(12) United States Patent
Tanikawa et al.

(10) Patent No.: US 9,045,466 B2
(45) Date of Patent: Jun. 2, 2015

(54) AMIDINE COMPOUND OR SALT THEREOF

(75) Inventors: Tetsuya Tanikawa, Toshima-ku (JP); Yasunobu Ushiki, Toshima-ku (JP); Fumihito Ushiyama, Toshima-ku (JP); Toru Yamaguchi, Toshima-ku (JP); Naoya Ono, Toshima-ku (JP); Keiko Yamamoto, Toshima-ku (JP); Risa Tsuruta, Toshima-ku (JP); Yasuhiro Tsutsui, Toyama (JP); Noritomo Fujino, Toyama (JP); Ayumu Mori, Toyama (JP)

(73) Assignees: TAISHO PHARMACEUTICAL CO., LTD, Tokyo (JP); TOYAMA CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 14/235,686

(22) PCT Filed: Jul. 27, 2012

(86) PCT No.: PCT/JP2012/069249
§ 371 (c)(1),
(2), (4) Date: Jan. 28, 2014

(87) PCT Pub. No.: WO2013/018735
PCT Pub. Date: Feb. 7, 2013

(65) Prior Publication Data
US 2014/0155597 A1 Jun. 5, 2014

(30) Foreign Application Priority Data
Jul. 29, 2011 (JP) .................................. 2011-167754

(51) Int. Cl.
| C07D 417/12 | (2006.01) |
|---|---|
| C07D 417/04 | (2006.01) |
| C07D 277/20 | (2006.01) |
| C07D 277/28 | (2006.01) |
| C07D 277/30 | (2006.01) |
| C07D 277/34 | (2006.01) |
| C07D 277/48 | (2006.01) |
| C07D 277/56 | (2006.01) |
| C07D 285/08 | (2006.01) |

(52) U.S. Cl.
CPC ............ *C07D 417/12* (2013.01); *C07D 417/04* (2013.01); *C07D 277/20* (2013.01); *C07D 277/28* (2013.01); *C07D 277/30* (2013.01); *C07D 277/34* (2013.01); *C07D 277/48* (2013.01); *C07D 277/56* (2013.01); *C07D 285/08* (2013.01)

(58) Field of Classification Search
CPC .................................................. C07D 417/04
USPC ................. 544/333, 405; 546/270.4; 548/202
See application file for complete search history.

(56) References Cited

U.S. PATENT DOCUMENTS

| 2008/0255196 A1 | 10/2008 | Kunz et al. |
| 2010/0093534 A1 | 4/2010 | Kunz et al. |

FOREIGN PATENT DOCUMENTS

| JP | 2009-507814 A | 2/2009 |
| JP | 2010-520905 A | 6/2010 |
| WO | 00/46184 A1 | 8/2000 |
| WO | 0217915 | 3/2002 |
| WO | 2004/037239 A1 | 5/2004 |

OTHER PUBLICATIONS

Hiroshi Nagase, Saishin Soyaku Kagaku, 1st volume, 1st edition, Technomics, Inc., Aug. 15, 1998, pp. 236 to 240.
Yamaguchi Hideyo, Clinical Microbiology, 1990, pp. 265-266, vol. 17, No. 3.
Mori Takeshi, Clinical Microbiology, 1994, pp. 277-283, vol. 21, No. 3.
Yamaguchi Hideyo, Clinical Microbiology, 2001, pp. 51-58, vol. 28, No. 1.
E Glyn V Evans et al., "Double blind, randomised study of continuous terbinafine compared with intermittent itraconazole in treatment of toenail onychomycosis", BMJ, Apr. 17, 1999, pp. 1031-1035, vol. 318.
Sigurgeirsson et al., "Long-term Effectiveness of Treatment With Terbinafine vs Itraconazole in Onychomycosis", Arch Dermatol., Mar. 2002, pp. 353-357, vol. 138.
J. New Rem. and Clin., 2007, pp. 228-236, vol. 56, vol. 9.
International Search Report of PCT/JP2012/069249 dated Oct. 2, 2012.
Communication for EP Application No. 12819674.8 dated Nov. 10, 2014, with Supplementary European Search Report (dated Oct. 29, 2014).

*Primary Examiner* — Brian McDowell
(74) *Attorney, Agent, or Firm* — Sughrue Mion, PLLC

(57) ABSTRACT

An amidine compound represented by formula (I)

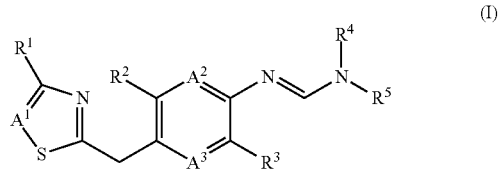

(wherein $A^1$ represents a nitrogen atom or a group represented by formula $CR^6$; $A^2$ and $A^3$ are the same as or different from each other and independently represent a nitrogen atom or a group represented by formula CH; $R^1$ represents an aryl group which may be substituted by 1 to 5 substituents independently selected from a substituent group (2) or the like; $R^2$ and $R^3$ are the same as or different from each other and independently represent a hydrogen atom, a halogen atom, a $C_{1-6}$ alkyl group, a $C_{1-6}$ haloalkyl group or a $C_{1-6}$ alkoxy group; and $R^4$ and $R^5$ are the same as or different from each other and independently represent a hydrogen atom, a $C_{1-6}$ haloalkyl group, a $C_{1-6}$ alkyl group or the like) or a salt thereof. The compound is useful as an anti-fungal agent.

5 Claims, No Drawings

AMIDINE COMPOUND OR SALT THEREOF

CROSS REFERENCE TO RELATED APPLICATIONS

This is a National Stage of International Application No. PCT/JP2012/069249 filed Jul. 27, 2012, claiming priority based on Japanese Patent Application No. 2011-167754 filed Jul. 29, 2011, the contents of all of which are incorporated herein by reference in their entirety.

TECHNICAL FIELD

The present invention relates to a novel amidine compound or a salt thereof, which has an antifungal activity against pathogenic fungi and an antifungal agent comprising the same.

BACKGROUND ART

In recent years, in association with the rapid progress of an aging society or a rise in chronic diseases such as lifestyle-related diseases, the risk of contracting deep mycosis and superficial mycosis caused by pathogenic fungi has also increased. Serious deep mycosis, such as invasive candidiasis, often threatens human life. The principal defensive mechanism of a host organism against fungi such as candida is originally considered to be brought about by nonspecific immunity mediated by neutrophils. When this defensive mechanism functions normally, there is a low risk of being infected by fungi. In recent years, however, the risk of contracting deep mycosis has been increased due to the increased number of patients having underlying diseases, such as malignant tumor and AIDS, which reduce the immune functions of organisms, frequent use of anticancer agents, immunosuppressants or the like, heavy use of antibacterial antibiotic substances or steroid hormones, long-term use of parenteral nutrition and intravenous catheters, etc. (Non Patent Document 1).

Only 9 types of drugs are available for such deep mycosis: amphotericin B, flucytosine, miconazole, fluconazole, itraconazole, voriconazole, posaconazole, caspofungin and micafungin. Amphotericin B has very strong antiseptic effects, but disadvantageously has adverse reactions such as renal toxicity resulting in limited clinical use. Flucytosine presents problems such as resistance and is therefore rarely used alone in current practice. Caspofungin and micafungin are weakly active against the genus *Cryptococcus*. All of the other drugs are collectively referred to as azole antifungal agents. These agents generally tend to be inferior in antiseptic effects on fungi to amphotericin B and however, are currently used most frequently in light of efficacy-safety tradeoffs (Non Patent Document 2).

Recently, fluconazole-resistant *Candida albicans* has been detected with high frequency from the oropharyngeal candidiasis lesions of AIDS patients who have received repeated doses of fluconazole. In addition, most of such resistant strains also exhibit cross resistance to itraconazole and other azole drugs. Furthermore, the segregation of resistant strains has also been reported as to non-AIDS patients affected by chronic mucocutaneous candidiasis or deep candidiasis (Non Patent Document 3). The resistance problem has a serious impact on the management of ever-increasing deep mycosis patients (Non Patent Document 3).

Meanwhile, trichophytosis unguium caused by *Trichophyton* is one type of superficial mycosis and is an intractable disease that requires 3 to 6 months for its treatment. Oral agents of itraconazole and terbinafine are currently used as therapeutic drugs in the treatment of this disease. Under the present circumstances, both the drugs, however, produce an insufficient cure rate, albeit differing depending on reports, and recurrence has also been found (Non Patent Documents 4 and 5). In addition, terbinafine must be taken every day for 6 months, and poor compliance attributed to the long-term administration has therefore been pointed out for this drug (Non Patent Document 6). Both of these drugs also produce adverse reactions in approximately 10% or more cases and have been confirmed to have abnormality in clinical laboratory test results including liver function test results of approximately 5% patients. Itraconazole is known to exhibit interaction with many other drugs and is thus difficult to use in combination with other agents. In this regard, itraconazole is not selected as a therapeutic drug in some cases.

Accordingly, there is a strong demand for the emergence of a therapeutic drug for deep mycosis that is superior in safety and pharmacological effects on resistant fungi to existing drugs, a therapeutic drug for trichophytosis unguium that has a better cure rate and incidence of recurrence and a shorter dosing period than those of existing drugs, or a drug that has better safety or drug interaction than that of existing drugs.

A compound that has an amidine structure and is useful as an antiseptic (Patent Document 1) is disclosed. This compound is also useful as an antifungal agent against particular fungi according to the disclosure (Patent Document 2). Nonetheless, neither of the documents state that this compound also has an antifungal activity against *Trichophyton*.

PRIOR ART DOCUMENTS

Patent Documents

Patent Document 1: International Publication No. WO 00/46184 pamphlet
Patent Document 2: International Publication No. WO 2004/037239 pamphlet

Non Patent Documents

Non Patent Document 1: Clinical Microbiology, Vol. 17, p. 265-266, 1990
Non Patent Document 2: Clinical Microbiology, Vol. 21, p. 277-283, 1994
Non Patent Document 3: Clinical Microbiology, Vol. 28, p. 51-58, 2001
Non Patent Document 4: BMJ. 318: 1031-5. 1999
Non Patent Document 5: Arch Dermatol. 138 (3): 353-7. 2002
Non Patent Document 6: J. New Rem. and Clin. 56 (9): 228-236. 2007

SUMMARY OF INVENTION

Technical Problem

An object of the present invention is to provide a novel compound that exhibits an antifungal activity against pathogenic fungi including fungi of the genera *Candida, Aspergillus* and *Trichophyton* and is pharmaceutically useful.

Solution to Problem

The present inventors have conducted diligent studies and consequently completed the present invention by finding that a compound represented by a formula (I):

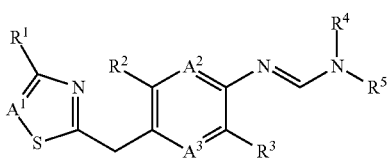

(wherein

A$^1$ represents a nitrogen atom or a group represented by a formula CR$^6$, where R$^6$ represents a hydrogen atom, a halogen atom, a cyano group or a group represented by a formula COR$^7$, where R$^7$ represents a hydroxy group, a C$_{1-6}$ alkoxy group, a C$_{1-6}$ alkyl group, an aryl group or a group represented by a formula NR$^8$R$^9$, where R$^8$ and R$^9$ are the same or different and represent a hydrogen atom or a C$_{1-6}$ alkyl group, or R$^8$ and R$^9$ represent, together with the nitrogen atom bonded thereto, a saturated heterocyclic ring which may be substituted with oxo group;

A$^2$ and A$^3$ are the same or different and represent a nitrogen atom or a group represented by a formula CH;

R$^1$ represents a C$_{3-6}$ cycloalkyl group which may be substituted with 1 to 5 substituents selected from Substituent Group 1, a C$_{1-6}$ alkyl group which may be substituted with 1 to 6 substituents selected from Substituent Group 1, an aryl group which may be substituted with 1 to 5 substituents selected from Substituent Group 2, a heterocyclic group which may be substituted with 1 to 5 substituents selected from Substituent Group 2, a group represented by a formula OR$^{10}$, a group represented by a formula COR$^{11}$, a group represented by a formula NR$^{12}$CO$_2$R$^{13}$, a group represented by a formula NR$^{14}$CONR$^{15}$R$^{16}$, a group represented by a formula NR$^{17}$COR$^{18}$, a group represented by a formula NR$^{19}$SO$_2$R$^{20}$ or a group represented by a formula OCONR$^{21}$R$^{22}$, where R$^{10}$, R$^{13}$, R$^{15}$, R$^{16}$, R$^{21}$ and R$^{22}$ are the same or different and represent a hydrogen atom, a C$_{1-6}$ alkyl group which may be substituted with 1 to 6 substituents selected from Substituent Group 1, a C$_{3-6}$ cycloalkyl group which may be substituted with 1 to 5 substituents selected from Substituent Group 1, an adamantyl group, an aryl group which may be substituted with 1 to 5 substituents selected from Substituent Group 2 or a heterocyclic group which may be substituted with 1 to 5 substituents selected from Substituent Group 2, R$^{11}$ represents a hydroxy group, a C$_{1-6}$ alkoxy group, a C$_{1-6}$ alkyl group which may be substituted with 1 to 6 substituents selected from Substituent Group 1, a C$_{3-6}$ cycloalkyl group which may be substituted with 1 to 5 substituents selected from Substituent Group 1, an adamantyl group, an aryl group which may be substituted with 1 to 5 substituents selected from Substituent Group 2, a heterocyclic group which may be substituted with 1 to 5 substituents selected from Substituent Group 2 or a group represented by a formula NR$^{23}$R$^{24}$, where R$^{23}$ and R$^{24}$ are the same or different and represent a hydrogen atom, a C$_{1-6}$ alkyl group which may be substituted with 1 to 6 substituents selected from Substituent Group 1 or a C$_{3-6}$ cycloalkyl group which may be substituted with 1 to 5 substituents selected from Substituent Group 1, R$^{12}$, R$^{14}$, R$^{17}$ and R$^{19}$ are the same or different and represent a hydrogen atom or a C$_{1-6}$ alkyl group, R$^{18}$ and R$^{20}$ are the same or different and represent a C$_{1-6}$ alkyl group which may be substituted with 1 to 6 substituents selected from Substituent Group 1, a C$_{3-6}$ cycloalkyl group which may be substituted with 1 to 5 substituents selected from Substituent Group 1, an adamantyl group, an aryl group which may be substituted with 1 to 5 substituents selected from Substituent Group 2 or a heterocyclic group which may be substituted with 1 to 5 substituents selected from Substituent Group 2, Substituent Group 1 is the group consisting of a halogen atom, an aryl group which may be substituted with 1 to 5 substituents selected from Substituent Group 2, a heterocyclic group which may be substituted with 1 to 5 substituents selected from Substituent Group 2, a group represented by a formula —OR$^{25}$, a group represented by a formula —COR$^{26}$, a group represented by a formula —NR$^{27}$R$^{28}$ and a group represented by a formula —SO$_2$R$^{29}$, where R$^{25}$ represents a hydrogen atom, a C$_{1-6}$ alkyl group, an aryl group which may be substituted with 1 to 5 substituents selected from Substituent Group 2 or a C$_{1-6}$ alkanoyl group, R$^{26}$ represents a hydroxy group, a C$_{1-6}$ alkoxy group or a group represented by a formula NR$^{30}$R$^{31}$, where R$^{30}$ and R$^{31}$ are the same or different and represent a hydrogen atom or a C$_{1-6}$ alkyl group, or R$^{30}$ and R$^{31}$ represent, together with the nitrogen atom bonded thereto, a saturated heterocyclic ring which may be substituted with oxo group, R$^{27}$ and R$^{28}$ are the same or different and represent a hydrogen atom or a C$_{1-6}$ alkyl group, R$^{29}$ represents a C$_{1-6}$ alkyl group, a C$_{3-6}$ cycloalkyl group, an aryl group which may be substituted with 1 to 5 substituents selected from Substituent Group 2 or a heterocyclic group which may be substituted with 1 to 5 substituents selected from Substituent Group 2, Substituent Group 2 is the group consisting of a halogen atom, an oxo group, a hydroxy group, a C$_{1-6}$ alkoxy group, a C$_{1-6}$ alkyl group, a C$_{1-6}$ haloalkyl group, a cyano group, a C$_{1-6}$ alkylsulfanyl group, a C$_{1-6}$ alkylsulfinyl group, a C$_{1-6}$ alkylsulfonyl group, an aminosulfonyl group, a C$_{1-6}$ alkylaminosulfonyl group and a group represented by a formula COR$^{32}$, where R$^{32}$ represents a hydroxy group, a C$_{1-6}$ alkoxy group or a group represented by a formula NR$^{33}$R$^{34}$, where R$^{33}$ and R$^{34}$ are the same or different and represent a hydrogen atom or a C$_{1-6}$ alkyl group, or R$^{33}$ and R$^{34}$ represent, together with the nitrogen atom bonded thereto, a saturated heterocyclic ring which may be substituted with oxo group;

R$^2$ and R$^3$ are the same or different and represent a hydrogen atom, a halogen atom, a C$_{1-6}$ alkyl group, a C$_{1-6}$ haloalkyl group or a C$_{1-6}$ alkoxy group;

R$^4$ and R$^5$ are the same or different and represent a hydrogen atom, a C$_{1-6}$ haloalkyl group or a C$_{1-6}$ alkyl group, wherein the C$_{1-6}$ alkyl group may be substituted with 1 to 3 substituents selected from the group consisting of a hydroxy group and a group represented by a formula COR$^{35}$, where R$^{35}$ represents a hydroxy group, a C$_{1-6}$ alkoxy group or a group represented by a formula NR$^{36}$R$^{37}$, where R$^{36}$ and R$^{37}$ are the same or different and represent a hydrogen atom or a C$_{1-6}$ alkyl group, or R$^{36}$ and R$^{37}$ represent, together with the nitrogen atom bonded thereto, a saturated heterocyclic ring which may be substituted with oxo group, or R$^4$ and R$^5$ represent, together with the nitrogen atom bonded thereto, a saturated heterocyclic ring which may be substituted with oxo group)

or a salt thereof has an antifungal activity.

Advantageous Effects of Invention

The compound represented by the formula (I) or the salt thereof has an antifungal activity against pathogenic fungi and is useful as an antifungal agent. In another aspect, the compound represented by the formula (I) or the salt thereof is also excellent in safety and is useful as an antifungal agent against fungi of the genera *Candida, Aspergillus* and *Trichophyton*.

DESCRIPTION OF EMBODIMENTS

In the present invention, $C_{x-y}$ means that the number of carbon atoms is x to y.

The $C_{1-6}$ alkyl group means a linear or branched alkyl group having 1 to 6 carbon atoms. Examples thereof can include methyl, ethyl, propyl, isopropyl, butyl, isobutyl, sec-butyl, tert-butyl, pentyl, isopentyl and hexyl.

The $C_{1-6}$ alkoxy group means a linear or branched alkoxy group having 1 to 6 carbon atoms. Examples thereof can include methoxy, ethoxy, propoxy, isopropoxy, butoxy, isobutoxy, sec-butoxy, tert-butoxy, pentyloxy, isopentyloxy and hexyloxy.

The halogen atom refers to a fluorine atom, a chlorine atom, a bromine atom or an iodine atom.

The $C_{1-6}$ haloalkyl group means a group in which any hydrogen atom in the $C_{1-6}$ alkyl group is replaced with a halogen atom. Examples thereof can include fluoromethyl, difluoromethyl, trifluoromethyl and trichloromethyl. The number of halogen atom substituents is preferably 1 to 3.

The $C_{1-6}$ alkylsulfanyl group means a linear or branched alkylsulfanyl group having 1 to 6 carbon atoms. Examples thereof can include methylsulfanyl, ethylsulfanyl, propylsulfanyl, isopropylsulfanyl, butylsulfanyl, isobutylsulfanyl, sec-butylsulfanyl, tert-butylsulfanyl, pentylsulfanyl, isopentylsulfanyl and hexylsulfanyl.

The $C_{1-6}$ alkylsulfinyl group means a linear or branched alkylsulfinyl group having 1 to 6 carbon atoms. Examples thereof can include methylsulfinyl, ethylsulfinyl, propylsulfinyl, isopropylsulfinyl, butylsulfinyl, isobutylsulfinyl, sec-butylsulfinyl, tert-butylsulfinyl, pentylsulfinyl, isopentylsulfinyl and hexylsulfinyl.

The $C_{1-6}$ alkylsulfonyl group means a linear or branched alkylsulfonyl group having 1 to 6 carbon atoms. Examples thereof can include methylsulfonyl, ethylsulfonyl, propylsulfonyl, isopropylsulfonyl, butylsulfonyl, isobutylsulfonyl, sec-butylsulfonyl, tert-butylsulfonyl, pentylsulfonyl, isopentylsulfonyl and hexylsulfonyl.

The $C_{1-6}$ alkylaminosulfonyl group means a group in which an amino group substituted by 1 or 2 $C_{1-6}$ alkyl groups exemplified above is bonded via $SO_2$. Examples thereof can include methylaminosulfonyl, dimethylaminosulfonyl, ethylaminosulfonyl and methylethylaminosulfonyl.

The $C_{3-6}$ cycloalkyl group refers to cyclopropyl, cyclobutyl, cyclopentyl or cyclohexyl.

The $C_{1-6}$ alkanoyl group means a linear or branched alkanoyl group having 1 to 6 carbon atoms. Examples thereof can include formyl, acetyl, propionyl, butyryl, isovaleryl and pivaloyl.

Examples of the heterocyclic groups can include monocyclic heterocyclic groups and bicyclic heterocyclic groups.

Examples of the monocyclic heterocyclic groups can include furyl, thienyl, 2-pyrrolyl, imidazolyl, 3-pyrazolyl, thiazolyl, isothiazolyl, oxazolyl, isoxazolyl, thiadiazolyl, imidazolidinyl, pyridyl, dihydropyridyl, pyrimidinyl, pyridazinyl, pyrazyl, pyrrolidinyl, piperazinyl, 2-piperidyl, 3-piperidyl, 4-piperidyl, 2-piperazinyl, 2-morpholinyl, 2-thiomorpholinyl, pyranyl, tetrahydropyranyl and tetrahydrothiopyranyl. The monocyclic heterocyclic group preferably contains 1 to 3 heteroatoms selected from a nitrogen atom, an oxygen atom and a sulfur atom as ring-constituting atoms and has 4 to 6 members. Among these monocyclic heterocyclic groups, a structure that contains at least one nitrogen atom as a ring-constituting atom and is free from an unsaturated bond is referred to as a saturated heterocyclic ring.

Examples of the bicyclic heterocyclic groups can include benzofuranyl, isobenzofuranyl, benzothienyl, indolyl, isoindolyl, indolizinyl, benzimidazolyl, benzoxazolyl, benzisoxazolyl, benzothiazolyl, 1H-indazolyl, purinyl, coumarinyl, chromenyl, quinolyl, isoquinolyl, phthalazinyl, naphthyridinyl, quinoxalinyl, quinazolinyl, cinnolinyl, chromanyl, isochromanyl, quinuclidinyl, 1,3-benzodioxanyl, 1,4-benzodioxanyl, benzomorpholinyl, benzomorpholonyl, 2,3-dihydro(1,4)dioxino(2,3-c)pyridin-7-yl, 3,4-dihydro-2H-pyrido(4,3-b)(1,4)oxazin-7-yl, 3-oxo-3,4-dihydro-2H-pyrido(3,2-b)(1,4)oxazin-6-yl, 3-oxo-3,4-dihydro-2H-pyrido(3,2-b)(1,4)thiazin-6-yl, 3-oxo-3,4-dihydro-2H-benzothiazin-6-yl, 3,4-dihydro-2H-pyrano(2,3-c)pyridin-6-yl, 3,4-dihydro-2H-(1,4)dioxepino(2,3-c)pyridin-8-yl, (1,3)dioxolo(4,5-c)pyridin-6-yl, 6-oxido-2,3-dihydro(1,4)dioxino(2,3-c)pyridin-7-yl, 7-oxo-5,6,7,8-tetrahydro-1,8-naphthyridin-2-yl, 5,6,7,8-tetrahydroquinoxalin-2-yl, 1,4-benzodithianyl, thieno(3,2-b)thiophen-2-yl and 7-oxo-7,8-dihydro-6H-pyrimido(5,4-b)(1,4)oxazin-4-yl.

Examples of the aryl groups can include phenyl, naphthyl, anthracenyl and phenanthrenyl.

Examples of the arylsulfonyl groups can include benzenesulfonyl, p-toluenesulfonyl and naphthalenesulfonyl.

In the compounds of the present invention, examples of the preferred compounds include the following compounds.

Preferred are the compounds wherein $A^1$ is a nitrogen atom or a group represented by a formula CH.

Preferred are the compounds wherein $A^2$ and $A^3$ are a group represented by a formula CH.

Preferred are the compounds wherein $R^1$ is a $C_{3-6}$ cycloalkyl group which may be substituted with 1 to 5 substituents selected from Substituent Group 1, a $C_{1-6}$ alkyl group which may be substituted with 1 to 6 substituents selected from Substituent Group 1, an aryl group which may be substituted with 1 to 5 substituents selected from Substituent Group 2, a heterocyclic group which may be substituted with 1 to 5 substituents selected from Substituent Group 2, a group represented by a formula $OR^{10}$, a group represented by a formula $COR^{11}$ or a group represented by a formula $NR^{12}CO_2R^{13}$.

Preferred are the compounds wherein $R^2$ and $R^3$ are the same or different and represent a hydrogen atom or a $C_{1-6}$ alkyl group. Further, more preferred are the compounds wherein $R^2$ and $R^3$ are the same or different and represent a $C_{1-6}$ alkyl group.

Preferred are the compounds wherein $R^4$ and $R^5$ are the same or different and represent a $C_{1-6}$ alkyl group, where the $C_{1-6}$ alkyl group may be substituted with 1 to 3 substituents selected from the group consisting of a hydroxy group and a group represented by a formula $COR^{35}$; or $R^4$ and $R^5$ represent, together with the nitrogen atom bonded thereto, a saturated heterocyclic ring which may be substituted with oxo group. Further, more preferred are the compounds wherein $R^4$ and $R^5$ are the same or different and represent a $C_{1-6}$ alkyl group.

The antifungal agent means a substance that is able to act on pathogenic fungi to thereby suppress their growth or kill the fungi. The antifungal agent may be a substance that prevents the propagation of the fungi or kills some fungi to decrease the number thereof.

Examples of the pathogenic fungi can include yeast-like fungi, filamentous fungi and *Zygomycetes*. Examples of the yeast-like fungi include the genus *Candida* (*Candida albicans*, *Candida glabrata*, *Candida guilliermondii*, *Candida krusei*, *Candida parapsilosis*, *Candida tropicalis*, etc.), the genus *Cryptococcus* (*Cryptococcus neoformans*, etc.), the genus *Malassezia* (*Malassezia furfur*, etc.) and the genus *Trichosporon* (*Trichosporon asahii*, etc.). Examples of the filamentous fungi include the genus *Aspergillus* (*Aspergillus fumigatus*, *Aspergillus terreus*, *Aspergillus niger*, *Aspergillus flavus*, etc.), the genus *Trichophyton* (*Trichophyton rubrum*, *Trichophyton mentagrophytes*, *Trichophyton tonsurans*, etc.), the genus *Fusarium* (*Fusarium solani*, etc.), the genus *Scedosporium* (*Scedosporium apiospermum*, etc.) and the genus *Microsporum* (*Microsporum canis*, etc.). Examples of the Zygomycetes include the genus *Mucor* (*Mucor plumbeus*, etc.), the genus *Rhizopus* (*Rhizopus oryzae*, etc.) and the genus *Absidia* (*Absidia corymbifera*, etc.).

The antifungal agent of the present invention exhibits excellent antifungal effects on species of fungi such as fungi of the genera *Candida*, *Aspergillus* and *Trichophyton* and exhibits better excellent antifungal effects on fungi of the genus *Trichophyton*.

In another aspect, the antifungal agent of the present invention exhibits excellent antifungal effects on fungal species such as *Candida albicans*, *Aspergillus fumigatus*, *Trichophyton rubrum*, *Trichophyton mentagrophytes*, *Malassezia furfur* and *Cryptococcus neoformans*.

The compound represented by the formula (I) or the salt thereof exhibits excellent safety. The safety is evaluated by various tests and can be evaluated by various safety tests selected from, for example, cytotoxicity tests, hERG tests, repeated dose toxicity tests, cytochrome P450 (CYP) activity inhibition tests, metabolic dependence inhibition tests, in vivo mouse micronucleus tests and in vivo rat liver UDS tests.

Examples of the salts of the compound of the formula (I) can include usually known salts of basic groups (e.g., an amino group) or acidic groups (e.g., a phenolic hydroxy group and a carboxy group).

Examples of the preferred salts include pharmacologically acceptable salts. The pharmacologically acceptable salt means a salt that is used in the chemotherapy and prevention of fungal infection. Examples thereof can include: salts with acids such as acetic acid, propionic acid, butyric acid, formic acid, trifluoroacetic acid, maleic acid, tartaric acid, citric acid, stearic acid, succinic acid, ethylsuccinic acid, malonic acid, lactobionic acid, gluconic acid, glucoheptonic acid, benzoic acid, methanesulfonic acid, ethanesulfonic acid, 2-hydroxyethanesulfonic acid, benzenesulfonic acid, p-toluenesulfonic acid (tosylic acid), laurylsulfuric acid, malic acid, aspartic acid, glutamic acid, adipic acid, cysteine, N-acetylcysteine, hydrochloric acid, hydrobromic acid, phosphoric acid, sulfuric acid, hydroiodic acid, nicotinic acid, oxalic acid, picric acid, thiocyanic acid, undecanoic acid, acrylic acid polymers and carboxyvinyl polymers; salts with inorganic bases, such as lithium salt, sodium salt, potassium salt, magnesium salt and calcium salt; organic amines such as morpholine and piperidine; and salts with amino acids.

The compound of the formula (I) or the salt thereof may form a hydrate or a solvate. They are also included in the present invention.

The compound of the present invention may have tautomers or stereoisomers such as geometric isomers. They are also included in the present invention.

The compound of the present invention may have compounds that function as prodrugs at the time of administration. They are also included in the present invention. The group of compounds that function as prodrugs preferably have the following features:

(1) the prodrug compound itself may have an antimicrobial activity, which is however not essential;

(2) the compound is converted after administration to a compound that exhibits the pharmacological activity of interest through the cleavage of a functional group functioning as a prodrug by an appropriate enzyme in vivo. In this case, the prodrug having an antimicrobial activity in itself may exhibit pharmacological effects as it is without being cleaved by an enzyme in vivo. Also, the prodrug and the compound cleaved by an enzyme in vivo may coexist; and (3) the prodrug is expected to have, for example, increased water solubility, enhanced or sustained pharmacological effects, reduced adverse reactions or toxicity, and improved stability. Particularly preferably, increased water solubility is expected. Use of the prodrug as, for example, an injection or drops achieves improvement in administration conditions such as reduction in the amount of a solution administered. This can be expected to increase the amount of the active ingredient or enhance pharmacological effects by a rise in serum concentration, for example.

The compound of the present invention can be made into a pharmaceutical preparation in combination with one or two or more pharmaceutically acceptable carriers, excipients or diluents. The carriers, excipients and diluents include water, lactose, dextrose, fructose, sucrose, sorbitol, mannitol, polyethylene glycol, propylene glycol, starch, gum, gelatin, alginate, calcium silicate, calcium phosphate, cellulose, water syrups, methylcellulose, polyvinylpyrrolidone, alkyl parahydroxybenzosorbate, talc, magnesium stearate, stearic acid, glycerin and various oils such as sesame oil, olive oil and soybean oil. These carriers, excipients or diluents are mixed, if necessary, with additives generally used, such as expanders, binders, disintegrants, pH adjusters and solubilizers. The compound of the present invention can be prepared as oral or parenteral drugs such as tablets, pills, capsules, granules, powders, solutions, emulsions, suspensions, ointments, injections or skin patches by a routine formulation technique.

The compound of the present invention can be administered orally or parenterally to an adult patient at a single dose of 1 to 5000 mg once a day or several times a day. The dose can be appropriately increased or decreased depending on the type of a disease to be treated, the age, body weight or symptoms of a patient, etc. Also, the compound of the present invention may be used in combination with other drugs.

Although the compound of the present invention can be synthesized, for example, by the following methods, the methods for producing the compound of the present invention should not be limited thereto.

General Production Method 1

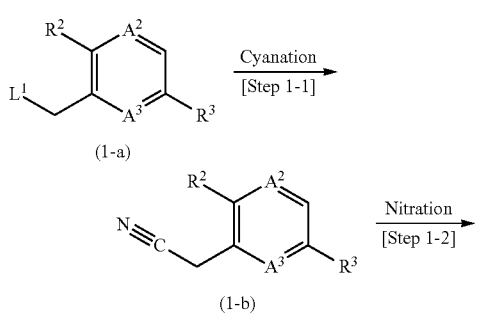

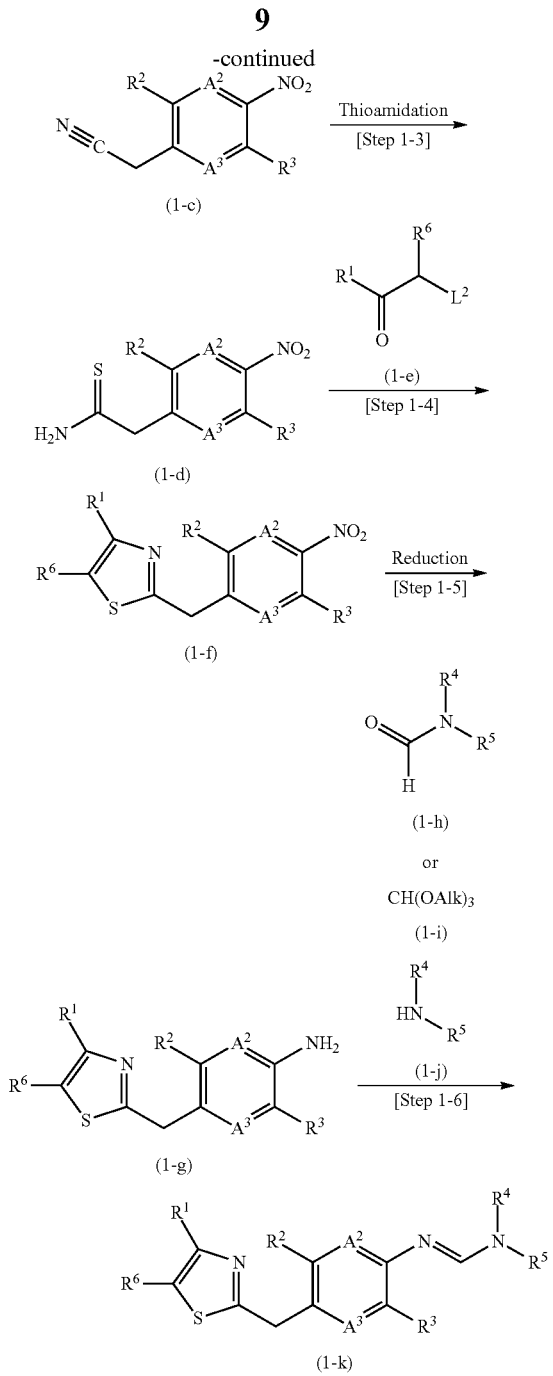

wherein $L^1$ and $L^2$ represent a leaving group such as a halogen atom, a $C_{1-6}$ alkylsulfonyl-O-group or an arylsulfonyl-O— group; Alk represents a $C_{1-6}$ alkyl group; and other groups $R^1$, $R^2$, $R^3$, $R^4$, $R^5$, $R^6$, $A^2$ and $A^3$ are as defined above.

Step 1-1

The compound of the general formula (1-b) can be produced through the reaction of a compound of the general formula (1-a) with sodium cyanide or potassium cyanide in an aprotic polar solvent (e.g., dimethyl sulfoxide, N,N-dimethylformamide, N,N-dimethylacetamide and 1-methyl-2-pyrrolidone), water, acetonitrile, or an alcoholic solvent (e.g., methanol and ethanol).

Step 1-2

The compound of the general formula (1-c) can be produced through the reaction of the compound of the general formula (1-b) with concentrated nitric acid or a mixture of concentrated nitric acid and sulfuric acid.

Step 1-3

The compound of the general formula (1-d) can be produced through the reaction of the compound of the general formula (1-c) with diethylphosphorodithioic acid or the like in the presence of an acid. This reaction can be performed by a method described in, for example, International Publication No. WO 06/137658 pamphlet and Journal of Medicinal Chemistry, Vol. 33, p. 2715-2720, 1990 or a method equivalent thereto. The solvent used in this reaction can be any solvent that has no adverse effect on the reaction. Examples thereof include esters such as ethyl acetate. Examples of the acids used in this reaction include hydrochloric acid. In this reaction, the amount of diethylphosphorodithioic acid or the like used can be 1 to 50 equivalents, preferably 1 to 5 equivalents, with respect to the compound of the general formula (1-c). The amount of the acid used can be 1 to 50 equivalents. This reaction can be carried out at 0° C. to 200° C., preferably 0° C. to 50° C., for 30 minutes to 48 hours.

Step 1-4

The compound of the general formula (1-f) can be produced through the reaction of the compound of the general formula (1-d) with a compound of the general formula (1-e). This reaction can be performed by a method described in, for example, International Publication No. WO 05/115382 pamphlet and U.S. Patent No. 20060052420 or a method equivalent thereto. The solvent used in this reaction can be any solvent that has no adverse effect on the reaction. Examples thereof include: alcohols such as methanol, ethanol, 2-propanol and 2-methyl-2-propanol; aprotic polar solvents such as N,N-dimethylformamide, N,N-dimethylacetamide and 1-methyl-2-pyrrolidone; halogenated hydrocarbons such as chloroform and dichloroethane; aromatic hydrocarbons such as benzene, toluene and xylene; ethers such as tetrahydrofuran, anisole, ethylene glycol dimethyl ether, diethylene glycol dimethyl ether, diethylene glycol diethyl ether and ethylene glycol monomethyl ether; sulfoxides such as dimethyl sulfoxide; ketones such as acetone and 2-butanone; nitriles such as acetonitrile; and water. These solvents may be mixed for use. In this reaction, the amount of the compound of the general formula (1-e) used can be 1 to 50 equivalents, preferably 1 to 5 equivalents, with respect to the compound of the general formula (1-d). This reaction can be carried out at 0° C. to 200° C., preferably room temperature to 150° C., for 30 minutes to 48 hours.

Step 1-5

The compound of the general formula (1-g) can be produced through the hydrogenation of the compound of the general formula (1-f) in the presence of a catalyst such as palladium-carbon, Raney nickel or palladium hydroxide in an alcoholic solvent (e.g., methanol and ethanol), an ether solvent (e.g., tetrahydrofuran and dioxane), a halogen solvent (e.g., methylene chloride and chloroform), or an aromatic hydrocarbon solvent (e.g., toluene and xylene). Alternatively, the compound of the general formula (1-g) may be produced through the reaction of the compound of the general formula (1-f) with a reducing agent, for example, iron (powder) or tin chloride, in the presence of hydrochloric acid or ammonium chloride in an aqueous solution of an alcohol such as methanol or ethanol. The reducing agent is used in an amount of 2 to 5 equivalents with respect to the compound of the general formula (1-f). This reaction can be carried out at room temperature to solvent reflux temperature. The reaction time is 30 minutes to 24 hours.

Step 1-6

The compound of the present invention of the general formula (1-k) can be produced through the reaction of the compound of the general formula (1-g) with carbamoyl chloride obtained through the reaction of a compound of the general formula (1-h) with, for example, oxalyl chloride or phosphoryl chloride. This reaction can be performed by a method described in, for example, Journal of Organic Chemistry, Vol. 73, p. 8954-8959, 2008 and International Publication No. WO 09/045,830 pamphlet or a method equivalent thereto. The solvent used in this reaction can be any solvent that has no adverse effect on the reaction. Examples thereof include: halogenated hydrocarbons such as chloroform and dichloroethane; and ethers such as tetrahydrofuran, anisole, ethylene glycol dimethyl ether, diethylene glycol dimethyl ether, diethylene glycol diethyl ether and ethylene glycol monomethyl ether. These solvents may be mixed for use. In this reaction, the amount of the compound of the general formula (1-h) used can be 1 to 50 equivalents, preferably 1 to 5 equivalents, with respect to the compound of the general formula (1-g). In this reaction, the amount of oxalyl chloride or phosphoryl chloride or the like used can be 1 to 50 equivalents, preferably 1 to 5 equivalents, with respect to the compound of the general formula (1-h). This reaction can be carried out at −78° C. to 200° C., preferably 0° C. to 50° C., for 30 minutes to 48 hours.

Alternatively, the compound of the present invention of the general formula (1-k) may be produced through the reaction of amine of the general formula (1-j) with a formimidate compound obtained through the reaction of the compound of the general formula (1-g) with a compound of the general formula (1-i) in the presence of an acid catalyst such as (+)-10-camphorsulfonic acid or p-toluenesulfonic acid. The solvent used in this reaction can be any solvent that has no adverse effect on the reaction and is preferably an aqueous solution of an alcohol such as methanol or ethanol.

General Production Method 2

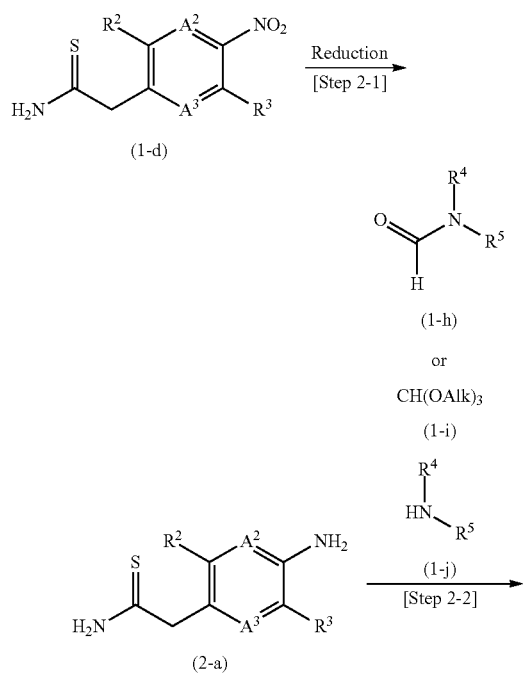

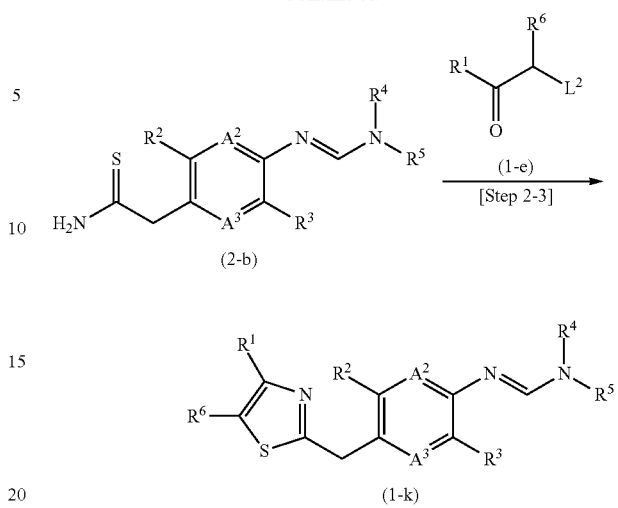

wherein $L^2$, Alk, $R^1$, $R^2$, $R^3$, $R^4$, $R^5$, $R^6$, $A^2$ and $A^3$ are as defined above.

Step 2-1

The compound of the general formula (2-a) can be produced through the reduction of a nitro group in a compound of the general formula (1-d) in the same way as in "Step 1-5".

Step 2-2

The compound of the general formula (2-b) can be produced through the reaction of the compound of the general formula (2-a) with a compound of the general formula (1-h) or with a compound of the general formula (1-i) and a compound of the general formula (1-j) in the same way as in "Step 1-6".

Step 2-3

The compound of the present invention of the general formula (1-k) can be produced through the reaction of the compound of the general formula (2-b) with a compound of the general formula (1-e) in the same way as in "Step 1-4".

General Production Method 3

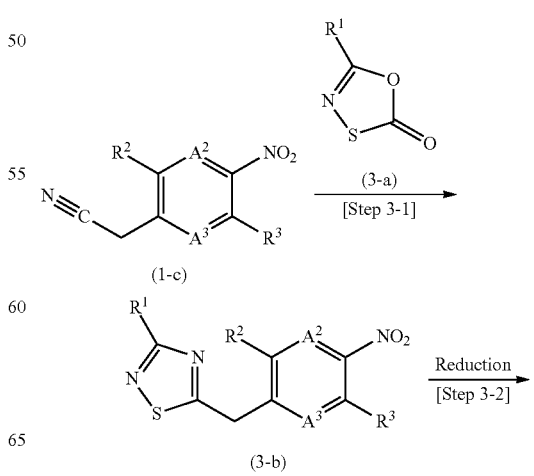

-continued

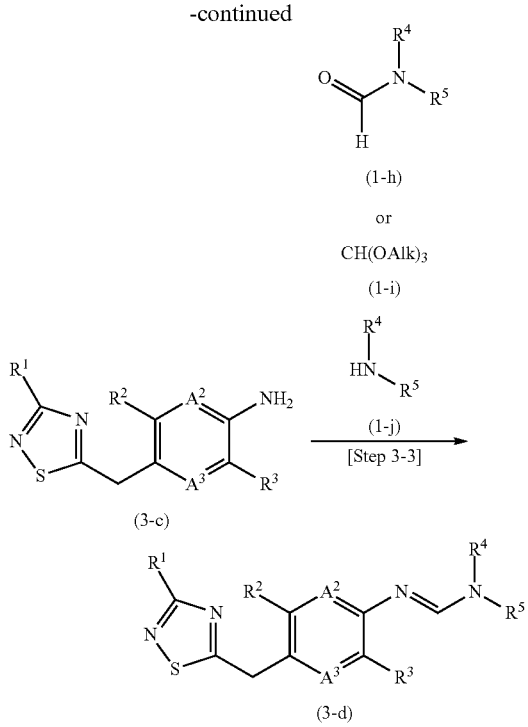

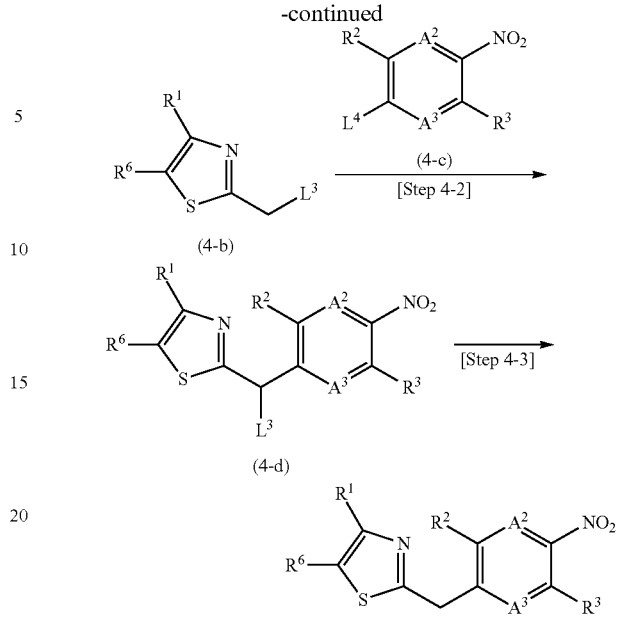

wherein $L^3$ represents a cyano group or an optionally protected carboxy group; $L^4$ represents a leaving group such as a halogen atom, a $C_{1-6}$ alkylsulfonyl-O— group or an arylsulfonyl-O— group; and other groups $L^2$, $R^1$, $R^2$, $R^3$, $R^6$, $A^2$ and $A^3$ are as defined above.

Step 4-1

The compound of the general formula (4-b) can be produced through the reaction of a compound of the general formula (1-e) with a compound of the general formula (4-a) in the same way as in "Step 1-4".

Step 4-2

For example, 1-chloro-2,5-dimethyl-4-nitrobenzene is known as a compound of the general formula (4-c). The compound of the general formula (4-d) can be produced through the reaction of the compound of the general formula (4-b) with the compound of the general formula (4-c) in the presence of a base. The solvent used in this reaction can be any solvent that has no adverse effect on the reaction. Examples thereof include: aprotic polar solvents such as N,N-dimethylformamide, N,N-dimethylacetamide and 1-methyl-2-pyrrolidone; and ethers such as tetrahydrofuran, anisole, ethylene glycol dimethyl ether, diethylene glycol dimethyl ether, diethylene glycol diethyl ether and ethylene glycol monomethyl ether. Amides are preferred.

Examples of the bases used in this reaction include: organic bases such as sodium methoxide, sodium ethoxide, potassium tert-butoxide, pyridine, dimethylaminopyridine and triethylamine; and inorganic bases such as sodium hydride, sodium hydroxide, potassium hydroxide, sodium bicarbonate, potassium carbonate and sodium carbonate. Examples of the preferred bases include potassium tert-butoxide.

The amount of the base used can be 1 to 20 equivalents with respect to the compound of the general formula (4-b) and is preferably 1 to 5 equivalents. The amount of the compound of the general formula (4-d) used can be 1 to 20 equivalents, preferably 1 to 5 equivalents, with respect to the compound of the general formula (4-b). This reaction can be carried out at 0 to 200° C., preferably 0 to 150° C., for 10 minutes to 48 hours.

wherein Alk, $R^1$, $R^2$, $R^3$, $R^4$, $R^5$, $A^2$ and $A^3$ are as defined above.

Step 3-1

The compound of the general formula (3-b) can be produced through the [3+2] cyclization reaction of a compound of the general formula (1-c) in an aromatic hydrocarbon solvent such as o-dichlorobenzene, m-xylene or decalin. This reaction can be carried out at room temperature to solvent reflux temperature, preferably 150° C. to 200° C.

Step 3-2

The compound of the general formula (3-c) can be produced through the reduction of a nitro group in the compound of the general formula (3-b) in the same way as in "Step 1-5".

Step 3-3

The compound of the present invention of the general formula (3-d) can be produced through the reaction of the compound of the general formula (3-c) with a compound of the general formula (1-h) or with a compound of the general formula (1-i) and a compound of the general formula (1-j) in the same way as in "Step 1-6".

General Production Method 4

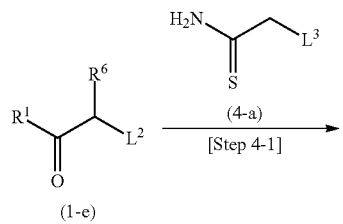

Step 4-3

The compound of the general formula (1-f) can be produced through the decarboxylation reaction of the compound of the general formula (4-d) in the presence or absence of an acid. The solvent used in this reaction can be any solvent that has no adverse effect on the reaction. Examples thereof include: aprotic polar solvents such as N,N-dimethylformamide, N,N-dimethylacetamide and 1-methyl-2-pyrrolidone; and ethers such as tetrahydrofuran, anisole, ethylene glycol dimethyl ether, diethylene glycol dimethyl ether, diethylene glycol diethyl ether and ethylene glycol monomethyl ether. Ethers are preferred.

Examples of the acids used, if desired, in this reaction include: inorganic acids such as hydrochloric acid, sulfuric acid, phosphoric acid, hydrogen chloride and hydrogen bromide; organic carboxylic acids such as acetic acid, trichloroacetic acid and trifluoroacetic acid; and organic sulfonic acids such as methanesulfonic acid and p-toluenesulfonic acid. Examples of the preferred acids include hydrochloric acid. The amount of the acid used can be 0.001 equivalents or more with respect to the compound of the general formula (4-d) and is preferably 0.01 to 5 equivalents. Also, the acid may be used as a solvent. This reaction can be carried out at 0 to 200° C., preferably 50 to 150° C., for 10 minutes to 48 hours. The compound of the general formula (1-f) can be converted to the compound of the present invention of the general formula (1-k) through "Step 1-5" and "Step 1-6" of General Production Method 1.

EXAMPLES

Hereinafter, the present invention will be described in more detail with reference to Reference Examples, Examples and Test Example. However, the present invention is not limited by these examples.

Abbreviations in Examples will be shown below.

The carrier used in silica gel chromatography was silica gel 60N manufactured by Kanto Chemical Co., Inc., SANP Cartridge HP-sil manufactured by Biotage Japan Ltd., or Reveleris Silica Cartridge manufactured by W. R. Grace & Co., unless otherwise specified. The carrier used in NH-type silica gel chromatography was Chromatorex NH-DM1020 manufactured by Fuji Silysia Chemical Ltd. or SANP Cartridge KP-NH manufactured by Biotage Japan Ltd., unless otherwise specified. Preparative silica gel thin-layer chromatography employed PLC plate silica gel $60F_{254}$ manufactured by Merck KGaA, and the NH type employed Chromatorex NH-DM1020 manufactured by Fuji Silysia Chemical Ltd. The phase separator used is manufactured by Biotage Japan Ltd. The HP-20 used is manufactured by SUPELCO (Sigma-Aldrich Corp.). NMR spectra represent proton NMR, and δ values were indicated by ppm using tetramethylsilane as an internal standard.

For LC-MS, HPLC was performed using Agilent 1100, and MS (ESI) measurement was performed using MicroMass Platform LC. The column, solvent and measurement conditions used are as follows:
Column: Waters, SunFire C18, 2.5 μm, 4.6×50 mm Column
Solvent: $CH_3CN$ (0.10% $CF_3COOH$), $H_2O$ (0.10% $CF_3COOH$)
Measurement conditions: gradient elution; 0 to 0.5 min. (10% $CH_3CN$), 5.5 min. (80% $CH_3CN$), and 6.0 to 6.3 min. (99% $CH_3CN$)

Preparative LC employed GILSON preparative HPLC system. The column, solvent and measurement conditions used in preparative LC are as follows:
Column: Waters, SunFire Prep C18, OBD 5.0 μm, 30×50 mm Column
Solvent: $CH_3CN$ (0.1% $CF_3COOH$), $H_2O$ (0.1% $CF_3COOH$)
Measurement conditions: gradient elution; 0 to 2 min. (10% $CH_3CN$), 11 min. (80% $CH_3CN$), and 13.5 min. (95% $CH_3CN$)

Further, the abbreviations used in Examples are shown hereinbelow:
(+)-CSA: (+)-10-camphorsulfonic acid
APCI: atmospheric pressure chemical ionization
aq.: aqueous solution
DMSO-$d_6$: hexadeuterated dimethyl sulfoxide
ESI: electrospray ionization
HATU: O-(7-azabenzotriazol-1-yl)-N,N,N',N'-tetramethyluronium hexafluorophosphate
HOBt.$H_2O$: 1-hydroxybenzotriazole monohydrate
LC: liquid chromatography
WSC.HCl: 1-ethyl-3-(3-dimethylaminopropyl)carbodiimide hydrochloride
s: singlet
br.s.: broad singlet
d: doublet
dd: double doublet
dt: double triplet
m: multiplet
t: triplet
td: triple doublet
tt: triple triplet
q: quartet
quin: quintet Reference Example 1-1

(2,5-Dimethyl-4-nitrophenyl)acetonitrile

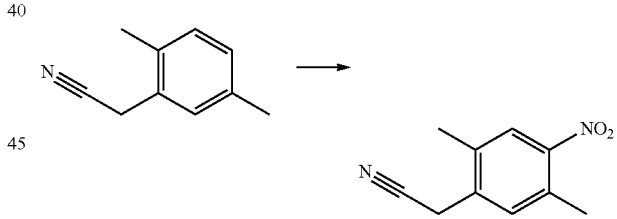

To (2,5-dimethylphenyl)acetonitrile (30 g), under ice cooling, fuming nitric acid (103 mL) was added dropwise, and the resultant was stirred for 30 minutes under ice cooling. Water was added thereto, followed by extraction with ethyl acetate. The organic layer was dried over magnesium sulfate, and the desiccant was filtered off. Then, the solvent was distilled off under reduced pressure. A saturated aqueous solution of sodium bicarbonate was added to the obtained residue, followed by extraction with ethyl acetate. The organic layer was dried over magnesium sulfate, and the desiccant was filtered off. Then, the solvent was distilled off under reduced pressure. The obtained residue was purified by silica gel column chromatography (NH-type silica gel; chloroform/ethyl acetate-gradient elution=100/0→90/10) and then further purified twice by silica gel column chromatography (OH-type silica gel; hexane/ethyl acetate-gradient elution=90/10→60/40) to obtain the title compound (12 g) as a pale yellow solid.

¹H NMR (600 MHz, CHLOROFORM-d) δppm 2.35-2.41 (3H, m), 2.58 (3H, s), 3.69 (2H, s), 7.36 (1H, s), 7.84 (1H, s)

Reference Example 1-2

2-(2,5-Dimethyl-4-nitrophenyl)ethanethioamide

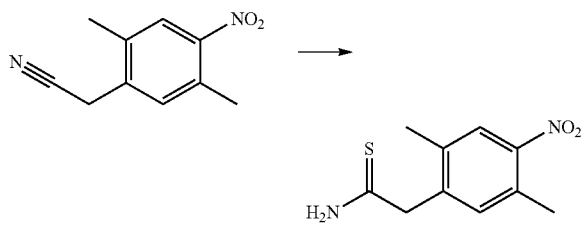

To the compound (6.0 g) obtained by the technique of Reference Example 1-1A, 4 mol/L hydrogen chloride/ethyl acetate solution (100 mL) and diethylphosphorodithioic acid (7.9 mL) were added, and the resultant was stirred at room temperature for 1 day. The deposited solid was collected by filtration and washed with hexane/ethyl acetate (=3/1) to obtain the title compound (6.3 g) as a pale yellow solid.

¹H NMR (600 MHz, CHLOROFORM-d) δppm 2.37 (3H, s), 2.58 (3H, s), 4.11 (2H, s), 6.53 (1H, br. s), 7.18 (1H, s), 7.45 (1H, br. s), 7.86 (1H, s)

Reference Example 1-3

2-(4-Amino-2,5-dimethylphenyl)ethanethioamide

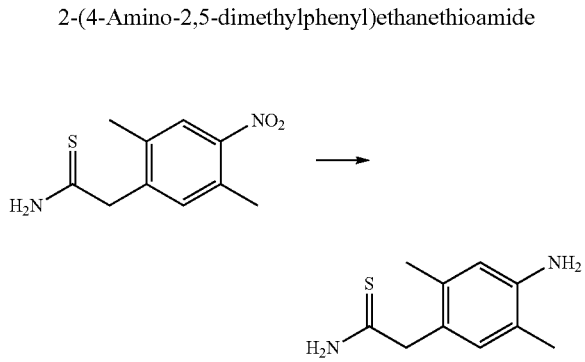

To a 1:1 ethanol/water (50 mL) solution of the compound (5.0 g) obtained by the technique of Reference Example 1-2, ammonium chloride (3.6 g) and iron powder (3.7 g) were added, and the resultant was heated to reflux for 2 hours. Insoluble material was filtered off, and the filtrate was concentrated under reduced pressure. A saturated aqueous solution of sodium bicarbonate was added to the obtained residue, followed by extraction with ethyl acetate. The organic layer was dried over magnesium sulfate, and the desiccant was filtered off. Then, the solvent was distilled off under reduced pressure to obtain the title compound (3.3 g) as a yellow solid.

¹H NMR (600 MHz, CHLOROFORM-d) δppm 2.12 (3H, s), 2.16 (3H, s), 3.61 (2H, br. s.), 3.99 (2H, s), 6.54 (1H, s), 6.73 (1H, br. s.), 6.82 (1H, s), 7.50 (1H, br. s)

Reference Example 1-4

N-Ethyl-N-methylformamide

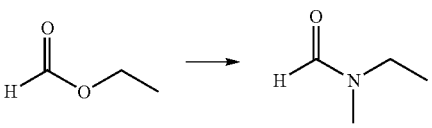

To an ethanol (25 mL) solution of N-ethyl-N-methylamine (10 g) under ice cooling, ethyl formate (27 ml) was added, and the resultant was stirred at 65° C. for 2 hours. After standing to cool to room temperature and stirring for 30 minutes, the reaction solution was concentrated under reduced pressure to obtain the title compound (11 g) as a yellow oil.

¹H NMR (200 MHz, CHLOROFORM-d) δppm 1.06-1.27 (3H, m), 2.79-2.98 (3H, m), 3.19-3.48 (2H, m), 7.96-8.12 (1H, m)

Reference Example 1-5

2-[4-({(E)-[Ethyl(methyl)amino]methylidene}amino)-2,5-dimethylphenyl]ethanethioamide

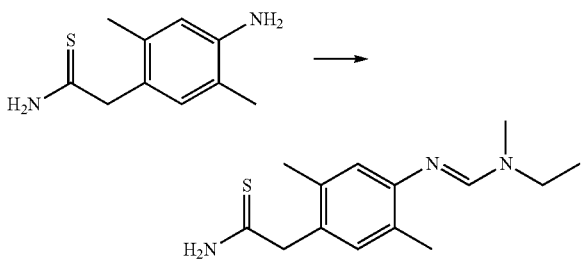

To a chloroform (15 mL) solution of the compound (2.4 g) obtained by the technique of Reference Example 1-4, oxalyl chloride (2.0 mL) was added, and the resultant was stirred at room temperature for 10 minutes. Then, a chloroform (10 mL) solution of the compound (3.3 g) obtained by the technique of Reference Example 1-3 was added thereto, and the resultant was stirred at room temperature for 1 day. A saturated aqueous solution of sodium bicarbonate was added thereto, followed by extraction with chloroform. The organic layer was dried over magnesium sulfate, and the desiccant was filtered off. Then, the solvent was distilled off under reduced pressure. The obtained residue was purified by silica gel column chromatography (OH-type silica gel; chloroform/methanol-gradient elution=100/0→91/9) and then further purified by silica gel column chromatography (NH-type silica gel; hexane/ethyl acetate-gradient elution=66/34→20/80) to obtain the title compound (1.0 g) as a brown oil.

¹H NMR (600 MHz, CHLOROFORM-d) δppm 1.19-1.23 (3H, m), 2.20 (3H, s), 2.22 (3H, s), 3.00 (3H, s), 3.28-3.44 (2H, m), 4.04 (2H, s), 6.60 (1H, s), 6.66-6.74 (1H, m), 6.91 (1H, s), 7.38-7.54 (2H, m)

Reference Example 2-1

2-(2,5-Dimethyl-4-nitrobenzyl)-4-(4-methylphenyl)-1,3-thiazole hydrobromide

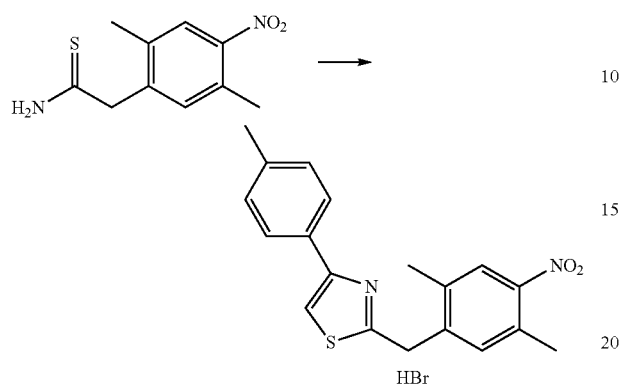

To a 2-propanol (10 mL) suspension of the compound (0.20 g) obtained by the technique of Reference Example 1-2, 2-bromo-4'-methylacetophenone (0.21 g) was added, and the resultant was stirred at 80° C. for 1 hour in a nitrogen atmosphere. After standing to cool at room temperature, the resulting deposit was filtered and washed with 2-propanol to obtain the title compound (0.19 g) as a white solid.

$^1$H NMR (600 MHz, CHLOROFORM-d) δppm 2.39-2.46 (6H, m), 2.59 (3H, s), 5.14 (2H, br. s.), 7.36 (2H, d, J=8.3 Hz), 7.40 (1H, s), 7.47 (1H, s), 7.90 (1H, s), 8.01 (2H, d, J=8.3 Hz)

Reference Example 2-2

2,5-Dimethyl-4-{[4-(4-methylphenyl)-1,3-thiazol-2-yl]methyl}aniline hydrobromide

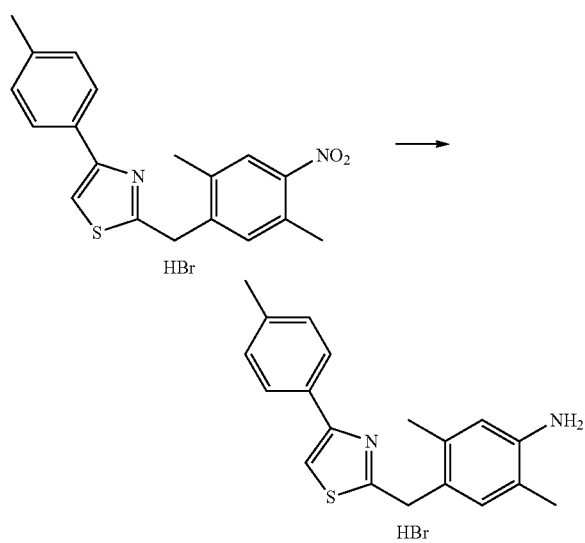

To a methanol (10 mL) suspension of the compound (0.19 g) obtained by the technique of Reference Example 2-1, 10% palladium-carbon (93 mg) was added, and the resultant was stirred at room temperature for 19 hours in a hydrogen atmosphere. Insoluble material was filtered off, and the filtrate was concentrated under reduced pressure to obtain the title compound (0.16 g) as a white solid.

$^1$H NMR (600 MHz, DMSO-d$_6$) δppm 2.19 (3H, s), 2.25 (3H, s), 2.32 (3H, s), 4.30 (2H, s), 6.94 (1H, s), 7.17 (1H, s), 7.23 (2H, d, J=7.8 Hz), 7.81 (2H, d, J=7.8 Hz), 7.85 (1H, s)

Reference Example 3-1

5-Tert-butylpyrazine-2-carbonitrile

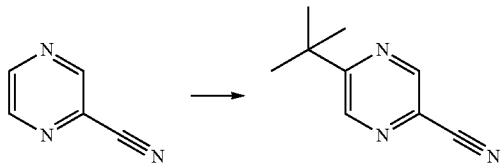

To an aqueous (1.5 L) solution of 2-cyanopyrazine (60 g), pivalic acid (56 mL) and ammonium peroxodisulfate (100 g) were added, then silver nitrate (146 g) was added, and the resultant was stirred at 80° C. for 2.5 hours. The reaction solution was extracted with ethyl acetate. Ethyl acetate was further added to the extract, and the suspension was filtered. Saturated saline was added to the filtrate, followed by extraction with ethyl acetate. The organic layer was dried over magnesium sulfate, and the desiccant was filtered off. Then, the solvent was distilled off under reduced pressure. The obtained residue was purified twice by silica gel column chromatography (OH-type silica gel; hexane/ethyl acetate-gradient elution=95/5→50/50) to obtain the title compound (54 g) as a pale yellow solid.

$^1$H NMR (200 MHz, CHLOROFORM-d) δppm 1.43 (9H, s), 8.77 (1H, d, J=1.8 Hz), 8.83 (1H, d, J=1.8 Hz)

Reference Example 3-2

1-(5-Tert-butylpyrazin-2-yl)ethanone

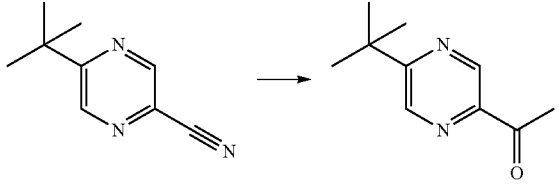

To a tetrahydrofuran (300 mL) solution of the compound (15 g) obtained by the technique of Reference Example 3-1, under ice cooling, a 3 mol/L methyl magnesium bromide/diethyl ether solution (62 mL) was added, and the resultant was stirred for 4 hours under ice cooling. The reaction solution was added to ice-cold water, and the resultant was adjusted to around pH 2.0 by the addition of a 6 mol/L aqueous hydrochloric acid solution under ice cooling and stirred for 30 minutes. After extraction with ethyl acetate, the organic layer was dried over magnesium sulfate, and the desiccant was filtered off. Then, the solvent was distilled off under reduced pressure. The obtained residue was purified by silica gel column chromatography (OH-type silica gel; hexane/ethyl acetate-gradient elution=100/0→83/17) to obtain the title compound (8.3 g) as a yellow solid.

¹H NMR (600 MHz, CHLOROFORM-d) δppm 1.43 (9H, s), 2.70 (3H, s), 8.69 (1H, d, J=1.2 Hz), 9.14 (1H, d, J=1.2 Hz)

Reference Example 3-3

2-Bromo-1-(5-tert-butylpyrazin-2-yl)ethanone hydrobromide

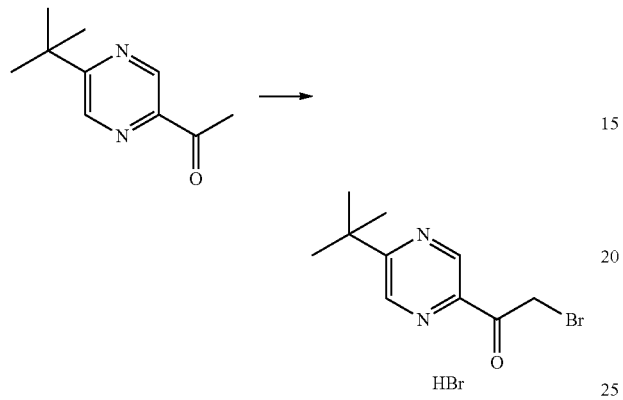

To an ethanol (80 mL) solution of the compound (8.0 g) obtained by the technique of Reference Example 3-2, acetic acid (100 mL), a 20 to 30% hydrobromic acid/ethanol solution (12 mL) and bromine (1.9 mL) were added, and the resultant was stirred at 70° C. for 1 hour under sealed conditions. Then, bromine (0.60 mL) was further added thereto, and the resultant was further stirred at 70° C. for 1 hour under sealed conditions. The reaction solution was concentrated under reduced pressure to obtain the title compound (16 g) as a pale yellow solid.

Reference Example 3-4

2-Tert-butyl-5-[2-(2,5-dimethyl-4-nitrobenzyl)-1,3-thiazol-4-yl]pyrazine

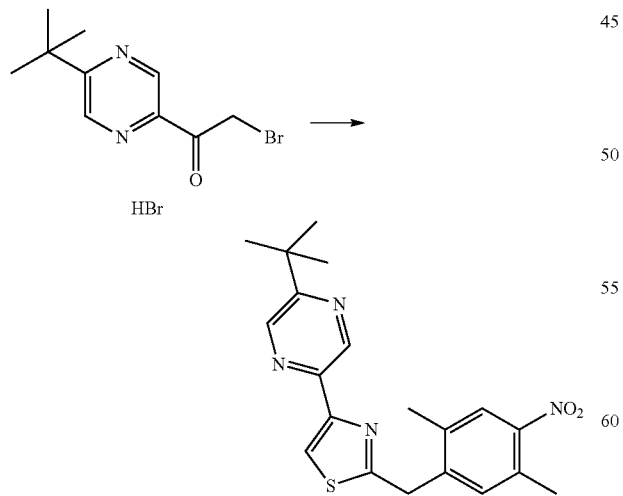

To a 2-propanol (50 mL) suspension of the compound (2.0 g) obtained by the technique of Reference Example 1-2, the compound (4.6 g) obtained by the technique of Reference Example 3-3 was added, and the resultant was stirred at 80° C. for 30 minutes and then stirred at room temperature for 15 hours. The solvent was distilled off under reduced pressure. A saturated aqueous solution of sodium bicarbonate was added to the obtained residue, followed by extraction with ethyl acetate. The organic layer was dried over magnesium sulfate, and the desiccant was filtered off. Then, the solvent was distilled off under reduced pressure. The obtained residue was purified by silica gel column chromatography (OH-type silica gel; hexane/ethyl acetate-gradient elution=100/0→70/30) to obtain the title compound (3.4 g) as an orange oil.

¹H NMR (600 MHz, CHLOROFORM-d) δppm 1.42 (9H, s), 2.42 (3H, s), 2.57 (3H, s), 4.42 (2H, s), 7.25 (1H, s), 7.86 (1H, s), 7.93 (1H, s), 8.62 (1H, d, J=1.5 Hz), 9.21 (1H, d, J=1.5 Hz)

Reference Example 3-5

4-{[4-(5-Tert-butylpyrazin-2-yl)-1,3-thiazol-2-yl]methyl}-2,5-dimethylaniline

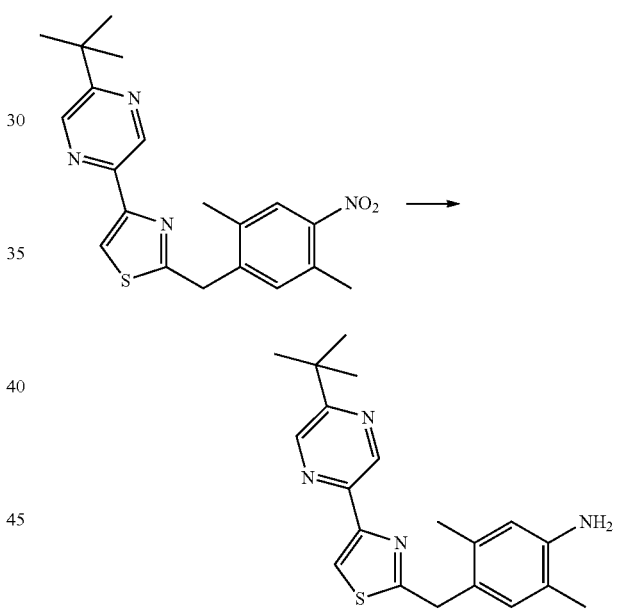

To a methanol (60 mL) solution of the compound (3.1 g) obtained by the technique of Reference Example 3-4, 10% palladium-carbon (0.31 g) was added, and the resultant was stirred at room temperature for 6 days in a hydrogen atmosphere. The reaction mixture was filtered through Celite, and the filtrate was concentrated under reduced pressure. The obtained residue was purified by silica gel column chromatography (OH-type silica gel; hexane/ethyl acetate-gradient elution=100/0→50/50) to obtain the title compound (1.2 g) as a yellow solid.

¹H NMR (600 MHz, CHLOROFORM-d) δppm 1.42 (9H, s), 2.15 (3H, s), 2.23 (3H, s), 3.44-3.66 (2H, m), 4.26 (2H, s), 6.55 (1H, s), 6.97 (1H, s), 7.85 (1H, s), 8.61 (1H, d, J=1.7 Hz), 9.23 (1H, d, J=1.7 Hz)

Reference Example 4-1

5-(1,1,1-Trifluoro-2-methylpropan-2-yl)pyrazine-2-carbonitrile

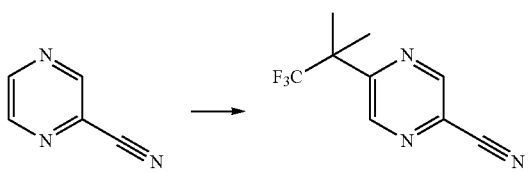

To an aqueous (50 mL) solution of 2-cyanopyrazine (6.7 mL), 3,3,3-Trifluoro-2,2-dimethylpropionic acid (10 g) and ammonium peroxodisulfate (22 g) were added, then silver nitrate (16 g) was added, and the resultant was stirred at 80° C. for 8 hours. The reaction solution was subjected to extraction with ethyl acetate. The organic layer was dried over magnesium sulfate, and the desiccant was filtered off. Then, the solvent was distilled off under reduced pressure. The obtained residue was purified by silica gel column chromatography (OH-type silica gel; hexane/ethyl acetate-gradient elution=100/0→75/25) to obtain the title compound (0.28 g) as a pale yellow oil.

$^1$H NMR (600 MHz, CHLOROFORM-d) δppm 1.67 (6H, s), 8.83-8.96 (2H, m)

Reference Example 4-2

1-[5-(1,1,1-Trifluoro-2-methylpropan-2-yl)pyrazin-2-yl]ethanone

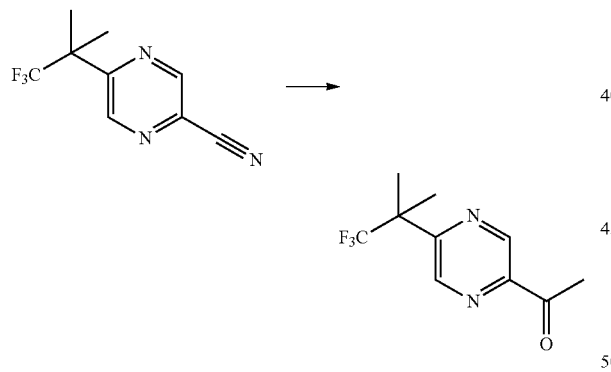

To a tetrahydrofuran (5.0 mL) solution of the compound (0.28 g) obtained by the technique of Reference Example 4-1, under ice cooling, a 3 mol/L methyl magnesium bromide/diethyl ether solution (0.87 mL) was added, and the resultant was stirred for 4 hours under ice cooling. The reaction solution was added to ice-cold water, and the resultant was adjusted to around pH 2.0 by the addition of a 6 mol/L aqueous hydrochloric acid solution under ice cooling and stirred for 30 minutes. After extraction with ethyl acetate, the organic layer was dried over magnesium sulfate, and the desiccant was filtered off. Then, the solvent was distilled off under reduced pressure. The obtained residue was purified by silica gel column chromatography (OH-type silica gel; hexane/ethyl acetate-gradient elution=100/0→83/17) to obtain the title compound (0.12 g) as a yellow solid.

$^1$H NMR (600 MHz, CHLOROFORM-d) δppm 1.67 (6H, s), 2.72 (3H, s), 8.84 (1H, s), 9.20 (1H, d, J=1.7 Hz)

Reference Example 4-3

2-Bromo-1-[5-(1,1,1-trifluoro-2-methylpropan-2-yl)pyrazin-2-yl]ethanone hydrobromide

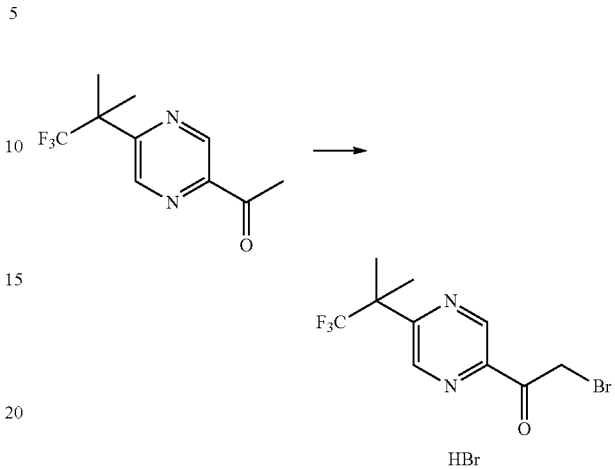

To an ethanol (10 mL) solution of the compound (0.11 g) obtained by the technique of Reference Example 4-2, acetic acid (12 mL), a 20 to 30% hydrobromic acid/ethanol solution (0.20 mL) and bromine (20 μL) were added, and the resultant was stirred at 70° C. for 1 hour under sealed conditions. Then, bromine (10 μL) was further added thereto, and the resultant was further stirred at 70° C. for 1 hour under sealed conditions. The reaction solution was concentrated under reduced pressure to obtain the title compound (0.15 g) as a light brown solid.

Reference Example 4-4

2-[2-(2,5-Dimethyl-4-nitrobenzyl)-1,3-thiazol-4-yl]-5-(1,1,1-trifluoro-2-methylpropan-2-yl)pyrazine

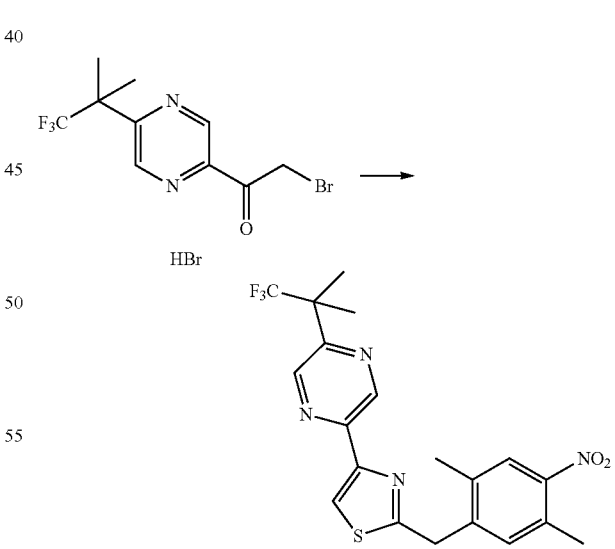

To a 2-propanol (1.0 mL) suspension of the compound (86 mg) obtained by the technique of Reference Example 1-2, the compound (0.15 g) obtained by the technique of Reference Example 4-3 was added, and the resultant was stirred at 80° C. for 2 hours. The reaction solution was concentrated under reduced pressure. The obtained residue was purified by silica gel column chromatography (OH-type silica gel; hexane/ ethyl acetate-gradient elution=100/0→66/34) to obtain the title compound (0.10 g) as a pale yellow foam.

$^1$H NMR (600 MHz, CHLOROFORM-d) δppm 1.67 (6H, s), 2.42 (3H, s), 2.58 (3H, s), 4.42 (2H, s), 7.25 (1H, s), 7.87 (1H, s), 8.02 (1H, s), 8.75 (1H, s), 9.28 (1H, s)

Reference Example 4-5

2,5-Dimethyl-4-({4-[5-(1,1,1-trifluoro-2-methylpropan-2-yl)pyrazin-2-yl]-1,3-thiazol-2-yl}methyl)aniline

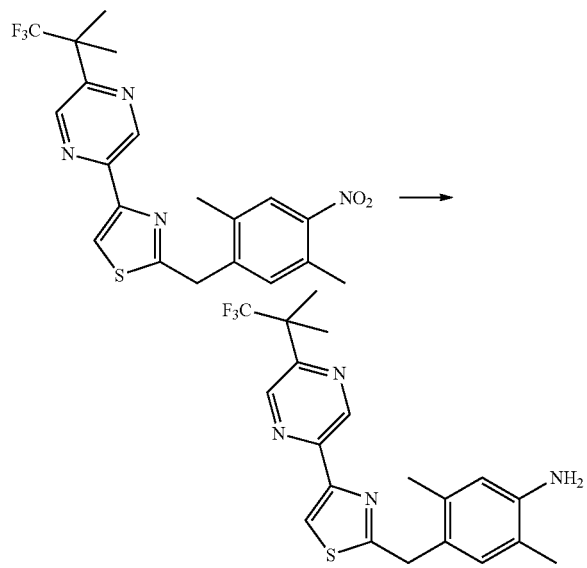

To a methanol (1 mL) solution of the compound (0.10 g) obtained by the technique of Reference Example 4-4, 10% palladium-carbon (31 mg) was added, and the resultant was stirred at room temperature for 4 hours in a hydrogen atmosphere. The reaction mixture was filtered through Celite, and the filtrate was concentrated under reduced pressure. The obtained residue was purified by silica gel column chromatography (OH-type silica gel; hexane/ethyl acetate-gradient elution=100/0→50/50) to obtain the title compound (88 mg) as a pale yellow foam.

$^1$H NMR (600 MHz, CHLOROFORM-d) δppm 1.67 (6H, s), 2.15 (3H, s), 2.23 (3H, s), 3.56 (2H, br. s.), 4.26 (2H, s), 6.55 (1H, s), 6.97 (1H, s), 7.94 (1H, s), 8.74 (1H, s), 9.31 (1H, s)

Reference Example 5-1

Methyl 2-bromo-3-(4-chlorophenyl)-3-oxopropanoate

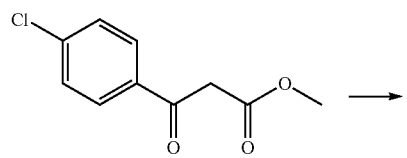

-continued

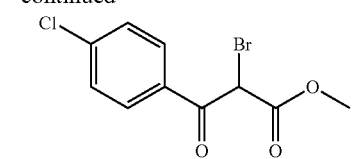

To a chloroform (20 mL) solution of methyl 3-(4-chlorophenyl)-3-oxopropanoate (1.0 g), bromine (0.12 mL) was added, and the resultant was stirred at 70° C. for 1 hour under sealed conditions. Then, bromine (0.12 mL) was further added thereto, and the resultant was further stirred at 70° C. for 1 hour under sealed conditions. The reaction solution was concentrated under reduced pressure. The obtained residue was purified by silica gel column chromatography (OH-type silica gel; hexane/ethyl acetate-gradient elution=100/0→75/25) to obtain the title compound (0.44 g) as a pale yellow oil.

$^1$H NMR (600 MHz, CHLOROFORM-d) δppm 3.84 (3H, s), 5.61 (1H, s), 7.48 (2H, d, J=8.6 Hz), 7.94 (2H, d, J=8.6 Hz)

Reference Example 5-2

Methyl 4-(4-chlorophenyl)-2-(2,5-dimethyl-4-nitrobenzyl)-1,3-thiazole-5-carboxylate

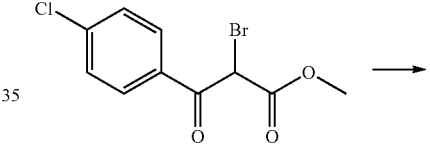

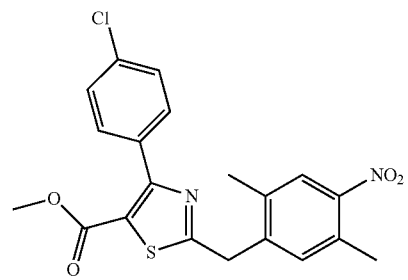

To a 2-propanol (5.0 mL) suspension of the compound (0.34 g) obtained by the technique of Reference Example 1-2, the compound (0.44 g) obtained by the technique of Reference Example 5-1 was added, and the resultant was stirred at 80° C. for 2 hours. A saturated aqueous solution of sodium bicarbonate was added thereto, followed by extraction with ethyl acetate. The organic layer was dried over magnesium sulfate, and the desiccant was filtered off. Then, the solvent was distilled off under reduced pressure. The obtained residue was purified by silica gel column chromatography (OH-type silica gel; hexane/ethyl acetate-gradient elution=100/0→50/50) to obtain the title compound (0.23 g) as a colorless solid.

$^1$H NMR (600 MHz, CHLOROFORM-d) δppm 2.40 (3H, s), 2.58 (3H, s), 3.78 (3H, s), 4.35 (2H, s), 7.25 (1H, s), 7.41 (2H, d, J=8.6 Hz), 7.72 (2H, d, J=8.6 Hz), 7.87 (1H, s)

Reference Example 5-3

Methyl 2-(4-amino-2,5-dimethylbenzyl)-4-(4-chlorophenyl)-1,3-thiazole-5-carboxylate

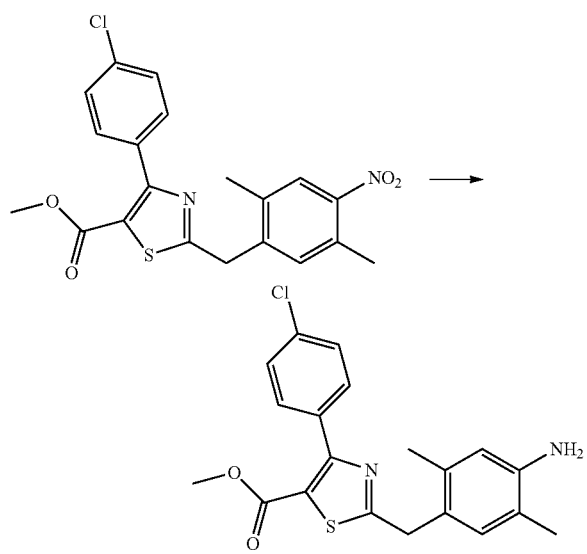

A 1:1 ethanol/water (2.0 mL) solution of the compound (0.10 g) obtained by the technique of Reference Example 5-2, ammonium chloride (38 mg) and iron powder (40 mg) were added to, and the resultant was heated to reflux for 2 hours. Insoluble material was filtered off, and the filtrate was concentrated under reduced pressure. A saturated aqueous solution of sodium bicarbonate was added to the obtained residue, followed by extraction with ethyl acetate. The organic layer was dried over magnesium sulfate, and the desiccant was filtered off. Then, the solvent was distilled off under reduced pressure to obtain the title compound (87 mg) as a brown foam.

$^1$H NMR (600 MHz, CHLOROFORM-d) δppm 2.15 (3H, s), 2.21 (3H, s), 3.61 (2H, br. s.), 3.74 (3H, s), 4.19 (2H, s), 6.56 (1H, s), 6.96 (1H, s), 7.40 (2H, d, J=8.6 Hz), 7.73 (2H, d, J=8.6 Hz)

Reference Example 6-1

Methyl 2-bromo-3-(4-methylphenyl)-3-oxopropanoate

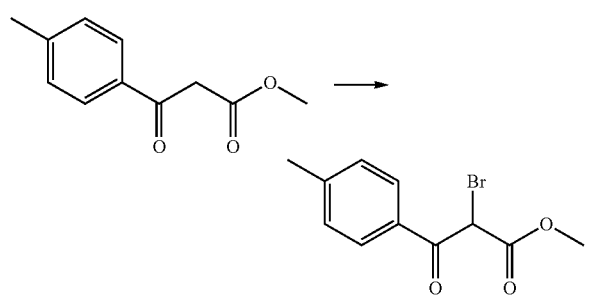

To a chloroform (20 mL) solution of methyl 3-(4-methylphenyl)-3-oxopropanoate (1.0 g), bromine (0.12 mL) was added, and the resultant was stirred at 70° C. for 1 hour under sealed conditions. Then, bromine (0.12 mL) was further added thereto, and the resultant was further stirred at 70° C. for 1 hour under sealed conditions. The reaction solution was concentrated under reduced pressure to obtain the title compound (1.3 g) as a brown oil.

$^1$H NMR (600 MHz, CHLOROFORM-d) δppm 2.44 (3H, s), 3.83 (3H, s), 5.66 (1H, s), 7.30 (2H, d, J=8.0 Hz), 7.89 (2H, d, J=8.0 Hz)

Reference Example 6-2

Methyl 2-(2,5-dimethyl-4-nitrobenzyl)-4-(4-methylphenyl)-1,3-thiazole-5-carboxylate

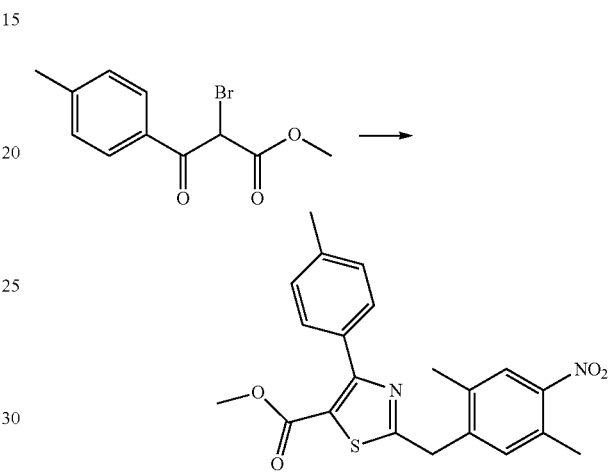

To a 2-propanol (20 mL) suspension of the compound (1.1 g) obtained by the technique of Reference Example 1-2, the compound (1.3 g) obtained by the technique of Reference Example 6-1 was added, and the resultant was stirred at 80° C. for 2 hours. A saturated aqueous solution of sodium bicarbonate was added thereto, followed by extraction with ethyl acetate. The organic layer was dried over magnesium sulfate, and the desiccant was filtered off. Then, the solvent was distilled off under reduced pressure. The obtained residue was purified by silica gel column chromatography (OH-type silica gel; hexane/ethyl acetate-gradient elution=100/0→50/50) to obtain the title compound (0.45 g) as a yellow oil.

1H NMR (600 MHz, CHLOROFORM-d) δppm 2.36-2.44 (6H, m), 2.58 (3H, s), 3.77 (3H, s), 4.35 (2H, s), 7.23-7.28 (3H, m), 7.65 (2H, d, J=8.3 Hz), 7.87 (1H, s)

Reference Example 6-3

Methyl 2-(4-amino-2,5-dimethylbenzyl)-4-(4-methylphenyl)-1,3-thiazole-5-carboxylate

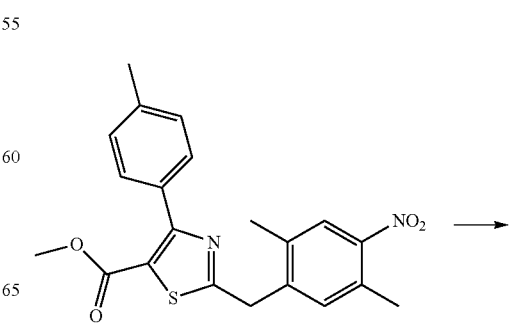

-continued

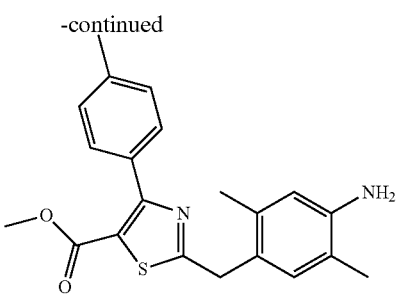

To a 1:1 ethanol/water (2.0 mL) solution of the compound (0.45 g) obtained by the technique of Reference Example 6-2, ammonium chloride (0.18 mg) and iron powder (0.19 g) were added, and the resultant was heated to reflux for 2 hours. Insoluble material was filtered off, and the filtrate was concentrated under reduced pressure. A saturated aqueous solution of sodium bicarbonate was added to the obtained residue, followed by extraction with ethyl acetate. The organic layer was dried over magnesium sulfate, and the desiccant was filtered off. Then, the solvent was distilled off under reduced pressure to obtain the title compound (0.28 g) as a brown foam.

$^1$H NMR (600 MHz, CHLOROFORM-d) δppm 2.15 (3H, s), 2.21 (3H, s), 2.40 (3H, s), 3.59 (2H, br. s), 3.73 (3H, s), 4.19 (2H, s), 6.55 (1H, s), 6.96 (1H, s), 7.23 (2H, d, J=7.8 Hz), 7.64-7.67 (2H, m)

Reference Example 6-4

2-(2,5-Dimethyl-4-nitrobenzyl)-4-(4-methylphenyl)-1,3-thiazole-5-carboxylic acid

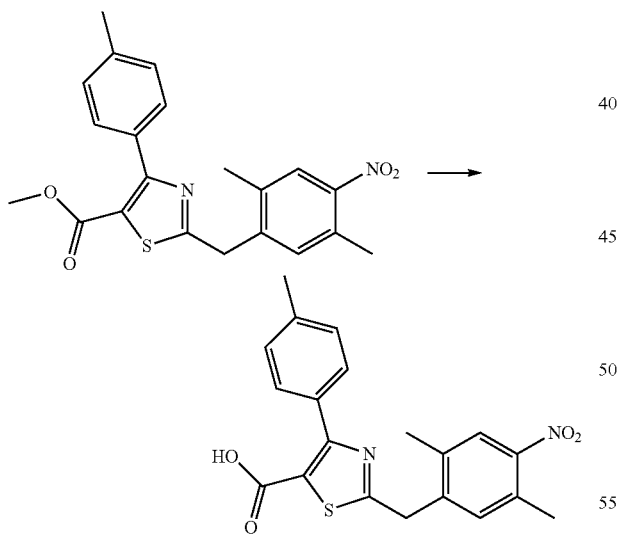

To a methanol (20 mL) solution of the compound (0.80 g) obtained by the technique of Reference Example 6-2, a 1 mol/L aqueous sodium hydroxide solution (6.1 mL) was added, and the resultant was stirred at room temperature for 4 hours. Water was added to the reaction solution, followed by extraction with ethyl acetate. The organic layer was dried over magnesium sulfate, and the desiccant was filtered off. Then, the solvent was distilled off under reduced pressure. The obtained solid was washed with chloroform/methanol (=100/1) to obtain the title compound (0.32 g) as a pale yellow solid.

1H NMR (600 MHz, DMSO-d$_6$) δppm 2.35 (3H, s), 2.37 (3H, s), 2.49 (3H, s), 4.45 (2H, s), 7.22 (2H, d, J=8.0 Hz), 7.48 (1H, s), 7.60 (2H, d, J=8.0 Hz), 7.89 (1H, s), 13.24 (1H, br. s)

Reference Example 6-5

2-(2,5-Dimethyl-4-nitrobenzyl)-N-methyl-4-(4-methylphenyl)-1,3-thiazole-5-carboxamide

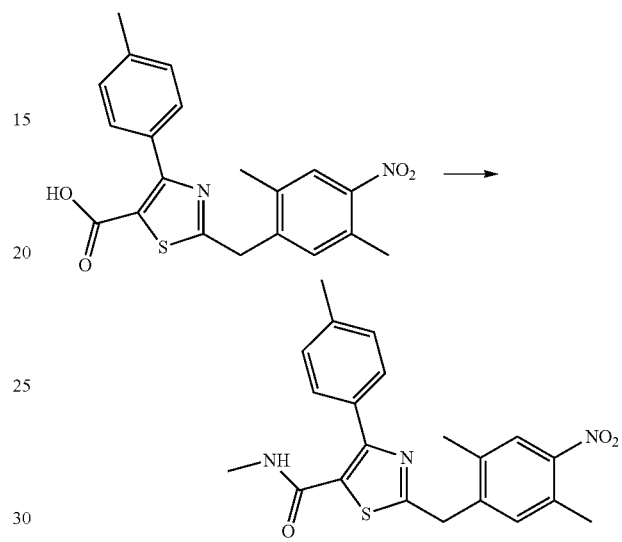

To a N,N-dimethylformamide (1.0 mL) solution of the compound (0.15 g) obtained by the technique of Reference Example 6-4, dimethylamine hydrochloride (40 mg), WSC.HCl (0.11 g), HOBt.H$_2$O (90 mg) and triethylamine (0.16 mL) were added, and the resultant was stirred at room temperature for 1 day. Water was added to the reaction solution, followed by extraction with ethyl acetate. The organic layer was dried over magnesium sulfate, and the desiccant was filtered off. Then, the solvent was distilled off under reduced pressure. The obtained residue was purified by silica gel column chromatography (NH-type silica gel; hexane/ethyl acetate-gradient elution=100/0→34/66) to obtain the title compound (0.12 g) as a colorless solid.

$^1$H NMR (600 MHz, CHLOROFORM-d) δppm 2.40 (3H, s), 2.42 (3H, s), 2.57 (3H, s), 2.78 (3H, d, J=5.0 Hz), 4.32 (2H, s), 5.69-5.75 (1H, m), 7.24 (1H, s), 7.29 (2H, d, J=7.8 Hz), 7.50 (2H, d, J=7.8 Hz), 7.85 (1H, s)

Reference Example 6-6

2-(4-Amino-2,5-dimethylbenzyl)-N-methyl-4-(4-methylphenyl)-1,3-thiazole-5-carboxamide

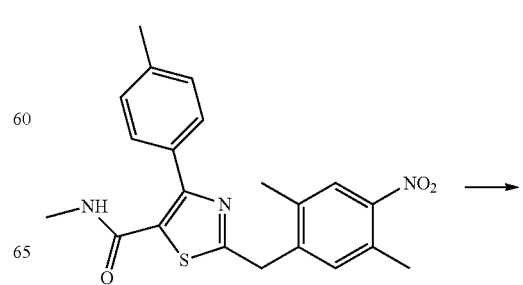

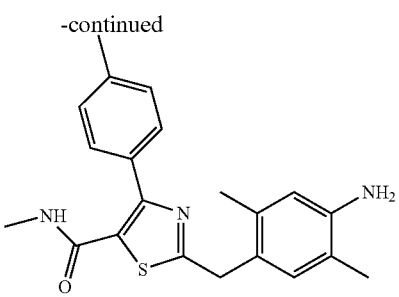

To a 1:1 ethanol/water (2.0 mL) solution of the compound (0.10 g) obtained by the technique of Reference Example 6-5, ammonium chloride (41 mg) and iron powder (42 mg) were added, and the resultant was heated to reflux for 2 hours. Insoluble material was filtered off, and the filtrate was concentrated under reduced pressure. A saturated aqueous solution of sodium bicarbonate was added to the obtained residue, followed by extraction with ethyl acetate. The organic layer was dried over magnesium sulfate, and the desiccant was filtered off. Then, the solvent was distilled off under reduced pressure to obtain the title compound (92 mg) as a yellow solid.

$^1$H NMR (600 MHz, CHLOROFORM-d) δppm 2.14 (3H, s), 2.21 (3H, s), 2.41 (3H, s), 2.76 (3H, d, J=5.0 Hz), 3.55 (2H, br. s.), 4.16 (2H, s), 5.65-5.69 (1H, m), 6.53 (1H, s), 6.95 (1H, s), 7.27 (2H, d, J=7.8 Hz), 7.52 (2H, d, J=7.8 Hz)

Reference Example 6-7

2-(2,5-Dimethyl-4-nitrobenzyl)-4-(4-methylphenyl)-1,3-thiazole-5-carboxamide

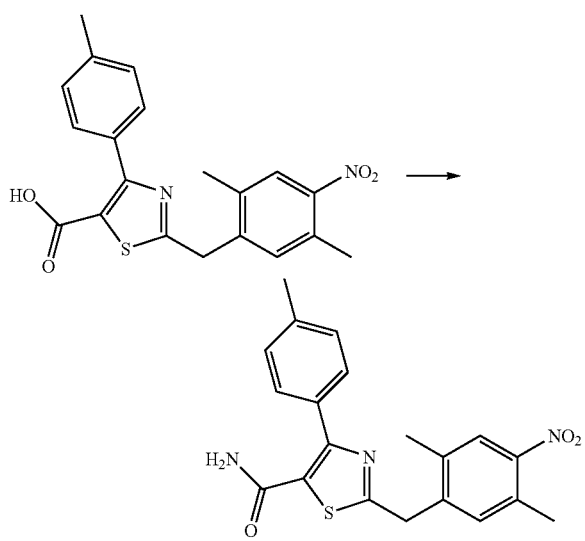

To a N,N-dimethylformamide (1.0 mL) solution of the compound (0.20 g) obtained by the technique of Reference Example 6-4, ammonium chloride (42 mg), WSC.HCl (0.15 g), HOBt.H$_2$O (0.12 g) and triethylamine (0.22 mL) were added, and the resultant was stirred at room temperature for 1 day. Water was added to the reaction solution, followed by extraction with ethyl acetate. The organic layer was dried over magnesium sulfate, and the desiccant was filtered off. Then, the solvent was distilled off under reduced pressure. The obtained residue was purified by silica gel column chromatography (NH-type silica gel; hexane/ethyl acetate-gradient elution=100/0→25/75) to obtain the title compound (0.18 g) as a green solid.

$^1$H NMR (600 MHz, CHLOROFORM-d) δppm 2.40 (3H, s), 2.42 (3H, s), 2.57 (3H, s), 4.32 (2H, s), 5.45-5.76 (2H, m), 7.25 (1H, s), 7.30 (2H, d, J=7.8 Hz), 7.51 (2H, d, J=7.8 Hz), 7.86 (1H, s)

Reference Example 6-8

2-(4-Amino-2,5-dimethylbenzyl)-4-(4-methylphenyl)-1,3-thiazole-5-carboxamide

To a 1:1 ethanol/water (2.0 mL) solution of the compound (0.10 g) obtained by the technique of Reference Example 6-7, ammonium chloride (42 mg) and iron powder (44 mg) were added, and the resultant was heated to reflux for 2 hours. Insoluble material was filtered off, and the filtrate was concentrated under reduced pressure. A saturated aqueous solution of sodium bicarbonate was added to the obtained residue, followed by extraction with ethyl acetate. The organic layer was dried over magnesium sulfate, and the desiccant was filtered off. Then, the solvent was distilled off under reduced pressure to obtain the title compound (73 mg) as a yellow solid.

$^1$H NMR (600 MHz, CHLOROFORM-d) δppm 2.14 (3H, s), 2.22 (3H, s), 2.41 (3H, s), 3.56 (2H, br. s.), 4.16 (2H, s), 5.29-5.72 (2H, m), 6.54 (1H, s), 6.95 (1H, s), 7.29 (2H, d, J=7.8 Hz), 7.53 (2H, d, J=7.8 Hz)

Reference Example 7-1

N-(2-Hydroxyethyl)-N-methylformamide

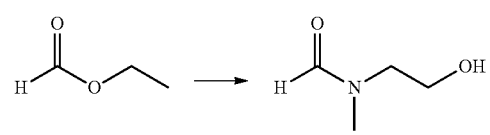

To an ethanol (4.0 mL) solution of 2-(methylamino)ethanol (2.0 g), ethyl formate (4.0 ml) was added, and the resultant was stirred at 70° C. for 1.5 hours. After standing to cool to room temperature and stirring for 10 minutes, the reaction solution was concentrated under reduced pressure to obtain the title compound (2.6 g) as a pale yellow liquid.

$^1$H NMR (200 MHz, CHLOROFORM-d) δppm 2.83-3.11 (3H, m), 3.30-3.59 (2H, m), 3.64-3.89 (2H, m), 7.97-8.16 (1H, m)

Reference Example 7-2

N-{2-[(4-Methoxybenzyl)oxy]ethyl}-N-methylformamide

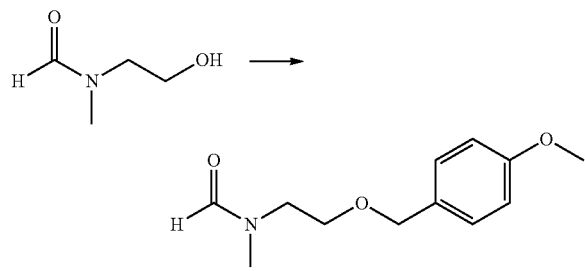

To a tetrahydrofuran (5.0 mL) solution of the compound (0.53 g) obtained by the technique of Reference Example 7-1, under ice cooling, 60% sodium hydride (0.23 g) was added, and the resultant was stirred for 10 minutes. Then, 1-(chloromethyl)-4-methoxybenzene (0.84 mL) was added thereto, and the resultant was stirred at room temperature for 1 hour. Water and ethyl acetate were added to the reaction solution, and the resultant was stirred for 15 minutes. Then, an aqueous layer was subjected to extraction with ethyl acetate. The extract was washed with saturated saline and dried over magnesium sulfate, and the desiccant was then filtered off. The solvent was distilled off under reduced pressure. The obtained residue was purified by silica gel column chromatography (OH-type silica gel; chloroform/methanol-gradient elution=100/0→98/2) to obtain the title compound (0.38 g) as a colorless oil.

$^1$H NMR (200 MHz, CHLOROFORM-d) δppm 2.82-3.07 (3H, m), 3.34-3.44 (1H, m), 3.47-3.63 (3H, m), 3.81 (3H, s), 4.45 (2H, s), 6.82-6.93 (2H, m), 7.17-7.28 (3H, m), 8.05 (1H, d, J=2.6 Hz)

Reference Example 7-3

N'-(2,5-Dimethyl-4-{[4-(4-methylphenyl)-1,3-thiazol-2-yl]methyl}phenyl)-N-{2-[(4-methoxybenzyl)oxy]ethyl}-N-methylimidoformamide

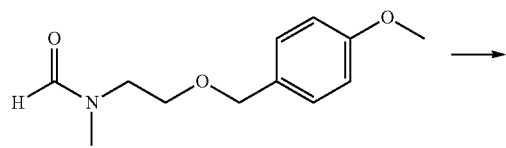

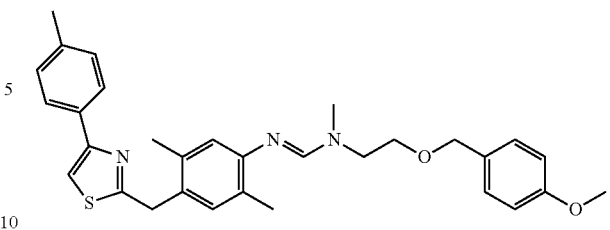

To a chloroform (4.0 mL) solution of the compound (0.12 g) obtained by the technique of Reference Example 7-2, oxalyl chloride (45 µL) was added, and the resultant was stirred at room temperature for 10 minutes. Then, a chloroform (4.0 mL) solution of the compound (0.11 g) obtained by the technique of Reference Example 2-2 was added thereto, and the resultant was stirred at room temperature for 1.5 hours. A saturated aqueous solution of sodium bicarbonate was added to the reaction solution, and the resultant was stirred for 15 minutes, followed by extraction with chloroform. The organic layer was dried over magnesium sulfate, and the desiccant was filtered off. Then, the solvent was distilled off under reduced pressure. The obtained residue was purified by silica gel column chromatography (NH-type silica gel; hexane/ethyl acetate-gradient elution=85/15→70/30) to obtain the title compound (0.11 g) as a pale yellow oil.

$^1$H NMR (600 MHz, CHLOROFORM-d) δppm 2.01 (3H, s), 2.22 (6H, br. s.), 2.38 (3H, s), 3.05 (2H, br. s.), 3.52-3.67 (2H, m), 3.79 (3H, s), 4.28 (2H, s), 4.48 (2H, s), 6.57 (1H, s), 6.85-6.89 (3H, m), 7.04 (1H, s), 7.20-7.27 (5H, m), 7.78 (2H, d, J=8.3 Hz)

Reference Example 8

Tert-butyl N-formyl-N-methylglycinate

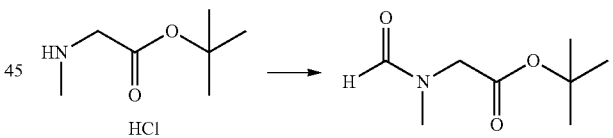

To an ethanol (10 mL) suspension of tert-butyl N-methylglycinate hydrochloride (3.0 g), under ice cooling, triethylamine (2.3 mL) was added, and the resultant was stirred at room temperature for 20 minutes. Then, ethyl formate (2.7 ml) was added thereto, and the resultant was stirred at 70° C. for 1 hour. After standing to cool to room temperature and stirring for 4 hours, the reaction solution was concentrated under reduced pressure. The obtained residue was dissolved by the addition of water and a 10:1 chloroform/methanol solution. An organic layer was separated, and an aqueous layer was subjected to extraction with a 10:1 chloroform/methanol solution. The organic layers were dried over magnesium sulfate, and the desiccant was filtered off. Then, the solvent was distilled off under reduced pressure to obtain the title compound (1.9 g) as a light brown oil.

$^1$H NMR (600 MHz, CHLOROFORM-d) δppm 1.47 (9H, s), 3.25 (3H, s), 3.99 (2H, s), 8.10 (1H, s)

Reference Example 9-1

Methyl 4-[2-(2,5-dimethyl-4-nitrobenzyl)-1,3-thiazol-4-yl]benzoate hydrobromide

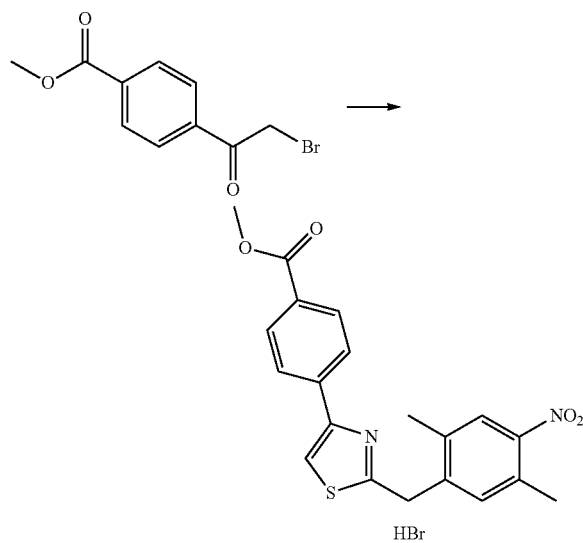

To a 2-propanol (3.0 mL) suspension of the compound (0.10 g) obtained by the technique of Reference Example 1-2, methyl 4-(2-bromoacetyl)-benzoate (0.11 g) was added, and the resultant was stirred at 80° C. for 2.5 hours and then left overnight at room temperature. The deposited solid was filtered and washed with 2-propanol to obtain the title compound (0.12 g) as a slightly gray solid.

$^1$H NMR (600 MHz, CHLOROFORM-d) δppm 2.42 (3H, s), 2.58 (3H, s), 3.94 (3H, s), 4.42 (2H, s), 7.25 (1H, s), 7.50 (1H, s), 7.87 (1H, s), 7.96 (2H, d, J=8.3 Hz), 8.09 (2H, d, J=8.3 Hz)

Reference Example 9-2

Methyl 4-[2-(4-amino-2,5-dimethylbenzyl)-1,3-thiazol-4-yl]benzoate

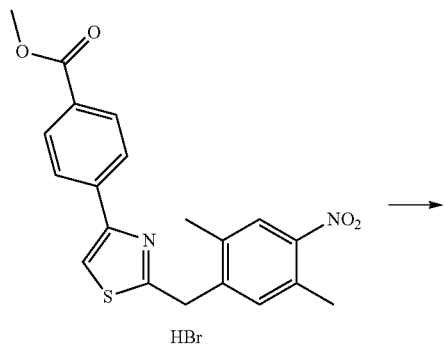

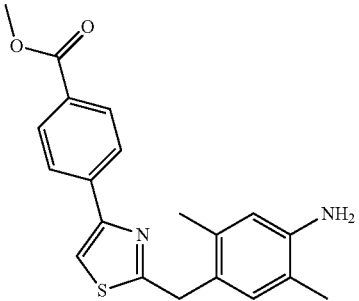

To an ethanol (4.4 mL) solution of the compound (0.11 g) obtained by the technique of Reference Example 9-1, 10% palladium-carbon (33 mg) was added, and the resultant was stirred at room temperature for 24 hours in a hydrogen atmosphere. Insoluble material was filtered off through Celite, and the filtrate was concentrated under reduced pressure. The obtained residue was purified by silica gel column chromatography (OH-type silica gel; hexane/ethyl acetate-gradient elution=90/10→70/30) to obtain the title compound (40 mg) as a pale yellow solid.

$^1$H NMR (600 MHz, CHLOROFORM-d) δppm 2.15 (3H, s), 2.23 (3H, s), 3.56 (2H, br. s.), 3.93 (3H, s), 4.25 (2H, s), 6.55 (1H, s), 6.97 (1H, s), 7.43 (1H, d, J=1.2 Hz), 7.97 (2H, d, J=7.0 Hz), 8.06-8.11 (2H, m)

Reference Example 9-3

4-[2-(2,5-Dimethyl-4-nitrobenzyl)-1,3-thiazol-4-yl]benzoic acid

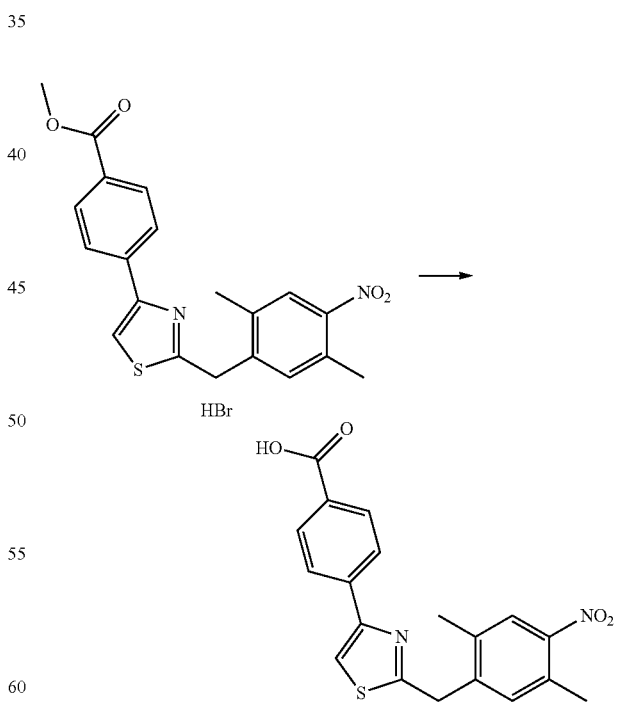

To a 1:1 water/tetrahydrofuran (6.0 mL) solution of the compound (0.28 g) obtained by the technique of Reference Example 9-1, lithium hydroxide monohydrate (46 mg) was added, and the resultant was stirred at room temperature for 25 hours. A 1 mol/L aqueous hydrochloric acid solution was added to the reaction solution, and the deposited solid was collected by filtration to obtain the title compound (0.22 g) as a pale yellow solid.

$^1$H NMR (600 MHz, DMSO-d$_6$) δppm 2.39 (6H, s), 4.50 (2H, s), 7.47 (1H, s), 7.89 (1H, s), 7.98-8.01 (2H, m), 8.03-8.06 (2H, m), 8.18 (1H, s)

Reference Example 9-4

N-Tert-butyl-4-[2-(2,5-dimethyl-4-nitrobenzyl)-1,3-thiazol-4-yl]benzamide

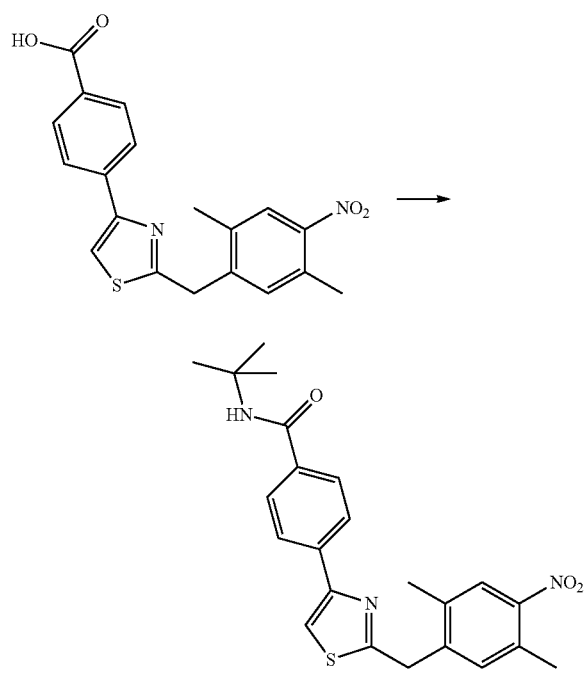

To a N,N-dimethylformamide (2.0 mL) solution of the compound (0.22 g) obtained by the technique of Reference Example 9-3, tert-butylamine (90 µL), WSC.HCl (0.17 g), HOBt.H$_2$O (0.14 g) and triethylamine (0.24 mL) were added, and the resultant was stirred at room temperature for 24 hours. Then, tert-butylamine (90 µL) was further added thereto, and the resultant was stirred at room temperature for 8 hours. Water was added to the reaction solution, followed by extraction with chloroform. An organic layer was separated using a phase separator, and the solvent was distilled off under reduced pressure. The obtained residue was purified by silica gel column chromatography (OH-type silica gel; hexane/ethyl acetate-gradient elution=90/10→70/30) to obtain the title compound (0.16 g) as a pale yellow oil.

$^1$H NMR (600 MHz, CHLOROFORM-d) δppm 1.48-1.50 (9H, m), 2.39-2.51 (3H, m), 2.55-2.66 (3H, m), 4.40 (2H, s), 5.92-5.99 (1H, m), 7.25 (1H, s), 7.46 (1H, s), 7.76-7.81 (2H, m), 7.89-7.94 (2H, m), 8.01 (1H, s)

Reference Example 9-5

4-[2-(4-Amino-2,5-dimethylbenzyl)-1,3-thiazol-4-yl]-N-tert-butylbenzamide

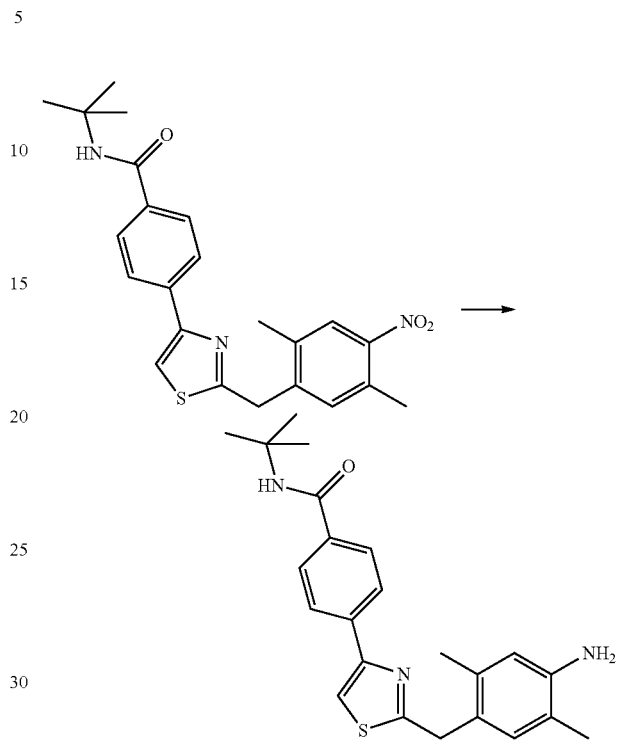

To an ethanol (6.4 mL) solution of the compound (0.16 g) obtained by the technique of Reference Example 9-4, 10% palladium-carbon (48 mg) was added, and the resultant was stirred at room temperature for 20 hours in a hydrogen atmosphere. Insoluble material was filtered off through Celite, and the filtrate was concentrated under reduced pressure. The obtained residue was purified by silica gel column chromatography (OH-type silica gel; hexane/ethyl acetate-gradient elution=70/30→50/50) to obtain the title compound (0.11 g) as a yellow foam.

$^1$H NMR (600 MHz, CHLOROFORM-d) δppm 1.49 (9H, s), 2.15 (3H, s), 2.23 (3H, s), 4.25 (2H, s), 5.91-5.99 (1H, m), 6.55 (1H, s), 6.97 (1H, s), 7.39 (1H, s), 7.76 (2H, d, J=8.7 Hz), 7.94 (2H, d, J=8.7 Hz)

Reference Example 10-1

(4-Methylphenyl)-1,3,4-oxathiazol-2-one

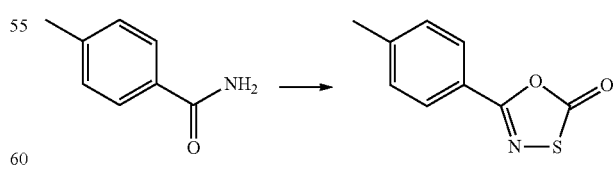

To a toluene (60 mL) suspension of 4-methylbenzamide (20 g), chlorocarbonylsulfenyl chloride (15 mL) was added, and the resultant was stirred at 120° C. for 3 hours. The reaction solution was concentrated under reduced pressure. The obtained solid was washed with hexane to obtain the title compound (24 g) as a colorless solid.

$^1$H NMR (200 MHz, DMSO-d$_6$) δppm 2.40 (3H, s), 7.39 (2H, d, J=8.3 Hz), 7.82 (2H, d, J=8.3 Hz)

Reference Example 10-2

5-(2,5-Dimethyl-4-nitrobenzyl)-3-(4-methylphenyl)-1,2,4-thiadiazole

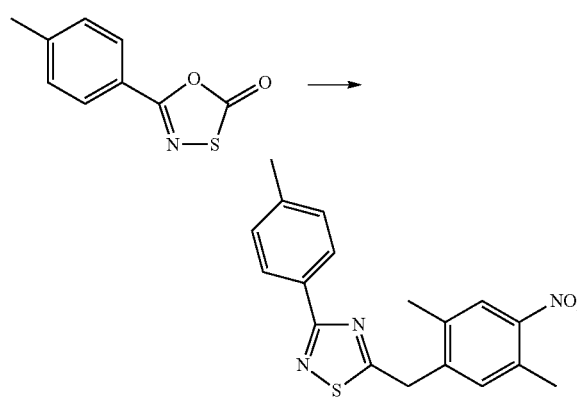

To a decahydronaphthalene (7.0 mL) suspension of the compound (0.73 g) obtained by the technique of Reference Example 10-1, the compound (0.58 g) obtained by the technique of Reference Example 1-1 was added, and the resultant was stirred overnight at 160° C. The reaction mixture was purified by column chromatography (OH-type silica gel; hexane/ethyl acetate-gradient elution=100/0→70/30) to obtain the title compound (32 mg) as a light brown solid.

$^1$H NMR (600 MHz, CHLOROFORM-d) δppm 2.39-2.44 (6H, m), 2.58 (3H, s), 4.47 (2H, s), 7.26-7.29 (3H, m), 7.88 (1H, s), 8.16 (2H, d, J=8.3 Hz)

Reference Example 10-3

2,5-Dimethyl-4-{[3-(4-methylphenyl)-1,2,4-thiadiazol-5-yl]methyl}aniline

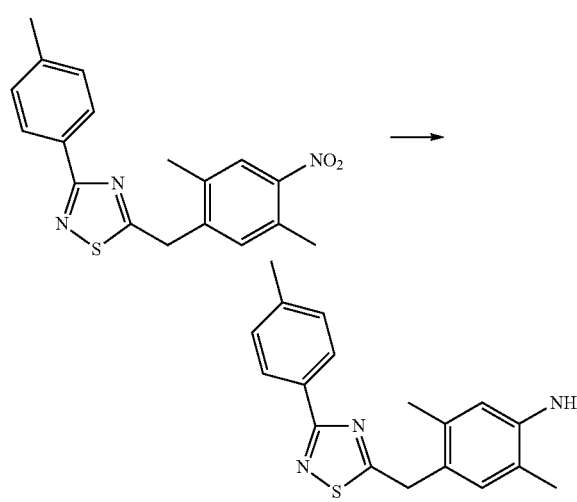

To a methanol (10 mL) solution of the compound (46 mg) obtained by the technique of Reference Example 10-2, 10% palladium-carbon (46 mg) was added, and the resultant was stirred at room temperature for 21 hours in a hydrogen atmosphere. Insoluble material was filtered off through Celite, and the filtrate was concentrated under reduced pressure. The obtained residue was purified by silica gel column chromatography (OH-type silica gel; hexane/ethyl acetate-gradient elution=100/0→60/40) to obtain the title compound (32 mg) as a yellow solid.

1H NMR (600 MHz, CHLOROFORM-d) δppm 2.15 (3H, s), 2.21 (3H, s), 2.41 (3H, s), 3.60 (2H, br. s.), 4.29 (2H, s), 6.56 (1H, s), 6.98 (1H, s), 7.25-7.29 (2H, m), 8.16 (2H, d, J=8.3 Hz)

Reference Example 11-1

4-(4-Tert-butylphenyl)-2-(2,5-dimethyl-4-nitrobenzyl)-1,3-thiazole

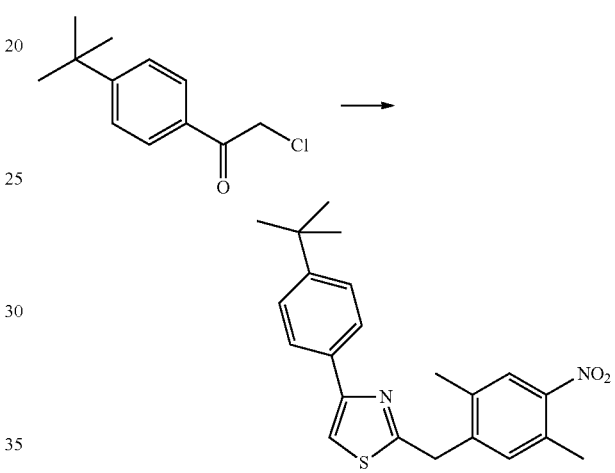

To a suspension of the compound (5.0 mL) obtained by the technique of Reference Example 1-2, 1-(4-tert-butylphenyl)-2-chloroethanone (0.22 g) was added, and the resultant was stirred at 80° C. for 3.5 hours and then left overnight at room temperature. The deposited solid was filtered and washed with 2-propanol to obtain the title compound (0.29 g) as a colorless solid.

$^1$H NMR (600 MHz, CHLOROFORM-d) δppm 1.35 (9H, s), 2.40 (3H, s), 2.57 (3H, s), 4.39 (2H, s), 7.24 (1H, s), 7.32 (1H, s), 7.44 (2H, d, J=8.3 Hz), 7.80 (2H, d, J=8.3 Hz), 7.85 (1H, s)

Reference Example 11-2

4-{[4-(4-Tert-butylphenyl)-1,3-thiazol-2-yl]methyl}-2,5-dimethylaniline

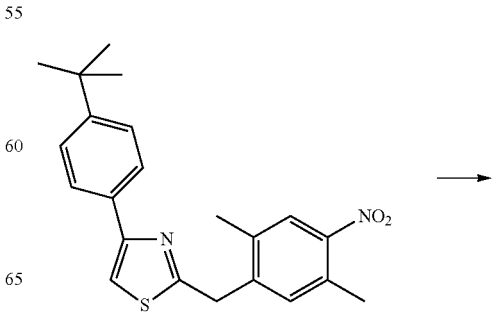

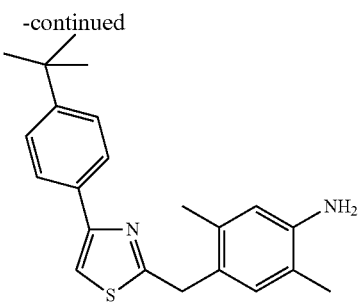

To an ethanol (11 mL) solution of the compound (0.27 g) obtained by the technique of Reference Example 11-1, 10% palladium-carbon (80 mg) was added, and the resultant was stirred at room temperature for 2 hours in a hydrogen atmosphere. Insoluble material was filtered off through Celite, and the filtrate was concentrated under reduced pressure. The obtained residue was purified by silica gel column chromatography (NH-type silica gel; hexane/ethyl acetate-gradient elution=90/10→70/30) to obtain the title compound (0.13 g) as a yellow solid.

$^1$H NMR (600 MHz, CHLOROFORM-d) δppm 1.34 (9H, s), 2.14 (3H, s), 2.22 (3H, s), 4.24 (2H, s), 6.54 (1H, s), 6.96 (1H, s), 7.25 (1H, s), 7.40-7.45 (2H, m), 7.78-7.84 (2H, m)

Reference Example 12-1

[2-(2,5-Dimethyl-4-nitrobenzyl)-1,3-thiazol-4-yl](phenyl)methanone hydrobromide

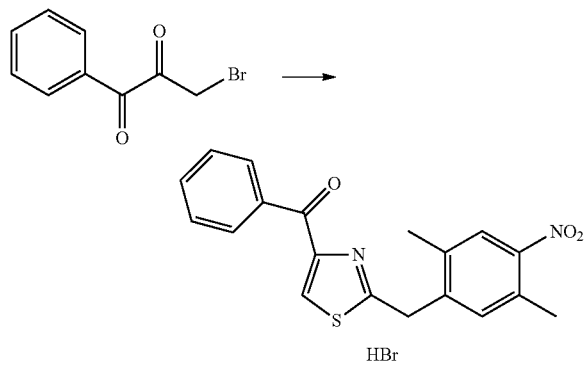

To a 2-propanol (10 mL) suspension of the compound (0.38 g) obtained by the technique of Reference Example 1-2, 3-bromo-1-phenylpropane-1,2-dione (0.38 g) was added, and the resultant was stirred at 70° C. for 1.5 hours in a nitrogen atmosphere. The reaction solution was concentrated under reduced pressure. Then, diethyl ether was added to the obtained residue, and the suspension was filtered. The solid was washed with diethyl ether to obtain [2-(2,5-dimethyl-4-nitrobenzyl)-1,3-thiazol-4-yl](phenyl)methanone hydrobromide (0.26 g) as a light brown solid. A deposit formed during the course of concentration of the obtained filtrate under reduced pressure was filtered to obtain the title compound (0.18 g).

$^1$H NMR (600 MHz, DMSO-$d_6$) δppm 2.37 (3H, s), 2.49 (3H, s), 4.53 (2H, s), 7.48 (1H, s), 7.54 (2H, t, J=7.8 Hz), 7.64-7.69 (1H, m), 7.90 (1H, s), 8.05 (2H, dd, J=7.8, 1.2 Hz), 8.46 (1H, s)

Reference Example 12-2

[2-(4-Amino-2,5-dimethylbenzyl)-1,3-thiazol-4-yl](phenyl)methanone

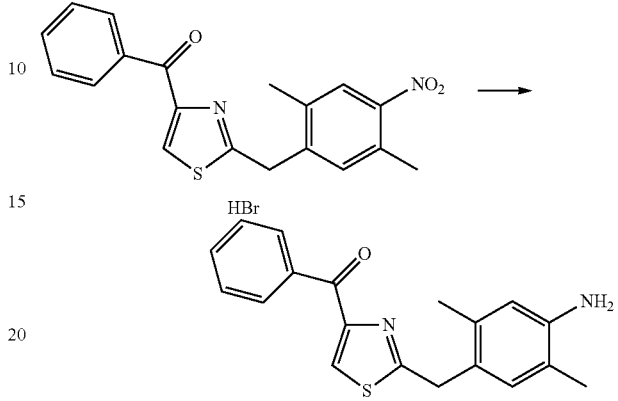

To an ethanol (15 mL) solution of the compound (0.24 g) obtained by the technique of Reference Example 12-1, 10% palladium-carbon (73 mg) was added, and the resultant was stirred at 50° C. for 38 hours in a hydrogen atmosphere. Insoluble material was filtered off through Celite, and the filtrate was concentrated under reduced pressure. The obtained residue was purified by silica gel column chromatography (NH-type silica gel; hexane/ethyl acetate-gradient elution=90/10→75/25) to obtain the title compound (87 mg) as a brown oil.

$^1$H NMR (600 MHz, CHLOROFORM-d) δppm 2.15 (3H, s), 2.21 (3H, s), 4.27 (2H, s), 6.55 (1H, s), 6.97 (1H, s), 7.46-7.52 (2H, m), 7.56-7.62 (1H, m), 8.01 (1H, s), 8.15 (2H, d, J=7.0 Hz)

Reference Example 13-1

5-Tert-butyl-N-methoxy-N-methyl-1,3-thiazole-2-carboxamide

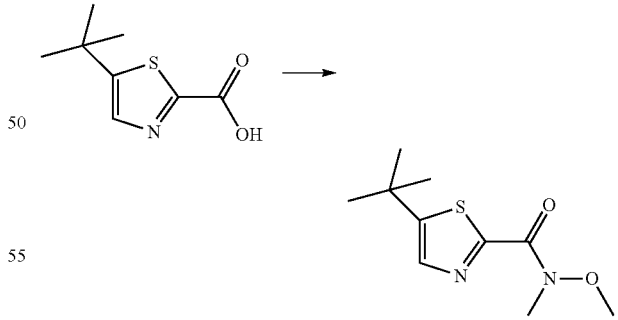

To a N,N-dimethylformamide (25 mL) solution of 5-tert-butyl-1,3-thiazole-2-carboxylic acid (2.5 g), N,O-dimethylhydroxylamine hydrochloride (2.0 g), WSC.HCl (3.9 g), HOBt.H$_2$O (3.1 g) and triethylamine (7.1 g) were added, and the resultant was stirred at room temperature for 1 day. Water was added to the reaction solution, followed by extraction with ethyl acetate. The organic layer was dried over magnesium sulfate, and the desiccant was filtered off. Then, the solvent was distilled off under reduced pressure. The obtained residue was purified by silica gel column chromatography (NH-type silica gel; hexane/ethyl acetate-gradient elution=100/0→50/50) to obtain the title compound (3.1 g) as a colorless oil.

$^1$H NMR (600 MHz, CHLOROFORM-d) δppm 1.47 (9H, s), 3.36 (3H, s), 3.77 (3H, s), 8.41 (1H, s)

Reference Example 13-2

1-(5-Tert-butyl-1,3-thiazol-2-yl)ethanone

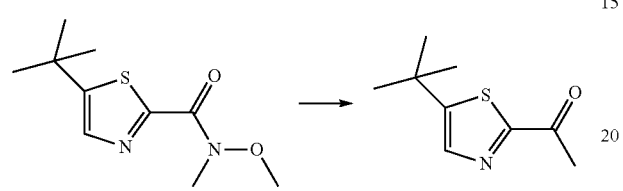

To a tetrahydrofuran (30 mL) solution of the compound (3.1 g) obtained by the technique of Reference Example 13-1, under ice cooling, a 3 mol/L methyl magnesium bromide/diethyl ether solution (6.8 mL) was added, and the resultant was stirred for 2 hours under ice cooling. The reaction solution was added to ice-cold water, and the resultant was adjusted to around pH 2.0 by the addition of a 6 mol/L aqueous hydrochloric acid solution under ice cooling and stirred for 30 minutes. After extraction with ethyl acetate, the organic layer was dried over magnesium sulfate, and the desiccant was filtered off. Then, the solvent was distilled off under reduced pressure. The obtained residue was purified by silica gel column chromatography (OH-type silica gel; hexane/ethyl acetate-gradient elution=100/0→66/34) to obtain the title compound (1.9 g) as a colorless solid.

$^1$H NMR (600 MHz, CHLOROFORM-d) δppm 1.46 (9H, s), 2.56 (3H, s), 8.19 (1H, s)

Reference Example 13-3

2-Bromo-1-(5-tert-butyl-1,3-thiazol-2-yl)ethanone hydrobromide

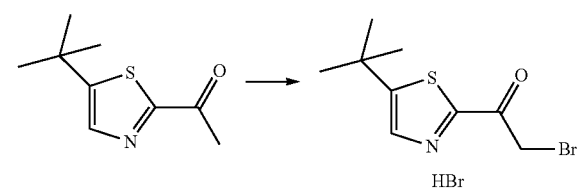

To an ethanol (5.0 mL) solution of the compound (0.50 g) obtained by the technique of Reference Example 13-2, acetic acid (5.5 mL), a 20 to 30% hydrobromic acid/ethanol solution (0.75 mL) and bromine (0.11 mL) were added, and the resultant was stirred at 70° C. for 1 hour under sealed conditions. Then, bromine (80 μL) was further added thereto, and the resultant was further stirred at 70° C. for 1 hour under sealed conditions. The reaction solution was concentrated under reduced pressure to obtain the title compound (0.94 g) as a light brown solid.

Reference Example 14-1

2-Bromo-1-(5-fluoropyridin-3-yl)ethanone hydrobromide

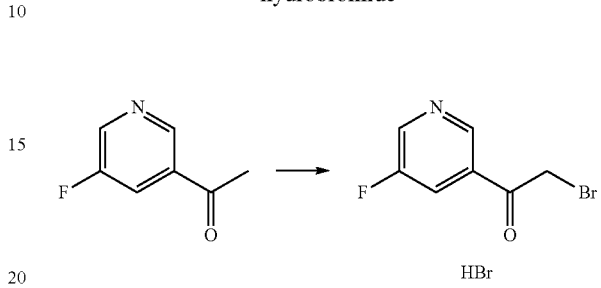

To an ethanol (5.0 mL) solution of 1-(5-fluoropyridin-3-yl)ethanone (0.50 g), acetic acid (6.0 mL) was added, then a 20 to 30% hydrobromic acid/ethanol solution (1.0 mL) and bromine (0.30 mL) were added under ice cooling, and the resultant was stirred at 70° C. for 45 minutes. The reaction solution was concentrated under reduced pressure to obtain the title compound (1.30 g) as a faint orange solid.

Reference Example 14-2

3-[2-(2,5-Dimethyl-4-nitrobenzyl)-1,3-thiazol-4-yl]-5-fluoropyridine dihydrobromide

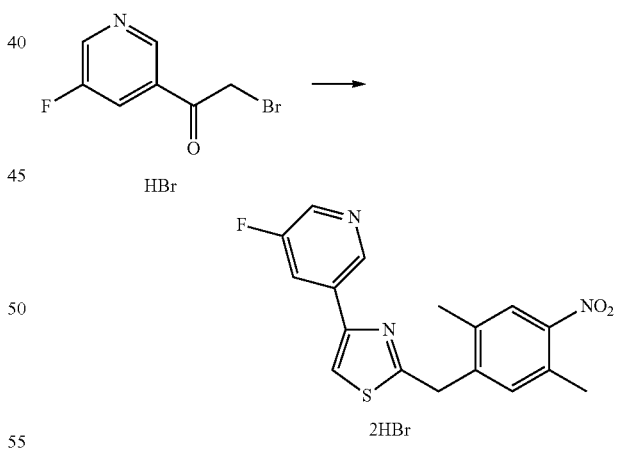

To a 2-propanol (6.0 mL) suspension of the compound (0.20 g) obtained by the technique of Reference Example 1-2, the compound (0.27 g) obtained by the technique of Reference Example 14-1 was added, and the resultant was stirred at 80° C. for 2.5 hours and then left at room temperature for 1 hour. The deposited solid was filtered and washed with 2-propanol to obtain the title compound (0.17 g) as a fawn solid.

$^1$H NMR (600 MHz, CHLOROFORM-d) δppm 2.40 (3H, s), 2.59 (3H, s), 4.41 (2H, s), 7.24 (1H, s), 7.87-7.90 (2H, m), 8.56 (1H, s), 8.58-8.63 (1H, m), 9.23 (1H, d, J=1.2 Hz)

Reference Example 14-3

4-{[4-(5-Fluoropyridin-3-yl)-1,3-thiazol-2-yl]methyl}-2,5-dimethylaniline

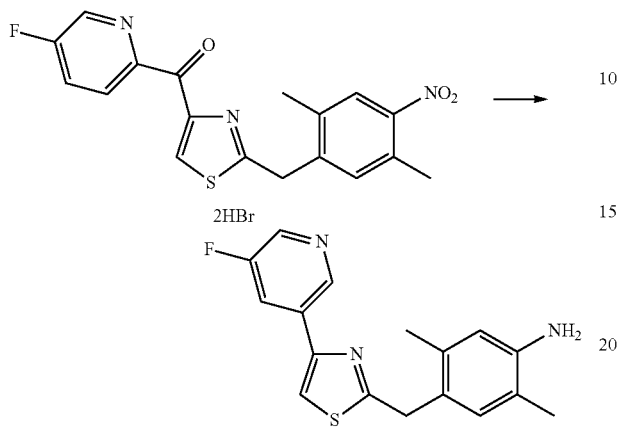

To an ethanol (6.7 mL) solution of the compound (0.17 g) obtained by the technique of Reference Example 14-2, 10% palladium-carbon (50 mg) was added, and the resultant was stirred at room temperature for 22 hours in a hydrogen atmosphere. Insoluble material was filtered off through Celite. Again, 10% palladium-carbon (50 mg) was added to the filtrate, and the resultant was stirred at 40° C. for 4 hours in a hydrogen atmosphere. Insoluble material was filtered off through Celite, and the filtrate was concentrated under reduced pressure. The obtained residue was purified by silica gel column chromatography (OH-type silica gel; hexane/ethyl acetate-gradient elution=90/10→60/40) to obtain the title compound (82 mg) as a pale yellow solid.

$^1$H NMR (600 MHz, CHLOROFORM-d) δppm 2.15 (3H, s), 2.23 (3H, s), 3.57 (2H, br. s.), 4.24 (2H, s), 6.55 (1H, s), 6.96 (1H, s), 7.44 (1H, s), 7.91-7.98 (1H, m), 8.41 (1H, d, J=2.9 Hz), 8.91 (1H, t, J=1.4 Hz)

Reference Example 15

3-(Bromoacetyl)-6-tert-butylpyridin-2(1H)-one

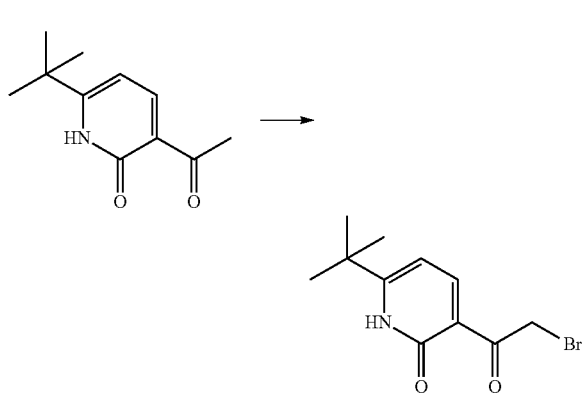

To a tetrahydrofuran (5.0 mL) solution of 3-(acetyl)-6-tert-butylpyridin-2(1H)-one (0.50 g), 5,5-dibromobarbituric acid (0.41 g) was added, and the resultant was heated to reflux for 2 hours. A deposit formed during the course of concentration of the reaction solution under reduced pressure was filtered to obtain the title compound (0.28 g) as a light brown solid.

Reference Example 16

2-Bromo-1-(5-methoxypyrazin-2-yl)ethanone

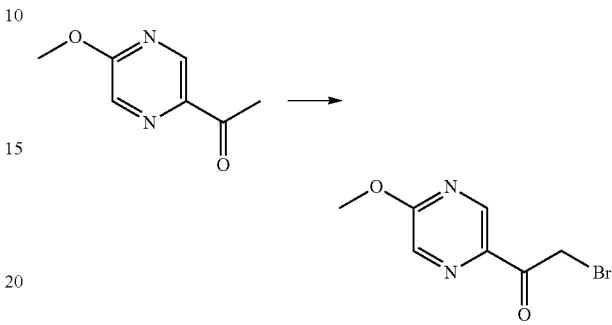

To a chloroform (7.0 mL) solution of 1-(5-methoxypyrazin-2-yl)ethanone (0.35 g), tetrabutylammonium tribromide (1.2 g) was added, and the resultant was heated to reflux for 1 hour. After standing to cool to room temperature, the reaction solution was diluted with chloroform, and a 10% aqueous sodium thiosulfate solution was added to the dilution, followed by extraction with chloroform. An organic layer was separated using a phase separator, and the solvent was distilled off under reduced pressure. The obtained residue was purified by silica gel column chromatography (OH-type silica gel; hexane/ethyl acetate-gradient elution=95/5→80/20) to obtain the title compound (26 mg) as a white solid.

$^1$H NMR (600 MHz, CHLOROFORM-d) δppm 4.07 (3H, s), 4.69 (2H, s), 8.21 (1H, d, J=0.8 Hz), 8.88 (1H, s)

Reference Example 17-1

2-(2,5-Dimethyl-4-nitrobenzyl)-4-(propan-2-yloxy)-1,3-thiazole

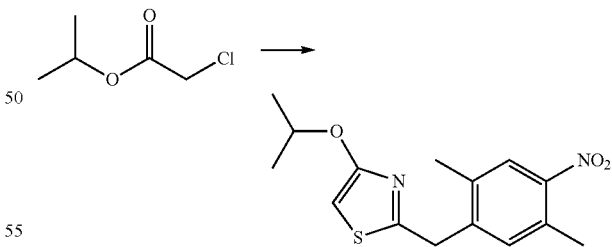

To a 2-propanol (5.0 mL) suspension of the compound (0.21 g) obtained by the technique of Reference Example 1-2, isopropyl chloroacetate (0.58 mL) was added, and the resultant was stirred at 80° C. for 4 hours, followed by standing to cool to room temperature. The deposited solid was filtered off, and the filtrate was concentrated under reduced pressure. The obtained residue was purified by silica gel column chromatography (NH-type silica gel; hexane/ethyl acetate-gradient elution=95/5→50/50) to obtain the title compound (94 mg) as a yellow oil.

Reference Example 17-2

2,5-Dimethyl-4-{[4-(propan-2-yloxy)-1,3-thiazol-2-yl]methyl}aniline

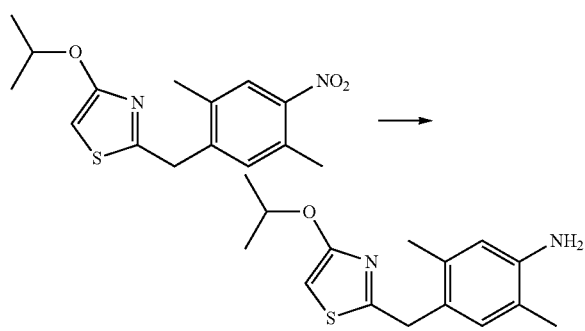

To an ethanol (3.0 mL) solution of the compound (85 mg) obtained by the technique of Reference Example 17-1, 20% palladium hydroxide (26 mg) was added, and the resultant was stirred at 50° C. for 18 hours in a hydrogen atmosphere. Insoluble material was filtered off, and the filtrate was washed with ethanol and chloroform and then concentrated under reduced pressure. The obtained residue was purified by silica gel column chromatography (OH-type silica gel; hexane/ethyl acetate-gradient elution=90/10→75/25) to obtain the title compound (49 mg) as a brown oil.

Reference Example 18

3-Bromo-1-[4-(trifluoromethyl)phenyl]propane-1,2-dione

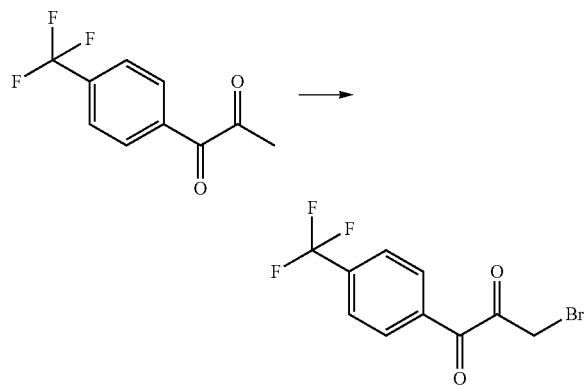

To a chloroform (6.0 mL) solution of 1-[4-(trifluoromethyl)phenyl]propane-1,2-dione (0.65 g), bromine (0.62 mL) was added, and the resultant was stirred at 70° C. for 6 hours. After standing to cool to room temperature, a 10% aqueous sodium thiosulfate solution was added thereto, followed by extraction with chloroform. An organic layer was separated using a phase separator, and the solvent was distilled off under reduced pressure to obtain the title compound (1.1 g) as a yellow oil.

Reference Example 19

2-Bromo-1-(5-methylpyrazin-2-yl)ethanone

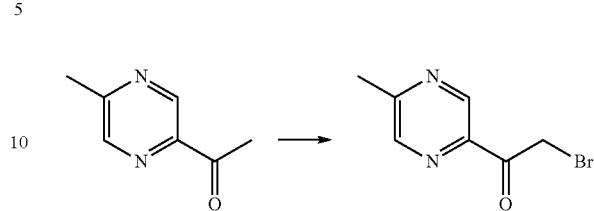

To a chloroform (28 mL) solution of 1-(5-methylpyrazin-2-yl)ethanone (1.9 g), under ice cooling in a nitrogen atmosphere, 2,6-lutidine (2.7 mL) and trimethylsilyl trifluoromethanesulfonate (3.0 mL) were added, and the resultant was stirred for 30 minutes. Then, N-bromosuccinimide (3.0 g) was added thereto, and the resultant was stirred at room temperature for 1 hour. Water was added to the reaction solution, and the resultant was stirred for 15 minutes, followed by extraction with chloroform. An organic layer was separated using a phase separator, and the solvent was distilled off under reduced pressure. The obtained residue was purified by silica gel column chromatography (OH-type silica gel; hexane/ethyl acetate-gradient elution=90/10→60/40) and then further purified by hexane/ethyl acetate-gradient elution (=90/10→80/20) to obtain the title compound (2.1 g) as a pale yellow solid.

$^1$H NMR (600 MHz, CHLOROFORM-d) δppm 2.62-2.73 (3H, m), 4.73 (2H, s) 8.52 (1H, s), 9.17 (1H, d, J=1.7 Hz)

Reference Example 20-1

2,5-Dimethyl-5-nitropyridine-1-oxide

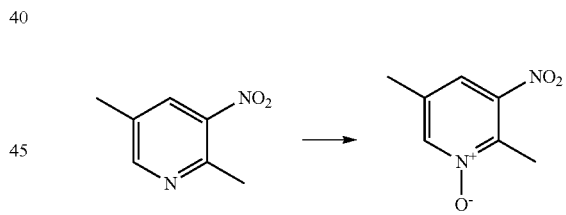

To a chloroform (10 mL) solution of 2,5-dimethyl-5-nitropyridine (1.2 g), under ice cooling in a nitrogen atmosphere, carbamide peroxide (1.9 g) and trifluoroacetic anhydride (2.3 mL) were added dropwise, and the resultant was stirred for 30 minutes under ice cooling and then stirred at room temperature for 13 hours. Water was added to the reaction mixture, followed by extraction with chloroform. The obtained organic layer was washed with a 10% aqueous sodium thiosulfate solution and then dried over sodium sulfate, and the desiccant was filtered off. Then, the solvent was distilled off under reduced pressure. The obtained residue was purified by silica gel column chromatography (OH-type silica gel; chloroform/ethyl acetate-gradient elution=100/0→0/100) to obtain the title compound (1.0 g) as a yellow solid.

$^1$H NMR (200 MHz, CHLOROFORM-d) δppm 2.38 (3H, d, J=0.9 Hz), 2.68 (3H, s), 7.54 (1H, s), 8.32 (1H, s)

Reference Example 20-2

2-Chloro-3,6-dimethyl-5-nitropyridine

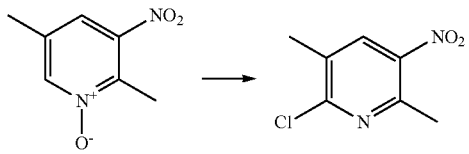

To the compound (0.98 g) obtained by the technique of Reference Example 20-1, phosphoryl chloride (6.0 mL) was added, and the resultant was heated to reflux for 2 hours. The reaction mixture was allowed to cool to room temperature and then added to ice water, followed by extraction with chloroform twice. Combined organic layers were washed with saturated saline and dried over sodium sulfate, and the desiccant was filtered off. Then, the solvent was distilled off under reduced pressure. The obtained residue was purified by silica gel column chromatography (OH-type silica gel; hexane/ethyl acetate-gradient elution=100/0→75/25) to obtain the title compound (0.56 g) as a pale yellow solid.

$^1$H NMR (200 MHz, CHLOROFORM-d) δppm 2.45 (3H, s), 2.82 (3H, s), 8.18 (1H, s)

Reference Example 20-3

Tert-butyl cyano(3,6-dimethyl-5-nitropyridin-2-yl)acetate

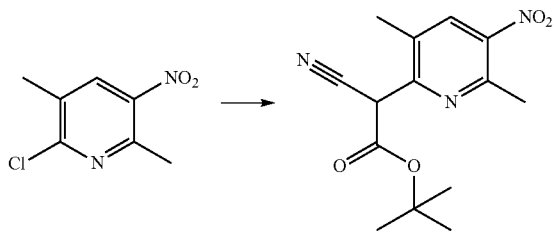 [SMILES: Cc1cc([N+](=O)[O-])c(C)nc1Cl ; Cc1cc([N+](=O)[O-])c(C)nc1C(C#N)C(=O)OC(C)(C)C]

To a tetrahydrofuran (5.0 mL) solution of the compound (0.45 g) obtained by the technique of Reference Example 20-2, tert-butyl cyanoacetate (0.51 g) and potassium carbonate (0.83 g) were added, and the resultant was heated to reflux for 16 hours. Then, tert-butyl cyanoacetate (0.51 g) was further added thereto, and the resultant was heated to reflux for 16 hours. After standing to cool to room temperature, the solvent was distilled off under reduced pressure. Water was added to the obtained residue, followed by extraction with ethyl acetate. The organic layer was dried over magnesium sulfate, and the desiccant was filtered off. Then, the solvent was distilled off under reduced pressure to obtain the title compound (0.40 g) as an orange solid.

Reference Example 20-4

(3,6-Dimethyl-5-nitropyridin-2-yl)acetonitrile

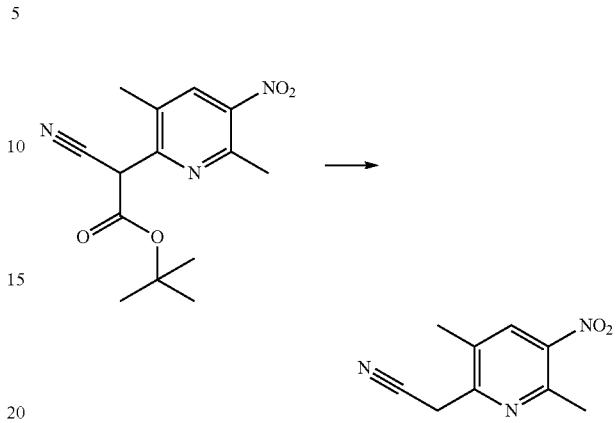

To a toluene (5.0 mL) solution of the compound (0.40 g) obtained by the technique of Reference Example 20-3, p-toluenesulfonic acid monohydrate (42 mg) was added, and the resultant was heated to reflux for 1 day. After standing to cool to room temperature, a saturated aqueous solution of sodium bicarbonate was added thereto, followed by extraction with ethyl acetate. The organic layer was dried over magnesium sulfate, and the desiccant was filtered off. Then, the solvent was distilled off under reduced pressure. The obtained residue was purified by silica gel column chromatography (OH-type silica gel; hexane/ethyl acetate-gradient elution=100/0→75/25) to obtain the title compound (0.16 g) as an orange solid.

1H NMR (600 MHz, CHLOROFORM-d) δppm 2.46 (3H, s), 2.83 (3H, s), 3.93 (2H, s), 8.13 (1H, s)

Reference Example 20-5

2-(3,6-Dimethyl-5-nitropyridin-2-yl)ethanethioamide hydrochloride

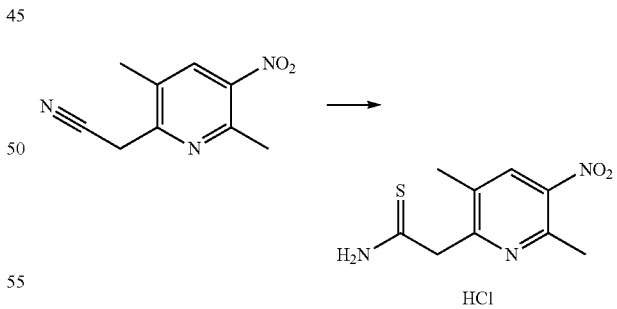

To the compound (0.10 g) obtained by the technique of Reference Example 20-4, a 4 mol/L hydrogen chloride/ethyl acetate solution (2.0 mL) and diethylphosphorodithioic acid (0.13 mL) were added, and the resultant was stirred at room temperature for 1 day. The deposited solid was collected by filtration and washed with hexane/ethyl acetate (=3/1) to obtain the title compound (0.10 g) as a yellow solid.

$^1$H NMR (600 MHz, DMSO-$d_6$) δppm 2.40 (3H, s), 2.68 (3H, s), 4.10 (2H, s), 8.23 (1H, s), 9.39-9.70 (2H, m)

Reference Example 20-6

2,5-Dimethyl-6-{[4-(4-methylphenyl)-1,3-thiazol-2-yl]methyl}-3-nitropyridine

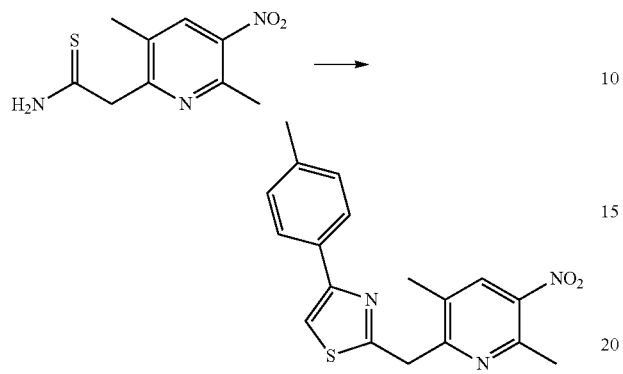

To a 2-propanol (2.0 mL) suspension of the compound (0.10 g) obtained by the technique of Reference Example 20-5, 2-bromo-4'-methylacetophenone (91 mg) was added, and the resultant was stirred at 80° C. for 4 hours. A saturated aqueous solution of sodium bicarbonate was added thereto, followed by extraction with ethyl acetate. The organic layer was dried over magnesium sulfate, and the desiccant was filtered off. Then, the solvent was distilled off under reduced pressure. The obtained residue was purified by silica gel column chromatography (OH-type silica gel; hexane/ethyl acetate-gradient elution=100/0→66/34) to obtain the title compound (83 mg) as a red solid.

$^1$H NMR (600 MHz, DMSO-$d_6$) δppm 2.32 (3H, s), 2.47 (3H, s), 2.71 (3H, s), 4.65 (2H, s), 7.23 (2H, d, J=8.2 Hz), 7.80 (2H, d, J=8.2 Hz), 7.92 (1H, s), 8.30-8.36 (1H, m)

Reference Example 20-7

2,5-Dimethyl-6-{[4-(4-methylphenyl)-1,3-thiazol-2-yl]methyl}pyridin-3-amine

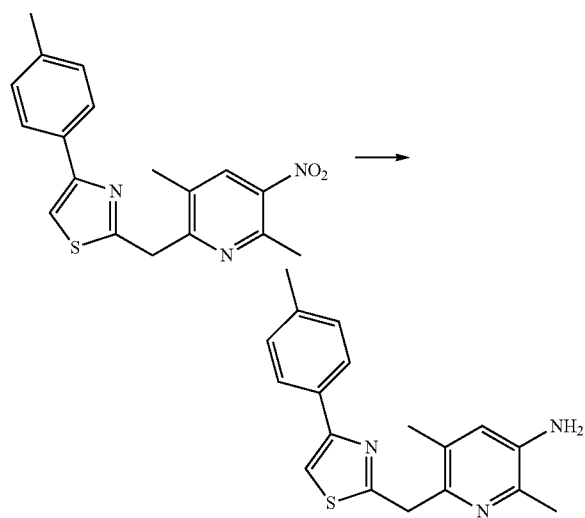

To a 1:1 ethanol/water (1.0 mL) solution of the compound (80 mg) obtained by the technique of Reference Example 20-6, ammonium chloride (38 mg) and iron powder (39 mg) were added, and the resultant was heated to reflux for 2 hours. Insoluble material was filtered off, and the filtrate was concentrated under reduced pressure. A saturated aqueous solution of sodium bicarbonate was added to the obtained residue, followed by extraction with ethyl acetate. The organic layer was dried over magnesium sulfate, and the desiccant was filtered off. Then, the solvent was distilled off under reduced pressure. The obtained residue was purified by silica gel column chromatography (NH-type silica gel; hexane/ethyl acetate-gradient elution=100/0→50/50) to obtain the title compound (27 mg) as a red solid.

$^1$H NMR (600 MHz, CHLOROFORM-d) δppm 2.26 (3H, s), 2.37 (3H, s), 2.41 (3H, s), 3.52 (2H, br. s.), 4.47 (2H, s), 6.76 (1H, s), 7.21 (2H, d, J=8.0 Hz), 7.25 (1H, s), 7.77 (2H, d, J=8.0 Hz)

Reference Example 21-1

4,4'-Bi-1,3-thiazol-2-ylacetonitrile

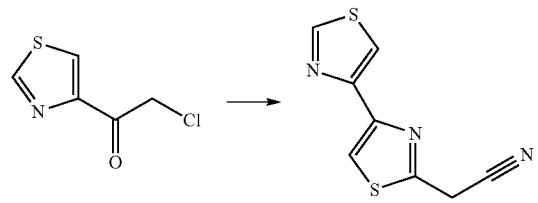 [SMILES: O=C(CCl)c1cscn1 ; N#CCc1nc(-c2cscn2)cs1]

A N,N-dimethylformamide (49 mL) suspension of 2-chloro-1-(1,3-thiazol-4-yl)ethanone (4.9 g), 2-cyanoethanethioamide (3.3 g) and potassium carbonate (4.6 g) was stirred at 60° C. for 1 hour in a nitrogen atmosphere. The reaction mixture was cooled to room temperature, and water and ethyl acetate were added thereto. An organic layer was separated and dried over anhydrous magnesium sulfate, and the solvent was distilled off under reduced pressure. The residue was purified by silica gel column chromatography (eluent: hexane/ethyl acetate=3/1). Isopropyl ether was added to the residue, and the solid was collected by filtration to obtain the title compound (2.8 g) as a faint orange solid.

$^1$H NMR (400 MHz, CHLOROFORM-d) δppm 4.18 (2H, s), 7.84 (1H, s), 7.87 (1H, d, J=1.9 Hz), 8.85 (1H, d, J=2.2 Hz)

Reference Example 21-2

4,4'-Bi-1,3-thiazol-2-yl(2,5-dimethyl-4-nitrophenyl)acetonitrile

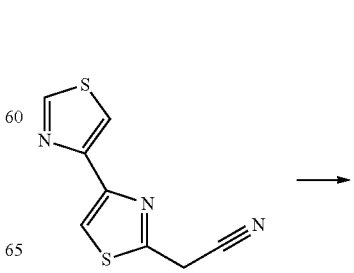

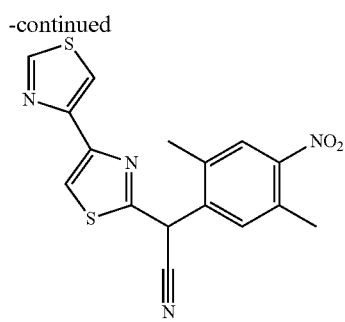

To a N,N-dimethylformamide (1.0 mL) solution of the compound (50 mg) obtained by the technique of Reference Example 21-1, at room temperature in a nitrogen atmosphere, 1-chloro-2,5-dimethyl-4-nitrobenzene (49 mg) was added, then potassium tert-butoxide (30 mg) was added at 69° C., and the resultant was stirred at 60 to 70° C. for 50 minutes. 1-Chloro-2,5-dimethyl-4-nitrobenzene (22 mg) and potassium tert-butoxide (14 mg) were added to the reaction mixture, and the resultant was stirred at the same temperature as above for 40 minutes. The reaction mixture was ice-cold, and acetic acid (22 µL), water and ethyl acetate were added thereto. An organic layer was separated, washed with a saturated aqueous solution of sodium chloride, and dried over anhydrous magnesium sulfate. The solvent was distilled off under reduced pressure. The obtained residue was purified by silica gel column chromatography (eluent: hexane/ethyl acetate=3/1). Ethyl ether and isopropyl ether were added thereto, and the solid was collected by filtration to obtain the title compound (29 mg) as a brownish yellow solid.

$^1$H NMR (400 MHz, CHLOROFORM-d) δppm 2.45 (3H, s), 2.63 (3H, s), 5.73 (1H, s), 7.60 (1H, s), 7.83-7.91 (3H, m), 8.84 (1H, d, J=2.0 Hz)

Reference Example 21-3

2-(2,5-Dimethyl-4-nitrobenzyl)-4,4'-bi-1,3-thiazole

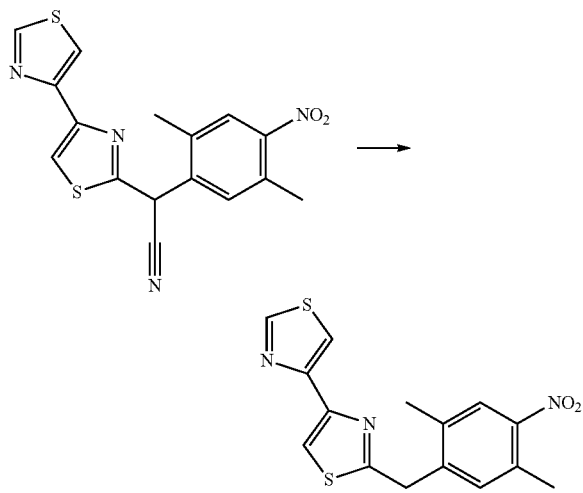

To a dioxane (4.3 mL) solution of the compound (0.43 g) obtained by the technique of Reference Example 21-2 at room temperature, 12 mol/L hydrochloric acid (4.3 mL) was added, and the resultant was stirred for 4 hours and 40 minutes under heating to reflux. The reaction mixture was cooled to room temperature, and water and ethyl acetate were added thereto. The resultant was adjusted to pH 10 with a 1 mol/L aqueous sodium hydroxide solution. An organic layer was separated and dried over anhydrous magnesium sulfate, and the solvent was distilled off under reduced pressure. The obtained residue was purified by silica gel column chromatography (eluent: toluene/ethyl acetate=10/1). Isopropyl ether was added thereto, and the solid was collected by filtration to obtain the title compound (0.30 g) as a slightly red solid.

$^1$H NMR (400 MHz, CHLOROFORM-d) δppm 2.40 (3H, s), 2.57 (3H, s), 4.39 (2H, s), 7.24 (1H, s), 7.72 (1H, s), 7.83 (1H, d, J=2.2 Hz), 7.86 (1H, s), 8.84 (1H, d, J=2.2 Hz)

Reference Example 21-4

4-(4,4'-Bi-1,3-thiazol-2-ylmethyl)-2,5-dimethylaniline

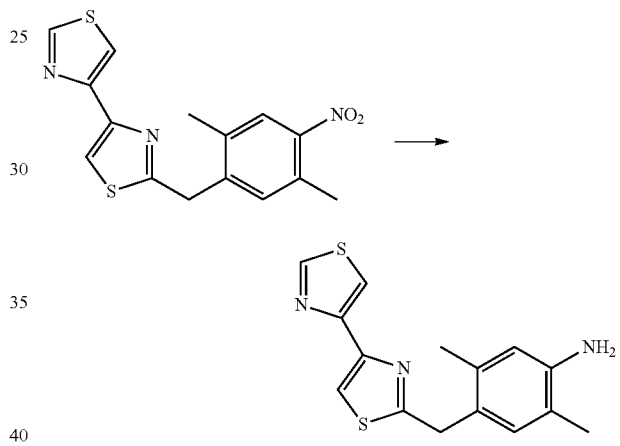

To an ethanol (3.0 mL)-ethyl acetate (3.0 mL) suspension of the compound (0.30 g) obtained by the technique of Reference Example 21-3, at room temperature, 10% palladium-carbon (60 mg) was added, and the resultant was stirred at 50° C. for 40 minutes in a hydrogen atmosphere. Insoluble material was filtered off, and the solvent was distilled off under reduced pressure. Methanol (3.0 mL), acetic acid (1.0 mL) and 10% palladium-carbon (60 mg) were added to the obtained residue, and the resultant was stirred at 40 to 50° C. for 1 hour and 45 minutes in a hydrogen atmosphere. Methanol (3.0 mL), acetic acid (1.0 mL) and 10% palladium-carbon (60 mg) were added to the reaction mixture, and the resultant was stirred at 40 to 50° C. for 10 minutes in a hydrogen atmosphere. The reaction mixture was cooled to room temperature, and chloroform was added thereto. Insoluble material was filtered off, and the solvent was distilled off under reduced pressure. Ethyl ether and isopropyl ether were added to the residue, and the solid was collected by filtration to obtain the title compound (0.24 g) as a light brown solid.

$^1$H NMR (400 MHz, CHLOROFORM-d) δppm 2.15 (3H, s), 2.21 (3H, s), 3.3-4.0 (2H, broad), 4.24 (2H, s), 6.55 (1H, s), 6.96 (1H, s), 7.65 (1H, s), 7.84 (1H, d, J=2.2 Hz), 8.83 (1H, d, J=2.0 Hz),

Reference Example 22

4-((4-(4-Chlorophenyl)-1,3-thiazol-2-yl)methyl)-2,5-dimethylaniline

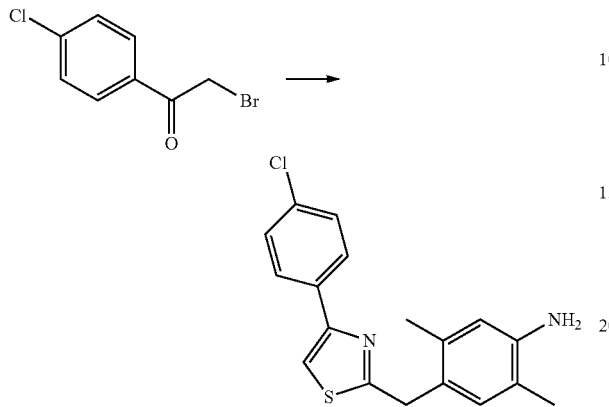

To an isopropyl alcohol (2.0 mL) solution of the compound (0.20 g) obtained by the technique of Reference Example 1-2 at room temperature, 2-bromo-4'-chloroacetophenone (0.25 g) was added, and the resultant was stirred at 80 to 90° C. for 1 hour and 20 minutes. 12 mol/L hydrochloric acid (1.0 mL) and tin(II) chloride (0.50 g) were added thereto, and the resultant was stirred at the same temperature as above for 2 hours. The reaction mixture was cooled to room temperature, and water (10 mL), ethyl acetate (10 mL) and a 20% aqueous sodium hydroxide solution (4 mL) were added thereto. Insoluble material was filtered off. An organic layer was separated, and an aqueous layer was subjected to extraction with ethyl acetate. The organic layer and the extract were combined, washed with a saturated aqueous solution of sodium chloride, and dried over anhydrous magnesium sulfate. The solvent was distilled off under reduced pressure. The obtained residue was purified by flash silica gel column chromatography (hexane/ethyl acetate-gradient elution=80/20→67:33) to obtain the title compound (0.11 g) as a light brown solid.

$^1$H NMR (400 MHz, CHLOROFORM-d) δppm 2.15 (3H, s), 2.22 (3H, s), 3.52-3.68 (2H, broad), 4.23 (2H, s), 6.55 (1H, s), 6.96 (1H, s), 7.29 (1H, s), 7.35-7.41 (2H, m), 7.80-7.86 (2H, m)

Reference Example 23

2,5-Dimethyl-4-((4-methyl-1,3-thiazol-2-yl)methyl)aniline

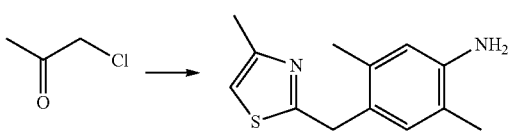

The title compound was obtained by the same technique as in Reference Example 22 from the compound obtained by the technique of Reference Example 1-2 and chloroacetone.

$^1$H NMR (400 MHz, CHLOROFORM-d) δppm 2.13 (3H, s), 2.18 (3H, s), 2.42 (3H, s), 3.48-3.60 (2H, broad), 4.15 (2H, s), 6.52 (1H, s), 6.66-6.70 (1H, m), 6.93 (1H, s)

Reference Example 24

4-((4-(4-Chlorophenyl)-1,3-thiazol-2-yl)methyl)aniline

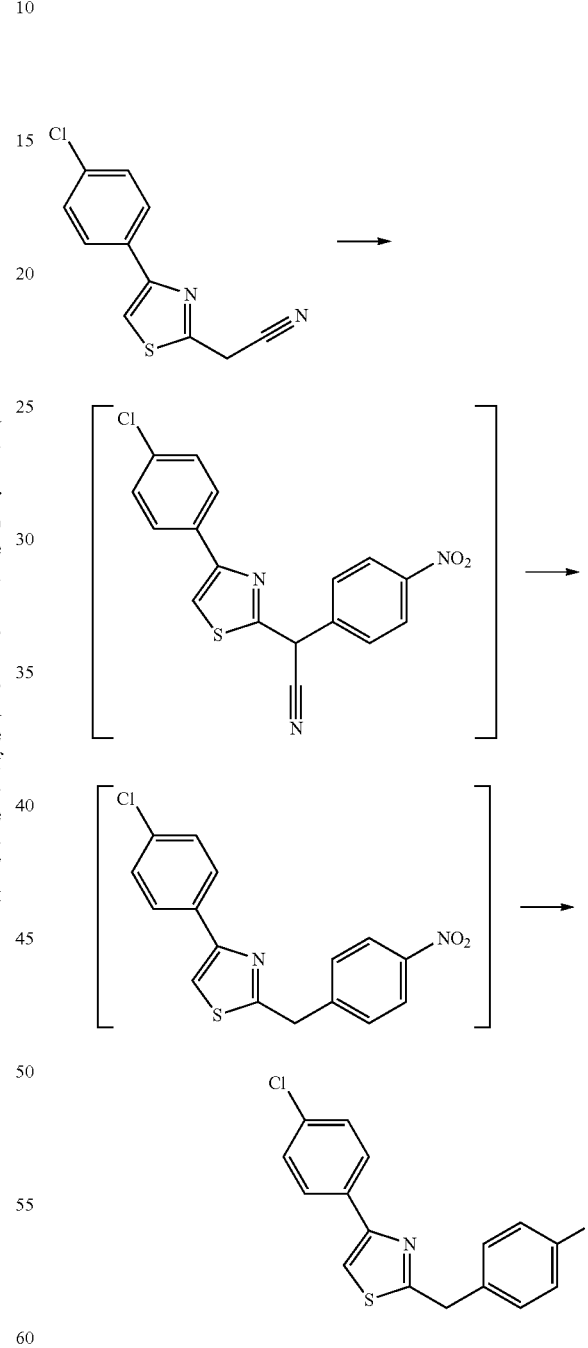

The title compound was obtained by the same technique as in Reference Examples 21-2 to 21-4 from (4-(4-chlorophenyl)-1,3-thiazol-2-yl)acetonitrile.

$^1$H NMR (400 MHz, CHLOROFORM-d) δppm 3.61-3.70 (2H, broad), 4.26 (2H, s), 6.65-6.71 (2H, m), 7.12-7.17 (2H, m), 7.31 (1H, s), 7.35-7.41 (2H, m), 7.80-7.85 (2H, m)

Reference Example 25-1

2-(2,5-Dimethyl-4-nitrobenzyl)-1,3-thiazole-4-carboxylic acid

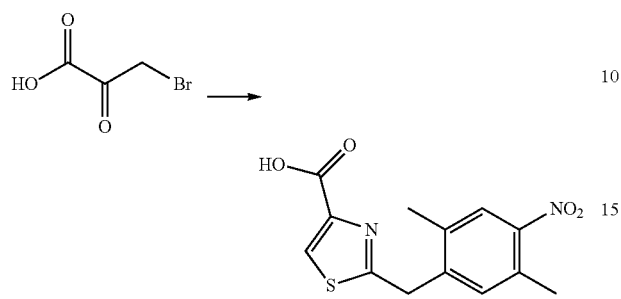

To a 2-propanol (9.0 mL) suspension of the compound (0.20 g) obtained by the technique of Reference Example 1-2, 3-bromopyruvic acid (0.15 g) was added, and the resultant was stirred at 80° C. for 30 minutes. After standing to cool to room temperature, a 1 mol/L aqueous hydrochloric acid solution was added to the reaction solution, followed by extraction with chloroform. Then, an aqueous layer was purified using a synthetic adsorbent (HP-20). The solvent was distilled off under reduced pressure. The obtained residue was purified by silica gel column chromatography (OH-type silica gel; chloroform/methanol-gradient elution=99/1→40/60) to obtain the title compound (0.23 g) as a pale yellow solid.

$^1$H NMR (600 MHz, DMSO-$d_6$) δppm 2.32 (3H, s), 2.47 (3H, s), 4.37 (2H, s), 7.39 (1H, s), 7.56 (1H, s), 7.86 (1H, s)

Reference Example 25-2

N-Cyclohexyl-2-(2,5-dimethyl-4-nitrobenzyl)-1,3-thiazole-4-carboxamide

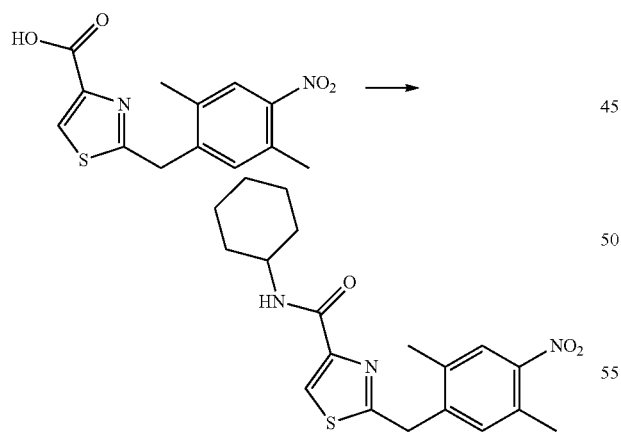

To a N,N-dimethylformamide (3.0 mL) solution of the compound (0.10 g) obtained by the technique of Reference Example 25-1, cyclohexylamine (40 μL) and N,N-diisopropylethylamine (0.30 mL) were added, and the resultant was stirred for 5 minutes. Then, HATU (0.16 g) was added thereto, and the resultant was stirred at room temperature for 2 hours. A saturated aqueous solution of sodium bicarbonate was added to the reaction solution, followed by extraction with chloroform. An organic layer was separated using a phase separator, and the solvent was distilled off under reduced pressure. The obtained residue was purified by silica gel column chromatography (OH-type silica gel; hexane/ethyl acetate-gradient elution=100/0→70/30) to obtain the title compound (0.13 g) as a pale yellow solid.

$^1$H NMR (600 MHz, CHLOROFORM-d) δppm 1.05-1.48 (5H, m), 1.62-2.05 (5H, m), 2.37 (3H, s) 2.57 (3H, s), 3.90-4.00 (1H, m), 4.32 (2H, s), 7.15 (1H, d, J=8.3 Hz), 7.18 (1H, s), 7.86 (1H, s), 7.98 (1H, s)

Reference Example 25-3

2-(4-Amino-2,5-dimethylbenzyl)-N-cyclohexyl-1,3-thiazole-4-carboxamide

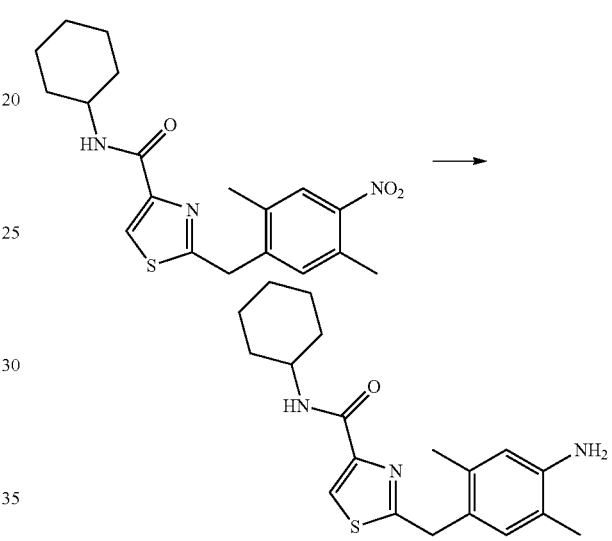

To an ethanol (5.0 mL) solution of the compound (0.12 g) obtained by the technique of Reference Example 25-2, 20% palladium hydroxide (36 mg) was added, and the resultant was stirred at room temperature for 24 hours in a hydrogen atmosphere. Insoluble material was filtered off through Celite, and the filtrate was washed with chloroform and then concentrated under reduced pressure. The obtained residue was purified by silica gel column chromatography (NH-type silica gel; hexane/ethyl acetate-gradient elution=90/10→80/20) to obtain the title compound (0.11 g) as a pale yellow foam.

$^1$H NMR (600 MHz, CHLOROFORM-d) δppm 1.06-1.48 (5H, m), 1.62-2.05 (5H, m), 2.14 (3H, s), 2.18 (3H, s), 3.90-3.98 (1H, m), 4.15 (2H, s), 6.54 (1H, s), 6.90 (1H, s), 7.22 (1H, d, J=7.8 Hz), 7.90 (1H, s)

Reference Example 26-1

[2-(2,5-Dimethyl-4-nitrobenzyl)-1,3-thiazol-4-yl](piperidin-1-yl)methanone

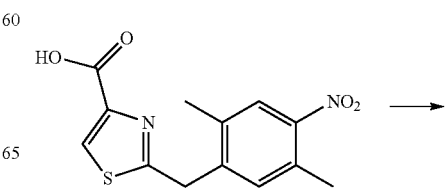

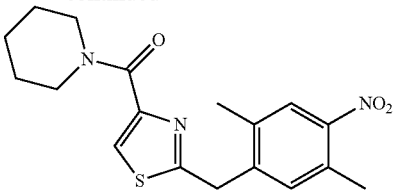

To a N,N-dimethylformamide (3.0 mL) solution of the compound (0.12 g) obtained by the technique of Reference Example 25-1, piperidine (50 μL) and N,N-diisopropylethylamine (0.36 mL) were added, and the resultant was stirred for 5 minutes. Then, HATU (0.19 g) was added thereto, and the resultant was stirred at room temperature for 1 hour. A saturated aqueous solution of sodium bicarbonate was added to the reaction solution, followed by extraction with chloroform. An organic layer was separated using a phase separator, and the solvent was distilled off under reduced pressure. The obtained residue was purified by silica gel column chromatography (OH-type silica gel; hexane/ethyl acetate-gradient elution=100/0→80/20) to obtain the title compound (0.12 g) as a pale yellow oil.

$^1$H NMR (600 MHz, CHLOROFORM-d) δppm 1.59-1.75 (6H, m), 2.37 (3H, s), 2.56 (3H, s), 3.56-3.76 (4H, m), 4.34 (2H, s), 7.21 (1H, s), 7.70 (1H, s), 7.85 (1H, s)

Reference Example 26-2

[2-(4-Amino-2,5-dimethylbenzyl)-1,3-thiazol-4-yl](piperidin-1-yl)methanone

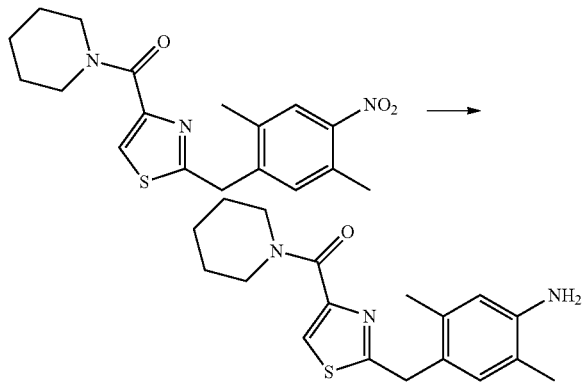

To an ethanol (4.4 mL) solution of the compound (0.11 g) obtained by the technique of Reference Example 26-1, 20% palladium hydroxide (33 mg) was added, and the resultant was stirred at room temperature for 18 hours in a hydrogen atmosphere. Insoluble material was filtered off through Celite, and the filtrate was washed with chloroform and then concentrated under reduced pressure. The obtained residue was purified by silica gel column chromatography (NH-type silica gel; hexane/ethyl acetate-gradient elution=90/10→80/20) to obtain the title compound (95 mg) as a pale yellow solid.

$^1$H NMR (600 MHz, CHLOROFORM-d) δppm 1.64-1.74 (6H, m), 2.13 (3H, s), 2.18 (3H, s), 3.63-3.76 (4H, m), 4.18 (2H, s), 6.53 (1H, s), 6.92 (1H, s), 7.61 (1H, s)

Reference Example 27

2-Bromo-1-(6-methylpyridin-3-yl)ethanone

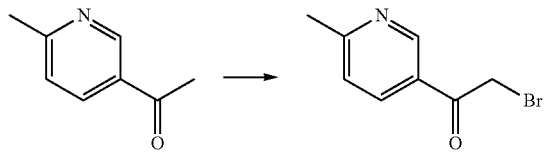

To a chloroform (6.5 mL) solution of 1-(6-methylpyridin-3-yl)ethanone (0.43 g), under ice cooling in a nitrogen atmosphere, 2,6-lutidine (0.63 mL) and trimethylsilyl trifluoromethanesulfonate (0.69 mL) were added, and the resultant was stirred for 30 minutes. Then, N-bromosuccinimide (0.63 g) was added thereto, and the resultant was stirred at room temperature for 1 hour. Water was added to the reaction solution, and the resultant was stirred for 15 minutes, followed by extraction with chloroform. An organic layer was separated using a phase separator, and the solvent was distilled off under reduced pressure. The obtained residue was purified by silica gel column chromatography (OH-type silica gel; hexane/ethyl acetate-gradient elution=90/10→70/30) to obtain the title compound (0.24 g) as a light brown solid.

$^1$H NMR (600 MHz, CHLOROFORM-d) δppm 2.66 (3H, s), 4.41 (2H, s), 7.30 (1H, d, J=7.8 Hz), 8.17 (1H, dd, J=7.8, 2.1 Hz), 9.09 (1H, d, J=2.1 Hz)

Reference Example 28

2-Bromo-1-(2,5-difluoro-4-methylphenyl)ethanone

To a chloroform (3.5 mL) solution of 1-(2,5-difluoro-4-methylphenyl)ethanone (0.23 g), under ice cooling in a nitrogen atmosphere, 2,6-lutidine (0.27 mL) and trimethylsilyl trifluoromethanesulfonate (0.32 mL) were added, and the resultant was stirred for 30 minutes. Then, N-bromosuccinimide (0.27 g) was added thereto, and the resultant was stirred for 30 minutes under ice cooling. Water was added to the reaction solution, and the resultant was stirred for 15 minutes, followed by extraction with chloroform. An organic layer was separated using a phase separator, and the solvent was distilled off under reduced pressure. The obtained residue was purified by silica gel column chromatography (OH-type silica gel; hexane/ethyl acetate-gradient elution=99/1→95/5) to obtain the title compound (0.31 g) as a white solid.

$^1$H NMR (600 MHz, CHLOROFORM-d) δppm 2.34 (3H, d, J=1.7 Hz), 4.48 (2H, d, J=2.5 Hz), 7.02 (1H, dd, J=10.9, 5.6 Hz), 7.58 (1H, dd, J=9.5, 5.6 Hz)

Reference Example 29

2-Bromo-1-(2-fluoro-4-methylphenyl)ethanone

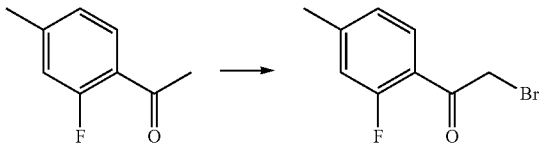

To a chloroform (7.5 mL) solution of 1-(2-fluoro-4-methylphenyl)ethanone (0.50 g), under ice cooling in a nitrogen atmosphere, 2,6-lutidine (0.65 mL) and trimethylsilyl trifluoromethanesulfonate (0.71 mL) were added, and the resultant was stirred for 30 minutes. Then, N-bromosuccinimide (0.64 g) was added thereto, and the resultant was stirred for 30 minutes under ice cooling. Water was added to the reaction solution, and the resultant was stirred for 10 minutes, followed by extraction with chloroform. An organic layer was separated using a phase separator, and the solvent was distilled off under reduced pressure. The obtained residue was purified by silica gel column chromatography (OH-type silica gel; hexane/ethyl acetate-gradient elution=99/1→95/5) to obtain the title compound (0.72 g) as a white solid.

$^1$H NMR (600 MHz, CHLOROFORM-d) δppm 2.42 (3H, s), 4.50 (2H, d, J=2.1 Hz), 6.95-7.00 (1H, m), 7.04-7.10 (1H, m), 7.85 (1H, t, J=7.8 Hz)

Reference Example 30-1

[2-(2,5-Dimethyl-4-nitrobenzyl)-1,3-thiazol-4-yl]methyl acetate

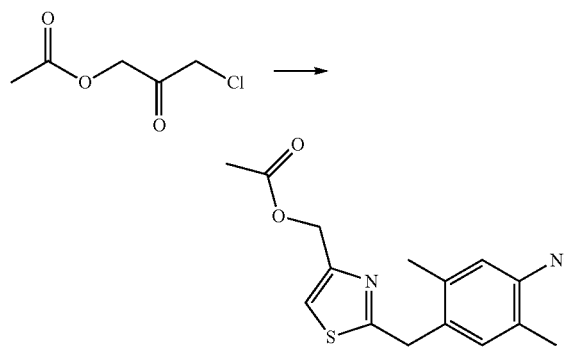

To a 2-propanol (15 mL) solution of the compound (1.4 g) obtained by the technique of Reference Example 1-2, 3-chloro-2-oxopropyl acetate (0.75 mL) and triethylamine (0.65 mL) were added, and the resultant was stirred at 80° C. for 4 hours. The reaction solution was allowed to cool to room temperature and then concentrated under reduced pressure. The obtained residue was purified by silica gel column chromatography (OH-type silica gel; hexane/ethyl acetate-gradient elution=100/0→0/100) to obtain the title compound (1.1 g) as a brown oil.

$^1$H NMR (600 MHz, CHLOROFORM-d) δppm 2.12 (3H, s), 2.36 (3H, s), 2.57 (3H, s), 4.34 (2H, s), 5.19 (2H, s), 7.18 (1H, s), 7.21 (1H, s), 7.85 (1H, s)

Reference Example 30-2

[2-(2,5-Dimethyl-4-nitrobenzyl)-1,3-thiazol-4-yl]methanol

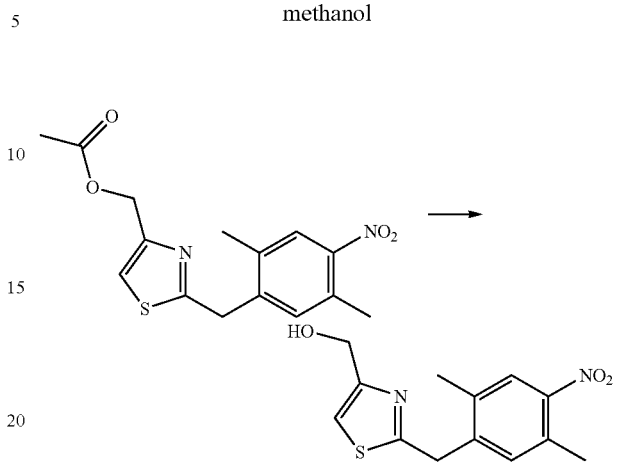

To a methanol (20 mL) solution of the compound (1.1 g) obtained by the technique of Reference Example 30-1, under ice cooling, a 28% sodium methoxide/methanol solution (0.20 g) was added, and the resultant was stirred for 30 minutes under ice cooling. The reaction solution was added to a saturated aqueous solution of ammonium chloride, followed by extraction with ethyl acetate. The organic layer was dried over magnesium sulfate, and the desiccant was filtered off. Then, the solvent was distilled off under reduced pressure to obtain the title compound (0.75 g) as a brown solid.

$^1$H NMR (600 MHz, CHLOROFORM-d) δppm 2.36 (3H, s), 2.56 (3H, s), 4.33 (2H, s), 4.76 (2H, s), 7.09 (1H, s), 7.20 (1H, s), 7.84 (1H, s)

Reference Example 30-3

4-(Bromomethyl)-2-(2,5-dimethyl-4-nitrobenzyl)-1,3-thiazole

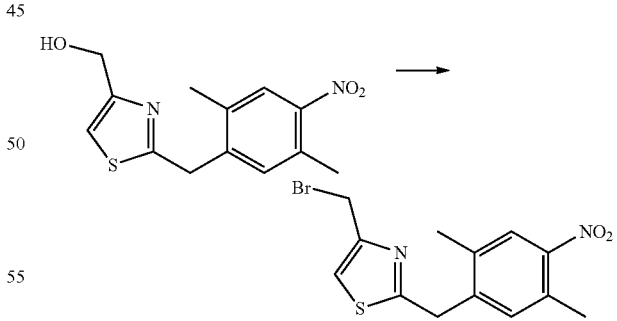

To a tetrahydrofuran (15 mL) solution of the compound (0.75 g) obtained by the technique of Reference Example 30-2, carbon tetrabromide (1.3 g) and triphenylphosphine (1.1 g) were added, and the resultant was stirred at room temperature for 1 day. The reaction solution was concentrated under reduced pressure. The obtained residue was purified by silica gel column chromatography (OH-type silica gel; hexane/ethyl acetate-gradient elution=100/0→66/34) to obtain the title compound (0.79 g) as a pale yellow solid.

¹H NMR (600 MHz, CHLOROFORM-d) δppm 2.36 (3H, s), 2.57 (3H, s), 4.34 (2H, s), 4.56 (2H, s), 7.18-7.23 (2H, m), 7.85 (1H, s)

Reference Example 30-4

2-(2,5-Dimethyl-4-nitrobenzyl)-4-[(4-methylphenoxy)methyl]-1,3-thiazole

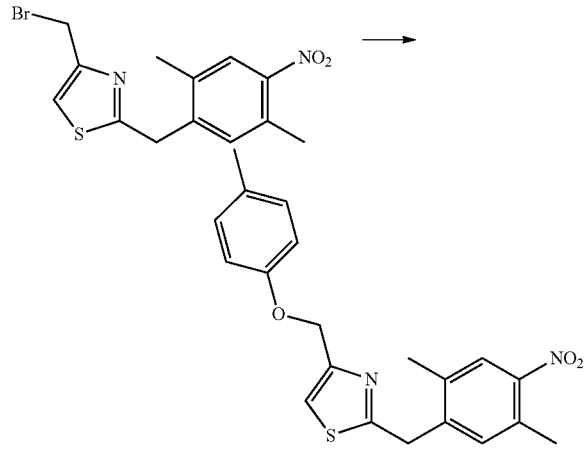

To an acetone (1.0 mL) solution of the compound (50 mg) obtained by the technique of Reference Example 30-3, 4-methylphenol (16 mg) and potassium carbonate (45 mg) were added, and the resultant was stirred at room temperature for 4 hours and then heated to reflux for 5 hours. Insoluble material was filtered off, and the filtrate was concentrated under reduced pressure. The obtained residue was purified by silica gel column chromatography (OH-type silica gel; hexane/ethyl acetate-gradient elution=100/0→66/34) to obtain the title compound (37 mg) as a pale yellow oil.

¹H NMR (600 MHz, CHLOROFORM-d) δppm 2.29 (3H, s), 2.36 (3H, s), 2.56 (3H, s), 4.35 (2H, s), 5.15 (2H, s), 6.88 (2H, d, J=8.7 Hz), 7.09 (2H, d, J=8.7 Hz), 7.19-7.23 (2H, m), 7.85 (1H, s)

Reference Example 30-5

2,5-Dimethyl-4-({4-[(4-methylphenoxy)methyl]-1,3-thiazol-2-yl}methyl)aniline

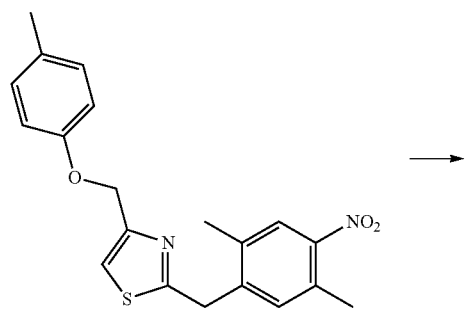

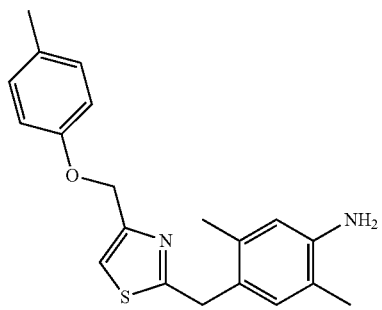

To a 50% aqueous ethanol solution (2.0 mL) of the compound (37 mg) obtained by the technique of Reference Example 30-4, ammonium chloride (16 mg) and iron powder (17 mg) were added, and the resultant was heated to reflux for 2 hours. Insoluble material was filtered off, and the filtrate was concentrated under reduced pressure. A saturated aqueous solution of sodium bicarbonate was added to the obtained residue, followed by extraction with ethyl acetate. The organic layer was dried over magnesium sulfate, and the desiccant was filtered off. Then, the solvent was distilled off under reduced pressure to obtain the title compound (23 mg) as a light brown solid.

¹H NMR (600 MHz, CHLOROFORM-d) δppm 2.14 (3H, s), 2.19 (3H, s), 2.29 (3H, s), 3.55 (2H, br. s.), 4.19 (2H, s), 5.14 (2H, s), 6.53 (1H, s), 6.89 (2H, d, J=8.7 Hz), 6.93 (1H, s), 7.08 (2H, d, J=8.7 Hz), 7.12 (1H, t, J=1.0 Hz)

Reference Example 31-1

2,2-Dibromo-1-(5-methylpyrimidin-2-yl)ethanone

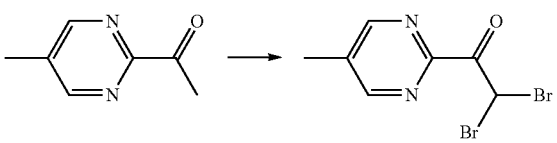

To a chloroform (3.0 mL) solution of 1-(5-methylpyrimidin-2-yl)ethanone (0.20 g), under ice cooling in a nitrogen atmosphere, 2,6-lutidine (0.30 mL) and trimethylsilyl trifluoromethanesulfonate (0.32 mL) were added, and the resultant was stirred for 30 minutes. Then, N-bromosuccinimide (0.32 g) was added thereto, and the resultant was stirred at room temperature for 40 minutes. Water was added to the reaction solution, and the resultant was stirred for 15 minutes, followed by extraction with chloroform. An organic layer was separated using a phase separator, and the solvent was distilled off under reduced pressure. The obtained residue was purified by silica gel column chromatography (OH-type silica gel; hexane/ethyl acetate-gradient elution=80/20→60/40) to obtain the title compound (0.21 g) as a colorless solid.

¹H NMR (600 MHz, CHLOROFORM-d) δppm 2.46 (3H, s), 7.48 (1H, s), 8.76-8.80 (2H, m)

Reference Example 31-2

2-[2-(2,5-Dimethyl-4-nitrobenzyl)-1,3-thiazol-4-yl]-5-methylpyrimidine

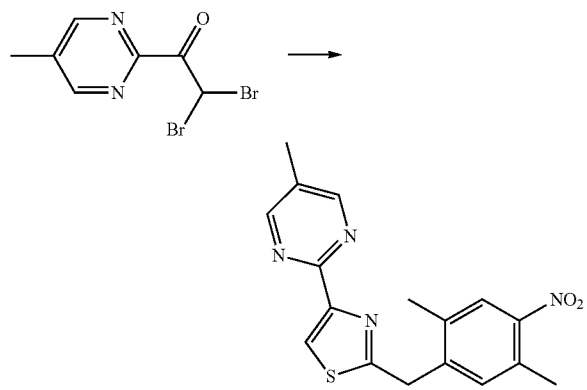

To a 2-propanol (3.0 mL) solution of the compound (0.11 g) obtained by the technique of Reference Example 31-1, the compound (85 mg) obtained by the technique of Reference Example 1-2 was added, and the resultant was stirred at 80° C. for 1 hour. After standing to cool to room temperature, the reaction solution was concentrated under reduced pressure. The obtained residue was purified by silica gel column chromatography (NH-type silica gel; hexane/ethyl acetate-gradient elution=60/40→20/80) to obtain the title compound (26 mg) as a yellow solid.

$^1$H NMR (600 MHz, CHLOROFORM-d) δppm 2.37 (3H, s), 2.37 (3H, s), 2.56 (3H, s), 4.49 (2H, s), 7.25 (1H, s), 7.86 (1H, s), 8.18 (1H, s), 8.66 (2H, s)

Reference Example 31-3

2,5-Dimethyl-4-{[4-(5-methylpyrimidin-2-yl)-1,3-thiazol-2-yl]methyl}aniline

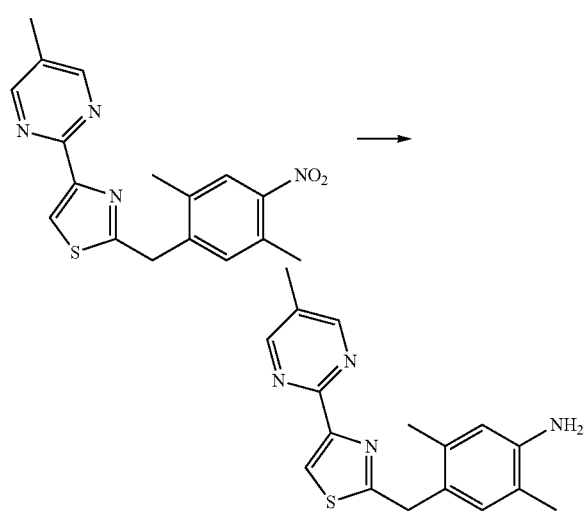

To an ethanol (3.0 mL) solution of the compound (45 mg) obtained by the technique of Reference Example 31-2, 20% palladium hydroxide (14 mg) was added, and the resultant was stirred at room temperature for 19 hours in a hydrogen atmosphere. After catalytic exchange, the resultant was further stirred at room temperature for 1 hour. Insoluble material was filtered off through Celite, and the filtrate was concentrated under reduced pressure. The residue was dried to obtain the title compound (42 mg) as a pale yellow solid.

$^1$H NMR (600 MHz, CHLOROFORM-d) δppm 2.14 (3H, s), 2.19 (3H, s), 2.35 (3H, s), 3.56 (2H, br. s.), 4.32 (2H, s), 6.55 (1H, s), 6.97 (1H, s), 8.09 (1H, s), 8.64 (2H, s)

Reference Example 32-1

2-(2,5-Dimethyl-4-nitrobenzyl)-4-[(propan-2-yloxy)methyl]-1,3-thiazole

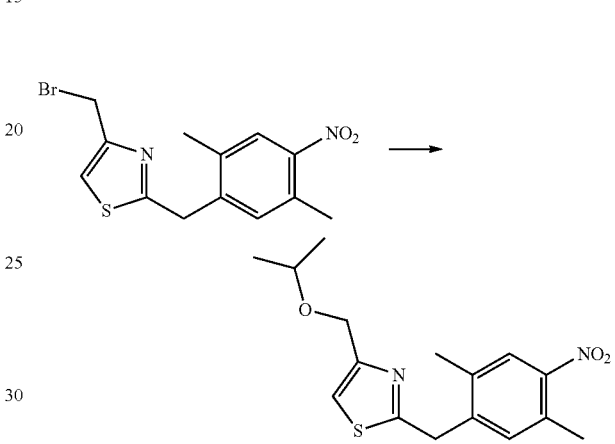

To a 2-propanol (10 mL) solution of the compound (0.19 g) obtained by the technique of Reference Example 30-3, silver oxide (0.66 g) was added, and the resultant was heated to reflux for 1 day. Then, insoluble material was filtered off, and the filtrate was concentrated under reduced pressure. The obtained residue was purified by silica gel column chromatography (NH-type silica gel; hexane/ethyl acetate-gradient elution=95/5→66/34) to obtain the title compound (0.10 g) as a colorless oil.

$^1$H NMR (600 MHz, CHLOROFORM-d) δppm 1.24 (6H, d, J=5.8 Hz), 2.35 (3H, s), 2.56 (3H, s), 3.71-3.80 (1H, m), 4.33 (2H, s), 4.61 (2H, s), 7.12 (1H, s), 7.19 (1H, s), 7.84 (1H, s)

Reference Example 32-2

2,5-Dimethyl-4-({4-[(propan-2-yloxy)methyl]-1,3-thiazol-2-yl}methyl)aniline

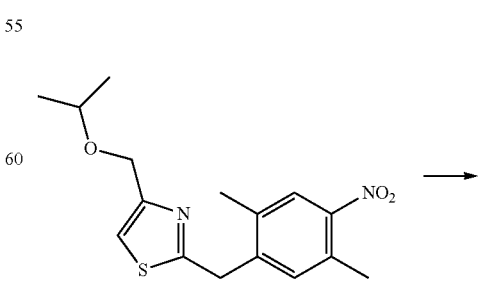

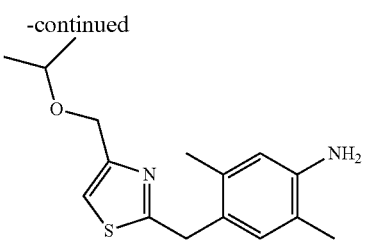

To a 50% aqueous ethanol solution (2.0 mL) of the compound (0.10 g) obtained by the technique of Reference Example 32-1, ammonium chloride (50 mg) and iron powder (52 mg) were added, and the resultant was heated to reflux for 2 hours. Insoluble material was filtered off, and the filtrate was concentrated under reduced pressure. A saturated aqueous solution of sodium bicarbonate was added to the obtained residue, followed by extraction with ethyl acetate. The organic layer was dried over magnesium sulfate, and the desiccant was filtered off. Then, the solvent was distilled off under reduced pressure to obtain the title compound (73 mg) as a pale yellow oil.

$^1$H NMR (600 MHz, CHLOROFORM-d) δppm 1.23 (6H, d, J=6.2 Hz), 2.13 (3H, s), 2.17 (3H, s), 3.55-3.80 (3H, m), 4.17 (2H, s), 4.61 (2H, s), 6.53 (1H, s), 6.92 (1H, s), 7.03 (1H, s)

Reference Example 33

2-Bromo-1-(3-methylpyrazin-2-yl)ethanone

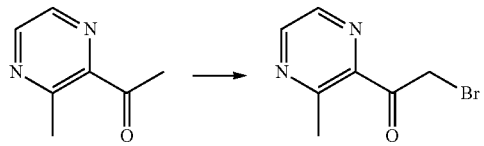

To a chloroform (7.5 mL) solution of 1-(3-methylpyrazin-2-yl)ethanone (0.50 g), under ice cooling in a nitrogen atmosphere, 2,6-lutidine (0.75 mL) and trimethylsilyl trifluoromethanesulfonate (0.80 mL) were added, and the resultant was stirred for 30 minutes. Then, N-bromosuccinimide (0.73 g) was added thereto, and the resultant was stirred for 1 hour under ice cooling. Water was added to the reaction solution, and the resultant was stirred for 10 minutes, followed by extraction with chloroform. An organic layer was separated using a phase separator, and the solvent was distilled off under reduced pressure. The obtained residue was purified by silica gel column chromatography (OH-type silica gel; hexane/ethyl acetate-gradient elution=95/5→85/15) to obtain the title compound (0.58 g) as a brown solid.

$^1$H NMR (600 MHz, CHLOROFORM-d) δppm 2.87 (3H, s), 4.79 (2H, s), 8.50 (1H, d, J=2.1 Hz), 8.65 (1H, d, J=2.1 Hz)

Reference Example 34-1

2,2-Dibromo-1-(6-methylpyridazin-3-yl)ethanone

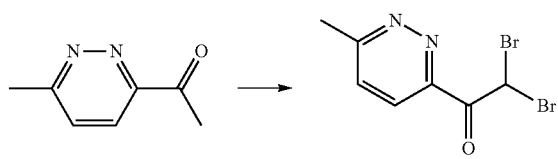

To a chloroform (7.5 mL) solution of 1-(6-methylpyridazin-3-yl)ethanone (0.50 g), under ice cooling in a nitrogen atmosphere, 2,6-lutidine (0.72 mL) and trimethylsilyl trifluoromethanesulfonate (0.79 mL) were added, and the resultant was stirred for 30 minutes. Then, N-bromosuccinimide (0.71 g) was added thereto, and the resultant was stirred for 1 hour under ice cooling. Water was added to the reaction solution, and the resultant was stirred for 10 minutes, followed by extraction with chloroform. An organic layer was separated using a phase separator, and the solvent was distilled off under reduced pressure. The obtained residue was purified by silica gel column chromatography (OH-type silica gel; hexane/ethyl acetate-gradient elution=95/5→85/15) to obtain the title compound (0.34 g) as a pale yellow solid.

$^1$H NMR (600 MHz, CHLOROFORM-d) δppm 2.86 (3H, s), 7.57 (1H, d, J=8.7 Hz), 7.73 (1H, s), 8.15 (1H, d, J=8.7 Hz)

Reference Example 34-2

3-[2-(2,5-Dimethyl-4-nitrobenzyl)-1,3-thiazol-4-yl]-6-methylpyridazine

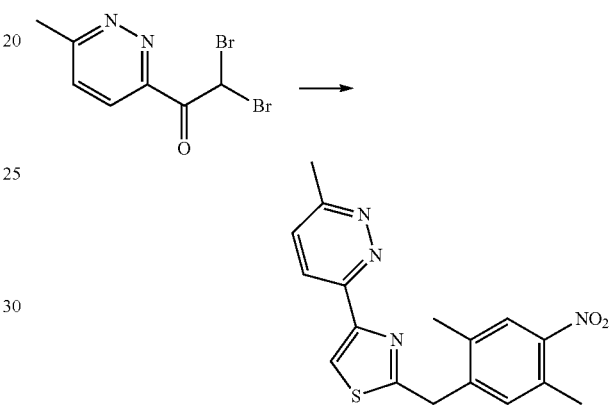

To a 2-propanol (8.0 mL) solution of the compound (0.20 g) obtained by the technique of Reference Example 1-2, the compound (0.26 g) obtained by the technique of Reference Example 34-1 was added, and the resultant was stirred at 80° C. for 1 hour. After standing to cool to room temperature, a saturated aqueous solution of sodium bicarbonate was added thereto, followed by extraction with chloroform. An organic layer was separated using a phase separator, and the solvent was distilled off under reduced pressure. The obtained residue was purified by silica gel column chromatography (NH-type silica gel; hexane/ethyl acetate-gradient elution=90/10→70/30) to obtain the title compound (86 mg) as a pale yellow solid.

$^1$H NMR (600 MHz, CHLOROFORM-d) δppm 2.41 (3H, s), 2.58 (3H, s), 2.75 (3H, s), 4.40 (2H, s), 7.24 (1H, s), 7.39 (1H, d, J=8.7 Hz), 7.87 (1H, s), 8.11 (1H, d, J=8.7 Hz), 8.26 (1H, s)

Reference Example 34-3

2,5-Dimethyl-4-{[4-(6-methylpyridazin-3-yl)-1,3-thiazol-2-yl]methyl}aniline

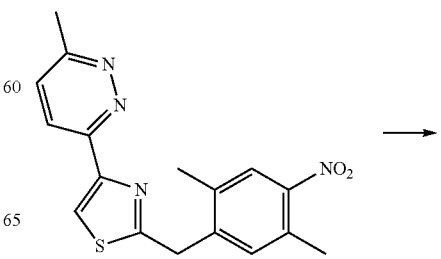

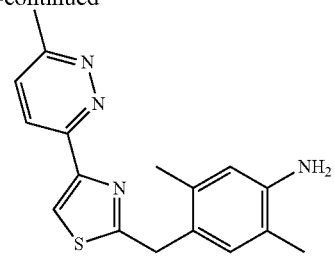

To an ethanol (4.0 mL) solution of the compound (83 mg) obtained by the technique of Reference Example 34-2, 20% palladium hydroxide (25 mg) was added, and the resultant was stirred at room temperature for 15 hours in a hydrogen atmosphere. After catalytic exchange, the resultant was further stirred at room temperature for 1 hour. Insoluble material was filtered off through Celite, and the filtrate was concentrated under reduced pressure. The residue was dried to obtain the title compound (78 mg) as a pale yellow solid.

$^1$H NMR (600 MHz, CHLOROFORM-d) δppm 2.13 (3H, s), 2.22 (3H, s), 2.74 (3H, s), 3.57 (2H, br. s.), 4.24 (2H, s), 6.55 (1H, s), 6.96 (1H, s), 7.38 (1H, d, J=8.7 Hz), 8.15 (1H, d, J=8.7 Hz), 8.18 (1H, s)

Reference Example 35

4-(Bromoacetyl)-1-methylpyridin-2(1H)-one

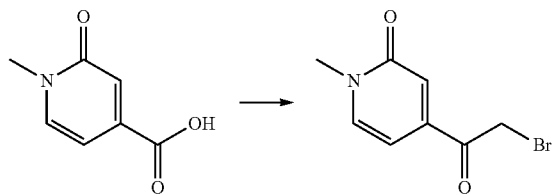

To a chloroform solution (6.0 mL) of 1-methyl-2-oxo-1,2-dihydropyridine-4-carboxylic acid (0.10 g), under ice cooling, oxalyl chloride (0.28 mL) and one drop of N,N-dimethylformamide were added, and the resultant was stirred at room temperature for 1 hour. The reaction solution was concentrated under reduced pressure, followed by azeotropy with toluene. Chloroform (6.0 mL) was added to the residue, then (diazomethyl)trimethylsilane (0.49 mL) was slowly added dropwise under ice cooling, and the resultant was stirred at room temperature for 16 hours. The reaction solution was concentrated under reduced pressure. Ethyl acetate (6.0 mL) was added to the obtained residue, then a 33% hydrobromic acid/acetic acid solution (0.13 mL) was slowly added dropwise under ice cooling, and the resultant was stirred at room temperature for 1 hour. A saturated aqueous solution of sodium bicarbonate was added to the reaction solution, followed by extraction with chloroform. An organic layer was separated using a phase separator, and the solvent was distilled off under reduced pressure.

Then, the residue was dried to obtain the title compound (85 mg) as a crude product.

MS (ESI-APCI): 230[M+H]+

Reference Example 36

2-Bromo-1-[4-({[tert-butyl(dimethyl)silyl]oxy}methyl)phenyl]ethanone

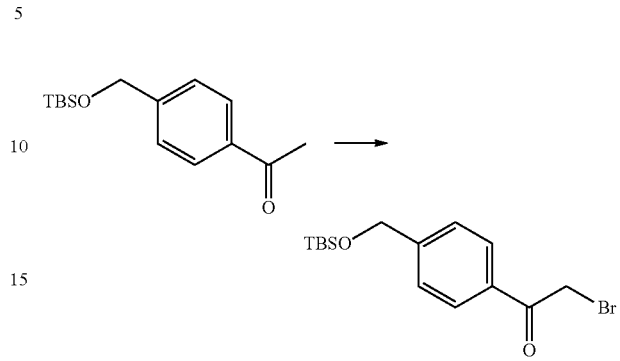

To a chloroform (7.5 mL) solution of 1-[4-({[tert-butyl(dimethyl)silyl]oxy}methyl)phenyl]ethanone (0.23 g), under ice cooling in a nitrogen atmosphere, 2,6-lutidine (0.17 mL) and trimethylsilyl trifluoromethanesulfonate (0.19 mL) were added, and the resultant was stirred for 30 minutes. Then, N-bromosuccinimide (0.17 g) was added thereto, and the resultant was stirred for 30 minutes under ice cooling. Water was added to the reaction solution, and the resultant was stirred for 10 minutes, followed by extraction with chloroform. An organic layer was separated using a phase separator, and the solvent was distilled off under reduced pressure. The obtained residue was purified by silica gel column chromatography (OH-type silica gel; hexane/ethyl acetate-gradient elution=100/0→75/25) to obtain the title compound (0.26 g) as a colorless oil.

$^1$H NMR (600 MHz, CHLOROFORM-d) δppm 0.12 (6H, s), 0.96 (9H, s), 4.45 (2H, s), 4.81 (2H, s), 7.45 (2H, d, J=8.3 Hz), 7.96 (2H, d, J=8.3 Hz)

Reference Example 37

2-[4-({(E)-[Ethyl(methyl)amino]methylidene}amino)-2,5-dimethylbenzyl]-1,3-thiazole-4-carboxylic acid hydrobromide

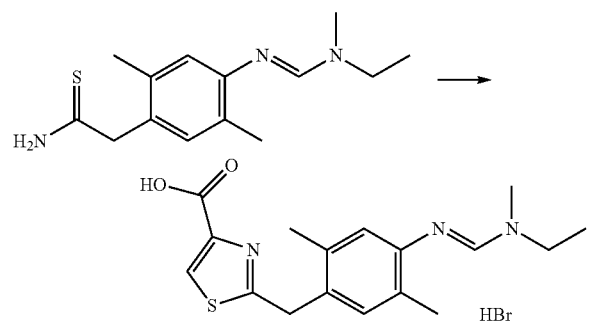

To a 2-propanol (10 mL) solution of the compound (0.26 g) obtained by the technique of Reference Example 1-5, 3-bromo-2-oxopropanoic acid (0.17 g) was added, and the resultant was stirred at 80° C. for 30 minutes. After standing to cool to room temperature, diethyl ether (20 mL) was added to the reaction solution. The deposited solid was collected by filtration, washed with diethyl ether (10 mL), and dried to obtain the title compound (0.33 g) as a white solid.

$^1$H NMR (600 MHz, DMSO-d$_6$) δppm 1.17-1.31 (3H, m), 2.21-2.31 (6H, m), 3.13-3.29 (3H, m), 3.54-3.67 (2H, m), 4.36 (2H, s), 7.22 (1H, br. s.), 7.27 (1H, s), 8.25-8.35 (1H, m), 8.42 (1H, br. s.), 10.48 (1H, br. s.), 12.97 (1H, br. s.)

Reference Example 38-1

5-(1-Ethoxyethenyl)-2-methylpyrimidine

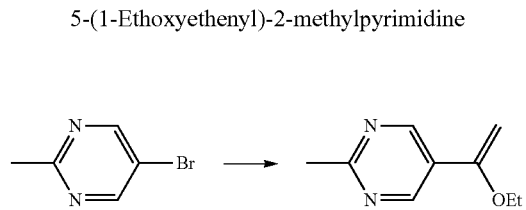

To a N,N-dimethylformamide (10 mL) solution of 5-bromo-2-methylpyrimidine (0.50 g), tributyl(1-ethoxyethenyl)stannane (1.5 g) and bis(triphenylphosphine)palladium(II) dichloride (0.14 g) were added, and the resultant was stirred at 100° C. for 1 hour. After standing to cool to room temperature, an aqueous potassium fluoride solution (20 mL) and diethyl ether (20 mL) were added to the reaction solution, and the resultant was stirred. Insoluble material was filtered off through Celite, and the filtrate was subjected to extraction with diethyl ether. The organic layer was dried over magnesium sulfate, and the desiccant was filtered off. Then, the solvent was distilled off under reduced pressure. The obtained residue was purified by silica gel column chromatography (OH-type silica gel; hexane/ethyl acetate-gradient elution=90/10→75/25) to obtain the title compound (0.48 g) as a pale yellow solid.

$^1$H NMR (600 MHz, CHLOROFORM-d) δppm 1.43 (3H, t, J=6.8 Hz), 2.74 (3H, s), 3.94 (2H, q, J=6.8 Hz), 4.31 (1H, d, J=3.3 Hz), 4.67 (1H, d, J=3.3 Hz), 8.82 (2H, s)

Reference Example 38-2

1-(2-Methylpyrimidin-5-yl)ethanone

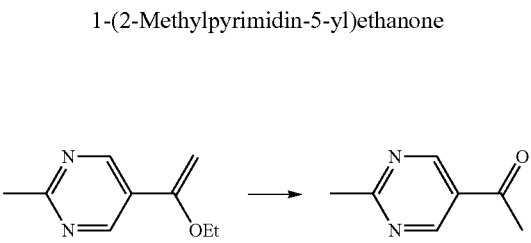

To an acetone (8.0 mL) solution of the compound (0.47 g) obtained by the technique of Reference Example 38-1, a 1.0 mol/L aqueous hydrochloric acid solution (2.0 mL) was added, and the resultant was stirred at room temperature for 24 hours. Water and a saturated aqueous solution of sodium bicarbonate were added to the reaction solution, and the resultant was stirred, followed by extraction with chloroform. An organic layer was separated using a phase separator, and the solvent was distilled off under reduced pressure to obtain the title compound (0.40 g) as a pale yellow solid.

$^1$H NMR (600 MHz, CHLOROFORM-d) δppm 2.63 (3H, s), 2.80-2.84 (3H, m), 9.13 (2H, s)

Reference Example 38-3

2-Bromo-1-(2-methylpyrimidin-5-yl)ethanone

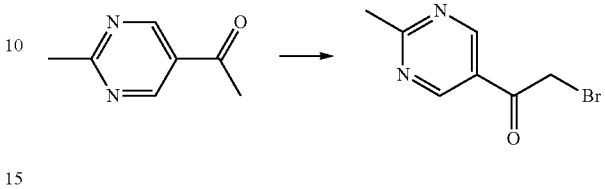

To a chloroform (6.0 mL) solution of the compound (0.39 g) obtained by the technique of Reference Example 38-2, under ice cooling in a nitrogen atmosphere, 2,6-lutidine (0.57 mL) and trimethylsilyl trifluoromethanesulfonate (0.62 mL) were added, and the resultant was stirred for 30 minutes. Then, N-bromosuccinimide (0.56 g) was added thereto, and the resultant was stirred for 1 hour under ice cooling. Water was added to the reaction solution, and the resultant was stirred for 10 minutes, followed by extraction with chloroform. An organic layer was separated using a phase separator, and the solvent was distilled off under reduced pressure. The obtained residue was purified by silica gel column chromatography (OH-type silica gel; hexane/ethyl acetate-gradient elution=95/5→85/15) to obtain the title compound (0.25 g) as a pale yellow solid.

$^1$H NMR (600 MHz, CHLOROFORM-d) δppm 2.84 (3H, s), 4.36 (2H, s), 9.18 (2H, s)

Reference Example 39

3-(Bromoacetyl)-N-methylbenzamide

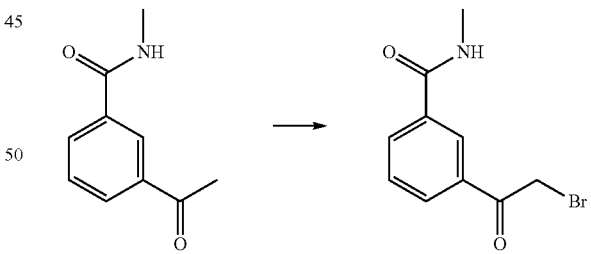

To an acetic acid (2.4 mL) solution of 3-acetyl-N-methylbenzamide (0.33 g), at room temperature, an acetic acid (0.30 mL) solution of bromine (95 μL) was added dropwise, and the resultant was stirred at room temperature for 3.5 hours and then stirred at 60° C. for 1 hour. The reaction solution was concentrated under reduced pressure and then dried to obtain the title compound (0.50 g) as a yellow oil.

$^1$H NMR (600 MHz, CHLOROFORM-d) δppm 3.06 (3H, s), 4.49 (2H, s), 6.27 (1H, br. s.), 7.57-7.62 (1H, m), 8.05 (1H, d, J=7.8 Hz), 8.11 (1H, d, J=7.4 Hz), 8.35 (1H, s)

Reference Example 40

4-(Bromoacetyl)-N-methylcyclohexanecarboxamide

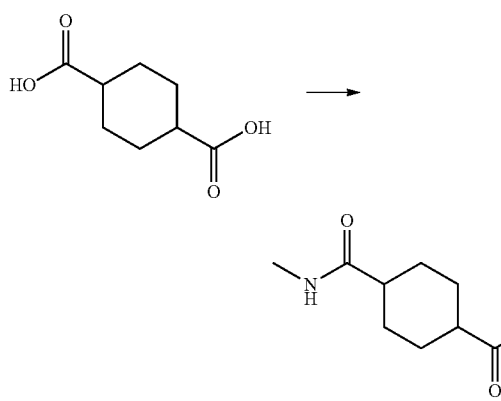

To a chloroform solution (6.0 mL) of cyclohexane-1,4-dicarboxylic acid (0.30 g), under ice cooling, oxalyl chloride (0.75 mL) and N,N-dimethylformamide (2.0 µl) were added, and the resultant was stirred at room temperature for 24 hours. The reaction solution was concentrated under reduced pressure. Tetrahydrofuran (6.0 mL) was added to the obtained residue, then a 2.0 mol/L methylamine/tetrahydrofuran solution (1.7 mL) was added under ice cooling, and the resultant was stirred for 3 hours under ice cooling under sealed conditions. The reaction solution was concentrated under reduced pressure. Chloroform (6.0 mL) was added to the residue, then (diazomethyl)trimethylsilane (1.3 mL) was slowly added dropwise under ice cooling, and the resultant was stirred at room temperature for 1.5 hours. The reaction solution was concentrated under reduced pressure. Ethyl acetate (8.0 mL) was added to the obtained residue, then a 33% hydrobromic acid/acetic acid solution (0.34 mL) was slowly added dropwise under ice cooling, and the resultant was stirred at room temperature for 50 minutes. A saturated aqueous solution of sodium bicarbonate was added to the reaction solution, followed by extraction with chloroform. An organic layer was separated using a phase separator, and the solvent was distilled off under reduced pressure. Then, the residue was dried to obtain the title compound (0.23 g) as a crude product.

MS (ESI-APCI): 262[M+H]+

Reference Example 41

2-{2-[4-({(E)-[Ethyl(methyl)amino]methylidene}amino)-2,5-dimethylbenzyl]-1,3-thiazol-4-yl}benzoic acid hydrobromide

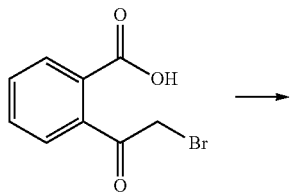

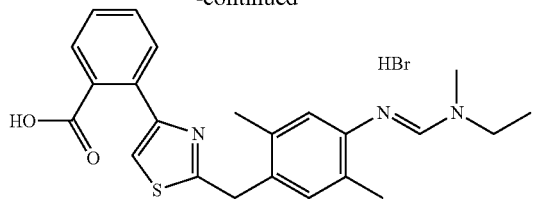

To a 2-propanol (3.0 mL) solution of the compound (70 mg) obtained by the technique of Reference Example 1-5, 2-(bromoacetyl)benzoic acid (0.11 g) was added, and the resultant was stirred at 80° C. for 1.5 hours. After standing to cool to room temperature, diethyl ether was added thereto. The deposited solid was collected by filtration to obtain the title compound (92 mg) as a pale green solid.

$^1$H NMR (600 MHz, DMSO-d$_6$) δppm 1.18-1.31 (3H, m), 2.20-2.33 (6H, m), 3.16-3.31 (3H, m), 3.56-3.64 (2H, m), 4.33 (2H, s), 7.08-7.32 (3H, m), 7.41-7.56 (2H, m), 7.58-7.65 (2H, m), 8.25-8.45 (1H, m), 9.30-9.59 (1H, m), 10.45-10.63 (1H, m)

Reference Example 42-1

1-Oxo-2,3-dihydro-1H-isoindole-5-carboxylic acid

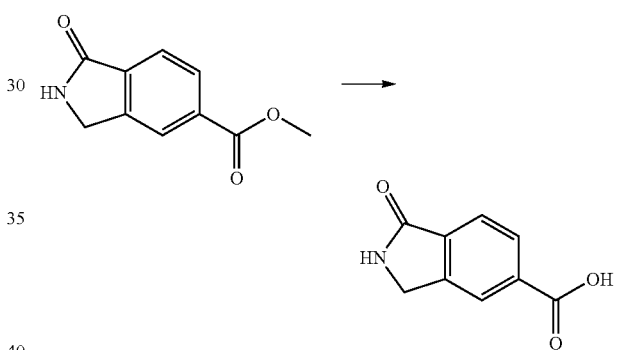

To a methanol (5.0 mL) solution of methyl 1-oxo-2,3-dihydro-1H-isoindole-5-carboxylate (0.33 g), a 1 mol/L aqueous sodium hydroxide solution (4.3 mL) was added, and the resultant was stirred at room temperature for 24 hours. A 1 mol/L aqueous hydrochloric acid solution was added to the reaction solution. The deposited solid was collected by filtration and dried to obtain the title compound (0.29 g) as a white solid.

$^1$H NMR (600 MHz, DMSO-d$_6$) δppm 4.44 (2H, s), 7.77 (1H, d, J=7.8 Hz), 8.04 (1H, d, J=7.8 Hz), 8.13 (1H, s), 8.77 (1H, br. s.), 13.24 (1H, br. s.)

Reference Example 42-2

N-Methoxy-N-methyl-1-oxo-2,3-dihydro-1H-isoindole-5-carboxamide

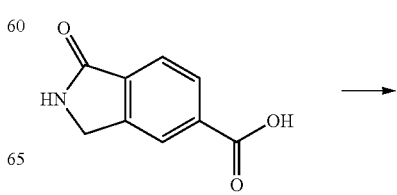

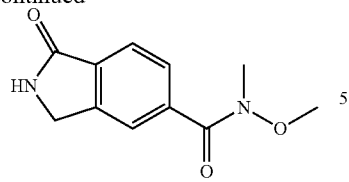

To a N,N-dimethylformamide (5.0 mL) solution of the compound (0.28 g) obtained by the technique of Reference Example 42-1, N-methoxymethanamine hydrochloride (0.23 mg), WSC.HCl (0.45 g), HOBt.H$_2$O (0.36 g) and triethylamine (0.83 mL) were added, and the resultant was stirred at room temperature for 1 day. Water was added to the reaction solution, followed by extraction with ethyl acetate. The organic layer was dried over magnesium sulfate, and the desiccant was filtered off. Then, the solvent was distilled off under reduced pressure. The obtained residue was purified by silica gel column chromatography (NH-type silica gel; chloroform/methanol-gradient elution=100/0→91/9) to obtain the title compound (90 mg) as a white solid.

$^1$H NMR (600 MHz, CHLOROFORM-d) δppm 3.39 (3H, s), 3.55 (3H, s), 4.50 (2H, s), 6.49 (1H, br. s.), 7.73-7.81 (2H, m), 7.88-7.94 (1H, m)

Reference Example 42-3

5-Acetyl-2,3-dihydro-1H-isoindol-1-one

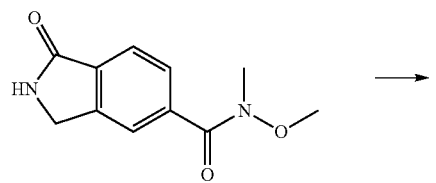

To a tetrahydrofuran (2.0 mL) solution of the compound (90 mg) obtained by the technique of Reference Example 42-2, under ice cooling, a 3.0 mol/L methyl magnesium bromide/diethyl ether solution (0.20 mL) was added, and the resultant was stirred for 2 hours under ice cooling. Then, a 3.0 mol/L methyl magnesium bromide/diethyl ether solution (0.20 mL) was further added thereto, and the resultant was stirred for 2 hours and further stirred at room temperature for 3 weeks. The reaction solution was added to ice-cold water, and the resultant was adjusted to around pH 2.0 by the addition of a 6 mol/L aqueous hydrochloric acid solution under ice cooling and stirred for 30 minutes. After extraction with ethyl acetate, the organic layer was dried over magnesium sulfate, and the desiccant was filtered off. Then, the solvent was distilled off under reduced pressure. The obtained residue was purified by silica gel column chromatography (OH-type silica gel; hexane/ethyl acetate-gradient elution=50/50→0/100) to obtain the title compound (16 mg) as a colorless solid.

$^1$H NMR (600 MHz, CHLOROFORM-d) δppm 2.68 (3H, s), 4.53 (2H, s), 6.49 (1H, br. s.), 7.97 (1H, d, J=8.3 Hz), 8.05-8.11 (2H, m)

Reference Example 42-4

5-(Bromoacetyl)-2,3-dihydro-1H-isoindol-1-one

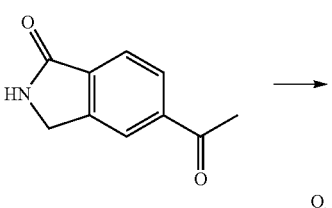

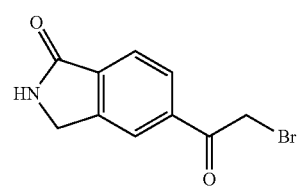

To an acetic acid (0.30 mL) solution of the compound (15 mg) obtained by the technique of Reference Example 42-3, at room temperature, an acetic acid (0.10 mL) solution of bromine (4.0 μL) was added dropwise, and the resultant was stirred at room temperature for 2 hours and then stirred at 80° C. for 2.5 hours. An acetic acid (0.10 mL) solution of bromine (2.0 μL) was further added thereto, and the resultant was further stirred at 80° C. for 1 hour. After standing to cool to room temperature, the reaction solution was concentrated under reduced pressure. The residue was dried to obtain the title compound (21 mg) as a pale yellow solid.

$^1$H NMR (600 MHz, DMSO-d$_6$) δppm 4.41-4.50 (2H, m), 5.00 (2H, s), 7.82 (1H, d, J=7.8 Hz), 8.10 (1H, d, J=7.8 Hz), 8.20 (1H, s), 8.82-8.89 (1H, m)

Reference Example 43-1

5-(1-Ethoxyethenyl)-N-methylpyrazine-2-carboxamide

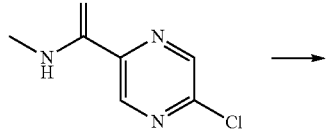

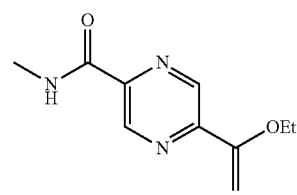

To a N,N-dimethylformamide (3.0 mL) solution of 5-chloro-N-methylpyrazine-2-carboxamide (0.25 g), tributyl (1-ethoxyethenyl)stannane (0.53 ml) and bis(triphenylphosphine)palladium(II) dichloride (55 mg) were added, and the resultant was stirred at 100° C. for 3 hours. After standing to cool to room temperature, the reaction solution was concentrated under reduced pressure, followed by azeotropy with toluene. The obtained residue was purified by silica gel column chromatography (NH-type silica gel; hexane/ethyl acetate-gradient elution=70/30→40/60) to obtain the title compound (0.23 g) as a pale yellow solid.

$^1$H NMR (600 MHz, CHLOROFORM-d) δppm 1.47 (3H, t, J=6.4 Hz), 3.06 (3H, d, J=5.4 Hz), 4.02 (2H, q, J=6.4 Hz), 4.55 (1H, d, J=2.5 Hz), 5.57 (1H, d, J=2.5 Hz), 7.72-7.81 (1H, m), 8.83 (1H, d, J=1.2 Hz), 9.30 (1H, d, J=1.2 Hz)

Reference Example 43-2

5-Acetyl-N-methylpyrazine-2-carboxamide

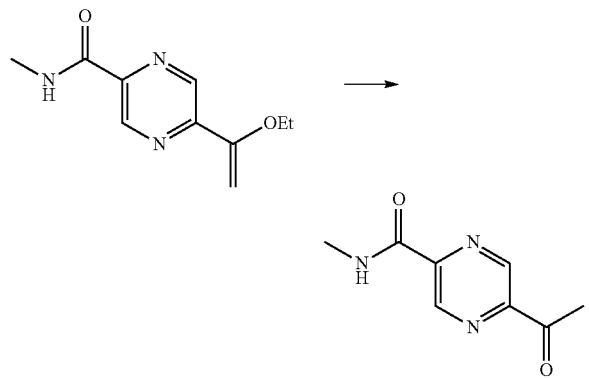

To an acetone (3.0 mL) solution of the compound (0.23 g) obtained by the technique of Reference Example 43-1, a 1.0 mol/L aqueous hydrochloric acid solution (0.70 mL) was added, and the resultant was stirred at room temperature for 2.5 hours. The deposited solid was collected by filtration and dried to obtain the title compound (0.23 g) as a white solid.

$^1$H NMR (600 MHz, CHLOROFORM-d) δppm 2.76 (3H, s), 3.08 (3H, d, J=5.0 Hz), 7.75-7.92 (1H, m), 9.14 (1H, d, J=1.7 Hz), 9.44 (1H, d, J=1.7 Hz)

Reference Example 43-3

5-(Bromoacetyl)-N-methylpyrazine-2-carboxamide hydrobromide

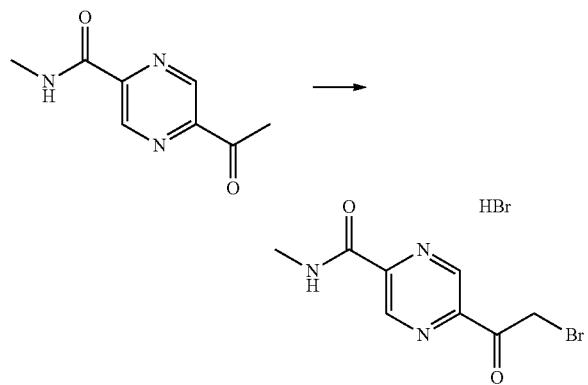

To an acetic acid (1.6 mL) solution of the compound (0.20 g) obtained by the technique of Reference Example 43-2, at room temperature, an acetic acid (0.60 mL) solution of bromine (59 μL) was added dropwise, and the resultant was stirred at 80° C. for 1.5 hours and then stirred overnight at room temperature. The deposited solid was collected by filtration and dried to obtain the title compound (0.22 g) as an ocher solid.

$^1$H NMR (600 MHz, DMSO-d$_6$) δppm 2.85 (3H, d, J=5.0 Hz), 5.05 (2H, s), 9.05-9.10 (1H, m), 9.19 (1H, d, J=1.7 Hz), 9.28 (1H, d, J=1.7 Hz)

Reference Example 44-1

5-Acetyl-N,2-dimethylbenzamide

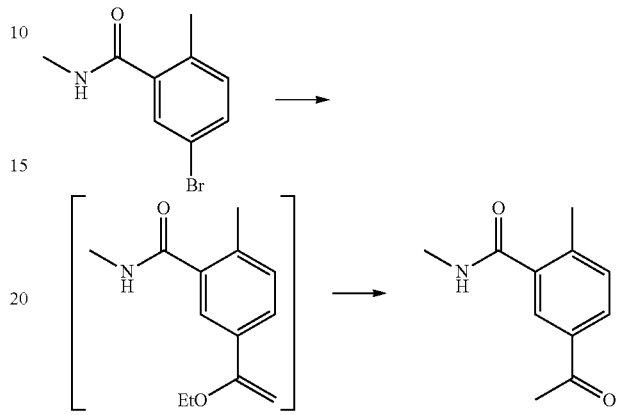

To a N,N-dimethylformamide (4.3 mL) solution of 5-bromo-N,2-dimethylbenzamide (0.43 g) obtained by a method described in the patent document (PCT Int. Appl., 2011045258, 21 Apr. 2011), tributyl(1-ethoxyethenyl)stannane (0.71 ml) and bis(triphenylphosphine)palladium(II) dichloride (67 mg) were added, and the resultant was stirred at 100° C. for 2 hours. After standing to cool to room temperature, insoluble material was filtered off through Celite, and the filtrate was concentrated under reduced pressure. The obtained residue was purified by silica gel column chromatography (OH-type silica gel; hexane/ethyl acetate-gradient elution=70/30→49/51). A 1.0 mol/L aqueous hydrochloric acid solution (2.0 mL) was added to an acetone (8.0 mL) solution of the obtained pale yellow oil (0.57 g), and the resultant was stirred at room temperature for 1 hour. Water and a saturated aqueous solution of sodium bicarbonate were added to the reaction solution, followed by extraction with chloroform. An organic layer was separated using a phase separator, and the solvent was distilled off under reduced pressure. Then, the residue was dried. The obtained residue was purified by silica gel column chromatography (OH-type silica gel; hexane/ethyl acetate-gradient elution=60/40→25/75) to obtain the title compound (0.22 g) as a white solid.

$^1$H NMR (600 MHz, CHLOROFORM-d) δppm 2.52 (3H, s), 2.59 (3H, s), 3.02 (3H, d, J=5.0 Hz), 5.78-5.89 (1H, m), 7.32 (1H, d, J=8.3 Hz), 7.88 (1H, dd, J=8.3, 1.7 Hz), 7.95 (1H, d, J=1.7 Hz)

Reference Example 44-2

5-(Bromoacetyl)-N,2-dimethylbenzamide

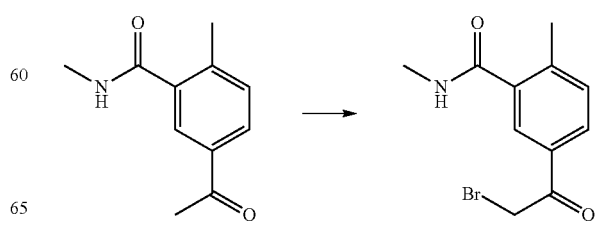

To a chloroform (2.0 mL) solution of the compound (0.10 g) obtained by the technique of Reference Example 44-1, under ice cooling in a nitrogen atmosphere, 2,6-lutidine (0.10 mL) and trimethylsilyl trifluoromethanesulfonate (0.11 mL) were added, and the resultant was stirred for 1 hour. Then, N-bromosuccinimide (0.10 g) was added thereto, and the resultant was stirred for 30 minutes under ice cooling. Water was added to the reaction solution, and the resultant was stirred for 10 minutes, followed by extraction with chloroform. An organic layer was separated using a phase separator, and the solvent was distilled off under reduced pressure. The obtained residue was purified by silica gel column chromatography (OH-type silica gel; hexane/ethyl acetate-gradient elution=60/40→15/85) to obtain the title compound (70 mg) as a white solid.

$^1$H NMR (600 MHz, CHLOROFORM-d) δppm 2.53 (3H, s), 3.03 (3H, d, J=5.0 Hz), 4.41 (2H, s), 5.75-5.88 (1H, m), 7.36 (1H, d, J=7.8 Hz), 7.91 (1H, dd, J=7.8, 1.7 Hz), 7.98 (1H, d, J=1.7 Hz)

Reference Example 45

4-(Chloromethyl)-2-(2,5-dimethyl-4-nitrobenzyl)-1,3-thiazole

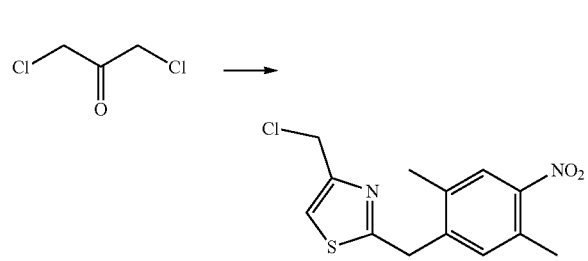

To a 2-propanol (5.0 mL) solution of the compound (0.48 g) obtained by the technique of Reference Example 1-2, 1,3-dichloropropan-2-one (0.27 g) was added, and the resultant was stirred at 80° C. for 4 hours. The reaction solution was allowed to cool to room temperature and then concentrated under reduced pressure. The obtained residue was purified by silica gel column chromatography (OH-type silica gel; hexane/ethyl acetate-gradient elution=100/0→75/25) to obtain the title compound (0.42 g) as a brown solid.

$^1$H NMR (600 MHz, CHLOROFORM-d) δppm 2.36 (3H, s), 2.57 (3H, s), 4.34 (2H, s), 4.67 (2H, s), 7.21 (2H, s), 7.85 (1H, s)

Reference Example 46

2-Bromo-1-(3,5-dimethylpyrazin-2-yl)ethanone

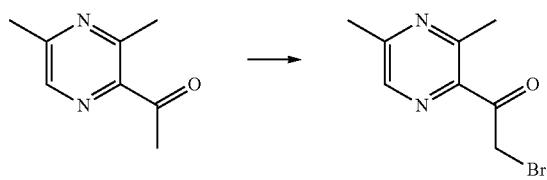

To a chloroform (2.0 mL) solution of 1-(3,5-dimethylpyrazin-2-yl)ethanone (41 mg), under ice cooling in a nitrogen atmosphere, 2,6-lutidine (54 μL) and trimethylsilyl trifluoromethanesulfonate (59 μL) were added, and the resultant was stirred for 1 hour. Then, N-bromosuccinimide (53 mg) was added thereto, and the resultant was stirred at room temperature for 30 minutes. Water was added to the reaction solution, and the resultant was stirred for 10 minutes, followed by extraction with chloroform. An organic layer was separated using a phase separator, and the solvent was distilled off under reduced pressure. The obtained residue was purified by silica gel column chromatography (OH-type silica gel; hexane/ethyl acetate-gradient elution=95/5→67/33) to obtain the title compound (35 mg) as a crude product.

MS (ESI-APCI): 229[M+H]+

Reference Example 47-1

4-{[2-(2,5-Dimethyl-4-nitrobenzyl)-1,3-thiazol-4-yl]methoxy}-N-methylbenzamide

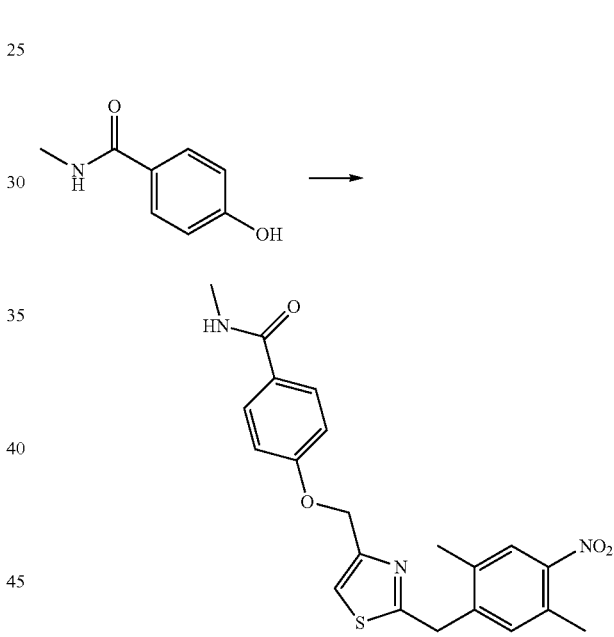

To an acetone (2.0 mL) solution of the compound (0.10 g) obtained by the technique of Reference Example 45, 4-hydroxy-N-methylbenzamide (51 mg) and potassium carbonate (0.10 g) were added, and the resultant was stirred at room temperature for 4 hours and then heated to reflux for 5 hours. Insoluble material was filtered off, and the filtrate was concentrated under reduced pressure. The obtained residue was purified by silica gel column chromatography (OH-type silica gel; hexane/ethyl acetate-gradient elution=100/0→66/34) to obtain the title compound (9.1 mg) as a pale yellow solid.

$^1$H NMR (600 MHz, CHLOROFORM-d) δppm 2.36 (3H, s), 2.57 (3H, s), 3.01 (3H, d, J=5.0 Hz), 4.35 (2H, s), 5.21 (2H, s), 6.00-6.10 (1H, m), 7.01 (2H, d, J=8.7 Hz), 7.21 (1H, s), 7.23 (1H, s), 7.72 (2H, d, J=8.7 Hz), 7.85 (1H, s)

Reference Example 47-2

4-{[2-(4-Amino-2,5-dimethylbenzyl)-1,3-thiazol-4-yl]methoxy}-N-methylbenzamide

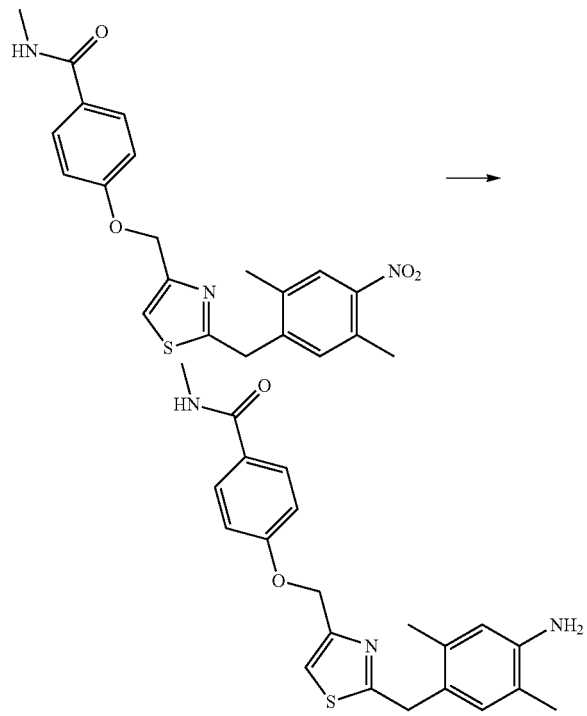

To a 50% aqueous ethanol solution (2.0 mL) of the compound (41 mg) obtained by the technique of Reference Example 47-1, ammonium chloride (16 mg) and iron powder (17 mg) were added, and the resultant was heated to reflux for 2 hours. Insoluble material was filtered off, and the filtrate was concentrated under reduced pressure. A saturated aqueous solution of sodium bicarbonate was added to the obtained residue, followed by extraction with ethyl acetate. The organic layer was dried over magnesium sulfate, and the desiccant was filtered off. Then, the solvent was distilled off under reduced pressure to obtain the title compound (32 mg) as a light brown solid.

$^1$H NMR (600 MHz, CHLOROFORM-d) δppm 2.14 (3H, s), 2.19 (3H, s), 3.00 (3H, d, J=5.0 Hz), 3.75 (2H, br. s.), 4.20 (2H, s), 5.20 (2H, s), 5.97-6.07 (1H, m), 6.55 (1H, s), 6.94 (1H, s), 7.01 (2H, d, J=8.7 Hz), 7.14 (1H, s), 7.72 (2H, d, J=8.7 Hz)

Reference Example 48-1

Methyl 2-acetyl-5-methylbenzoate

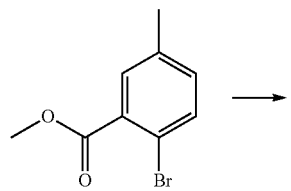

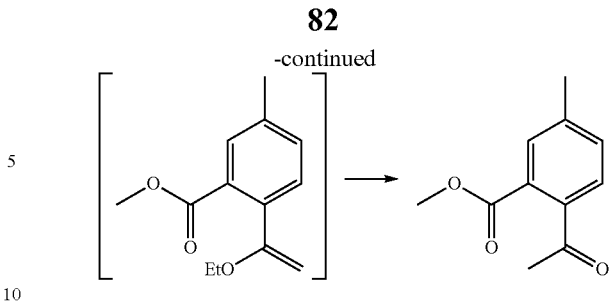

To a N,N-dimethylformamide (8.5 mL) solution of methyl 2-bromo-5-methylbenzoate (752 mg), tributyl(1-ethoxyethenyl)stannane (1.22 mL) and bis(triphenylphosphine)palladium(II) dichloride (115.1 mg) were added, and the resultant was stirred at 100° C. for 1 hour. The reaction solution was allowed to cool to room temperature and then filtered through Celite, and the filtrate was concentrated under reduced pressure. Acetone (10 mL) and a 1 mol/L aqueous hydrochloric acid solution (3.0 mL) were added to the obtained residue, and the resultant was stirred at room temperature for 1 hour. Water was added to the reaction solution, followed by extraction operation twice using chloroform. Organic layers were separated from aqueous layers using a phase separator. The organic layers were concentrated under reduced pressure. The obtained residue was purified by silica gel column chromatography (OH-type silica gel; hexane/ethyl acetate-gradient elution=86/14→65/35) to obtain the title compound (0.49 g) as a pale yellow oil.

$^1$H NMR (600 MHz, CHLOROFORM-d) δppm 2.42 (3H, s), 2.53 (3H, s), 3.90 (3H, s), 7.34-7.37 (1H, m), 7.38-7.41 (1H, m), 7.59 (1H, s)

Reference Example 48-2

Methyl 2-(bromoacetyl)-5-methylbenzoate

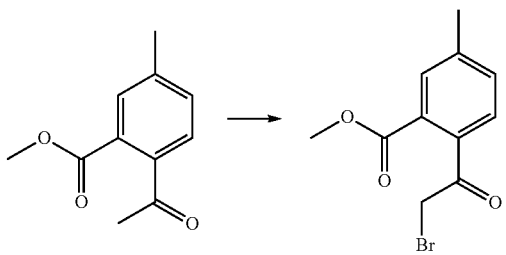

To a chloroform (7.3 mL) solution of the compound (0.48 g) obtained by the technique of Reference Example 48-1, under ice cooling in a nitrogen atmosphere, 2,6-lutidine (0.50 mL) and trimethylsilyl trifluoromethanesulfonate (0.55 mL) were added, and the resultant was stirred for 1 hour. Then, N-bromosuccinimide (0.50 g) was added thereto, and the resultant was stirred for 30 minutes under ice cooling. Water was added to the reaction solution, and the resultant was stirred for 10 minutes, followed by extraction with chloroform. An organic layer was separated using a phase separator, and the solvent was distilled off under reduced pressure. The obtained residue was purified by silica gel column chromatography (OH-type silica gel; hexane/ethyl acetate-gradient elution=88/12→67/33) to obtain the title compound (0.59 g) as a white solid.

¹H NMR (600 MHz, CHLOROFORM-d) δppm 2.44 (3H, s), 3.91 (3H, s), 4.32 (2H, s), 7.32 (1H, d, J=7.8 Hz), 7.40-7.44 (1H, m), 7.78 (1H, s)

Reference Example 49-1

Methyl 4-[2-(2,5-dimethyl-4-nitrobenzyl)-1,3-thiazol-4-yl]benzoate hydrobromide

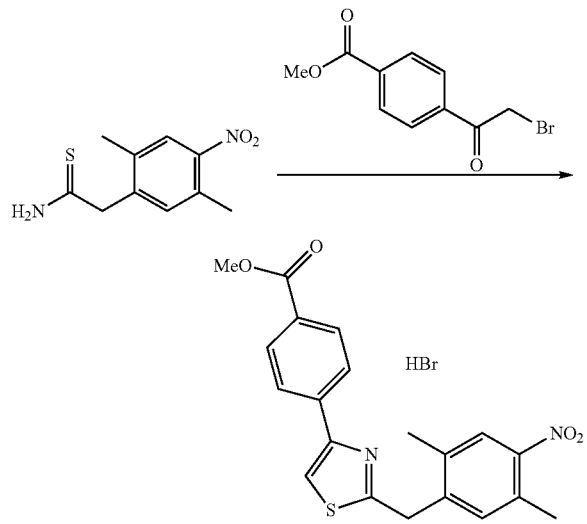

To a 2-propanol (180 mL) solution of the compound (8.30 g) obtained by the technique of Reference Example 1-5, methyl 4-(bromoacetyl)benzoate (9.51 g) was added, and the resultant was stirred at 80° C. for 2 hours. The deposited solid was collected by filtration and washed with 2-propanol to obtain the title compound (12.94 g) as a pale yellow solid.

¹H NMR (600 MHz, CHLOROFORM-d) δppm 2.42 (3H, s), 2.58 (3H, s), 3.95 (3H, s), 4.72 (2H, br. s.), 7.32 (1H, s), 7.58 (1H, s), 7.88 (1H, s), 8.07 (2H, d, J=8.3 Hz), 8.15 (2H, d, J=8.3 Hz)

Reference Example 49-2

4-[2-(2,5-Dimethyl-4-nitrobenzyl)-1,3-thiazol-4-yl]benzoic acid

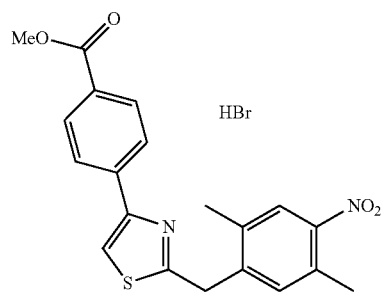

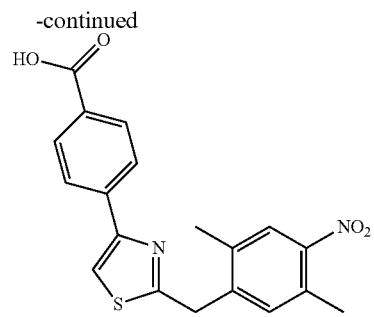

To a methanol (100 mL) solution of the compound (12.91 g) obtained by the technique of Reference Example 49-1, an aqueous sodium hydroxide solution (42.2 mL) was added, and the resultant was stirred at room temperature for 1 hour and then stirred at 50° C. for 1 hour. Tetrahydrofuran (70 mL) was further added thereto, and the resultant was stirred at 70° C. for 2 hours. After standing to cool to room temperature, a 1 mol/L aqueous hydrochloric acid solution was added thereto. The deposited crystals were collected by filtration to obtain the title compound (10.69 g) as a white solid.

¹H NMR (600 MHz, DMSO-d₆) δppm 2.39 (3H, s), 2.49 (3H, s), 4.50 (2H, s), 7.47 (1H, s), 7.90 (1H, s), 8.00 (2H, s), 8.03 (2H, s), 8.18 (1H, s)

Reference Example 49-3

4-[2-(2,5-Dimethyl-4-nitrobenzyl)-1,3-thiazol-4-yl]-N-methylbenzamide

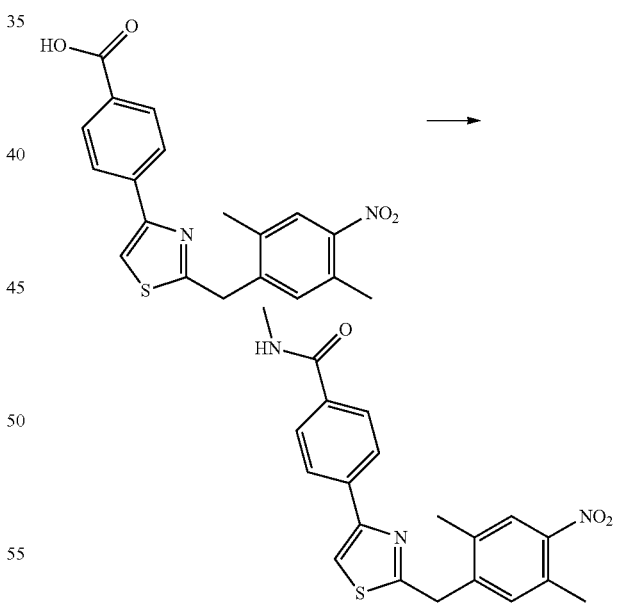

To a N,N-dimethylformamide (150 mL) solution of the compound (11.59 g) obtained by the technique of Reference Example 49-2, methylamine hydrochloride (2.34 g) and diisopropylethylamine (27.48 mL) were added, and the resultant was stirred at room temperature for 5 minutes. Then, HATU (14.36 g) was added thereto, and the resultant was stirred at room temperature for 30 minutes. A saturated aqueous solution of sodium bicarbonate was added to the reaction solution, followed by extraction operation three times with

85 ethyl acetate. The organic layers were dried over magnesium sulfate, and the desiccant was filtered off. The filtrate was concentrated under reduced pressure. The residue was purified by silica gel column chromatography (OH-type silica gel; chloroform/methanol-gradient elution=99/1→87/13 and NH-type silica gel; chloroform/methanol-gradient elution=99/1→87/13) to obtain the title compound (11.64 g) as a pale yellow solid.

$^1$H NMR (600 MHz, DMSO-d$_6$) δppm 2.39 (3H, s), 2.49 (3H, s), 2.80 (3H, d, J=4.5 Hz), 4.49 (2H, s), 7.47 (1H, s), 7.86-7.92 (3H, m), 8.00 (2H, d, J=8.3 Hz), 8.13 (1H, s), 8.42-8.50 (1H, m)

Reference Example 49-4

4-[2-(4-Amino-2,5-dimethylbenzyl)-1,3-thiazol-4-yl]-N-methylbenzamide

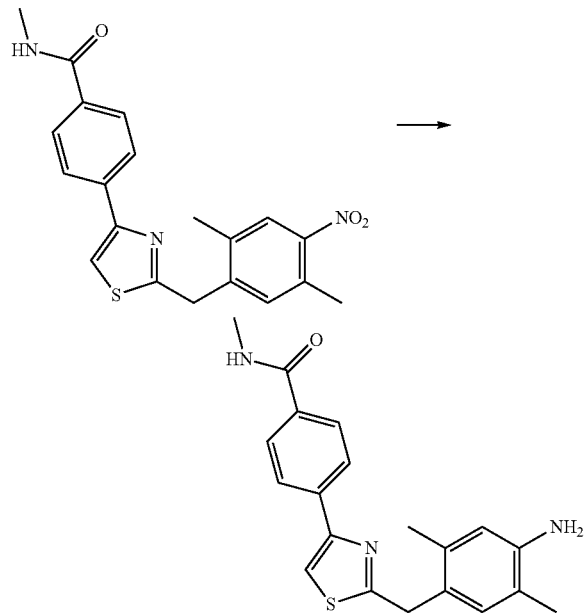

To an ethanol solution (466 mL) of the compound (11.64 g) obtained by the technique of Reference Example 49-3, palladium hydroxide (3.88 g) was added, and the resultant was stirred at room temperature for 16 hours in a hydrogen gas atmosphere. After exchange of palladium hydroxide, the resultant was further stirred for 18 hours. The catalyst was filtered off, and the filtrate was then concentrated under reduced pressure. The residue was crystallized from ethanol to obtain the title compound (2.88 g) as white crystals. The mother liquid was further concentrated and then solidified with diisopropyl ether to obtain the title compound (5.15 g) as a white solid.

$^1$H NMR (600 MHz, DMSO-d$_6$) δppm 2.01 (3H, s), 2.11 (3H, s), 2.79 (3H, d, J=4.5 Hz), 4.16 (2H, s), 4.71-4.75 (2H, m), 6.43-6.47 (1H, m), 6.85-6.88 (1H, m), 7.87-7.91 (2H, m), 7.99-8.02 (2H, m), 8.03 (1H, s), 8.43-8.48 (1H, m)

86

Reference Example 50-1

Propan-2-yl [2-(2,5-dimethyl-4-nitrobenzyl)-1,3-thiazol-4-yl]carbamate

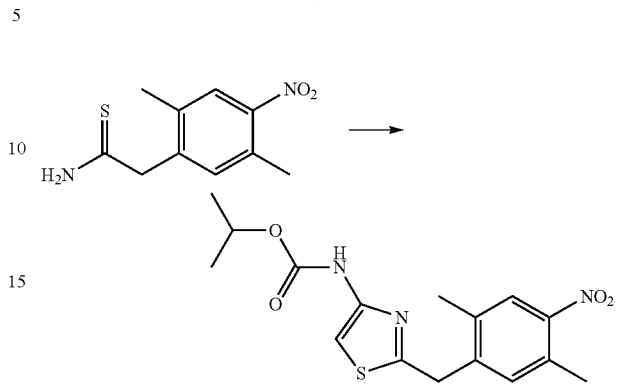

(A) To the compound (50 mg) obtained by the technique of Reference Example 1-2 and propan-2-yl (chloroacetyl)carbamate (60 mg), 2-propanol (1.0 mL) was added, and the resultant was heated to reflux for 1.5 hours in a nitrogen atmosphere. Propan-2-yl (chloroacetyl)carbamate (40 mg) was added to the reaction mixture, and the resultant was heated to reflux for 1 hour and 10 minutes. Propan-2-yl (chloroacetyl)carbamate (20 mg) was added to the reaction mixture, and the resultant was heated to reflux for 50 minutes. The reaction mixture was cooled to room temperature, and ethyl acetate and a saturated aqueous solution of sodium bicarbonate were added thereto.

(B) To the compound (0.50 g) obtained by the technique of Reference Example 1-2 and propan-2-yl (chloroacetyl)carbamate (0.60 g), 2-propanol (5.0 mL) was added, and the resultant was heated to reflux for 1 hour and 35 minutes in a nitrogen atmosphere. Propan-2-yl (chloroacetyl)carbamate (0.40 g) was added to the reaction mixture, and the resultant was heated to reflux for 1.5 hours. The reaction mixture was cooled to room temperature, and ethyl acetate and a saturated aqueous solution of sodium bicarbonate were added thereto. The reaction mixtures of (A) and (B) were combined, and an organic layer was separated. The organic layer was dried over anhydrous magnesium sulfate, and the solvent was distilled off under reduced pressure. The obtained residue was purified by silica gel column chromatography (hexane/ethyl acetate=3/1) to obtain the title compound (0.60 g) as a yellow oil.

$^1$H NMR (400 MHz, CHLOROFORM-d) δ ppm 1.29 (6H, d, J=6.1 Hz), 2.34 (3H, s), 2.56 (3H, s), 4.24 (2H, s), 4.97-5.08 (1H, m), 7.10-7.21 (2H, m), 7.55 (1H, s), 7.84 (1H, s)

Reference Example 50-2

Propan-2-yl [2-(4-amino-2,5-dimethylbenzyl)-1,3-thiazol-4-yl]carbamate

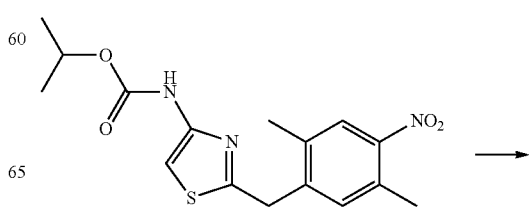

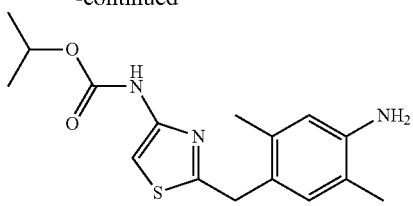

To the compound (0.60 g) obtained in Reference Example 50-1, ammonium chloride (0.92 g) and iron powder (0.48 g), an 80% aqueous ethanol solution (6.0 mL) was added, and the resultant was heated to reflux for 1 hour. The reaction mixture was cooled to room temperature, and a saturated aqueous solution of sodium bicarbonate and ethyl acetate was added thereto. Insoluble material was filtered off, and an organic layer was separated. The organic layer was dried over anhydrous magnesium sulfate, and the solvent was distilled off under reduced pressure. Diisopropyl ether was added to the obtained residue, and the solid was collected by filtration to obtain the title compound (0.45 g) as a faint orange solid.

$^1$H NMR (400 MHz, CHLOROFORM-d) δ ppm 1.29 (6H, d, J=6.0 Hz), 2.13 (3H, s), 2.16 (3H, s), 3.55 (2H, br. s.), 4.09 (2H, s), 4.96-5.07 (1H, m), 6.52 (1H, s), 6.90 (1H, s), 7.06 (1H, s), 7.61 (1H, s)

Example 1

2,5-Dimethyl-4-{[4-(4-methylphenyl)-1,3-thiazol-2-yl]methyl}-N-[(E)-pyrrolidin-1-ylmethylidene]aniline

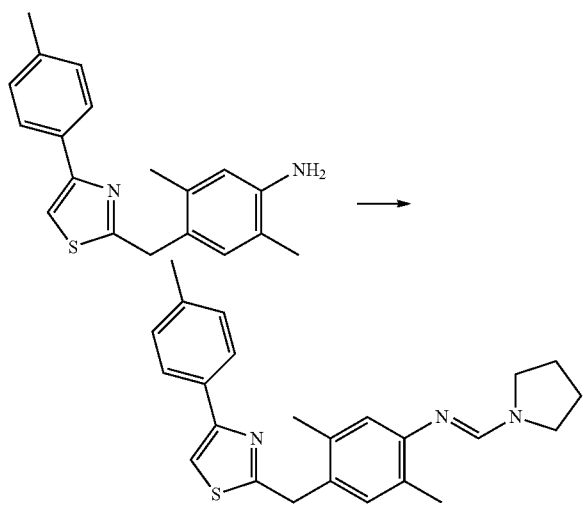

To the compound (0.15 g) obtained by the technique of Reference Example 2-2, triethyl orthoformate (2.0 mL) and (+)-CSA (11 mg) were added, and the resultant was stirred at 100° C. for 2.5 hours. The reaction mixture was concentrated under reduced pressure. Chloroform (2.0 mL) and pyrrolidine (0.12 μL) were added to the obtained residue at room temperature, and the resultant was stirred at room temperature for 80 hours. The reaction mixture was concentrated under reduced pressure. The obtained residue was purified by preparative LC and then freeze-dried. A saturated aqueous solution of sodium bicarbonate and chloroform were added to the obtained solid. An organic layer was separated using a phase separator and concentrated under reduced pressure to obtain the title compound (34 mg) as a reddish brown solid.

MS (ESI-APCI): 390[M+H]+

$^1$H NMR (600 MHz, CHLOROFORM-d) δppm 1.93-1.98 (4H, m), 2.24-2.26 (6H, m), 2.38 (3H, s), 3.49-3.53 (4H, m), 4.28 (2H, s), 6.60 (1H, s), 7.04 (1H, s), 7.21 (2H, d, J=8.0 Hz), 7.24 (1H, s), 7.67 (1H, s), 7.78 (2H, d, J=8.0 Hz)

Example 2

N'-(4-{[4-(5-Tert-butylpyrazin-2-yl)-1,3-thiazol-2-yl]methyl}-2,5-dimethylphenyl)-N-ethyl-N-methylimidoformamide dihydrochloride To a chloroform (10 mL) solution of N-ethyl-N-methylformamide (0.40 g), in a nitrogen atmosphere, oxalyl chloride (0.39 mL) was added, and the resultant was stirred at room temperature for 10 minutes. Then, a chloroform (10 mL) solution of the compound (1.2 g) obtained by the technique of Reference Example 3-5 was added thereto, and the resultant was stirred at room temperature for 1 hour. A saturated aqueous solution of sodium bicarbonate was added thereto, followed by extraction with chloroform. The organic layer was dried over magnesium sulfate, and the desiccant was filtered off. Then, the solvent was distilled off under reduced pressure. The obtained residue was purified by silica gel column chromatography (OH-type silica gel; chloroform/methanol-gradient elution=100/0→91/9) and then further purified by silica gel column chromatography (NH-type silica gel; hexane/ethyl acetate-gradient elution=100/0→50/50). Ethyl acetate was added to the obtained oil, then a 4 mol/L hydrogen chloride/ethyl acetate solution was added, and the deposited solid was collected by filtration to obtain the title compound (0.71 g) as a pale yellow solid.

MS (ESI-APCI): 422[M+H]+, 444[M+Na]+

$^1$H NMR (600 MHz, DMSO-$d_6$) δppm 1.22-1.29 (3H, m), 1.38 (9H, s), 2.29-2.34 (6H, m), 3.21-3.31 (3H, m), 3.59-3.70 (2H, m), 4.44 (2H, s), 7.21-7.27 (1H, m), 7.31 (1H, s), 8.19

(1H, s), 8.28-8.46 (1H, m), 8.77 (1H, d, J=1.7 Hz), 9.11 (1H, d, J=1.7 Hz), 10.73-10.93 (1H, m)

Example 3

N'-(2,5-Dimethyl-4-{[4-(4-methylphenyl)-1,3-thiazol-2-yl]methyl}phenyl)-N-ethyl-N-methylimidoformamide dihydrochloride

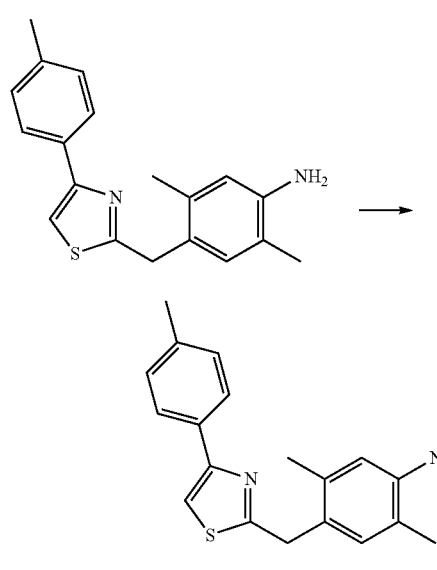

To a chloroform (1.0 mL) solution of N-ethyl-N-methylformamide (60 mg), in a nitrogen atmosphere, oxalyl chloride (59 μL) was added, and the resultant was stirred at room temperature for 10 minutes. Then, a chloroform (2.0 mL) solution of the compound (0.15 g) obtained by the technique of Reference Example 2-2 was added thereto, and the resultant was stirred at room temperature for 1 hour. The reaction solution was neutralized by the addition of a 2 mol/L aqueous sodium hydroxide solution. Then, an organic layer was separated, and the solvent was distilled off under reduced pressure. The obtained residue was purified by silica gel column chromatography (OH-type silica gel; hexane/ethyl acetate-gradient elution=80/20→20/80). A 4 mol/L hydrogen chloride/ethyl acetate solution (2.0 mL) was added to an ethyl acetate (1.0 mL) solution of the obtained pale pink oil (43 mg) in a nitrogen atmosphere, and the resultant was stirred at room temperature for 30 minutes. The deposited solid was collected by filtration and washed with ethyl acetate to obtain the title compound (38 mg) as a pale yellow solid.

MS (ESI-APCI): 378[M+H]+

$^1$H NMR (600 MHz, DMSO-$d_6$) δppm 1.22-1.29 (3H, m), 2.27-2.31 (3H, m), 2.33 (6H, s), 3.19-3.30 (3H, m), 3.58-3.69 (2H, m), 4.38 (2H, s), 7.19-7.27 (3H, m), 7.29 (1H, s), 7.81 (2H, d, J=8.3 Hz), 7.87 (1H, s), 8.27-8.45 (1H, m), 10.67-10.87 (1H, m)

Example 4

N'-[2,5-Dimethyl-4-({4-[5-(1,1,1-trifluoro-2-methyl-propan-2-yl)pyrazin-2-yl]-1,3-thiazol-2-yl}methyl)phenyl]-N-ethyl-N-methylimidoformamide hydrochloride

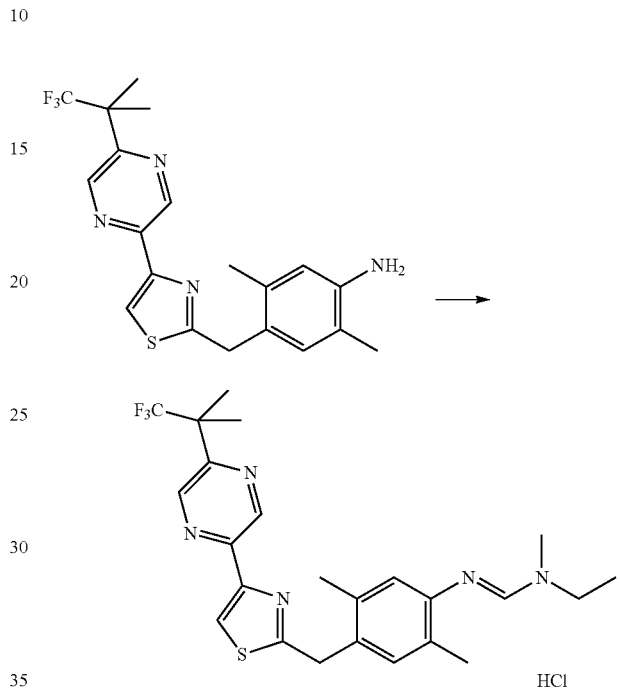

To a chloroform (0.50 mL) solution of N-ethyl-N-methylformamide (26 mg), in a nitrogen atmosphere, oxalyl chloride (25 μL) was added, and the resultant was stirred at room temperature for 10 minutes. Then, a chloroform (0.50 mL) solution of the compound (85 mg) obtained by the technique of Reference Example 4-5 was added thereto, and the resultant was stirred at room temperature for 1 hour. A saturated aqueous solution of sodium bicarbonate was added thereto, followed by extraction with chloroform. The organic layer was dried over magnesium sulfate, and the desiccant was filtered off. Then, the solvent was distilled off under reduced pressure. The obtained residue was purified by silica gel column chromatography (OH-type silica gel; chloroform/methanol-gradient elution=100/0→91/9). Ethyl acetate was added to the obtained oil, then a 4 mol/L hydrogen chloride/ethyl acetate solution was added, and the resultant was then concentrated under reduced pressure to obtain the title compound (79 mg) as a pale yellow solid.

MS (ESI-APCI): 476[M+H]+

$^1$H NMR (600 MHz, DMSO-$d_6$) δppm 1.23-1.30 (3H, m), 1.66 (6H, s), 2.28-2.35 (6H, m), 3.19-3.30 (3H, m), 3.59-3.68 (2H, m), 4.45 (2H, s), 7.22-7.27 (1H, m), 7.32 (1H, s), 8.28-8.45 (2H, m), 8.95 (1H, d, J=1.7 Hz), 9.20 (1H, d, J=1.7 Hz), 10.62-10.81 (1H, m)

Example 5

Methyl 4-(4-chlorophenyl)-2-[4-({(E)-[ethyl(methyl)amino]methylidene}amino)-2,5-dimethylbenzyl]-1,3-thiazole-5-carboxylate dihydrochloride

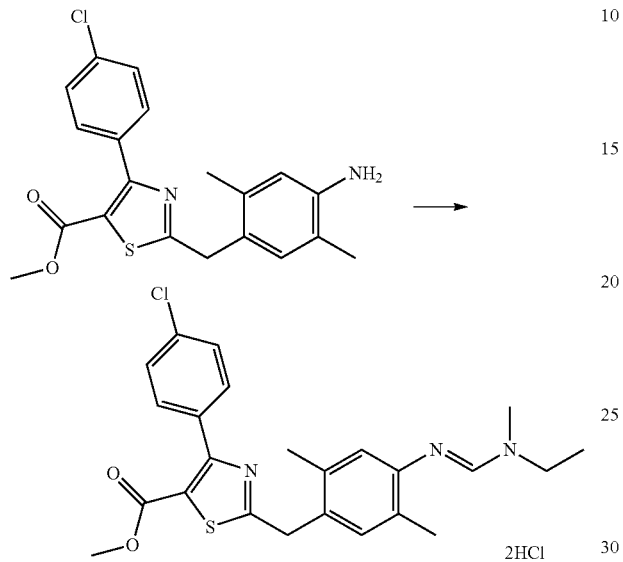

To a chloroform (0.50 mL) solution of N-ethyl-N-methylformamide (27 mg), in a nitrogen atmosphere, oxalyl chloride (26 μL) was added, and the resultant was stirred at room temperature for 10 minutes. Then, a chloroform (0.50 mL) solution of the compound (85 mg) obtained by the technique of Reference Example 5-3 was added thereto, and the resultant was stirred at room temperature for 1 hour. A saturated aqueous solution of sodium bicarbonate was added thereto, followed by extraction with chloroform. The organic layer was dried over magnesium sulfate, and the desiccant was filtered off. Then, the solvent was distilled off under reduced pressure. The obtained residue was purified by silica gel column chromatography (OH-type silica gel; chloroform/methanol-gradient elution=100/0→91/9) and then further purified by silica gel column chromatography (NH-type silica gel; hexane/ethyl acetate-gradient elution=100/0→66/34). Ethyl acetate was added to the obtained oil, then a 4 mol/L hydrogen chloride/ethyl acetate solution was added, and the resultant was then concentrated under reduced pressure. Methanol was added to the obtained yellow solid, then a 2 mol/L hydrogen chloride/methanol solution was added, and the resultant was then concentrated under reduced pressure to obtain the title compound (46 mg) as a yellow solid.

MS (ESI-APCI): 456[M+H]+

$^1$H NMR (600 MHz, DMSO-$d_6$) δppm 1.22-1.29 (3H, m), 2.28-2.33 (6H, m), 3.24-3.30 (3H, m), 3.59-3.72 (5H, m), 4.40 (2H, s), 7.24-7.26 (1H, m), 7.33 (1H, s), 7.52 (2H, d, J=8.7 Hz), 7.75 (2H, d, J=8.7 Hz), 8.28-8.45 (1H, m), 10.79-11.01 (1H, m)

Example 6

Methyl 2-[4-({(E)-[ethyl(methyl)amino]methylidene}amino)-2,5-dimethylbenzyl]-4-(4-methylphenyl)-1,3-thiazole-5-carboxylate dihydrochloride

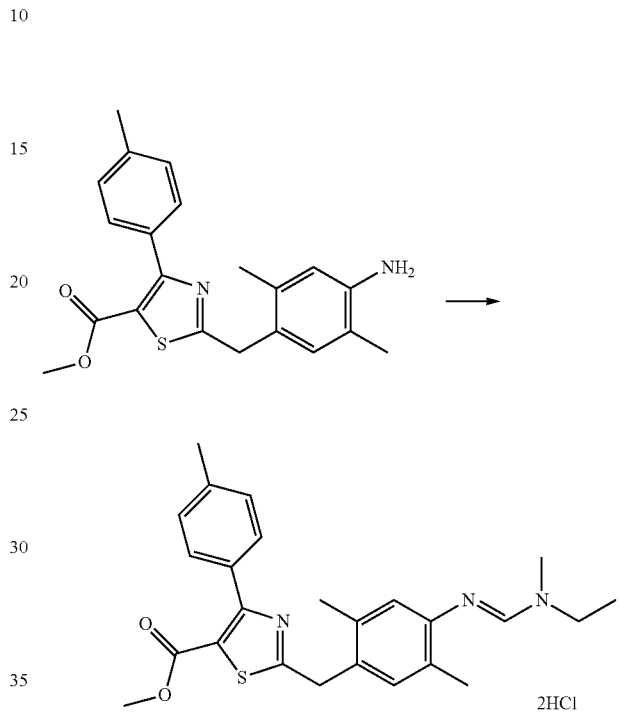

To a chloroform (2.5 mL) solution of N-ethyl-N-methylformamide (92 mg), in a nitrogen atmosphere, oxalyl chloride (90 μL) was added, and the resultant was stirred at room temperature for 10 minutes. Then, a chloroform (2.5 mL) solution of the compound (0.28 g) obtained by the technique of Reference Example 6-3 was added thereto, and the resultant was stirred at room temperature for 1 hour. A saturated aqueous solution of sodium bicarbonate was added thereto, followed by extraction with chloroform. The organic layer was dried over magnesium sulfate, and the desiccant was filtered off. Then, the solvent was distilled off under reduced pressure. The obtained residue was purified by silica gel column chromatography (NH-type silica gel; hexane/ethyl acetate-gradient elution=100/0→66/34). Methanol was added to the obtained yellow oil, then a 2 mol/L hydrogen chloride/methanol solution was added, and the resultant was then concentrated under reduced pressure to obtain the title compound (16 mg) as a yellow solid.

MS (ESI-APCI): 436[M+H]+

1H NMR (600 MHz, DMSO-$d_6$) δppm 1.23-1.29 (3H, m), 2.28-2.32 (6H, m), 2.36 (3H, s), 3.23-3.30 (3H, m), 3.60-3.73 (5H, m), 4.39 (2H, s), 7.22-7.27 (3H, m), 7.32 (1H, s), 7.61 (2H, d, J=7.8 Hz), 8.27-8.46 (1H, m), 10.74-10.97 (1H, m)

Example 7

Methyl N-{(E)-[(2,5-dimethyl-4-{[4-(4-methylphenyl)-1,3-thiazol-2-yl]methyl}phenyl)imino]methyl}-N-methylglycinate

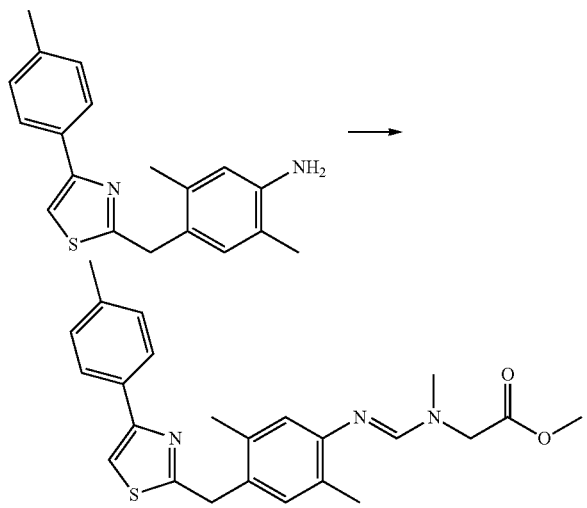

To a chloroform (6.0 mL) solution of methyl N-formyl-N-methylglycinate (0.12 g), in a nitrogen atmosphere, oxalyl chloride (79 µL) was added, and the resultant was stirred at room temperature for 10 minutes. Then, a chloroform (2.0 mL) solution of the compound (0.26 g) obtained by the technique of Reference Example 2-2 was added thereto, and the resultant was stirred at room temperature for 1.5 hours. A saturated aqueous solution of sodium bicarbonate was added thereto, and the resultant was stirred for 1 hour, followed by extraction with chloroform. The solvent was distilled off under reduced pressure. The obtained residue was purified by silica gel column chromatography (OH-type silica gel; hexane/ethyl acetate-gradient elution=95/5→30/70) and preparative silica gel thin-layer chromatography (OH-type silica gel; hexane/ethyl acetate=66/34) and then further purified by preparative LC to obtain the title compound (9.0 mg) as a white solid.

MS (ESI-APCI): 422[M+H]+

$^1$H NMR (600 MHz, CHLOROFORM-d) δppm 2.18 (3H, br. s.), 2.25 (3H, s), 2.38 (3H, s), 3.09 (3H, s), 3.77 (3H, s), 4.11-4.23 (2H, m), 4.28 (2H, s), 6.60 (1H, s), 7.04 (1H, s), 7.21 (2H, d, J=7.8 Hz), 7.24 (1H, s), 7.41-7.53 (1H, m), 7.71-7.83 (2H, m)

Example 8

2-[4-({(E)-[Ethyl(methyl)amino]methylidene}amino)-2,5-dimethylbenzyl]-4-(4-methylphenyl)-1,3-thiazole-5-carboxylic acid

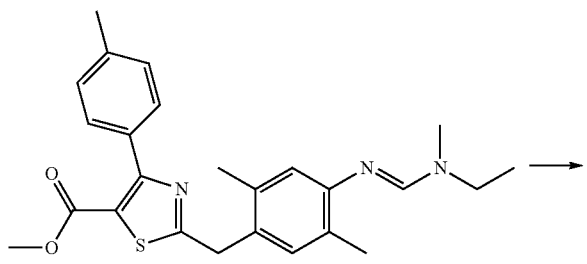

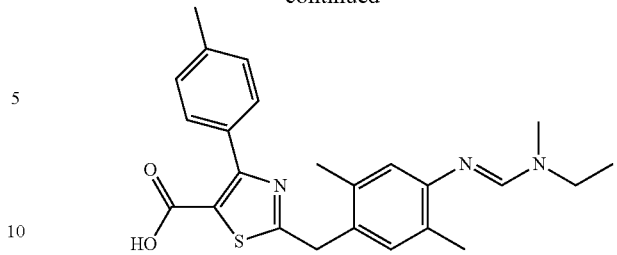

To a 1:1 water/tetrahydrofuran (2.0 mL) solution of the compound (0.15 g) obtained by the technique of Example 6, lithium hydroxide monohydrate (0.13 g) was added, and the resultant was stirred at room temperature for 4 hours. The reaction solution was added to a 1 mol/L aqueous hydrochloric acid solution, and the deposited solid was collected by filtration to obtain the title compound (19 mg) as a colorless solid.

MS (ESI-APCI): 422[M+H]+, 420[M−H]−

$^1$H NMR (600 MHz, DMSO-d$_6$) δppm 1.13 (3H, t, J=7.2 Hz), 2.14 (3H, s), 2.20 (3H, s), 2.35 (3H, s), 2.91-2.99 (2H, m), 3.26-3.30 (3H, m), 4.19 (2H, s), 6.66 (1H, s), 7.05 (1H, s), 7.21 (2H, d, J=8.3 Hz), 7.59-7.75 (3H, m)

Example 9

N'-(2,5-Dimethyl-4-{[4-(4-methylphenyl)-1,3-thiazol-2-yl]methyl}phenyl)-N-(2-hydroxyethyl)-N-methylimidoformamide

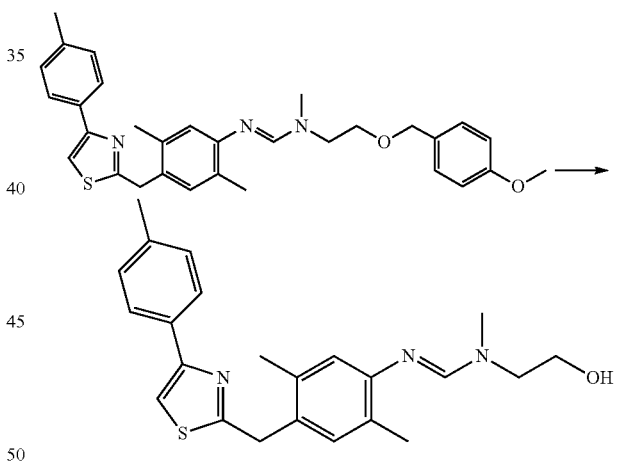

To a chloroform (2.0 mL) solution of the compound (93 mg) obtained by the technique of Reference Example 7-3, trifluoroacetic acid (2.0 mL) was added, and the resultant was stirred at room temperature for 1 hour. The reaction solution was concentrated under reduced pressure. Then, a saturated aqueous solution of sodium bicarbonate was added to the residue, and the resultant was stirred for 30 minutes, followed by extraction with chloroform. The solvent was distilled off under reduced pressure. The obtained residue was purified by preparative LC to obtain the title compound (28 mg) as a colorless oil.

MS (ESI-APCI): 394[M+H]+

$^1$H NMR (600 MHz, CHLOROFORM-d) δppm 2.23 (3H, s), 2.26 (3H, s), 2.38 (3H, s), 3.11 (3H, s), 3.57-3.70 (2H, m), 3.88 (2H, br. s.), 4.29 (2H, s), 6.61 (1H, s), 7.06 (1H, s), 7.22 (2H, d, J=7.8 Hz), 7.24 (1H, s), 7.58 (1H, s), 7.78 (2H, d, J=7.8 Hz)

Example 10

Tert-butyl N-{(E)-[(2,5-dimethyl-4-{[4-(4-methylphenyl)-1,3-thiazol-2-yl]methyl}phenyl)imino]methyl}-N-methylglycinate

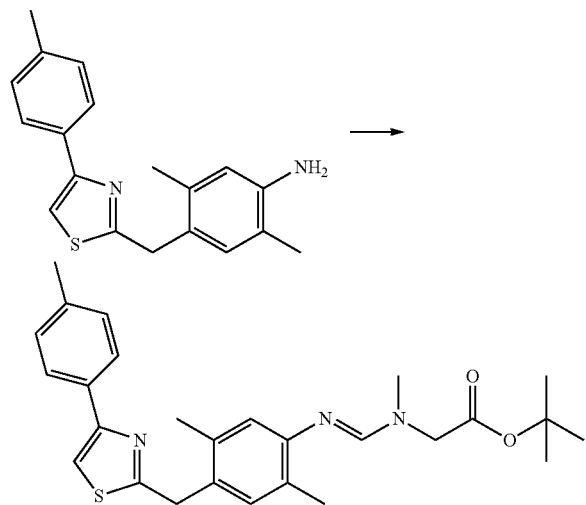

To a chloroform (6.0 mL) solution of the compound (0.32 g) obtained by the technique of Reference Example 8, in a nitrogen atmosphere, oxalyl chloride (0.16 mL) was added, and the resultant was stirred at room temperature for 10 minutes. Then, a chloroform (2.0 mL) solution of the compound (0.38 g) obtained by the technique of Reference Example 2-2 was added thereto, and the resultant was stirred at room temperature for 3 hours. A saturated aqueous solution of sodium bicarbonate was added thereto, and the resultant was stirred for 1 hour, followed by extraction with chloroform. An organic layer was separated using a phase separator, and the solvent was distilled off under reduced pressure. The obtained residue was purified by silica gel column chromatography (NH-type silica gel; hexane/ethyl acetate-gradient elution=95/5→80/20) to obtain the title compound (32 mg) as a yellow oil.

MS (ESI-APCI): 464[M+H]+

$^1$H NMR (600 MHz, CHLOROFORM-d) δppm 1.49 (9H, s), 2.20 (3H, br. s.), 2.25 (3H, s), 2.38 (3H, s), 3.07 (3H, s), 4.03-4.12 (2H, m), 4.28 (2H, s), 6.60 (1H, s), 7.04 (1H, s), 7.21 (2H, d, J=7.8 Hz), 7.24 (1H, s), 7.40-7.51 (1H, m), 7.78 (2H, d, J=7.8 Hz)

Example 11

N-{(E)-[(2,5-Dimethyl-4-{[4-(4-methylphenyl)-1,3-thiazol-2-yl]methyl}phenyl)imino]methyl}-N-methylglycine hydrochloride

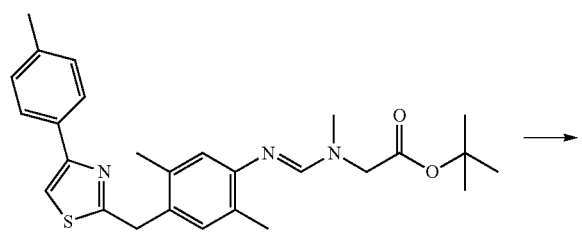

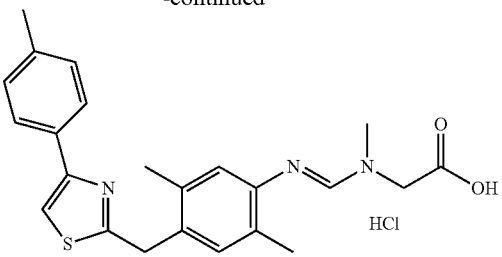

To a 1,4-dioxane (0.30 mL) solution of the compound (29 mg) obtained by the technique of Example 10, 4 mol/L hydrogen chloride in 1,4-dioxane (2.0 mL) was added, and the resultant was stirred at 70° C. for 1 hour. After standing to cool to room temperature, the reaction solution was concentrated under reduced pressure. Then, diethyl ether and methanol were added to the obtained residue, and the solid was collected by filtration to obtain the title compound (18 mg) as a pale yellow solid.

MS (ESI-APCI): 408[M+H]+, 406[M-H]-

$^1$H NMR (600 MHz, DMSO-d$_6$) δppm 2.23-2.31 (3H, m), 2.33 (6H, s), 3.24-3.34 (3H, m), 4.33-4.43 (2H, m), 4.43-4.56 (2H, m), 7.19 (1H, s), 7.24 (2H, d, J=7.8 Hz), 7.28-7.34 (1H, m), 7.81 (2H, d, J=7.8 Hz), 7.87 (1H, s), 8.43-8.60 (1H, m), 11.02-11.17 (1H, m)

Example 12

2-[4-({(E)-[Ethyl(methyl)amino]methylidene}amino)-2,5-dimethylbenzyl]-4-(4-methylphenyl)-1,3-thiazole-5-carboxamide

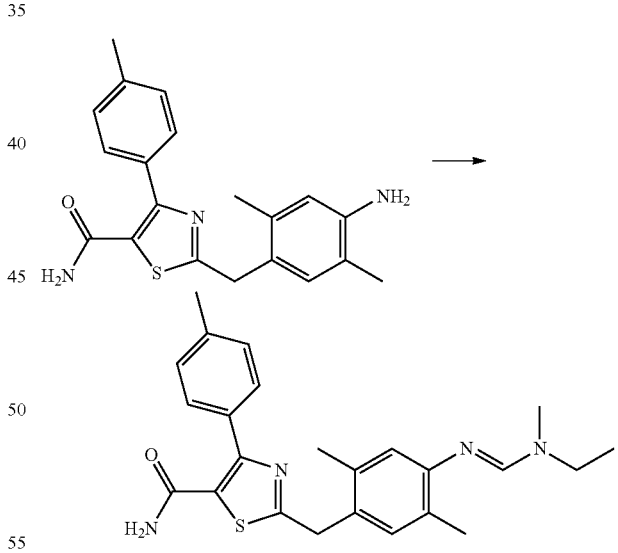

To a chloroform (1.0 mL) solution of N-ethyl-N-methylformamide (25 mg), in a nitrogen atmosphere, oxalyl chloride (25 μL) was added, and the resultant was stirred at room temperature for 10 minutes. Then, a chloroform (1.0 mL) solution of the compound (73 mg) obtained by the technique of Reference Example 6-8 was added thereto, and the resultant was stirred at room temperature for 1 hour. A saturated aqueous solution of sodium bicarbonate was added thereto, followed by extraction with chloroform. The organic layer was dried over magnesium sulfate, and the desiccant was filtered off. Then, the solvent was distilled off under reduced pressure. The obtained residue was purified by silica gel column chromatography (OH-type silica gel; chloroform/methanol-gradient elution=100/0→91/9) to obtain the title compound (38 mg) as a yellow solid.

MS (ESI-APCI): 421[M+H]+, 419[M−H]−

$^1$H NMR (600 MHz, CHLOROFORM-d) δppm 1.21 (3H, t, J=7.0 Hz), 2.23 (3H, s), 2.25 (3H, s), 2.41 (3H, s), 3.00 (3H, s), 3.27-3.46 (2H, m), 4.21 (2H, s), 5.31-5.71 (2H, m), 6.59 (1H, s), 7.03 (1H, s), 7.29 (2H, d, J=8.3 Hz), 7.41-7.46 (1H, m), 7.53 (2H, d, J=8.3 Hz)

Example 13

2-[4-({(E)-[Ethyl(methyl)amino]methylidene}amino)-2,5-dimethylbenzyl]-N-methyl-4-(4-methylphenyl)-1,3-thiazole-5-carboxamide

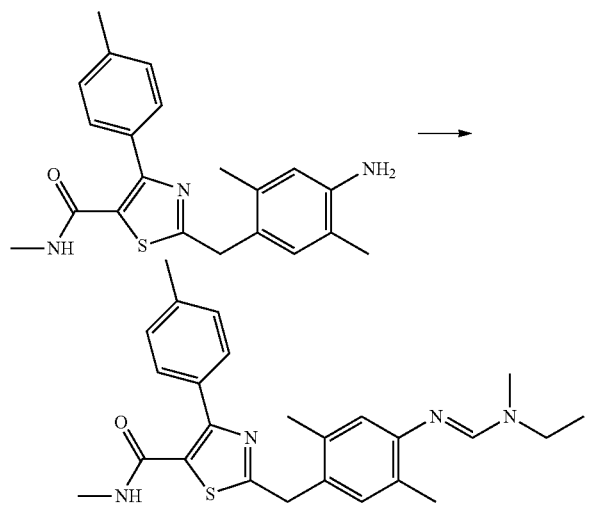

To a chloroform (1.0 mL) solution of N-ethyl-N-methylformamide (31 mg), in a nitrogen atmosphere, oxalyl chloride (31 µL) was added, and the resultant was stirred at room temperature for 10 minutes. Then, a chloroform (1.0 mL) solution of the compound (92 mg) obtained by the technique of Reference Example 6-6 was added thereto, and the resultant was stirred at room temperature for 1 hour. A saturated aqueous solution of sodium bicarbonate was added thereto, followed by extraction with chloroform. The organic layer was dried over magnesium sulfate, and the desiccant was filtered off. Then, the solvent was distilled off under reduced pressure. The obtained residue was purified by silica gel column chromatography (OH-type silica gel; chloroform/methanol-gradient elution=100/0→91/9) to obtain the title compound (47 mg) as a colorless solid.

MS (ESI-APCI): 435[M+H]+

$^1$H NMR (600 MHz, CHLOROFORM-d) δppm 1.20 (3H, t, J=7.2 Hz), 2.22 (3H, s), 2.23 (3H, s), 2.40 (3H, s), 2.75 (3H, d, J=5.0 Hz), 2.99 (3H, s), 3.25-3.47 (2H, m), 4.19 (2H, s), 5.63-5.70 (1H, m), 6.57 (1H, s), 7.02 (1H, s), 7.26 (2H, d, J=7.8 Hz), 7.40-7.45 (1H, m), 7.51 (2H, d, J=7.8 Hz)

Example 14

Methyl 4-{2-[4-({(E)-[ethyl(methyl)amino]methylidene}amino)-2,5-dimethylbenzyl]-1,3-thiazol-4-yl}benzoate dihydrochloride

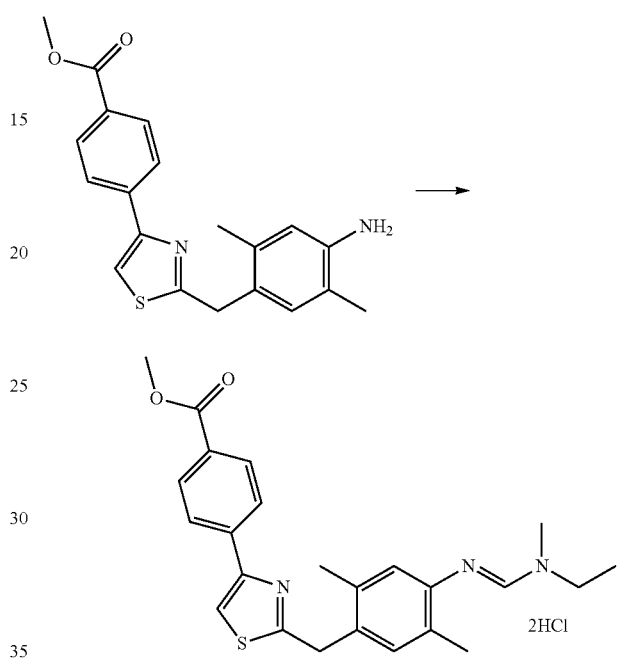

To a chloroform (0.5 mL) solution of N-ethyl-N-methylformamide (10 mg), in a nitrogen atmosphere, oxalyl chloride (10 µL) was added, and the resultant was stirred at room temperature for 10 minutes. Then, a chloroform (1.5 mL) solution of the compound (30 mg) obtained by the technique of Reference Example 9-2 was added thereto, and the resultant was stirred at room temperature for 3.5 hours. A saturated aqueous solution of sodium bicarbonate was added thereto, followed by extraction with chloroform. An organic layer was separated using a phase separator, and the solvent was distilled off under reduced pressure. The obtained residue was purified by silica gel column chromatography (NH-type silica gel; hexane/ethyl acetate-gradient elution=90/10→70/30). A 4 mol/L hydrogen chloride/ethyl acetate solution (1.0 mL) was added to an ethyl acetate (0.5 mL) solution of the obtained pale yellow oil (11 mg), and the resultant was stirred at room temperature for 1 hour. The reaction solution was concentrated under reduced pressure to obtain the title compound (13 mg) as a pale yellow solid.

MS (ESI-APCI): 422[M+H]+

$^1$H NMR (600 MHz, METHANOL-$d_3$) δppm 1.33-1.40 (3H, m), 2.32-2.39 (6H, m), 3.36 (3H, s), 3.63-3.71 (2H, m), 3.92 (3H, s), 4.43 (2H, s), 7.19 (1H, s), 7.32 (1H, s), 7.87 (1H, s), 7.95-8.10 (5H, m), 8.16-8.33 (1H, m)

Example 15

4-{2-[4-({(E)-[Ethyl(methyl)amino]methylidene}amino)-2,5-dimethylbenzyl]-1,3-thiazol-4-yl}benzoic acid

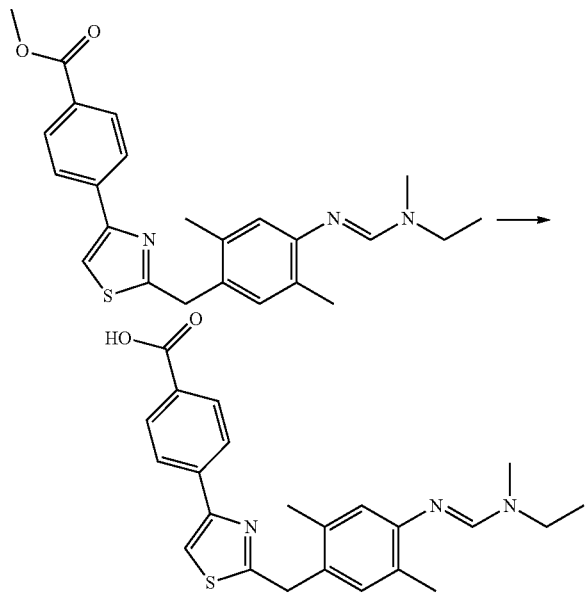

To a 1:1 water/tetrahydrofuran (3.0 mL) solution of the compound (0.13 g) obtained by the technique of Example 14, lithium hydroxide monohydrate (19 mg) was added, and the resultant was stirred at room temperature for 24 hours. A 1 mol/L aqueous hydrochloric acid solution was added to the reaction solution, followed by extraction with chloroform. An organic layer was separated using a phase separator, and the solvent was distilled off under reduced pressure to obtain the title compound (0.12 g) as a pale yellow solid.

MS (ESI-APCI): 408[M+H]+, 406[M−H]−

$^1$H NMR (600 MHz, CHLOROFORM-d) δppm 1.22 (3H, t, J=7.0 Hz), 2.26 (6H, s), 3.03 (3H, br. s.), 3.29-3.45 (2H, m), 4.30 (2H, s), 6.63 (1H, s), 7.06 (1H, s), 7.42-7.48 (2H, m), 7.99 (2H, d, J=8.7 Hz), 8.14 (2H, d, J=8.7 Hz)

Example 16

N'-(2,5-Dimethyl-4-{[3-(4-methylphenyl)-1,2,4-thiadiazol-5-yl]methyl}phenyl)-N-ethyl-N-methylimidoformamide

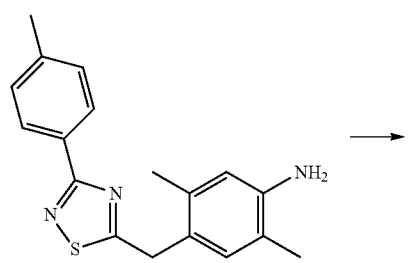

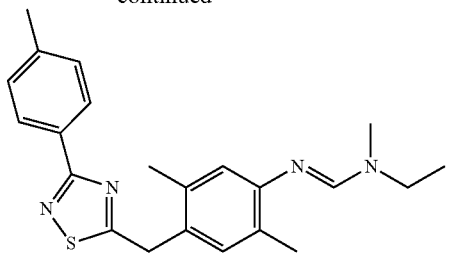

To a chloroform (1.0 mL) solution of N-ethyl-N-methylformamide (14 mg), in a nitrogen atmosphere, oxalyl chloride (14 µL) was added, and the resultant was stirred at room temperature for 10 minutes. Then, a chloroform (1.5 mL) solution of the compound (38 mg) obtained by the technique of Reference Example 10-3 was added thereto, and the resultant was stirred at room temperature for 1.5 hours. A saturated aqueous solution of sodium bicarbonate was added thereto, followed by extraction with chloroform. The organic layer was dried over magnesium sulfate, and the desiccant was filtered off. Then, the solvent was distilled off under reduced pressure. The obtained residue was purified by silica gel column chromatography (NH-type silica gel; hexane/ethyl acetate-gradient elution=100/0→70/30) to obtain the title compound (22 mg) as a yellow oil.

MS (ESI-APCI): 379[M+H]+

$^1$H NMR (600 MHz, CHLOROFORM-d) δppm 1.22 (3H, t, J=7.2 Hz), 2.22-2.26 (6H, m), 2.41 (3H, s), 3.01 (3H, s), 3.26-3.50 (2H, m), 4.33 (2H, s), 6.62 (1H, s), 7.06 (1H, s), 7.27 (2H, d, J=8.0 Hz), 7.43-7.50 (1H, m), 8.17 (2H, d, J=8.0 Hz)

Example 17

N'-(4-{[4-(4-Tert-butylphenyl)-1,3-thiazol-2-yl]methyl}-2,5-dimethylphenyl)-N-ethyl-N-methylimidoformamide dihydrochloride

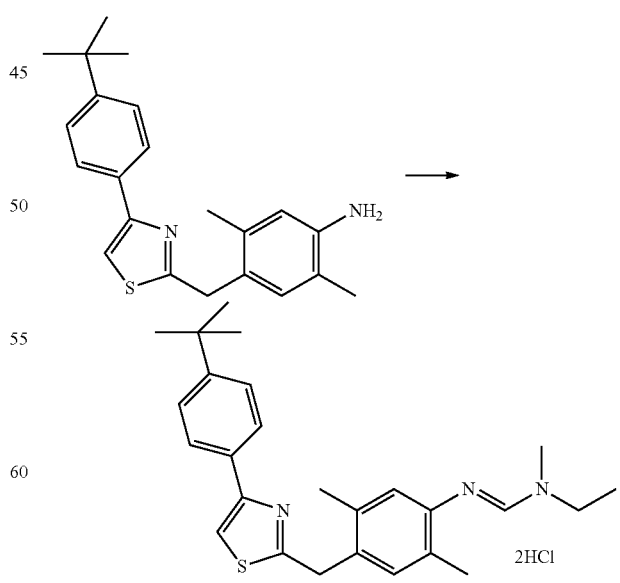

To a chloroform (1.5 mL) solution of N-ethyl-N-methylformamide (32 mg), in a nitrogen atmosphere, oxalyl chloride (50 μL) was added, and the resultant was stirred at room temperature for 10 minutes. Then, a chloroform (2.5 mL) solution of the compound (0.13 g) obtained by the technique of Reference Example 11-2 was added thereto, and the resultant was stirred at room temperature for 2 hours. A saturated aqueous solution of sodium bicarbonate was added thereto, followed by extraction with chloroform. An organic layer was separated using a phase separator, and the solvent was distilled off under reduced pressure. The obtained residue was purified by silica gel column chromatography (NH-type silica gel; hexane/ethyl acetate-gradient elution=90/10→80/20). A 4 mol/L hydrogen chloride/ethyl acetate solution (1.0 mL) was added to an ethyl acetate (0.5 mL) solution of the obtained pale yellow oil (86 mg), and the resultant was stirred at room temperature for 30 minutes. The reaction solution was concentrated under reduced pressure. Then, diethyl ether was added to the obtained residue, and the solid was collected by filtration to obtain the title compound (83 mg) as a pale yellow solid.

MS (ESI-APCI): 420 [M+H]+
$^1$H NMR (600 MHz, DMSO-$d_6$) δppm 1.26 (3H, s), 1.30 (9H, s), 2.26-2.34 (6H, m), 3.19-3.30 (3H, m), 3.52-3.67 (2H, m), 4.38 (2H, s), 7.20-7.25 (1H, m), 7.29 (1H, s), 7.45 (2H, d, J=8.7 Hz), 7.84 (2H, d, J=8.7 Hz), 7.86 (1H, s), 8.25-8.46 (1H, m), 10.58-10.79 (1H, m)

Example 18

N'-(4-{[4-(4-Cyanophenyl)-1,3-thiazol-2-yl]methyl}-2,5-dimethylphenyl)-N-ethyl-N-methylimidoformamide dihydrochloride

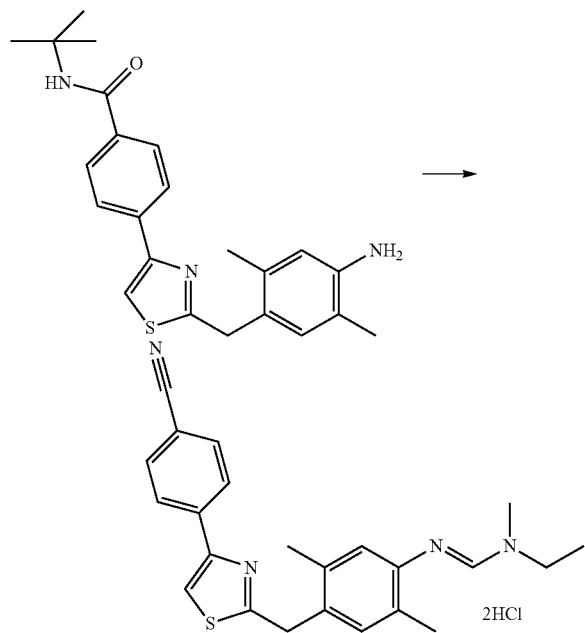

To a chloroform (2.0 mL) solution of N-ethyl-N-methylformamide (31 mg), in a nitrogen atmosphere, oxalyl chloride (30 μL) was added, and the resultant was stirred at room temperature for 10 minutes. Then, a chloroform (3.5 mL) solution of the compound (0.10 g) obtained by the technique of Reference Example 9-5 was added thereto, and the resultant was stirred at room temperature for 1 hour. A saturated aqueous solution of sodium bicarbonate was added thereto, followed by extraction with chloroform. An organic layer was separated using a phase separator, and the solvent was distilled off under reduced pressure. The obtained residue was purified by silica gel column chromatography (NH-type silica gel; hexane/ethyl acetate-gradient elution=90/10→75/25). A 4 mol/L hydrogen chloride/ethyl acetate solution (1.0 mL) was added to an ethyl acetate (0.5 mL) solution of the obtained oil (11 mg), and the resultant was stirred at room temperature for 1 hour. The reaction solution was concentrated under reduced pressure to obtain the title compound (14 mg) as a white solid.

MS (ESI-APCI): 389[M+H]+, 387[M−H]−
$^1$H NMR (600 MHz, METHANOL-$d_3$) δppm 1.34-1.40 (3H, m), 2.32-2.39 (6H, m), 3.28 (3H, s), 3.63-3.72 (2H, m), 4.42 (2H, s), 7.19 (1H, s), 7.32 (1H, s), 7.77 (2H, d, J=7.8 Hz), 7.92 (1H, s), 8.09 (2H, d, J=7.8 Hz), 8.15-8.34 (1H, m)

Example 19

N'-(2,5-Dimethyl-4-{[4-(phenylcarbonyl)-1,3-thiazol-2-yl]methyl}phenyl)-N-ethyl-N-methylimidoformamide dihydrochloride

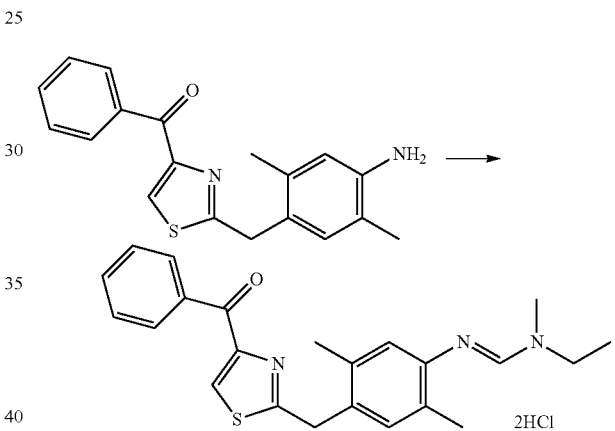

To a chloroform (1.5 mL) solution of N-ethyl-N-methylformamide (33 mg), in a nitrogen atmosphere, oxalyl chloride (30 μL) was added, and the resultant was stirred at room temperature for 10 minutes. Then, a chloroform (2.0 mL) solution of the compound (81 mg) obtained by the technique of Reference Example 12-2 was added thereto, and the resultant was stirred at room temperature for 2 hours. A saturated aqueous solution of sodium bicarbonate was added thereto, followed by extraction with chloroform. An organic layer was separated using a phase separator, and the solvent was distilled off under reduced pressure. The obtained residue was purified by silica gel column chromatography (NH-type silica gel; hexane/ethyl acetate-gradient elution=90/10→80/20). A 4 mol/L hydrogen chloride/ethyl acetate solution (1.0 mL) was added to an ethyl acetate (1.0 mL) solution of the obtained light brown oil (58 mg), and the resultant was stirred at room temperature for 30 minutes. The reaction solution was concentrated under reduced pressure. Diethyl ether was added to the obtained residue, and the solid was collected by filtration to obtain the title compound (42 mg) as a pale yellow solid.

MS (ESI-APCI): 392[M+H]+
$^1$H NMR (600 MHz, DMSO-$d_6$) δppm 1.20-1.30 (3H, m), 2.31 (6H, s), 3.19-3.31 (3H, m), 3.62 (2H, m), 4.43 (2H, s), 7.24 (1H, s), 7.32 (1H, s), 7.56 (2H, t, J=7.6 Hz), 7.68 (1H, s), 8.07 (2H, dd, J=7.6, 1.2 Hz), 8.43 (2H, s), 10.67-10.90 (1H, m)

Example 20

N'-{4-[(5-Tert-butyl-2,4'-bi-1,3-thiazol-2'-yl)methyl]-2,5-dimethylphenyl}-N-ethyl-N-methylimidoformamide dihydrochloride

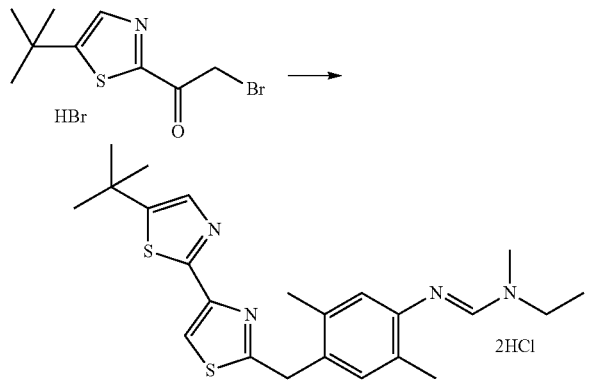

To a 2-propanol (1.0 mL) solution of the compound (35 mg) obtained by the technique of Reference Example 1-5, the compound (50 mg) obtained by the technique of Reference Example 13-3 was added, and the resultant was stirred at 80° C. for 2 hours. A saturated aqueous solution of sodium bicarbonate was added thereto, followed by extraction with ethyl acetate. The organic layer was dried over magnesium sulfate, and the desiccant was filtered off. Then, the solvent was distilled off under reduced pressure. The obtained residue was purified by silica gel column chromatography (NH-type silica gel; hexane/ethyl acetate-gradient elution=100/0→75/25). Ethyl acetate and a 4 mol/L hydrogen chloride/ethyl acetate solution were added to the obtained oil, and the resultant was then concentrated under reduced pressure to obtain the title compound (22 mg) as a colorless solid.

MS (ESI-APCI): 427[M+H]+
$^1$H NMR (600 MHz, DMSO-d$_6$) δppm 1.22-1.28 (3H, m), 1.40 (9H, s), 2.28-2.31 (6H, m), 3.20-3.30 (3H, m), 3.60-3.66 (2H, m), 4.36 (2H, s), 7.21-7.24 (1H, m), 7.28 (1H, s), 7.85 (1H, s), 8.06 (1H, s), 8.28-8.44 (1H, m), 10.56-10.79 (1H, m)

Example 21

N-Ethyl-N'-(4-{[4-(5-fluoropyridin-3-yl)-1,3-thiazol-2-yl]methyl}-2,5-dimethylphenyl)-N-methylimidoformamide trihydrochloride

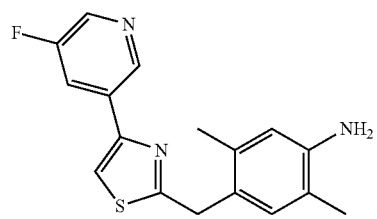

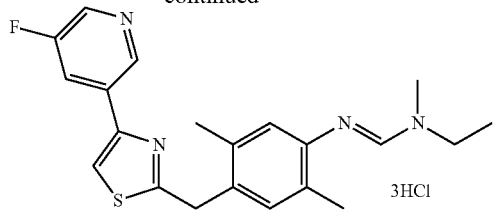

To a chloroform (1.0 mL) solution of N-ethyl-N-methylformamide (67 mg), in a nitrogen atmosphere, oxalyl chloride (30 μL) was added, and the resultant was stirred at room temperature for 10 minutes. Then, a chloroform (4.0 mL) solution of the compound (81 mg) obtained by the technique of Reference Example 14-3 was added thereto, and the resultant was stirred at room temperature for 6.5 hours. A saturated aqueous solution of sodium bicarbonate was added thereto, followed by extraction with chloroform. An organic layer was separated using a phase separator, and the solvent was distilled off under reduced pressure. The obtained residue was purified twice by silica gel column chromatography (OH-type silica gel; hexane/ethyl acetate-gradient elution=90/10→50/50). A 4 mol/L hydrogen chloride/ethyl acetate solution (2.0 mL) was added to an ethyl acetate (1.0 mL) solution of the obtained oil (30 mg), and the resultant was stirred at room temperature for 1 hour. The reaction solution was concentrated under reduced pressure. Hexane was added to the obtained residue, and the solid was collected by filtration to obtain the title compound (29 mg) as a pale yellow solid.

MS (ESI-APCI): 383 [M+H]+
$^1$H NMR (600 MHz, DMSO-d$_6$) δppm 1.22-1.29 (3H, m), 2.27-2.34 (6H, m), 3.22 (3H, s), 3.60-3.65 (2H, m), 4.42 (2H, s), 7.22-7.26 (1H, m), 7.31 (1H, s), 8.15-8.20 (1H, m), 8.27 (1H, s), 8.32 (1H, s), 8.56 (1H, d, J=2.9 Hz), 9.01-9.06 (1H, m), 10.58-10.75 (1H, m)

Example 22

N'-(4-{[4-(6-Tert-butyl-2-oxo-1,2-dihydropyridin-3-yl)-1,3-thiazol-2-yl]methyl}-2,5-dimethylphenyl)-N-ethyl-N-methylimidoformamide

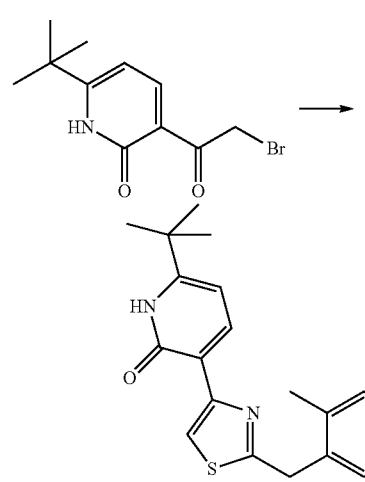

To a 2-propanol (1.0 mL) solution of the compound (31 mg) obtained by the technique of Reference Example 1-5, the compound (40 mg) obtained by the technique of Reference Example 15 was added, and the resultant was stirred at 80° C. for 2 hours. The deposited solid was collected by filtration. A saturated aqueous solution of sodium bicarbonate was added to the obtained yellow solid, followed by extraction with ethyl acetate. The organic layer was dried over magnesium sulfate, and the desiccant was filtered off. Then, the solvent was distilled off under reduced pressure to obtain the title compound (5.5 mg) as a pale yellow solid.

MS (ESI-APCI): 437[M+H]+, 459[M+Na]+, 435[M−H]−

$^1$H NMR (600 MHz, DMSO-$d_6$) δppm 1.19-1.31 (12H, m), 2.23-2.28 (6H, m), 3.08-3.17 (3H, m), 3.50-3.60 (2H, m), 4.32 (2H, s), 6.24 (1H, d, J=6.8 Hz), 7.19-7.27 (1H, m), 8.26 (1H, d, J=6.8 Hz), 8.34 (1H, s), 10.45-10.53 (1H, m), 11.10 (1H, s), 11.61 (1H, s)

Example 23

N'-[2,5-Dimethyl-4-{4-[4-(methylsulfonyl)phenyl]-1,3-thiazol-2-yl}methyl)phenyl]-N-ethyl-N-methylimidoformamide dihydrochloride

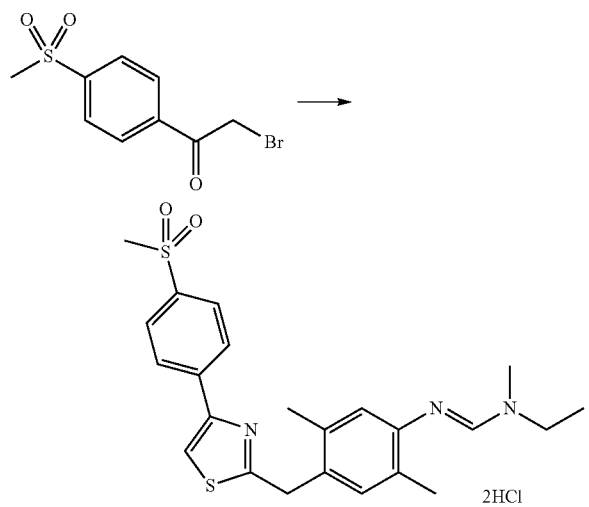

To a 2-propanol (2.0 mL) solution of the compound (30 mg) obtained by the technique of Reference Example 1-5, 2-bromo-1-[4-(methylsulfonyl)phenyl]-1-ethanone (32 mg) was added, and the resultant was stirred at 80° C. for 2 hours and then left overnight at room temperature. The reaction solution was concentrated, and the obtained residue was purified by preparative silica gel thin-layer chromatography (OH-type silica gel; chloroform/methanol=91/9). A 4 mol/L hydrogen chloride/ethyl acetate solution (1.0 mL) was added to an ethyl acetate (0.5 mL) solution of the obtained orange oil, and the resultant was stirred at room temperature for 1 hour. The reaction solution was concentrated under reduced pressure to obtain the title compound (14 mg) as a faint orange solid.

MS (ESI-APCI): 442[M+H]+, 440[M−H]−

$^1$H NMR (600 MHz, METHANOL-$d_3$) δppm 1.33-1.41 (3H, m), 2.32-2.39 (6H, m), 3.15 (3H, s), 3.28 (3H, br. s.), 3.62-3.71 (2H, m), 4.43 (2H, s), 7.19 (1H, s), 7.32 (1H, s), 7.95 (1H, s), 7.97-8.01 (2H, m), 8.10-8.34 (3H, m)

Example 24

N-Tert-butyl-4-{2-[4-({(E)-[ethyl(methyl)amino]methylidene}amino)-2,5-dimethylbenzyl]-1,3-thiazol-4-yl}benzamide dihydrochloride

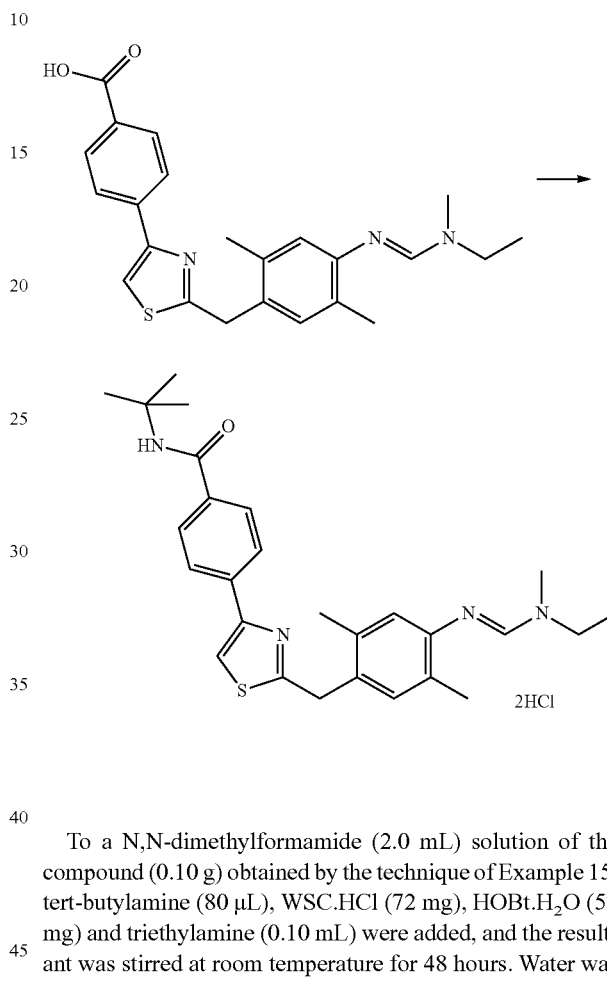

To a N,N-dimethylformamide (2.0 mL) solution of the compound (0.10 g) obtained by the technique of Example 15, tert-butylamine (80 μL), WSC.HCl (72 mg), HOBt.H$_2$O (57 mg) and triethylamine (0.10 mL) were added, and the resultant was stirred at room temperature for 48 hours. Water was added to the reaction solution, followed by extraction with chloroform. An organic layer was separated using a phase separator, and the solvent was distilled off under reduced pressure. The obtained residue was purified by silica gel column chromatography (NH-type silica gel; hexane/ethyl acetate-gradient elution=90/10→50/50). A 4 mol/L hydrogen chloride/ethyl acetate solution (2.0 mL) was added to an ethyl acetate (1.0 mL) solution of the obtained yellow oil (54 mg), and the resultant was stirred at room temperature for 1 hour. The reaction solution was concentrated under reduced pressure. Diethyl ether was added to the obtained residue, and the solid was collected by filtration to obtain the title compound (61 mg) as a pale yellow solid.

MS (ESI-APCI): 463[M+H]+, 461[M−H]−

$^1$H NMR (600 MHz, METHANOL-$d_3$) δppm 1.34-1.40 (3H, m), 1.47 (9H, s), 2.31-2.39 (6H, m), 3.28 (3H, br. s.), 3.64-3.71 (2H, m), 4.43 (2H, s), 7.20 (1H, s), 7.32 (1H, s), 7.75-7.99 (6H, m), 8.16-8.34 (1H, m)

Example 25

N'-(2,5-Dimethyl-4-{[4-phenyl-5-(phenylcarbonyl)-1,3-thiazol-2-yl]methyl}phenyl)-N-ethyl-N-methylimidoformamide dihydrochloride

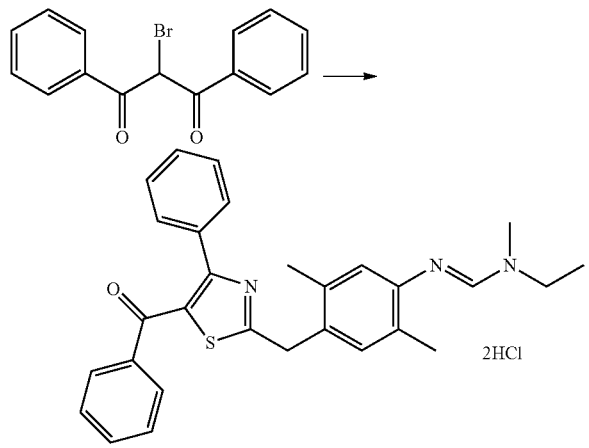

To a 2-propanol (1.0 mL) solution of the compound (25 mg) obtained by the technique of Reference Example 1-5, 2-bromo-1,3-diphenylpropane-1,3-dione (29 mg) was added, and the resultant was stirred at 80° C. for 2 hours. A saturated aqueous solution of sodium bicarbonate was added thereto, followed by extraction with ethyl acetate. The organic layer was dried over magnesium sulfate, and the desiccant was filtered off. Then, the solvent was distilled off under reduced pressure. The obtained residue was purified by silica gel column chromatography (NH-type silica gel; hexane/ethyl acetate-gradient elution=100/0→75/25) and then further purified (OH-type silica gel; chloroform/methanol-gradient elution=100/0→91/9). Ethyl acetate and a 4 mol/L hydrogen chloride/ethyl acetate solution were added to the obtained oil, and the resultant was then concentrated under reduced pressure to obtain the title compound (23 mg) as a colorless solid.

MS (ESI-APCI): 468[M+H]+, 466[M−H]−

$^1$H NMR (600 MHz, DMSO-d$_6$) δppm 1.23-1.28 (3H, m), 2.30-2.36 (6H, m), 3.22-3.29 (3H, m), 3.60-3.69 (2H, m), 4.46 (2H, s), 7.19-7.32 (6H, m), 7.36-7.41 (3H, m), 7.46-7.50 (1H, m), 7.57-7.60 (2H, m), 8.28-8.45 (1H, m), 10.71-10.91 (1H, m)

Example 26

N-Ethyl-N'-(4-{[4-(5-methoxypyrazin-2-yl)-1,3-thiazol-2-yl]methyl}-2,5-dimethylphenyl)-N-methylimidoformamide hydrobromide

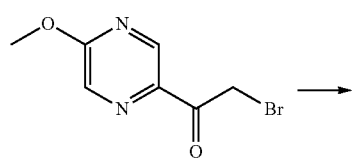

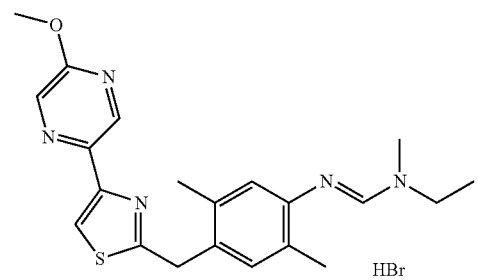

To a 2-propanol (1.0 mL) solution of the compound (30 mg) obtained by the technique of Reference Example 1-5, the compound (26 mg) obtained by the technique of Reference Example 16 was added, and the resultant was stirred at 80° C. for 2 hours, followed by standing to cool to room temperature. The deposited solid was collected by filtration to obtain the title compound (14 mg) as a yellow solid.

MS (ESI-APCI): 396 [M+H]+

$^1$H NMR (600 MHz, DMSO-d$_6$) δppm 1.27 (3H, s), 2.22-2.37 (6H, m), 3.12-3.25 (3H, m), 3.55-3.70 (2H, m), 4.02 (3H, s), 4.89 (2H, s), 7.13 (1H, s), 7.20-7.34 (1H, m), 7.47-7.63 (1H, m), 8.46 (2H, d, J=1.2 Hz), 9.01 (1H, d, J=1.2 Hz), 10.41-10.65 (1H, m)

Example 27

N'-[4-({4-[(4-Chlorophenyl)carbonyl]-1,3-thiazol-2-yl}methyl)-2,5-dimethylphenyl]-N-ethyl-N-methylimidoformamide hydrobromide

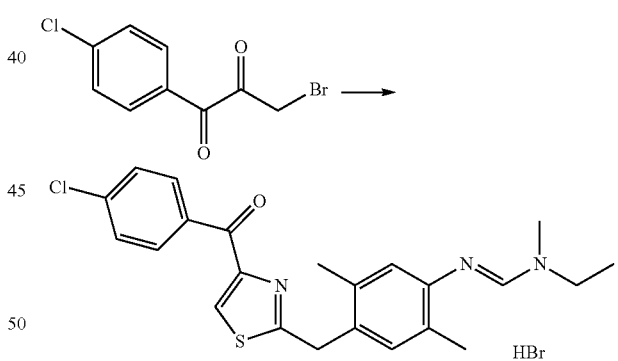

To a 2-propanol (1.0 mL) solution of the compound (35 mg) obtained by the technique of Reference Example 1-5, 1-(4-Chlorophenyl)propane-1,2-dione (46 mg) was added, and the resultant was stirred at 80° C. for 2 hours, followed by standing to cool to room temperature. The reaction solution was concentrated. 2-Propanol/diethyl ether (=1/10) was added to the obtained residue, and the deposited solid was collected by filtration to obtain the title compound (35 mg) as a light brown solid.

MS (ESI-APCI): 426 [M+H]+

$^1$H NMR (600 MHz, DMSO-d$_6$) δppm 1.22-1.31 (3H, m), 2.24-2.34 (6H, m), 3.16-3.31 (3H, m), 3.57-3.66 (2H, m), 4.44 (2H, s), 7.22-7.26 (1H, m), 7.32 (1H, s), 7.63 (2H, d, J=8.7 Hz), 8.12 (2H, d, J=8.7 Hz), 8.27-8.45 (1H, m), 8.48 (1H, s), 10.42-10.58 (1H, m)

Example 28

N-Ethyl-N'-{4-[(4-ethyl-1,3-thiazol-2-yl)methyl]-2,5-dimethylphenyl}-N-methylimidoformamide dihydrochloride

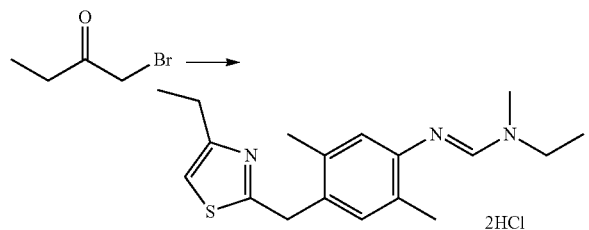

To a 2-propanol (2.0 mL) solution of the compound (30 mg) obtained by the technique of Reference Example 1-5, 1-bromo-2-butanone (17 mg) was added, and the resultant was stirred at 80° C. for 1 hour. The reaction solution was concentrated, and the obtained residue was purified by preparative silica gel thin-layer chromatography (NH-type silica gel; hexane/ethyl acetate=75/25). A 4 mol/L hydrogen chloride/ethyl acetate solution (1.0 mL) was added to an ethyl acetate (0.5 mL) solution of the obtained pale yellow oil (14 mg), and the resultant was stirred at room temperature for 1 hour. The reaction solution was concentrated under reduced pressure to obtain the title compound (17 mg) as a pale yellow solid.

MS (ESI-APCI): 316[M+H]+

$^1$H NMR (600 MHz, METHANOL-d$_3$) δppm 1.32-1.41 (6H, m), 2.28-2.38 (6H, m), 2.88 (2H, q, J=7.4 Hz), 3.29 (3H, br. s.), 3.65-3.74 (1H, m), 4.55 (2H, s), 7.26 (1H, s), 7.31 (1H, s), 7.46 (1H, s) 8.18-8.37 (1H, m)

Example 29

N'-{4-[(4-Tert-butyl-1,3-thiazol-2-yl)methyl]-2,5-dimethylphenyl}-N-ethyl-N-methylimidoformamide dihydrochloride

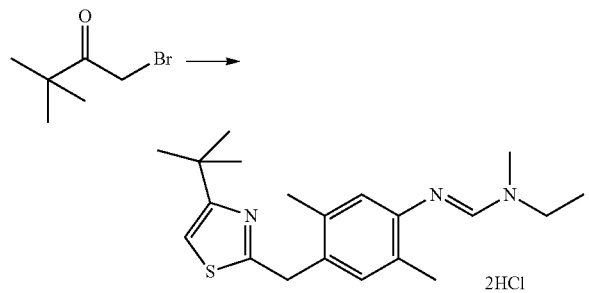

To a 2-propanol (2.0 mL) solution of the compound (30 mg) obtained by the technique of Reference Example 1-5, 1-bromo-3,3-dimethyl-2-butanone (20 mg) was added, and the resultant was stirred at 80° C. for 1 hour. The reaction solution was concentrated, and the obtained residue was purified by preparative silica gel thin-layer chromatography (NH-type silica gel; hexane/ethyl acetate=75/25). A 4 mol/L hydrogen chloride/ethyl acetate solution (1.0 mL) was added to an ethyl acetate (0.5 mL) solution of the obtained pale yellow oil, and the resultant was stirred at room temperature for 1 hour. The reaction solution was concentrated under reduced pressure to obtain the title compound (17 mg) as a pale yellow solid.

MS (ESI-APCI): 344[M+H]+

$^1$H NMR (600 MHz, METHANOL-d$_3$) δppm 1.33-1.42 (12H, m), 2.28-2.37 (6H, m), 3.29 (3H, br. s.), 3.64-3.73 (2H, m), 4.50 (2H, s), 7.24 (1H, s), 7.26-7.30 (1H, m), 7.32 (1H, s), 8.17-8.36 (1H, m)

Example 30

N'-{2,5-Dimethyl-4-[(4-{[(4-methylphenyl)sulfonyl]methyl}-1,3-thiazol-2-yl)methyl]phenyl}-N-ethyl-N-methylimidoformamide dihydrochloride

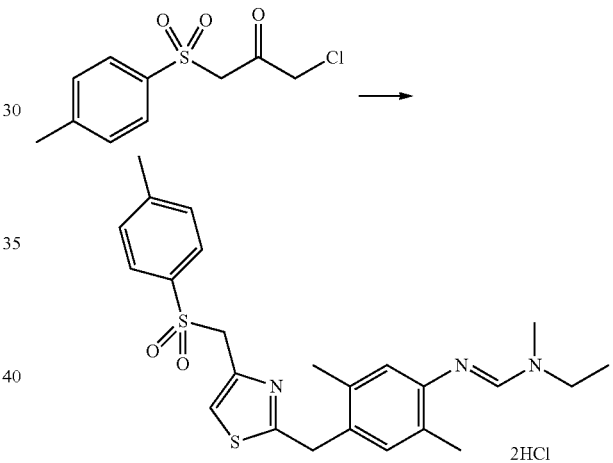

To a 2-propanol (2.0 mL) solution of the compound (30 mg) obtained by the technique of Reference Example 1-5, 3-chloro-1-((4-methylphenyl)sulfonyl)acetone (28 mg) was added, and the resultant was stirred at 80° C. for 3 hours. The reaction solution was concentrated, and the obtained residue was purified by preparative silica gel thin-layer chromatography (NH-type silica gel; hexane/ethyl acetate=50/50). A 4 mol/L hydrogen chloride/ethyl acetate solution (1.0 mL) was added to an ethyl acetate (0.5 mL) solution of the obtained pale yellow oil, and the resultant was stirred at room temperature for 1 hour. The reaction solution was concentrated under reduced pressure to obtain the title compound (17 mg) as a pale yellow solid.

MS (ESI-APCI): 456[M+H]+, 454[M−H]−

$^1$H NMR (600 MHz, METHANOL-d$_3$) δppm 1.35-1.40 (3H, m), 2.23 (3H, s), 2.30-2.35 (3H, m), 2.44 (3H, s), 3.28 (3H, s), 3.64-3.72 (2H, m), 4.27 (2H, s), 4.63 (2H, s), 7.17 (1H, s), 7.23 (1H, s), 7.27 (1H, s), 7.37 (2H, d, J=8.3 Hz), 7.61 (2H, d, J=8.3 Hz), 8.13-8.33 (1H, m)

Example 31

Ethyl {2-[4-({(E)-[ethyl(methyl)amino]methylidene}amino)-2,5-dimethylbenzyl]-1,3-thiazol-4-yl}carbamate dihydrochloride

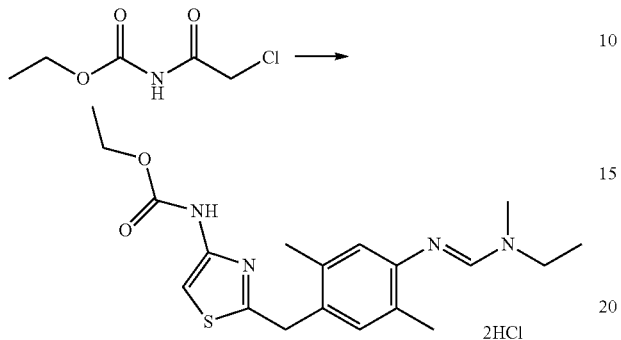

To a 2-propanol (2.0 mL) solution of the compound (30 mg) obtained by the technique of Reference Example 1-5, ethyl N-(2-chloroacetyl)carbamate (19 mg) was added, and the resultant was stirred at 80° C. for 3 hours. The reaction solution was concentrated, and the obtained residue was purified by preparative silica gel thin-layer chromatography (NH-type silica gel; hexane/ethyl acetate=50/50). A 4 mol/L hydrogen chloride/ethyl acetate solution (1.0 mL) was added to an ethyl acetate (0.5 mL) solution of the obtained pale yellow oil, and the resultant was stirred at room temperature for 1 hour. The reaction solution was concentrated under reduced pressure to obtain the title compound (4.0 mg) as a pale yellow solid.

MS (ESI-APCI): 375[M+H]+, 373[M−H]−

$^1$H NMR (600 MHz, METHANOL-$d_3$) δppm 1.27-1.32 (3H, m), 1.33-1.40 (3H, m), 2.26-2.35 (6H, m), 3.27 (3H, br. s.), 3.64-3.71 (2H, m), 4.15-4.22 (2H, m), 4.26 (2H, s), 7.06 (1H, br. s.), 7.16 (1H, br. s.), 7.25 (1H, s), 8.11-8.33 (1H, m)

Example 32

N'-(2,5-Dimethyl-4-{[4-(propan-2-yloxy)-1,3-thiazol-2-yl]methyl}phenyl)-N-ethyl-N-methylimidoformamide

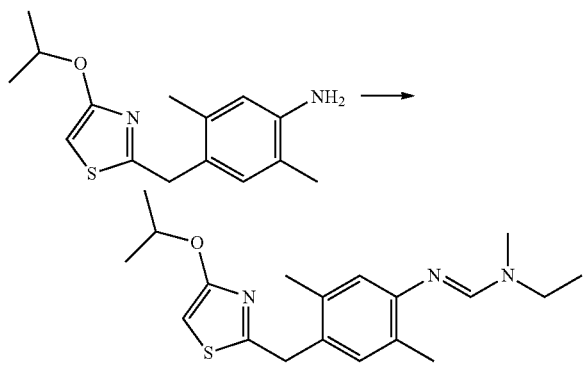

To a chloroform (1.0 mL) solution of N-ethyl-N-methylformamide (22 mg), in a nitrogen atmosphere, oxalyl chloride (20 μL) was added, and the resultant was stirred at room temperature for 10 minutes. Then, a chloroform (1.0 mL) solution of the compound (49 mg) obtained by the technique of Reference Example 17-2 was added thereto, and the resultant was stirred at room temperature for 2 hours. A saturated aqueous solution of sodium bicarbonate was added thereto, and the resultant was stirred at room temperature for 30 minutes, followed by extraction with chloroform. An organic layer was separated using a phase separator, and the solvent was distilled off under reduced pressure. The obtained residue was purified by preparative silica gel thin-layer chromatography (NH-type silica gel; hexane/ethyl acetate=66/34) and then further purified by preparative LC to obtain the title compound (15 mg) as a colorless oil.

MS (ESI-APCI): 346[M+H]+

$^1$H NMR (600 MHz, CHLOROFORM-d) δppm 1.21 (3H, t, J=7.2 Hz), 1.35 (6H, d, J=6.2 Hz), 2.21 (3H, s), 2.23 (3H, s), 2.99 (3H, s), 3.24-3.48 (2H, m), 4.12 (2H, s), 4.63 (1H, dt, J=12.1, 6.1 Hz), 5.87 (1H, s), 6.58 (1H, s), 7.00 (1H, s), 7.43 (1H, br. s.)

Example 33

N'-(4-{[5-(2,2-Dimethylpropanoyl)-4-phenyl-1,3-thiazol-2-yl]methyl}-2,5-dimethylphenyl)-N-ethyl-N-methylimidoformamide dihydrochloride

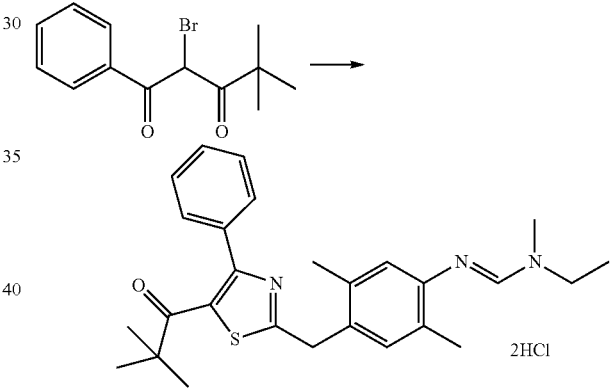

To a 2-propanol (1.0 mL) solution of the compound (25 mg) obtained by the technique of Reference Example 1-5, 2-bromo-4,4-dimethyl-1-phenyl-pentane-1,3-dione (27 mg) was added, and the resultant was stirred at 80° C. for 2 hours. A saturated aqueous solution of sodium bicarbonate was added thereto, followed by extraction with ethyl acetate. The organic layer was dried over magnesium sulfate, and the desiccant was filtered off. Then, the solvent was distilled off under reduced pressure. The obtained residue was purified by silica gel column chromatography (OH-type silica gel; chloroform/methanol-gradient elution=100/0→91/9) and then further purified (NH-type silica gel; hexane/ethyl acetate-gradient elution=100/0→75/25). Ethyl acetate and a 4 mol/L hydrogen chloride/ethyl acetate solution were added to the obtained oil, and the resultant was then concentrated under reduced pressure to obtain the title compound (11 mg) as a colorless solid.

MS (ESI-APCI): 448[M+H]+, 446[M−H]−

$^1$H NMR (600 MHz, DMSO-$d_6$) δppm 1.13 (9H, s), 1.23-1.27 (3H, m), 2.29-2.33 (6H, m), 3.21-3.30 (3H, m), 3.63-3.63 (2H, m), 4.43 (2H, s), 7.22-7.26 (1H, m), 7.34 (1H, s), 7.39-7.49 (5H, m), 8.27-8.44 (1H, m), 10.65-10.84 (1H, m)

Example 34

{2-[4-({(E)-[Ethyl(methyl)amino]methylidene}amino)-2,5-dimethylbenzyl]-1,3-thiazol-4-yl}methyl acetate dihydrochloride

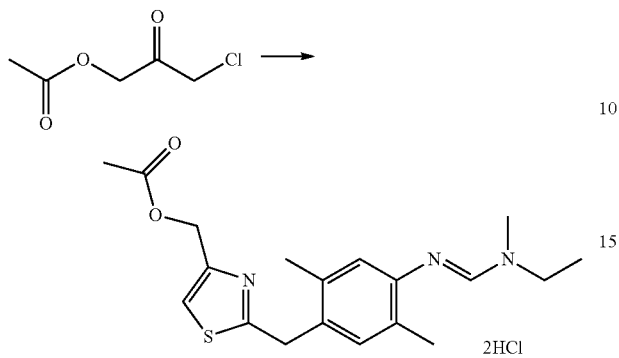

To a 2-propanol (1.0 mL) solution of the compound (28 mg) obtained by the technique of Reference Example 1-5, 1-acetoxy-3-chloroacetone (13 μL) was added, and the resultant was stirred at 80° C. for 2 hours. A saturated aqueous solution of sodium bicarbonate was added thereto, followed by extraction with ethyl acetate. The organic layer was dried over magnesium sulfate, and the desiccant was filtered off. Then, the solvent was distilled off under reduced pressure. The obtained residue was purified by silica gel column chromatography (NH-type silica gel; hexane/ethyl acetate-gradient elution=100/0→75/25). Ethyl acetate and a 4 mol/L hydrogen chloride/ethyl acetate solution were added to the obtained oil, and the resultant was then concentrated under reduced pressure to obtain the title compound (31 mg) as a colorless solid.

MS (ESI-APCI): 360[M+H]+

$^1$H NMR (600 MHz, DMSO-d$_6$) δppm 1.23-1.28 (3H, m), 2.06 (3H, s), 2.25-2.29 (6H, m), 3.19-3.30 (3H, m), 3.58-3.66 (2H, m), 4.32 (2H, s), 5.08 (2H, s), 7.18-7.23 (1H, m), 7.26 (1H, s), 7.51 (1H, s), 8.27-8.46 (1H, m), 10.51-10.74 (1H, m)

Example 35

Ethyl 2-[4-({(E)-[ethyl(methyl)amino]methylidene}amino)-2,5-dimethylbenzyl]-1,3-thiazole-4-carboxylate

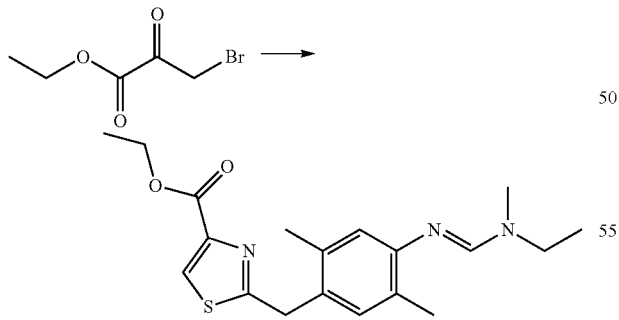

To a 2-propanol (2.0 mL) solution of the compound (69 mg) obtained by the technique of Reference Example 1-5, ethyl bromopyruvate (51 mg) was added, and the resultant was stirred at 80° C. for 1 hour. After standing to cool to room temperature, a saturated aqueous solution of sodium bicarbonate was added thereto, followed by extraction with chloroform. An organic layer was separated using a phase separator, and the solvent was distilled off under reduced pressure. The obtained residue was purified by silica gel column chromatography (NH-type silica gel; hexane/ethyl acetate-gradient elution=90/10→70/30) to obtain the title compound (68 mg) as a yellow oil.

MS (ESI-APCI): 360[M+H]+

$^1$H NMR (600 MHz, CHLOROFORM-d) δppm 1.21 (3H, t, J=7.2 Hz), 1.41 (3H, t, J=7.0 Hz), 2.18 (3H, s), 2.23 (3H, s), 3.00 (3H, s), 3.26-3.43 (2H, m), 4.28 (2H, s), 4.43 (2H, q, J=7.3 Hz), 6.59 (1H, s), 7.01 (1H, s), 7.39-7.49 (1H, m), 8.00 (1H, s)

Example 36

N'-{2,5-Dimethyl-4-[(4-{[4-(trifluoromethyl)phenyl]carbonyl}-1,3-thiazol-2-yl)methyl]phenyl}-N-ethyl-N-methylimidoformamide hydrobromide

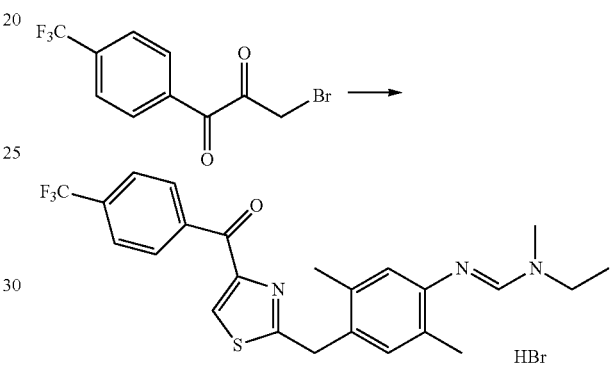

To a 2-propanol (1.0 mL) solution of the compound (43 mg) obtained by the technique of Reference Example 1-5, the compound (72 mg) obtained by the technique of Reference Example 18 was added, and the resultant was stirred at 80° C. for 3 hours, followed by standing to cool to room temperature. The reaction solution was concentrated. 2-Propanol/diethyl ether (=1/12) was added to the obtained residue, and the deposited solid was collected by filtration and washed with diethyl ether to obtain the title compound (48 mg) as a pale yellow solid.

MS (ESI-APCI): 460[M+H]+, 458[M-H]-

$^1$H NMR (600 MHz, DMSO-d$_6$) δppm 1.17-1.27 (3H, m), 2.26 (6H, d, J=6.6 Hz), 3.16 (3H, s), 3.53-3.62 (2H, m), 4.40 (2H, s), 7.18-7.24 (1H, m), 7.26-7.31 (1H, m), 7.86-7.93 (2H, m), 8.16-8.23 (2H, m), 8.25-8.43 (1H, m), 8.51 (1H, s), 10.39-10.54 (1H, m)

Example 37

N'-(2,5-Dimethyl-4-{[4-(5-methylpyrazin-2-yl)-1,3-thiazol-2-yl]methyl}phenyl)-N-ethyl-N-methylimidoformamide dihydrochloride

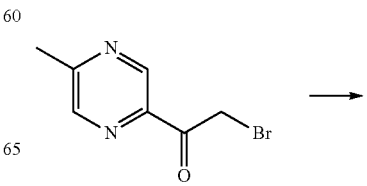

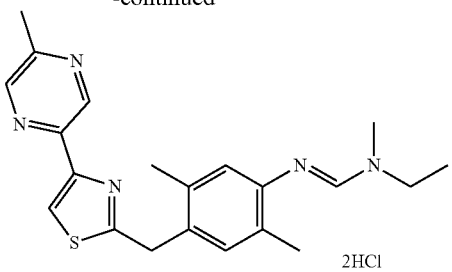

2HCl

To a 2-propanol (2.0 mL) solution of the compound (32 mg) obtained by the technique of Reference Example 1-5, the compound (39 mg) obtained by the technique of Reference Example 19 was added, and the resultant was stirred at 80° C. for 2 hours, followed by standing to cool to room temperature. The reaction solution was concentrated. 2-Propanol/diethyl ether (=1/12) was added to the obtained residue, and the deposited solid was collected by filtration and washed with diethyl ether. The obtained brown solid was purified by preparative LC. A 4 mol/L hydrogen chloride/ethyl acetate solution (1.0 mL) was added to an ethyl acetate (0.5 mL) solution of the obtained brown oil (28 mg), and the resultant was stirred at room temperature for 20 minutes. The reaction solution was concentrated under reduced pressure to obtain the title compound (31 mg) as a brown solid.

MS (ESI-APCI): 380[M+H]+

1H NMR (600 MHz, DMSO-$d_6$) δppm 1.26 (3H, d, J=7.0 Hz), 2.27-2.34 (6H, m), 2.53 (3H, s), 3.20-3.31 (3H, m), 3.62 (2H, s), 4.43 (2H, s), 7.20-7.27 (1H, m), 7.32 (1H, s), 8.19 (1H, s), 8.27-8.47 (1H, m), 8.57 (1H, s), 9.07 (1H, s), 10.70-10.90 (1H, m)

Example 38

N'-[4-({4-[(4-Chlorophenyl)(hydroxy)methyl]-1,3-thiazol-2-yl}methyl)-2,5-dimethylphenyl]-N-ethyl-N-methylimidoformamide

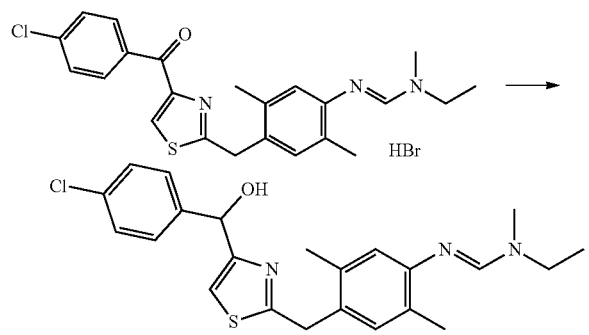

HBr

To a methanol (1.0 mL) solution of the compound (24 mg) obtained by the technique of Example 27, under ice cooling, sodium borohydride (1.0 mg) was added, and the resultant was stirred for 45 minutes under ice cooling and then stirred at room temperature for 15 minutes. The reaction solution was concentrated under reduced pressure. The obtained residue was purified by preparative LC to obtain the title compound (4.0 mg) as a yellow oil.

MS (ESI-APCI): 428[M+H]+, 426[M+H]+

1H NMR (600 MHz, CHLOROFORM-d) δppm 1.21 (3H, t, J=7.0 Hz), 2.20 (3H, s), 2.23 (3H, s), 3.01 (3H, br. s.), 3.25-3.58 (2H, m), 4.19 (2H, s), 5.85 (1H, s), 6.59 (1H, br. s.), 6.75 (1H, s) 6.99 (1H, s), 7.30-7.35 (2H, m), 7.36-7.40 (2H, m), 7.41-7.47 (1H, m)

Example 39

2-[4-({(E)-[Ethyl(methyl)amino]methylidene}amino)-2,5-dimethylbenzyl]-1,3-thiazole-4-carboxylic acid

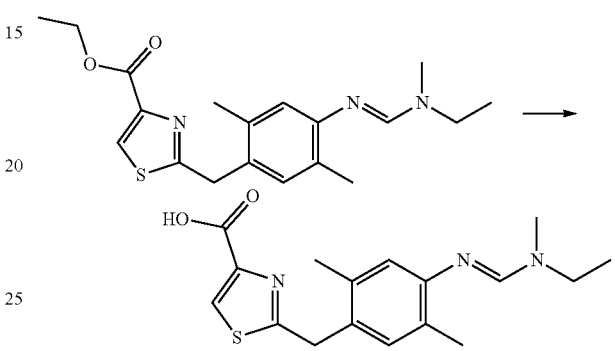

To a 1:1 water/tetrahydrofuran (2.0 mL) solution of the compound (28 mg) obtained by the technique of Example 35, lithium hydroxide monohydrate (4.9 mg) was added, and the resultant was stirred at room temperature for 24 hours. A 1 mol/L aqueous hydrochloric acid solution was added to the reaction solution, followed by extraction with chloroform. Then, an aqueous layer was purified using a synthetic adsorbent (HP-20) to obtain the title compound (29 mg) as a pale yellow solid.

MS (ESI-APCI): 332[M+H]+, 330[M−H]−

1H NMR (600 MHz, METHANOL-$d_3$) δppm 1.23-1.35 (3H, m), 2.13-2.33 (6H, m), 3.21 (3H, br. s.), 3.52-3.63 (2H, m), 4.29 (2H, br. s.), 7.00 (1H, br. s.), 7.19 (1H, br. s.), 7.82 (1H, br. s.), 7.91-7.99 (1H, m), 8.00-8.13 (1H, m)

Example 40

N-Ethyl-N'-(4-{[4-(hydroxymethyl)-1,3-thiazol-2-yl]methyl}-2,5-dimethylphenyl)-N-methylimidoformamide dihydrochloride

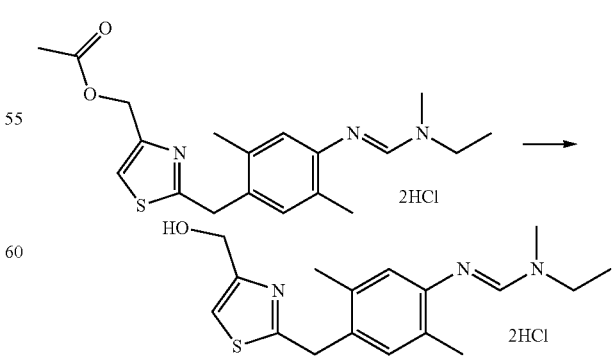

2HCl

To a methanol (1.0 mL) solution of the compound (20 mg) obtained by the technique of Example 34, under ice cooling, a 28% sodium methoxide/methanol solution (31 mg) was added, and the resultant was stirred for 2 hours under ice cooling. Water was added to the reaction solution, followed by extraction with ethyl acetate. The organic layer was dried over magnesium sulfate, and the desiccant was filtered off. Then, the solvent was distilled off under reduced pressure. Ethyl acetate and a 4 mol/L hydrogen chloride/ethyl acetate solution were added to the obtained yellow oil, and the resultant was then concentrated under reduced pressure to obtain the title compound (13 mg) as a colorless solid.

MS (ESI-APCI): 318.2[M+H]+

¹H NMR (600 MHz, DMSO-d₆) δppm 1.23-1.29 (3H, m), 2.25-2.29 (6H, m), 3.20-3.29 (3H, m), 3.60-3.65 (2H, m), 4.28 (2H, s), 4.50 (2H, s), 7.18-7.21 (1H, m), 7.23-7.26 (2H, m), 8.27-8.44 (1H, m), 10.54-10.70 (1H, m)

Example 41

4-{2-[4-({(E)-[Ethyl(methyl)amino]methylidene}amino)-2,5-dimethylbenzyl]-1,3-thiazol-4-yl}-N-methylbenzamide Example 42

N-Ethyl-4-{2-[4-({(E)-[ethyl(methyl)amino]methylidene}amino)-2,5-dimethylbenzyl]-1,3-thiazol-4-yl}-N-methylbenzamide

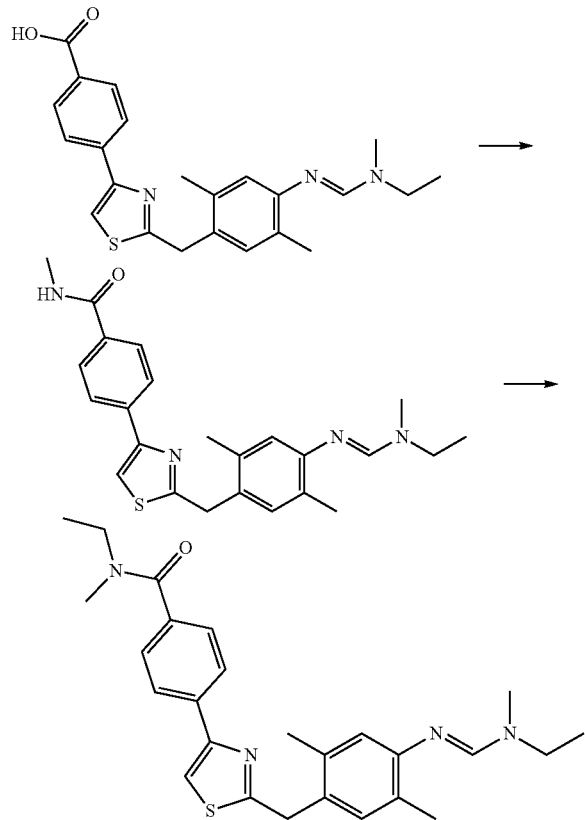

To a N,N-dimethylformamide (1.0 mL) solution of the compound (76 mg) obtained by the technique of Example 15, methylamine hydrochloride (35 mg), WSC.HCl (54 mg), HOBt.H₂O (43 mg) and triethylamine (80 μL) were added, and the resultant was stirred at room temperature for 4 hours. Water was added to the reaction solution, followed by extraction with chloroform. An organic layer was separated using a phase separator, and the solvent was distilled off under reduced pressure. The obtained residue was purified by preparative silica gel thin-layer chromatography (OH-type silica gel; chloroform/methanol=91/9) and silica gel column chromatography (OH-type silica gel; hexane/ethyl acetate-gradient elution=90/10→0/100) and then further purified by preparative LC to obtain the compound of Example 41 (10 mg) as a white solid. Also, the compound of Example 42 (4 mg) was obtained as a pale yellow oil.

Example 41

MS (ESI-APCI): 421[M+H]+, 419[M−H]

¹H NMR (600 MHz, CHLOROFORM-d) δppm 1.21 (3H, t, J=7.2 Hz), 2.24 (3H, s), 2.25 (3H, s), 3.00 (3H, s), 3.04 (3H, d, J=5.0 Hz), 3.26-3.47 (2H, m), 4.29 (2H, s), 6.10-6.18 (1H, m), 6.60 (1H, s), 7.05 (1H, s), 7.40 (1H, s), 7.45 (1H, br. s.), 7.81 (2H, d, J=8.3 Hz), 7.96 (2H, d, J=8.3 Hz)

Example 42

MS (ESI-APCI): 449[M+H]+

¹H NMR (600 MHz, CHLOROFORM-d) δppm 1.21 (3H, t, J=7.2 Hz), 1.26 (3H, s), 2.19-2.30 (6H, m), 2.91-3.14 (6H, m), 3.25-3.64 (4H, m), 4.29 (2H, s), 6.60 (1H, s), 7.05 (1H, s), 7.35 (1H, s), 7.45 (3H, m, J=7.0 Hz), 7.90-7.94 (2H, m)

Example 43

2-[4-({(E)-[Ethyl(methyl)amino]methylidene}amino)-2,5-dimethylbenzyl]-N-(propan-2-yl)-1,3-thiazole-4-carboxamide dihydrochloride

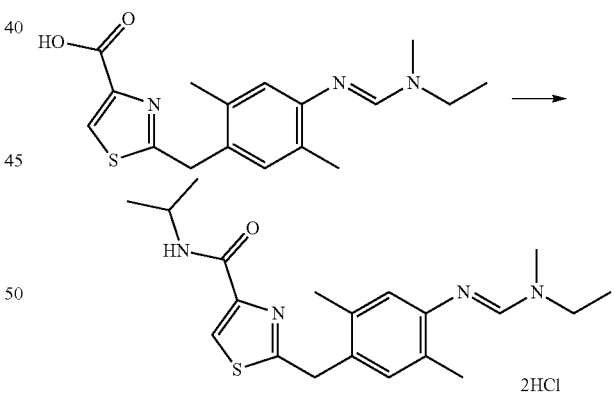

To a N,N-dimethylformamide (1.0 mL) solution of the compound (31 mg) obtained by the technique of Example 39, 2-propylamine (10 μL) and N,N-diisopropylethylamine (80 μL) were added, then HATU (42 mg) was added, and the resultant was stirred at room temperature for 2 hours. A saturated aqueous solution of sodium bicarbonate was added to the reaction solution, followed by extraction with chloroform. An organic layer was separated using a phase separator, and the solvent was distilled off under reduced pressure. The obtained residue was purified by silica gel column chromatography (OH-type silica gel; hexane/ethyl acetate-gradient elution=100/0→70/30). A 4 mol/L hydrogen chloride/ethyl acetate solution (1.0 mL) was added to an ethyl acetate (0.5 mL) solution of the obtained yellow oil, and the resultant was stirred at room temperature for 1 hour. The reaction solution was concentrated under reduced pressure to obtain the title compound (18 mg) as a pale yellow foam.

MS (ESI-APCI): 373[M+H]+, 371[M–H]–

$^1$H NMR (600 MHz, DMSO-d$_6$) δppm 1.17 (6H, d, J=6.6 Hz), 1.22-1.30 (3H, m), 2.23-2.31 (6H, m), 3.20-3.29 (3H, m), 3.59-3.67 (2H, m), 4.03-4.13 (1H, m), 4.36 (2H, s), 7.22-7.26 (1H, m), 7.28 (1H, s), 7.96 (1H, d, J=8.7 Hz), 8.07 (1H, s), 8.28-8.46 (1H, m), 10.53-10.71 (1H, m)

Example 44

N-Benzyl-2-[4-({(E)-[ethyl(methyl)amino]methylidene}amino)-2,5-dimethylbenzyl]-1,3-thiazole-4-carboxamide dihydrochloride

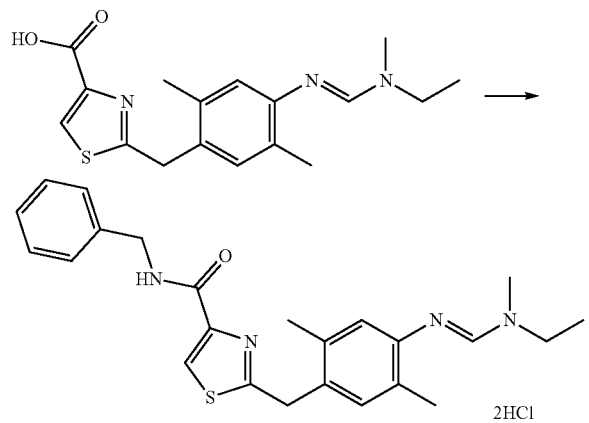

To a N,N-dimethylformamide (1.0 mL) solution of the compound (28 mg) obtained by the technique of Example 39, benzylamine (10 μL) and N,N-diisopropylethylamine (70 μL) were added, then HATU (38 mg) was added, and the resultant was stirred at room temperature for 2 hours. A saturated aqueous solution of sodium bicarbonate was added to the reaction solution, followed by extraction with chloroform. An organic layer was separated using a phase separator, and the solvent was distilled off under reduced pressure. The obtained residue was purified by silica gel column chromatography (OH-type silica gel; hexane/ethyl acetate-gradient elution=100/0→60/40) and then further purified by preparative silica gel thin-layer chromatography (NH-type silica gel; hexane/ethyl acetate=66/34). A 4 mol/L hydrogen chloride/ethyl acetate solution (1.0 mL) was added to an ethyl acetate (0.5 mL) solution of the obtained colorless oil (9.0 mg), and the resultant was stirred at room temperature for 1 hour. The reaction solution was concentrated under reduced pressure to obtain the title compound (10 mg) as a white solid.

MS (ESI-APCI): 421[M+H]+, 419[M–H]–

$^1$H NMR (600 MHz, DMSO-d$_6$) δppm 1.22-1.29 (3H, m), 2.25-2.30 (6H, m), 3.20-3.29 (3H, m), 3.59-3.65 (2H, m), 4.36 (2H, s), 4.45 (2H, d, J=6.6 Hz), 7.21-7.26 (2H, m), 7.28-7.33 (5H, m), 8.09-8.16 (1H, m), 8.27-8.45 (1H, m), 8.85 (1H, t, J=6.2 Hz), 10.53-10.70 (1H, m)

Example 45

N'-{4-[(4-Cyclopropyl-1,3-thiazol-2-yl)methyl]-2,5-dimethylphenyl}-N-ethyl-N-methylimidoformamide dihydrochloride

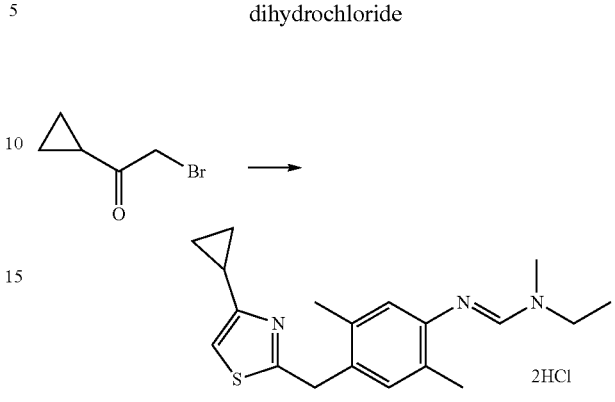

To a 2-propanol (1.0 mL) solution of the compound (26 mg) obtained by the technique of Reference Example 1-5, 2-bromo-1-cyclopropylethan-1-one (16 mg) was added, and the resultant was stirred at 80° C. for 30 minutes. After standing to cool to room temperature, a saturated aqueous solution of sodium bicarbonate was added thereto, followed by extraction with chloroform. An organic layer was separated using a phase separator, and the solvent was distilled off under reduced pressure. The obtained residue was purified by silica gel column chromatography (NH-type silica gel; hexane/ethyl acetate-gradient elution=95/5→70/30). A 4 mol/L hydrogen chloride/ethyl acetate solution (1.0 mL) was added to an ethyl acetate (0.5 mL) solution of the obtained yellow oil (22 mg), and the resultant was stirred at room temperature for 1 hour. The reaction solution was concentrated under reduced pressure to obtain the title compound (25 mg) as a white solid.

MS (ESI-APCI): 328[M+H]+

$^1$H NMR (600 MHz, DMSO-d$_6$) δppm 0.74-0.77 (2H, m), 0.85-0.89 (2H, m), 1.25 (3H, q, J=7.3 Hz), 1.99-2.05 (1H, m), 2.24-2.29 (6H, m), 3.21-3.29 (3H, m), 3.60-3.64 (2H, m), 4.23 (2H, s), 7.07 (1H, s), 7.18-7.21 (1H, m), 7.22 (1H, s), 8.23-8.45 (1H, m), 10.62-10.82 (1H, m)

Example 46

N'-(2,5-Dimethyl-4-{[4-(trifluoromethyl)-1,3-thiazol-2-yl]methyl}phenyl)-N-ethyl-N-methylimidoformamide dihydrochloride

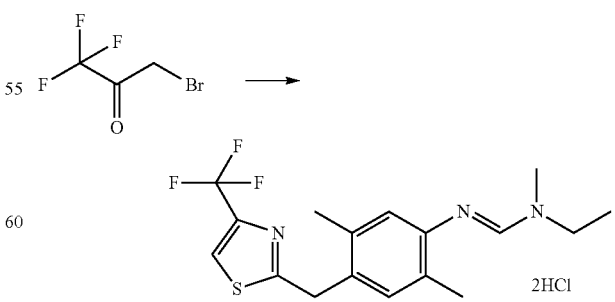

To a 2-propanol (1.0 mL) solution of the compound (23 mg) obtained by the technique of Reference Example 1-5, 3-bromo-1,1,1-trifluoroacetone (17 mg) was added, and the resultant was stirred at 80° C. for 8 hours. Then, a catalytic amount of p-toluenesulfonic acid monohydrate was added thereto, and the resultant was stirred at 80° C. for 6 hours. After standing to cool to room temperature, a saturated aqueous solution of sodium bicarbonate was added thereto, followed by extraction with chloroform. An organic layer was separated using a phase separator, and the solvent was distilled off under reduced pressure. The obtained residue was purified by silica gel column chromatography (NH-type silica gel; hexane/ethyl acetate-gradient elution=97/3→80/20). A 4 mol/L hydrogen chloride/ethyl acetate solution (1.0 mL) was added to an ethyl acetate (0.5 mL) solution of the obtained yellow oil (15 mg), and the resultant was stirred at room temperature for 1 hour. The reaction solution was concentrated under reduced pressure to obtain the title compound (17 mg) as a pale yellow foam.

MS (ESI-APCI): 356[M+H]+, 354[M−H]−

$^1$H NMR (600 MHz, DMSO-d$_6$) δppm 1.22-1.29 (3H, m), 2.24-2.31 (6H, m), 3.21-3.29 (3H, m), 3.57-3.69 (2H, m), 4.41 (2H, s), 7.19-7.25 (1H, m), 7.29 (1H, s), 8.25-8.47 (2H, m), 10.61-10.84 (1H, m)

Example 47

N'-(2,5-Dimethyl-6-{[4-(4-methylphenyl)-1,3-thiazol-2-yl]methyl}pyridin-3-yl)-N-ethyl-N-methylimidoformamide dihydrochloride

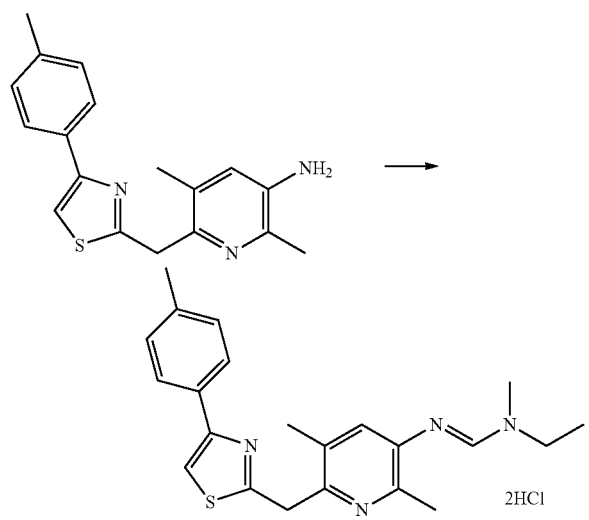

To a chloroform (0.5 mL) solution of N-ethyl-N-methylformamide (11 mg), in a nitrogen atmosphere, oxalyl chloride (10 μL) was added, and the resultant was stirred at room temperature for 10 minutes. Then, a chloroform (0.5 mL) solution of the compound (25 mg) obtained by the technique of Reference Example 20-7 was added thereto, and the resultant was stirred at room temperature for 1 hour. A saturated aqueous solution of sodium bicarbonate was added thereto, followed by extraction with chloroform. The organic layer was dried over magnesium sulfate, and the desiccant was filtered off. Then, the solvent was distilled off under reduced pressure. The obtained residue was purified by silica gel column chromatography (NH-type silica gel; hexane/ethyl acetate-gradient elution=100/0→50/50) to obtain the title compound (22 mg) as a yellow oil.

MS (ESI-APCI): 379[M+H]+, 401[M+Na]+

$^1$H NMR (600 MHz, CHLOROFORM-d) δppm 1.20-1.24 (3H, m), 2.28 (3H, s), 2.37 (3H, s), 2.51 (3H, s), 3.02 (3H, s), 3.28-3.38 (2H, m), 4.52 (2H, s), 6.83 (1H, s), 7.21 (2H, d, J=7.8 Hz), 7.25 (1H, s), 7.41-7.50 (1H, m), 7.77 (2H, d, J=7.8 Hz)

Example 48

N'-[4-(4,4'-Bi-1,3-thiazol-2-ylmethyl)-2,5-dimethylphenyl]-N-ethyl-N-methylimidoformamide hydrochloride

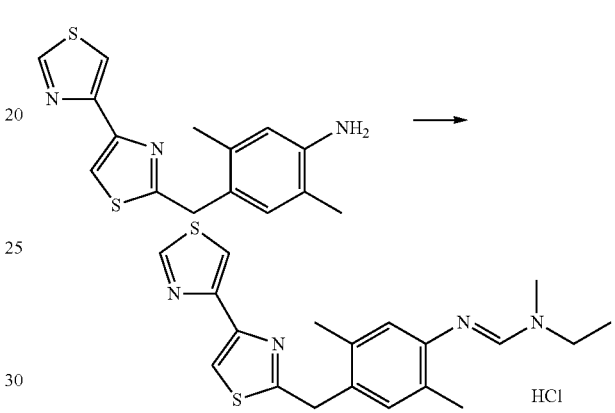

To an ethyl ether (1.0 mL) solution of N-ethyl-N-methylformamide (40 mg), at room temperature, phosphoryl chloride (30 μL) was added, and the resultant was stirred at room temperature for 45 minutes in a nitrogen atmosphere. The upper layer was removed from the reaction mixture. Ethyl ether was added to the lower layer, and the upper layer was removed. This operation was performed three times. Ethyl ether (1 mL) and the compound (50 mg) obtained by the technique of Reference Example 21-4 were added to the obtained oil at room temperature, and the resultant was stirred at room temperature for 2 hours and 20 minutes in a nitrogen atmosphere and stirred for 2 hours and 15 minutes under heating to reflux. The reaction mixture was cooled to room temperature and left overnight. Water was added thereto, and the resultant was adjusted to pH 9 with a saturated aqueous solution of sodium bicarbonate. An organic layer was separated and dried over anhydrous magnesium sulfate, and the solvent was distilled off under reduced pressure. The obtained residue was purified by silica gel column chromatography (eluent: chloroform:methanol=10:1). Ethyl acetate (1 mL), a 4.9 mol/L hydrogen chloride/ethyl acetate solution (0.1 mL) and ethanol were added thereto, and the solvent was distilled off under reduced pressure. Ethyl acetate was added to the obtained residue, and the solid was collected by filtration to obtain the title compound (35 mg) as a light brown solid.

$^1$H NMR (400 MHz, DMSO-d$_6$) δppm 1.22-1.30 (3H, m), 2.31 (6H, s), 3.23-3.30 (3H, m), 3.54-3.76 (2H, m), 4.39 (2H, s), 7.22-7.27 (1H, m), 7.30 (1H, s), 7.86 (1H, s), 7.98 (1H, d, J=2.0 Hz), 8.26-8.47 (1H, m), 9.18 (1H, d, J=2.0 Hz), 10.80-11.04 (1H, m)

Example 49

N'-(4-{[4-(4-Chlorophenyl)-1,3-thiazol-2-yl]methyl}-2,5-dimethylphenyl)-N-ethyl-N-methylimidoformamide hydrochloride

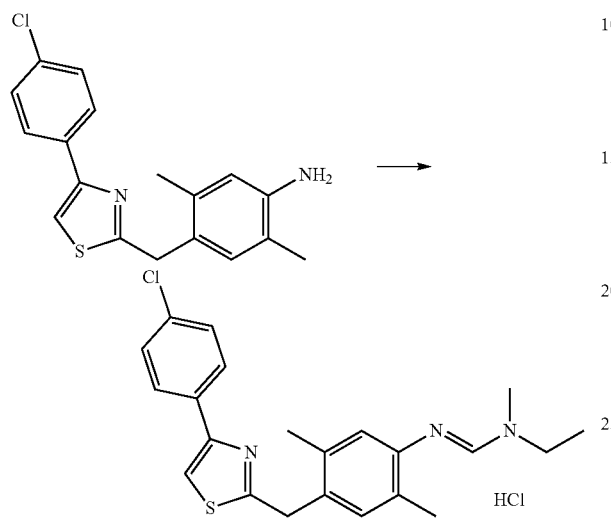

To a pyridine (1.0 mL) solution of the compound (0.10 g) obtained by the technique of Reference Example 22, at room temperature, N-ethyl-N-methylformamide (70 μL) and mesyl chloride (30 μL) were added, and the resultant was stirred at 60 to 70° C. for 1.5 hours. Mesyl chloride (30 μL) was added to the reaction mixture, and the resultant was stirred at 70 to 80° C. for 20 minutes. N-Ethyl-N-methylformamide (0.14 mL) and mesyl chloride (0.12 mL) were added thereto, and the resultant was stirred at the same temperature as above for 2 hours and 10 minutes. The solvent was distilled off under reduced pressure. Water and ethyl ether (20 mL) were added to the residue, and the resultant was adjusted to pH 8 with sodium bicarbonate. An organic layer was separated, and an aqueous layer was adjusted to pH 9 with potassium carbonate, followed by extraction with ethyl ether. The organic layer and the extract were combined, washed with water and a saturated aqueous solution of sodium chloride, and dried over anhydrous magnesium sulfate. The solvent was distilled off under reduced pressure. Ethyl ether, 4 mol/l-hydrogen chloride in dioxane (0.15 mL) and ethyl acetate were added to the obtained residue, and the solid was collected by filtration. Water and ethyl ether were added thereto, and an aqueous layer was saturated with potassium carbonate. An organic layer was separated, and an aqueous layer was subjected to extraction with ethyl ether. The organic layer and the extract were combined. Anhydrous magnesium sulfate and active carbon (20 mg) were added thereto, and the resultant was left for 30 minutes. Insoluble material was filtered off, and the solvent was distilled off under reduced pressure. Ethyl acetate and 4 mol/L hydrogen chloride in dioxane (0.15 mL) were added to the obtained residue, and the solid was collected by filtration to obtain the title compound (65 mg) as a brown solid.

$^1$H NMR (400 MHz, DMSO-$d_6$) δ ppm 1.21-1.29 (3H, m), 2.28-2.35 (6H, m), 3.21-3.31 (3H, m), 3.53-3.80 (2H, m), 4.39 (2H, s), 7.22-7.25 (1H, m), 7.30 (1H, s), 7.47-7.54 (2H, m), 7.92-7.98 (2H, m), 8.03 (1H, s), 8.28-8.46 (1H, m), 10.65-10.83 (1H, m)

Example 50

N'-{2,5-Dimethyl-4-[(4-methyl-1,3-thiazol-2-yl)methyl]phenyl}-N-ethyl-N-methylimidoformamide hydrochloride

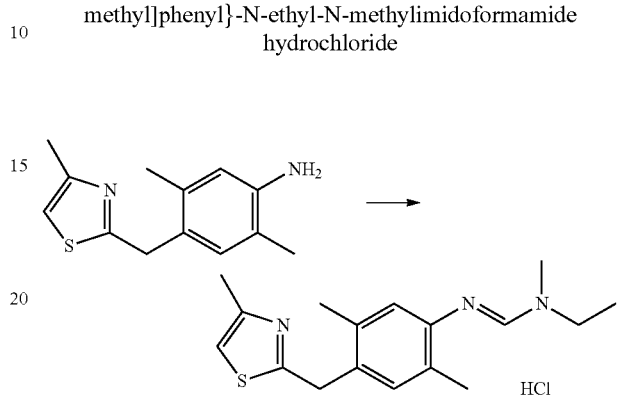

The title compound was obtained by the same technique as in Example 2 from the compound obtained by the technique of Reference Example 23.

$^1$H NMR (400 MHz, DMSO-$d_6$) δ ppm 1.21-1.30 (3H, m), 2.22-2.34 (9H, m), 3.20-3.29 (3H, m), 3.55-4.00 (2H, m), 4.27 (2H, s), 7.10 (1H, s), 7.17-7.22 (1H, m), 7.23 (1H, s), 8.26-8.45 (1H, m), 10.65-10.84 (1H, m)

Example 51

N'-(4-{[4-(4-Chlorophenyl)-1,3-thiazol-2-yl]methyl}phenyl)-N-ethyl-N-methylimidoformamide hydrochloride

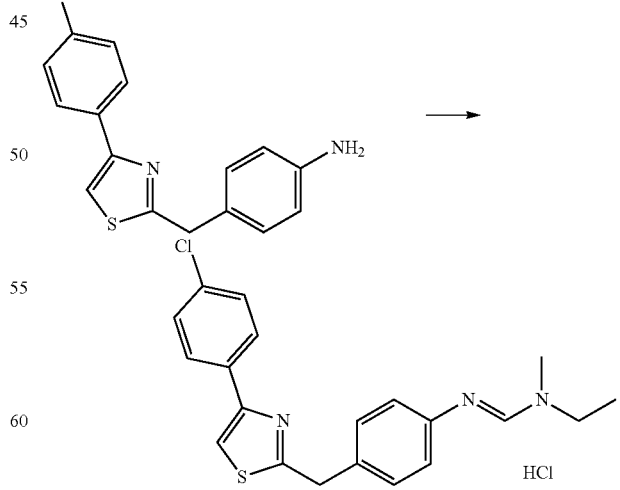

The title compound was obtained by the same technique as in Example 2 from the compound obtained by the technique of Reference Example 24.

¹H NMR (400 MHz, DMSO-d₆-D₂O) δ ppm 1.21-1.31 (3H, m), 3.19-3.34 (3H, m), 3.55-3.80 (2H, m), 4.41 (2H, s), 7.40-7.54 (6H, m), 7.90-8.00 (2H, m), 8.01 (1H, s), 8.57-8.73 (1H, m)

Example 52

N-Cyclohexyl-2-{[5-({(E)-[ethyl(methyl)amino]methylidene}amino)-3,6-dimethylpyridin-2-yl]methyl}-1,3-thiazole-4-carboxamide dihydrochloride

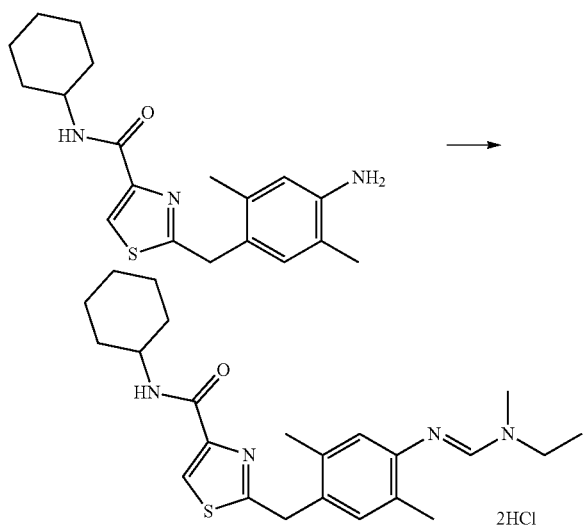

To a chloroform (2.0 mL) solution of N-ethyl-N-methylformamide (38 mg), in a nitrogen atmosphere, oxalyl chloride (40 μL) was added, and the resultant was stirred at room temperature for 10 minutes. Then, a chloroform (4.0 mL) solution of the compound (99 mg) obtained by the technique of Reference Example 25-3 was added thereto, and the resultant was stirred at room temperature for 30 minutes. A saturated aqueous solution of sodium bicarbonate was added thereto, followed by extraction with chloroform. An organic layer was separated using a phase separator, and the solvent was distilled off under reduced pressure. The obtained residue was purified by silica gel column chromatography (OH-type silica gel; hexane/ethyl acetate-gradient elution=95/5→50/50). A 4 mol/L hydrogen chloride/ethyl acetate solution (1.0 mL) was added to an ethyl acetate (0.5 mL) solution of the obtained orange foam (63 mg), and the resultant was stirred at room temperature for 1 hour. The reaction solution was concentrated under reduced pressure to obtain the title compound (70 mg) as a white solid.

MS (ESI-APCI): 413[M+H]+, 411[M-H]−

¹H NMR (600 MHz, DMSO-d₆) δppm 1.08-1.43 (8H, m), 1.54-1.83 (5H, m), 2.22-2.34 (6H, m), 3.19-3.31 (3H, m), 3.60-3.66 (2H, m), 3.71-3.79 (1H, m), 4.36 (2H, s), 7.22-7.27 (1H, m), 7.28 (1H, s), 7.93 (1H, d, J=8.7 Hz), 8.08 (1H, s), 8.27-8.47 (1H, m), 10.57-10.75 (1H, m)

Example 53

N'-(2,5-Dimethyl-6-{[4-(piperidin-1-ylcarbonyl)-1,3-thiazol-2-yl]methyl}pyridin-3-yl)-N-ethyl-N-methylimidoformamide dihydrochloride

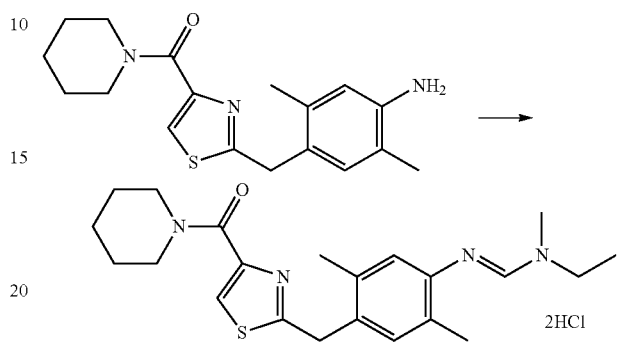

To a chloroform (2.0 mL) solution of N-ethyl-N-methylformamide (35 mg), in a nitrogen atmosphere, oxalyl chloride (30 μL) was added, and the resultant was stirred at room temperature for 10 minutes. Then, a chloroform (3.0 mL) solution of the compound (88 mg) obtained by the technique of Reference Example 26-2 was added thereto, and the resultant was stirred at room temperature for 30 minutes. A saturated aqueous solution of sodium bicarbonate was added thereto, followed by extraction with chloroform. An organic layer was separated using a phase separator, and the solvent was distilled off under reduced pressure. The obtained residue was purified by silica gel column chromatography (OH-type silica gel; hexane/ethyl acetate-gradient elution=95/5→50/50). A 4 mol/L hydrogen chloride/ethyl acetate solution (1.0 mL) was added to an ethyl acetate (0.5 mL) solution of the obtained pale yellow oil (58 mg), and the resultant was stirred at room temperature for 1 hour. The reaction solution was concentrated under reduced pressure to obtain the title compound (57 mg) as a pale yellow foam.

MS (ESI-APCI): 399[M+H]+, 397[M-H]−

¹H NMR (600 MHz, DMSO-d₆) δppm 1.22-1.28 (3H, m), 1.45-1.56 (4H, m), 1.59-1.65 (2H, m), 2.28 (6H, s), 3.19-3.28 (3H, m), 3.47-3.57 (4H, m), 3.58-3.68 (2H, m), 4.35 (2H, s), 7.20 (1H, br. s.), 7.26 (1H, s), 7.86 (1H, s), 8.24-8.46 (1H, m), 10.60-10.83 (1H, m)

Example 54

N-Ethyl-N'-(4-{[4-(3-fluoro-4-methylphenyl)-1,3-thiazol-2-yl]methyl}-2,5-dimethylphenyl)-N-methylimidoformamide dihydrochloride

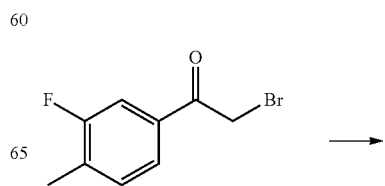

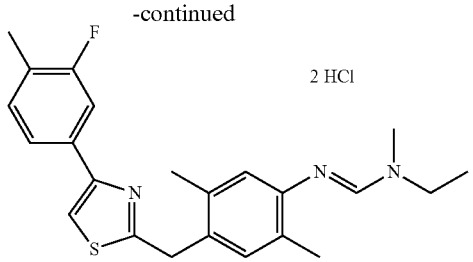

To a 2-propanol (1.0 mL) solution of the compound (30 mg) obtained by the technique of Reference Example 1-5, 2-bromo-1-(3-fluoro-4-methylphenyl)ethanone (26 mg) was added, and the resultant was stirred at 80° C. for 30 minutes. After standing to cool to room temperature, a saturated aqueous solution of sodium bicarbonate was added thereto, followed by extraction with ethyl acetate. The organic layer was dried over magnesium sulfate, and the desiccant was filtered off. Then, the solvent was distilled off under reduced pressure. The obtained residue was purified by silica gel column chromatography (NH-type silica gel; hexane/ethyl acetate-gradient elution=95/5→70/30). A 4 mol/L hydrogen chloride/ethyl acetate solution (1.0 mL) was added to an ethyl acetate (0.5 mL) solution of the obtained brown oil (39 mg), and the resultant was stirred at room temperature for 1 hour. The reaction solution was concentrated under reduced pressure to obtain the title compound (46 mg) as a pale yellow solid.

MS (ESI-APCI): 396[M+H]+
$^1$H NMR (600 MHz, DMSO-d$_6$) δppm 1.26 (3H, t, J=7.0 Hz), 2.23-2.34 (9H, m), 3.20-3.30 (3H, m), 3.60-3.68 (2H, m), 4.38 (2H, s), 7.20-7.37 (3H, m), 7.63-7.70 (2H, m), 8.00 (1H, s), 8.27-8.44 (1H, m), 10.61-10.79 (1H, m)

Example 55

N-Ethyl-N'-(4-{[4-(4-methoxyphenyl)-1,3-thiazol-2-yl]methyl}-2,5-dimethylphenyl)-N-methylimidoformamide hydrobromide

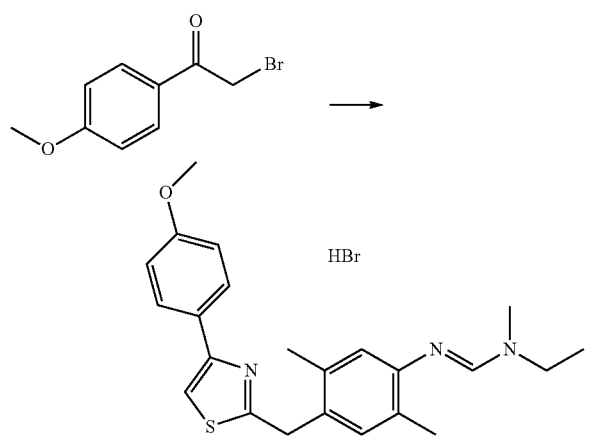

To a 2-propanol (1.0 mL) solution of the compound (30 mg) obtained by the technique of Reference Example 1-5, 2-bromo-1-(4-methoxyphenyl)ethanone (26 mg) was added, and the resultant was stirred at 80° C. for 30 minutes. After standing to cool to room temperature, the deposited solid was collected by filtration to obtain the title compound (27 mg) as a white solid.

MS (ESI-APCI): 394[M+H]+
$^1$H NMR (600 MHz, DMSO-d$_6$) δppm 1.21-1.28 (3H, m), 2.24-2.34 (6H, m), 3.18 (3H, br. s.), 3.57-3.64 (2H, m), 3.79 (3H, s), 4.36 (2H, s), 6.95-7.02 (2H, m), 7.20 (1H, br. s.), 7.28 (1H, br. s.), 7.77 (1H, s), 7.81-7.88 (2H, m), 8.24-8.43 (1H, m), 10.47 (1H, br. s.)

Example 56

N'-[2,5-Dimethyl-4-({4-[4-(trifluoromethyl)phenyl]-1,3-thiazol-2-yl}methyl)phenyl]-N-ethyl-N-methylimidoformamide

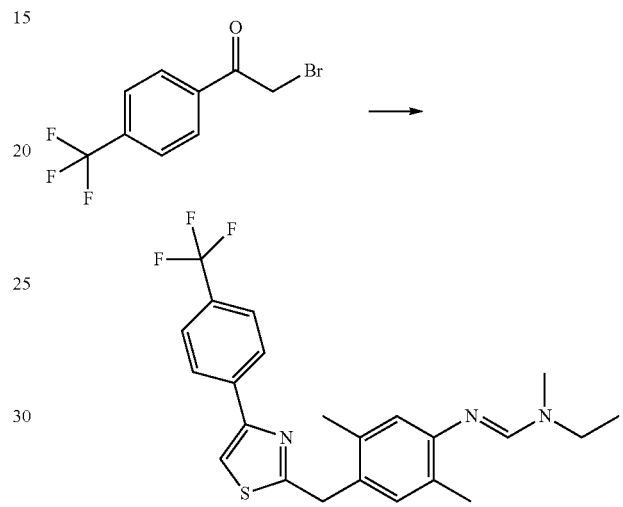

To a 2-propanol (1.0 mL) solution of the compound (30 mg) obtained by the technique of Reference Example 1-5, 2-bromo-1-[4-(trifluoromethyl)phenyl]ethanone (30 mg) was added, and the resultant was stirred at 80° C. for 45 minutes. After standing to cool to room temperature, a saturated aqueous solution of sodium bicarbonate was added thereto, followed by extraction with ethyl acetate. The organic layer was dried over magnesium sulfate, and the desiccant was filtered off. Then, the solvent was distilled off under reduced pressure. The obtained residue was purified by silica gel column chromatography (NH-type silica gel; hexane/ethyl acetate-gradient elution=95/5→70/30) to obtain the title compound (35 mg) as a yellow solid.

MS (ESI-APCI): 432[M+H]+, 430[M−H]−
$^1$H NMR (600 MHz, CHLOROFORM-d) δppm 1.21 (3H, t, J=7.2 Hz), 2.22-2.29 (6H, m), 3.00 (3H, s), 3.25-3.43 (2H, m), 4.29 (2H, s), 6.60 (1H, s), 7.05 (1H, s), 7.38-7.48 (2H, m), 7.66 (2H, d, J=8.3 Hz), 8.00 (2H, d, J=8.3 Hz)

Example 57

N'-(2,5-Dimethyl-4-{[4-(6-methylpyridin-3-yl)-1,3-thiazol-2-yl]methyl}phenyl)-N-ethyl-N-methylimidoformamide dihydrochloride

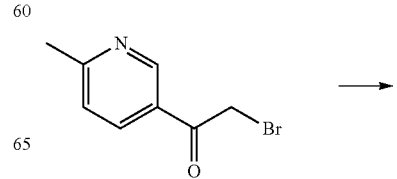

-continued

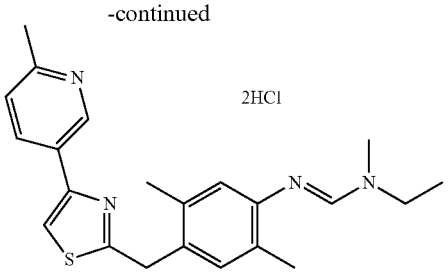

To a 2-propanol (1.0 mL) solution of the compound (30 mg) obtained by the technique of Reference Example 1-5, the compound (24 mg) obtained by the technique of Reference Example 27 was added, and the resultant was stirred at 80° C. for 30 minutes. After standing to cool to room temperature, a saturated aqueous solution of sodium bicarbonate was added thereto, followed by extraction with chloroform. An organic layer was separated using a phase separator, and the solvent was distilled off under reduced pressure. The obtained residue was purified by silica gel column chromatography (OH-type silica gel; hexane/ethyl acetate-gradient elution=90/10→50/50). A 4 mol/L hydrogen chloride/ethyl acetate solution (1.0 mL) was added to an ethyl acetate (0.5 mL) solution of the obtained yellow oil (38 mg), and the resultant was stirred at room temperature for 1 hour. The reaction solution was concentrated under reduced pressure to obtain the title compound (45 mg) as a pale yellow solid.

MS (ESI-APCI): 379[M+H]+, 377[M−H]−

$^1$H NMR (600 MHz, DMSO-d$_6$) δppm 1.19-1.29 (3H, m), 2.31 (6H, s), 2.76 (3H, s), 3.21-3.31 (3H, m), 3.69-3.78 (2H, m), 4.43 (2H, s), 7.21-7.28 (1H, m), 7.31 (1H, s), 7.95 (1H, d, J=8.3 Hz), 8.25-8.50 (2H, m), 8.87 (1H, d, J=8.3 Hz), 9.17 (1H, d, J=1.7 Hz), 10.87-11.12 (1H, m)

Example 58

N'-(4-{[4-(2,5-Difluoro-4-methylphenyl)-1,3-thiazol-2-yl]methyl}-2,5-dimethylphenyl)-N-ethyl-N-methylimidoformamide hydrobromide

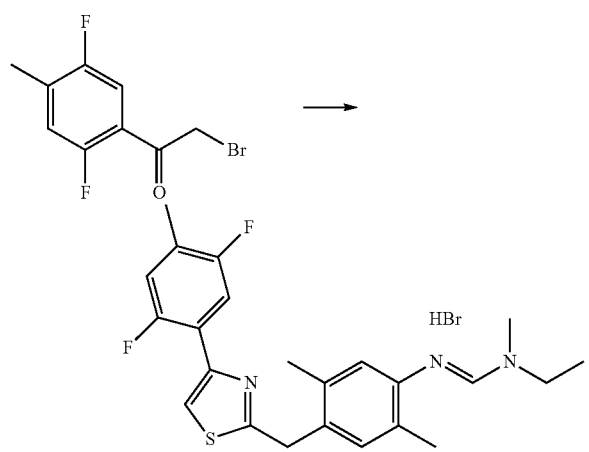

To a 2-propanol (1.0 mL) solution of the compound (30 mg) obtained by the technique of Reference Example 1-5, the compound (28 mg) obtained by the technique of Reference Example 28 was added, and the resultant was stirred at 80° C. for 1 hour. After standing to cool to room temperature, the deposited solid was collected by filtration to obtain the title compound (41 mg) as a yellow solid.

MS (ESI-APCI): 414[M+H]+, 412[M−H]−

$^1$H NMR (600 MHz, DMSO-d$_6$) δppm 1.22-1.30 (3H, m), 2.25-2.36 (9H, m), 3.19 (3H, br. s.), 3.54-3.68 (2H, m), 4.35-4.91 (2H, m), 7.11 (1H, s), 7.24-7.36 (1H, m), 7.36-7.43 (1H, m), 7.50 (1H, s), 7.71-7.88 (1H, m), 8.28-8.50 (1H, m), 10.49 (1H, br. s.)

Example 59

N-Ethyl-N'-(4-{[4-(2-fluoro-4-methylphenyl)-1,3-thiazol-2-yl]methyl}-2,5-dimethylphenyl)-N-methylimidoformamide dihydrochloride

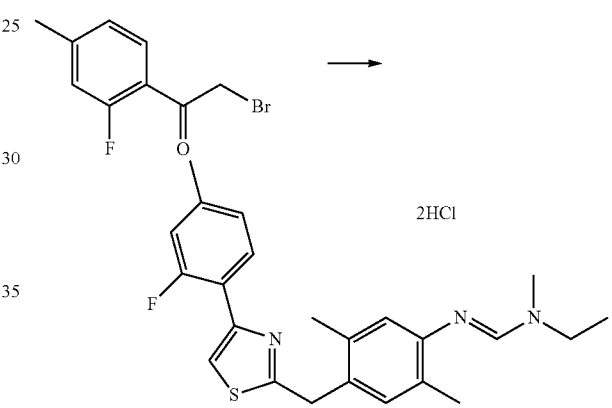

To a 2-propanol (1.0 mL) solution of the compound (30 mg) obtained by the technique of Reference Example 1-5, the compound (26 mg) obtained by the technique of Reference Example 29 was added, and the resultant was stirred at 80° C. for 1.5 hours. After standing to cool to room temperature, a saturated aqueous solution of sodium bicarbonate was added thereto, followed by extraction with chloroform. An organic layer was separated using a phase separator, and the solvent was distilled off under reduced pressure. The obtained residue was purified by silica gel column chromatography (NH-type silica gel; hexane/ethyl acetate-gradient elution=90/10→70/30). A 4 mol/L hydrogen chloride/ethyl acetate solution (1.0 mL) was added to an ethyl acetate (0.5 mL) solution of the obtained orange oil (33 mg), and the resultant was stirred at room temperature for 1 hour. The reaction solution was concentrated under reduced pressure to obtain the title compound (36 mg) as a pale yellow solid.

MS (ESI-APCI): 396[M+H]+

$^1$H NMR (600 MHz, DMSO-d$_6$) δppm 1.25 (3H, t, J=6.7 Hz), 2.24-2.37 (9H, m), 3.19-3.31 (3H, m), 3.62-3.71 (2H, m), 4.39 (2H, s), 7.07-7.25 (3H, m), 7.31 (1H, s), 7.75 (1H, d, J=2.1 Hz), 7.96 (1H, t, J=8.3 Hz), 8.28-8.45 (1H, m), 10.60-10.77 (1H, m)

Example 60

N'-[2,5-Dimethyl-4-({4-[(4-methylphenoxy)methyl]-1,3-thiazol-2-yl}methyl)phenyl]-N-ethyl-N-methylimidoformamide

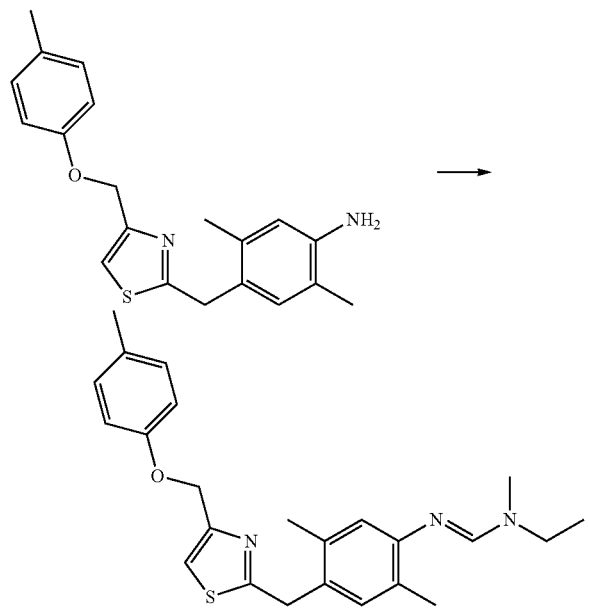

To a chloroform (0.5 mL) solution of N-ethyl-N-methylformamide (8.2 mg), in a nitrogen atmosphere, oxalyl chloride (7.1 µL) was added, and the resultant was stirred at room temperature for 10 minutes. Then, a chloroform (0.5 mL) solution of the compound (20 mg) obtained by the technique of Reference Example 30-5 was added thereto, and the resultant was stirred at room temperature for 1 hour. A saturated aqueous solution of sodium bicarbonate was added thereto, followed by extraction with chloroform. The organic layer was dried over magnesium sulfate, and the desiccant was filtered off. Then, the solvent was distilled off under reduced pressure. The obtained residue was purified by silica gel column chromatography (OH-type silica gel; chloroform/methanol-gradient elution=100/0→91/9) and then further purified by silica gel column chromatography (NH-type silica gel; hexane/ethyl acetate-gradient elution=100/0→66/34) to obtain the title compound (6.5 mg) as a colorless oil.

MS (ESI-APCI): 408[M+H]+
$^1$H NMR (600 MHz, CHLOROFORM-d) δppm 1.21 (3H, t, J=7.0 Hz), 2.19-2.26 (6H, m), 2.29 (3H, s), 3.01 (3H, br. s.), 3.27-3.43 (2H, m), 4.24 (2H, s), 5.15 (2H, s), 6.60 (1H, br. s.), 6.89 (2H, d, J=8.3 Hz), 7.02 (1H, s), 7.08 (2H, d, J=8.3 Hz), 7.12 (1H, s), 7.44 (1H, br. s.)

Example 61

N'-(2,5-Dimethyl-4-{[4-(5-methylpyridin-2-yl)-1,3-thiazol-2-yl]methyl}phenyl)-N-ethyl-N-methylimidoformamide dihydrochloride

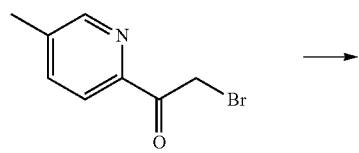

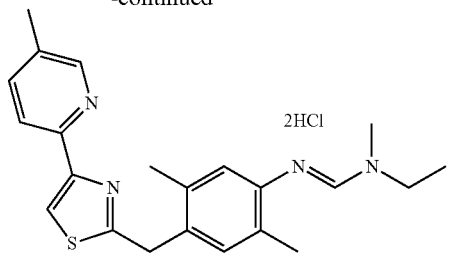

To a 2-propanol (1.0 mL) solution of the compound (30 mg) obtained by the technique of Reference Example 1-5, 2-bromo-1-(5-methylpyridin-2-yl)ethanone (24 mg) obtained by a method described in the patent document (WO2008/116665) was added, and the resultant was stirred at 80° C. for 30 minutes. After standing to cool to room temperature, a saturated aqueous solution of sodium bicarbonate was added thereto, followed by extraction with chloroform. An organic layer was separated using a phase separator, and the solvent was distilled off under reduced pressure. The obtained residue was purified by silica gel column chromatography (OH-type silica gel; hexane/ethyl acetate-gradient elution=90/10→70/30). A 4 mol/L hydrogen chloride/ethyl acetate solution (1.0 mL) was added to an ethyl acetate (0.5 mL) solution of the obtained orange oil (35 mg), and the resultant was stirred at room temperature for 1 hour. The reaction solution was concentrated under reduced pressure to obtain the title compound (40 mg) as a pale yellow solid.

MS (ESI-APCI): 379[M+H]+
$^1$H NMR (600 MHz, DMSO-d$_6$) δppm 1.26 (3H, t, J=7.0 Hz), 2.28-2.33 (6H, m), 2.37 (3H, s), 3.20-3.31 (3H, m), 3.62-3.70 (2H, m), 4.42 (2H, s), 7.21-7.26 (1H, m), 7.31 (1H, s), 7.83-7.93 (1H, m), 8.00-8.10 (1H, m), 8.25 (1H, br. s.), 8.43 (1H, d, J=12.8 Hz), 8.50 (1H, s), 10.56-10.87 (1H, m)

Example 62

N'-(2,5-Dimethyl-4-{[4-(5-methylpyrimidin-2-yl)-1,3-thiazol-2-yl]methyl}phenyl)-N-ethyl-N-methylimidoformamide dihydrochloride

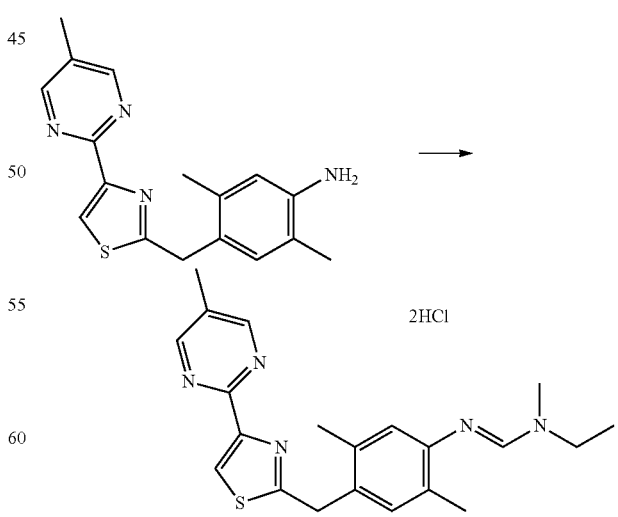

To a chloroform (0.50 mL) solution of N-ethyl-N-methylformamide (16 mg), in a nitrogen atmosphere, oxalyl chloride (20 µL) was added, and the resultant was stirred at room temperature for 10 minutes. Then, a chloroform (2.0 mL) solution of the compound (39 mg) obtained by the technique of Reference Example 31-3 was added thereto, and the resultant was stirred at room temperature for 40 minutes. A saturated aqueous solution of sodium bicarbonate was added thereto, followed by extraction with chloroform. An organic layer was separated using a phase separator, and the solvent was distilled off under reduced pressure. The obtained residue was purified by silica gel column chromatography (NH-type silica gel; hexane/ethyl acetate-gradient elution=95/5→80/20). Ethyl acetate (0.5 mL) was added to the obtained pale yellow oil, then a 4 mol/L hydrogen chloride/ethyl acetate solution (1.0 mL) was added, and the resultant was then concentrated under reduced pressure to obtain the title compound (14 mg) as a pale yellow solid.

MS (ESI-APCI): 380[M+H]+, 402[M+Na]+

$^1$H NMR (600 MHz, DMSO-$d_6$) δppm 1.19-1.30 (3H, m), 2.31 (9H, br. s.), 3.18-3.30 (3H, m), 3.57-3.69 (2H, m), 4.41 (2H, s), 7.20-7.25 (1H, m), 7.31 (1H, s), 8.25-8.48 (2H, m), 8.71 (2H, s), 10.61-10.83 (1H, m)

Example 63

N'-[2,5-Dimethyl-4-({4-[(propan-2-yloxy)methyl]-1,3-thiazol-2-yl}methyl)phenyl]-N-ethyl-N-methylimidoformamide dihydrochloride

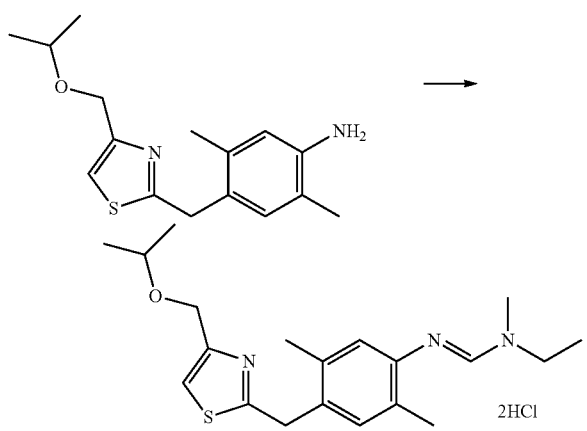

To a chloroform (1.0 mL) solution of N-ethyl-N-methylformamide (35 mg), in a nitrogen atmosphere, oxalyl chloride (30 μL) was added, and the resultant was stirred at room temperature for 10 minutes. Then, a chloroform (1.0 mL) solution of the compound (73 mg) obtained by the technique of Reference Example 32-2 was added thereto, and the resultant was stirred at room temperature for 1 hour. A saturated aqueous solution of sodium bicarbonate was added thereto, followed by extraction with chloroform. The organic layer was dried over magnesium sulfate, and the desiccant was filtered off. Then, the solvent was distilled off under reduced pressure. The obtained residue was purified by silica gel column chromatography (NH-type silica gel; hexane/ethyl acetate-gradient elution=100/0→66/34). Ethyl acetate (0.50 mL) was added to the obtained yellow oil, then a 4 mol/L hydrogen chloride/ethyl acetate solution (1.0 mL) was added, and the resultant was then concentrated under reduced pressure to obtain the title compound (70 mg) as a colorless foam.

MS (ESI-APCI): 360[M+H]+

$^1$H NMR (600 MHz, DMSO-$d_6$) δppm 1.12 (6H, d, J=6.2 Hz), 1.22-1.29 (3H, m), 2.22-2.30 (6H, m), 3.20-3.30 (3H, m), 3.58-3.70 (3H, m), 4.30 (2H, s), 4.47 (2H, s), 7.17-7.22 (1H, m), 7.24 (1H, s), 7.34 (1H, s), 8.25-8.46 (1H, m), 10.60-10.82 (1H, m)

Example 64

N'-(2,5-Dimethyl-4-{[4-(3-methylpyrazin-2-yl)-1,3-thiazol-2-yl]methyl}phenyl)-N-ethyl-N-methylimidoformamide dihydrochloride

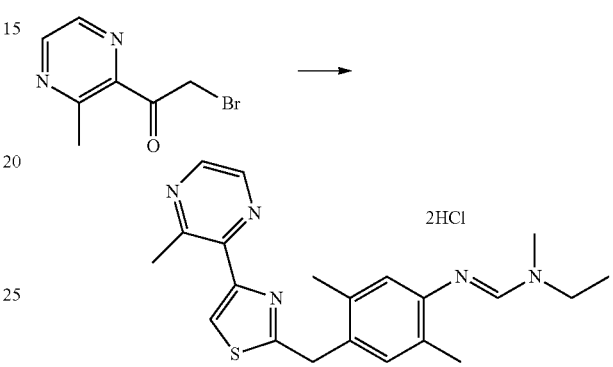

To a 2-propanol (1.0 mL) solution of the compound (25 mg) obtained by the technique of Reference Example 1-5, the compound (38 mg) obtained by the technique of Reference Example 33 was added, and the resultant was stirred at 80° C. for 45 minutes. After standing to cool to room temperature, a saturated aqueous solution of sodium bicarbonate was added thereto, followed by extraction with chloroform. An organic layer was separated using a phase separator, and the solvent was distilled off under reduced pressure. The obtained residue was purified by silica gel column chromatography (NH-type silica gel; hexane/ethyl acetate-gradient elution=100/0→70/30). A 4 mol/L hydrogen chloride/ethyl acetate solution (1.0 mL) was added to an ethyl acetate (0.5 mL)-methanol (0.5 mL) solution of the obtained yellow oil (35 mg), and the resultant was stirred at room temperature for 1 hour. The reaction solution was concentrated under reduced pressure to obtain the title compound (41 mg) as a pale yellow solid.

MS (ESI-APCI): 380[M+H]+

$^1$H NMR (600 MHz, DMSO-$d_6$) δppm 1.21-1.29 (3H, m), 2.26-2.34 (6H, m), 2.76 (3H, s), 3.14-3.24 (3H, m), 3.58-3.67 (2H, m), 4.43 (2H, s), 7.21-7.24 (1H, m), 7.32 (1H, s), 8.11 (1H, s), 8.26-8.44 (1H, m), 8.49-8.54 (2H, m), 10.63-10.81 (1H, m)

Example 65

N'-(2,5-Dimethyl-4-{[4-(pyrazin-2-yl)-1,3-thiazol-2-yl]methyl}phenyl)-N-ethyl-N-methylimidoformamide dihydrochloride

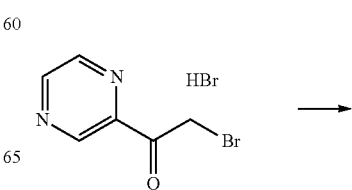

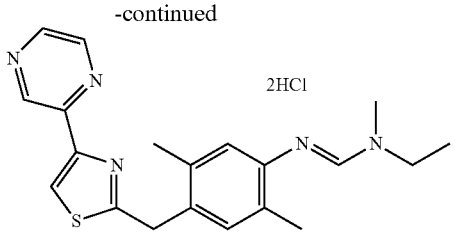

To a 2-propanol (1.0 mL) solution of the compound (30 mg) obtained by the technique of Reference Example 1-5, 2-bromo-1-(pyrazin-2-yl)ethanone hydrobromide (32 mg) was added, and the resultant was stirred at 80° C. for 2 hours. After standing to cool to room temperature, a saturated aqueous solution of sodium bicarbonate was added thereto, followed by extraction with chloroform. An organic layer was separated using a phase separator, and the solvent was distilled off under reduced pressure. The obtained residue was purified by silica gel column chromatography (NH-type silica gel; hexane/ethyl acetate-gradient elution=100/0→60/40). A 4 mol/L hydrogen chloride/ethyl acetate solution (1.0 mL) was added to an ethyl acetate (0.5 mL)-methanol (0.5 mL) solution of the obtained yellow oil (30 mg), and the resultant was stirred at room temperature for 1 hour. The reaction solution was concentrated under reduced pressure to obtain the title compound (35 mg) as a pale yellow solid.

MS (ESI-APCI): 366[M+H]+

$^1$H NMR (600 MHz, DMSO-d$_6$) δppm 1.26 (3H, t, J=6.7 Hz), 2.28-2.35 (6H, m), 3.19-3.31 (3H, m), 3.56-3.68 (2H, m), 4.45 (2H, s), 7.23-7.26 (1H, m), 7.33 (1H, s), 8.28 (1H, s), 8.29-8.47 (1H, m), 8.62 (1H, d, J=2.5 Hz), 8.66-8.70 (1H, m), 9.21 (1H, d, J=1.2 Hz), 10.58-10.77 (1H, m)

Example 66

N'-(2,5-Dimethyl-4-{[4-(6-methylpyridazin-3-yl)-1,3-thiazol-2-yl]methyl}phenyl)-N-ethyl-N-methylimidoformamide

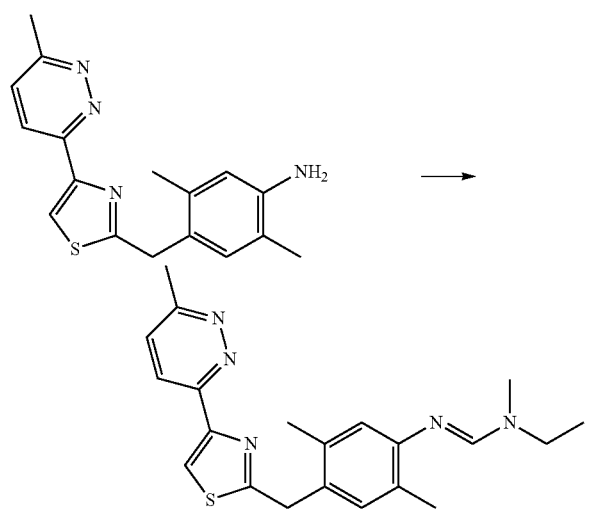

To a chloroform (1.0 mL) solution of N-ethyl-N-methylformamide (31 mg), in a nitrogen atmosphere, oxalyl chloride (30 μL) was added, and the resultant was stirred at room temperature for 10 minutes. Then, a chloroform (4.0 mL) solution of the compound (73 mg) obtained by the technique of Reference Example 34-3 was added thereto, and the resultant was stirred at room temperature for 1 hour. A saturated aqueous solution of sodium bicarbonate was added thereto, followed by extraction with chloroform. An organic layer was separated using a phase separator, and the solvent was distilled off under reduced pressure. The obtained residue was purified by silica gel column chromatography (NH-type silica gel; hexane/ethyl acetate-gradient elution=95/5→70/30) to obtain the title compound (47 mg) as a pale yellow solid.

MS (ESI-APCI): 380[M+H]+

$^1$H NMR (600 MHz, CHLOROFORM-d) δppm 1.21 (3H, t, J=7.0 Hz), 2.22-2.27 (6H, m), 2.74 (3H, s), 3.00 (3H, s), 3.23-3.47 (2H, m), 4.29 (2H, s), 6.60 (1H, s), 7.04 (1H, s), 7.38 (1H, d, J=8.7 Hz), 7.45 (1H, br. s.), 8.16 (1H, d, J=8.7 Hz), 8.18 (1H, s)

Example 67

N'-(2,5-Dimethyl-4-{[4-(1-methyl-2-oxo-1,2-dihydropyridin-4-yl)-1,3-thiazol-2-yl]methyl}phenyl)-N-ethyl-N-methylimidoformamide dihydrochloride

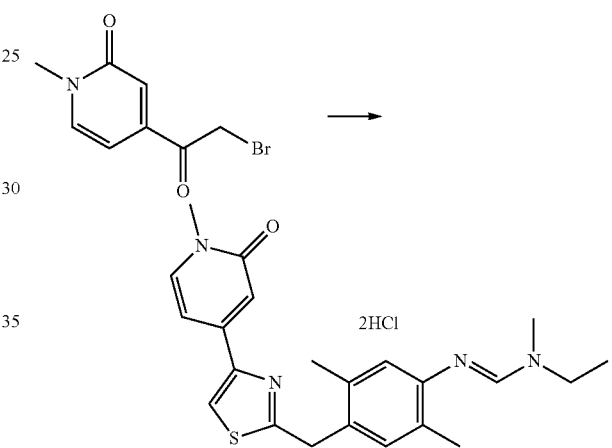

To a 2-propanol (2.0 mL) solution of the compound (25 mg) obtained by the technique of Reference Example 1-5, the compound (85 mg) obtained by the technique of Reference Example 35 was added, and the resultant was stirred at 90° C. for 3 hours. After standing to cool to room temperature, a saturated aqueous solution of sodium bicarbonate was added thereto, followed by extraction with chloroform. An organic layer was separated using a phase separator, and the solvent was distilled off under reduced pressure. The obtained residue was purified by silica gel column chromatography (OH-type silica gel; chloroform/methanol-gradient elution=99/1→83/17) and preparative silica gel thin-layer chromatography (OH-type silica gel; chloroform/methanol=10/1) and then further purified by preparative LC. A 4 mol/L hydrogen chloride/ethyl acetate solution (1.0 mL) was added to an ethyl acetate (0.5 mL) solution of the obtained light brown foam (26 mg), and the resultant was stirred at room temperature for 2 hours. The reaction solution was concentrated under reduced pressure to obtain the title compound (24 mg) as a white solid.

MS (ESI-APCI): 395[M+H]+, 393[M−H]−

$^1$H NMR (600 MHz, DMSO-d$_6$) δppm 1.25 (3H, t, J=7.0 Hz), 2.24-2.34 (6H, m), 3.17-3.31 (3H, m), 3.43 (3H, s), 3.61-3.66 (2H, m), 4.39 (2H, s), 6.74 (1H, dd, J=7.0, 2.1 Hz), 6.91 (1H, d, J=2.1 Hz), 7.18-7.25 (1H, m), 7.30 (1H, s), 7.75 (1H, d, J=7.0 Hz), 8.24 (1H, s), 8.28-8.46 (1H, m), 10.58-10.73 (1H, m)

Example 68

N-Ethyl-N-[4-({4-[4-(hydroxymethyl)phenyl]-1,3-thiazol-2-yl}methyl)-2,5-dimethylphenyl]-N-methylimidoformamide dihydrochloride

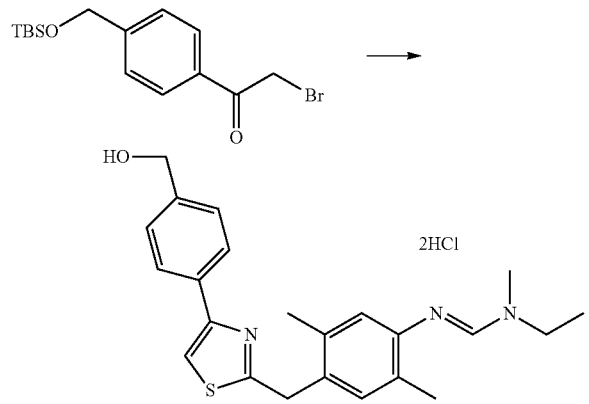

To a 2-propanol (2.0 mL) solution of the compound (60 mg) obtained by the technique of Reference Example 1-5, the compound (141 mg) obtained by the technique of Reference Example 36 was added, and the resultant was stirred at 80° C. for 90 minutes. After standing to cool to room temperature, a saturated aqueous solution of sodium bicarbonate was added thereto, followed by extraction with chloroform. An organic layer was separated using a phase separator, and the solvent was distilled off under reduced pressure. The obtained residue was purified by silica gel column chromatography (OH-type silica gel; hexane/ethyl acetate-gradient elution=100/0→0/100 and then chloroform/methanol=92/8). A 4 mol/L hydrogen chloride/ethyl acetate solution (1.0 mL) was added to an ethyl acetate (1.0 mL)-methanol (1.0 mL) solution of the obtained yellow oil (104 mg), and the resultant was stirred at room temperature for 1.5 hours. The reaction solution was concentrated under reduced pressure to obtain the title compound (78 mg) as a pale yellow solid.

MS (ESI-APCI): 394[M+H]+

$^{1}$H NMR (600 MHz, DMSO-$d_6$) δppm 1.19-1.29 (3H, m), 2.27-2.35 (6H, m), 3.15-3.37 (3H, m), 3.58-3.69 (2H, m), 4.39 (2H, s), 4.52 (2H, s), 7.18-7.26 (1H, m), 7.30 (1H, s), 7.37 (2H, d, J=8.7 Hz), 7.82-7.92 (3H, m), 8.25-8.47 (1H, m), 10.63-10.85 (1H, m)

Example 69

4-{2-[4-({(E)-[Ethyl(methyl)amino]methylidene}amino)-2,5-dimethylbenzyl]-1,3-thiazol-4-yl}-N-methylbenzenesulfonamide hydrobromide

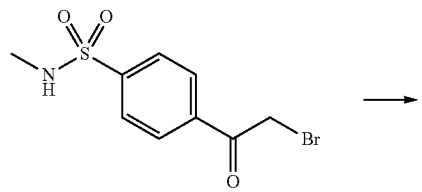

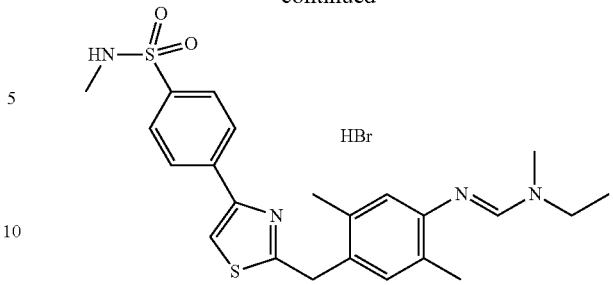

To a 2-propanol (1.0 mL) solution of the compound (30 mg) obtained by the technique of Reference Example 1-5, 4-(bromoacetyl)-N-methylbenzenesulfonamide (57 mg) obtained by a method described in the patent document (U.S. 2007/0049620) was added, and the resultant was stirred at 80° C. for 3 hours. The deposited solid was collected by filtration to obtain the title compound (40 mg) as a pale yellow solid.

MS (ESI-APCI): 457[M+H]+

$^{1}$H NMR (600 MHz, DMSO-$d_6$) δppm 1.20-1.29 (3H, m), 2.24-2.34 (6H, m), 2.43 (3H, d, J=5.0 Hz), 3.14-3.29 (3H, m), 3.55-3.66 (2H, m), 4.41 (2H, s), 7.23 (1H, br. s.), 7.30 (1H, br. s.), 7.45-7.50 (1H, m), 7.83 (2H, d, J=8.3 Hz), 8.14 (2H, d, J=8.3 Hz), 8.18 (1H, s), 8.26-8.48 (1H, m)

Example 70

N'-[2,5-Dimethyl-4-({4-[(4-methylpiperazin-1-yl)carbonyl]-1,3-thiazol-2-yl}methyl)phenyl]-N-ethyl-N-methylimidoformamide dihydrochloride

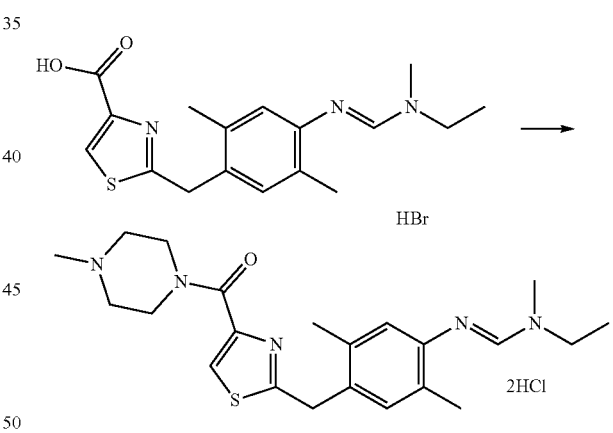

To a N,N-dimethylformamide (2.0 mL) solution of the compound (41 mg) obtained by the technique of Reference Example 37, 1-methylpiperazine (12 μL) and N,N-diisopropylethylamine (87 μL) were added, then HATU (45 mg) was added, and the resultant was stirred at room temperature for 1 hour. A saturated aqueous solution of sodium bicarbonate was added to the reaction solution, followed by extraction with chloroform. An organic layer was separated using a phase separator, and the solvent was distilled off under reduced pressure. The obtained residue was purified by silica gel column chromatography (NH-type silica gel; hexane/ethyl acetate-gradient elution=100/0→0/100). A 4 mol/L hydrogen chloride/ethyl acetate solution (2.0 mL) was added to an ethyl acetate (2.0 mL) solution of the obtained pale yellow oil (29 mg), and the resultant was stirred at room temperature for 10 minutes. Diethyl ether (4.0 mL) was added thereto, and the deposited gummy solid was collected by filtration and dried to obtain the title compound (27 mg) as a pale yellow solid.

MS (ESI-APCI): 414[M+H]+

$^1$H NMR (600 MHz, DMSO-$d_6$) δppm 1.22-1.28 (3H, m), 2.24-2.33 (6H, m), 2.74-2.81 (3H, m), 2.98-3.09 (2H, m), 3.21-3.31 (3H, m), 3.36-3.49 (2H, m), 3.54-3.68 (4H, m), 4.37 (2H, s), 4.46-4.55 (2H, m), 7.19-7.24 (1H, m), 7.27 (1H, s), 8.06-8.11 (1H, m), 8.27-8.45 (1H, m), 10.80-11.01 (1H, m), 11.23 (1H, br. s.)

Example 71

N-Cyclohexyl-2-[4-({(E)-[ethyl(methyl)amino]methylidene}amino)-2,5-dimethylbenzyl]-N-methyl-1,3-thiazole-4-carboxamide hydrochloride

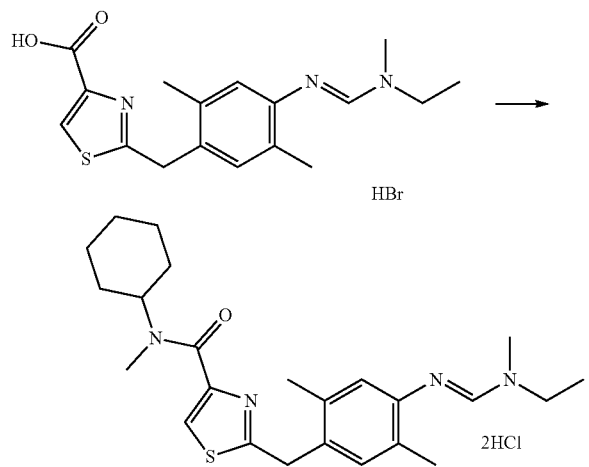

To a N,N-dimethylformamide (2.0 mL) solution of the compound (41 mg) obtained by the technique of Reference Example 37, N-methylcyclohexanamine (14 μL) and N,N-diisopropylethylamine (87 μL) were added, then HATU (45 mg) was added, and the resultant was stirred at room temperature for 1 hour. A saturated aqueous solution of sodium bicarbonate was added to the reaction solution, followed by extraction with chloroform. An organic layer was separated using a phase separator, and the solvent was distilled off under reduced pressure. The obtained residue was purified by preparative LC. A 4 mol/L hydrogen chloride/ethyl acetate solution (2.0 mL) was added to an ethyl acetate (2.0 mL) solution of the obtained yellow oil (34 mg), and the resultant was stirred at room temperature for 1 hour. The deposited gummy solid was collected by filtration and dried to obtain the title compound (33 mg) as a pale yellow foam.

MS (ESI-APCI): 427[M+H]+

$^1$H NMR (600 MHz, DMSO-$d_6$) δppm 0.96-1.14 (2H, m), 1.21-1.28 (3H, m), 1.29-1.83 (8H, m), 2.23-2.30 (6H, m), 2.80-2.92 (3H, m), 3.20-3.29 (3H, m), 3.57-4.30 (3H, m), 4.36 (2H, s), 7.17-7.30 (2H, m), 7.85 (1H, s), 8.24-8.45 (1H, m), 10.59-10.79 (1H, m)

Example 72

N'-(2,5-Dimethyl-4-{[4-(2-methylpyrimidin-5-yl)-1,3-thiazol-2-yl]methyl}phenyl)-N-ethyl-N-methylimidoformamide dihydrochloride

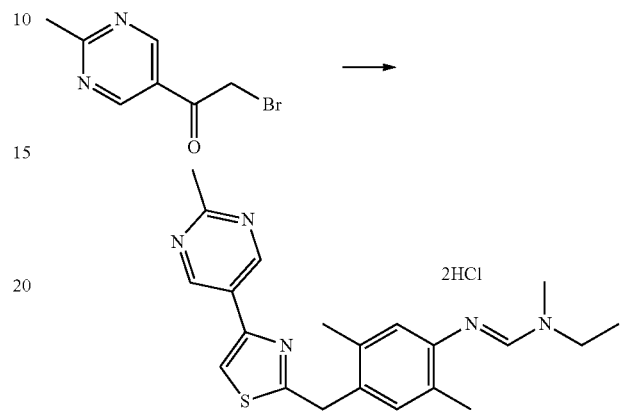

To a 2-propanol (1.0 mL) solution of the compound (34 mg) obtained by the technique of Reference Example 1-5, the compound (28 mg) obtained by the technique of Reference Example 38-3 was added, and the resultant was stirred at 80° C. for 1 hour. After standing to cool to room temperature, a saturated aqueous solution of sodium bicarbonate was added thereto, followed by extraction with chloroform. An organic layer was separated using a phase separator, and the solvent was distilled off under reduced pressure. The obtained residue was purified by silica gel column chromatography (NH-type silica gel; hexane/ethyl acetate-gradient elution=95/5→70/30). A 4 mol/L hydrogen chloride/ethyl acetate solution (1.0 mL) was added to an ethyl acetate (0.5 mL) solution of the obtained pale yellow solid (31 mg), and the resultant was stirred at room temperature for 2 hours. The reaction solution was concentrated under reduced pressure to obtain the title compound (33 mg) as a white solid.

MS (ESI-APCI): 380[M+H]+, 378[M−H]−

$^1$H NMR (600 MHz, DMSO-$d_6$) δppm 1.21-1.29 (3H, m), 2.27-2.34 (6H, m), 2.66 (3H, s), 3.19-3.30 (3H, m), 3.58-3.64 (2H, m), 4.42 (2H, s), 7.21-7.25 (1H, m), 7.31 (1H, s), 8.22 (1H, s), 8.27-8.45 (1H, m), 9.19 (2H, s), 10.62-10.81 (1H, m)

Example 73

N'-(2,5-Dimethyl-4-{[4-(1-methylpiperidin-4-yl)-1,3-thiazol-2-yl]methyl}phenyl)-N-ethyl-N-methylimidoformamide trihydrochloride

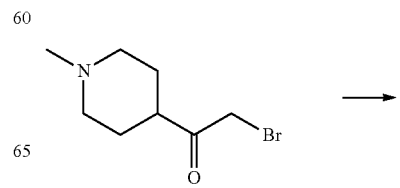

-continued

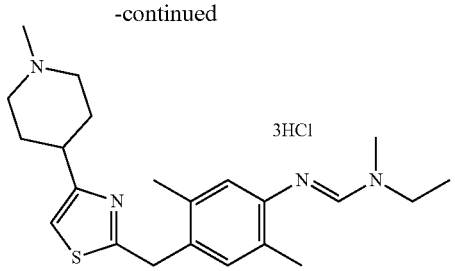

To a 2-propanol (2.0 mL) solution of the compound (30 mg) obtained by the technique of Reference Example 1-5, 2-bromo-1-(1-methylpiperidin-4-yl)ethanone (50 mg) obtained by a method described in the patent document (U.S. 2007/0049620) was added, and the resultant was stirred at 80° C. for 2 hours. After standing to cool to room temperature, a saturated aqueous solution of sodium bicarbonate was added thereto, followed by extraction with chloroform. An organic layer was separated using a phase separator, and the solvent was distilled off under reduced pressure. The obtained residue was purified by silica gel column chromatography (NH-type silica gel; hexane/ethyl acetate-gradient elution=95/5→70/30). A 4 mol/L hydrogen chloride/ethyl acetate solution (1.0 mL) was added to an ethyl acetate (0.5 mL) solution of the obtained orange oil (30 mg), and the resultant was stirred at room temperature for 2 hours. The reaction solution was concentrated under reduced pressure to obtain the title compound (38 mg) as a pale yellow solid.

MS (ESI-APCI): 385[M+H]+

$^1$H NMR (600 MHz, DMSO-d$_6$) δppm 1.25 (3H, t, J=7.4 Hz), 1.81-1.93 (2H, m), 2.09-2.18 (2H, m), 2.22-2.30 (6H, m), 2.75 (3H, d, J=4.5 Hz), 2.85-3.09 (4H, m), 3.21-3.30 (3H, m), 3.57-3.68 (3H, m), 4.29 (2H, s), 7.16-7.27 (2H, m), 8.22-8.44 (2H, m), 10.07-10.33 (1H, m), 10.62-10.82 (1H, m)

Example 74

N-Cyclopentyl-2-[4-({(E)-[ethyl(methyl)amino] methylidene}amino)-2,5-dimethylbenzyl]-1,3-thiazole-4-carboxamide

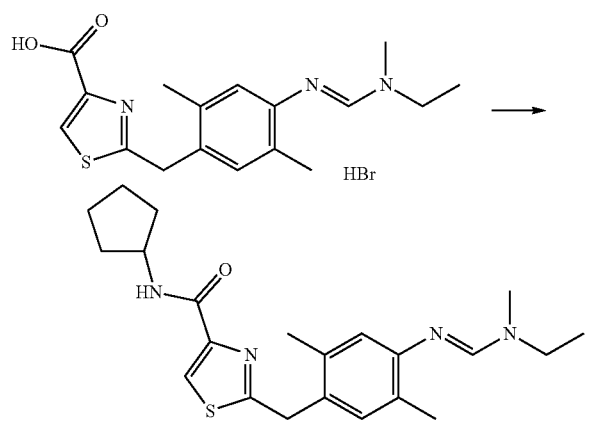

To a N,N-dimethylformamide (2.0 mL) solution of the compound (41 mg) obtained by the technique of Reference Example 37, cyclopentanamine (11 μL) and N,N-diisopropylethylamine (87 μL) were added, then HATU (45 mg) was added, and the resultant was stirred at room temperature for 1 hour. The reaction solution was purified by preparative LC to obtain the title compound (36 mg) as a pale yellow oil.

MS (ESI-APCI): 399[M+H]+

$^1$H NMR (600 MHz, CHLOROFORM-d) δppm 1.21 (3H, t, J=7.2 Hz), 1.49-1.82 (6H, m), 2.02-2.13 (2H, m), 2.18-2.26 (6H, m), 3.00 (3H, s), 3.22-3.47 (2H, m), 4.19 (2H, s), 4.33-4.43 (1H, m), 6.60 (1H, s), 6.99 (1H, s), 7.29 (1H, br. s.), 7.39-7.49 (1H, m), 7.89 (1H, s)

Example 75

N-Cyclobutyl-2-[4-({(E)-[ethyl(methyl)amino] methylidene}amino)-2,5-dimethylbenzyl]-1,3-thiazole-4-carboxamide

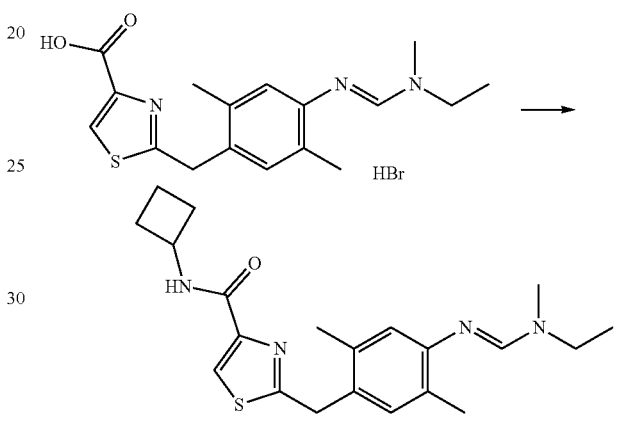

To a N,N-dimethylformamide (2.0 mL) solution of the compound (41 mg) obtained by the technique of Reference Example 37, cyclobutanamine (9.3 μL) and N,N-diisopropylethylamine (87 μL) were added, then HATU (45 mg) was added, and the resultant was stirred at room temperature for 1 hour. The reaction solution was purified by preparative LC to obtain the title compound (32 mg) as a colorless oil.

MS (ESI-APCI): 385[M+H]+

$^1$H NMR (600 MHz, CHLOROFORM-d) δppm 1.21 (3H, t, J=7.0 Hz), 1.73-1.82 (2H, m), 1.98-2.09 (2H, m), 2.17-2.26 (6H, m), 2.36-2.46 (2H, m), 3.00 (3H, br. s.), 3.23-3.44 (2H, m), 4.20 (2H, s), 4.53-4.62 (1H, m), 6.60 (1H, s), 6.99 (1H, s), 7.40-7.48 (2H, m), 7.89 (1H, s)

Example 76

N-Tert-butyl-2-[4-({(E)-[ethyl(methyl)amino] methylidene}amino)-2,5-dimethylbenzyl]-1,3-thiazole-4-carboxamide

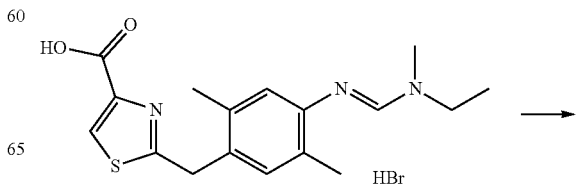

-continued

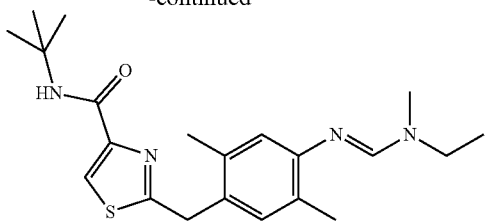

To a N,N-dimethylformamide (2.0 mL) solution of the compound (41 mg) obtained by the technique of Reference Example 37, 2-methylpropan-2-amine (12 μL) and N,N-diisopropylethylamine (87 μL) were added, then HATU (45 mg) was added, and the resultant was stirred at room temperature for 1 hour. The reaction solution was purified by preparative LC to obtain the title compound (32 mg) as a colorless oil.

MS (ESI-APCI): 387[M+H]+

$^1$H NMR (600 MHz, CHLOROFORM-d) δppm 1.21 (3H, t, J=7.2 Hz), 1.48 (9H, s), 2.17-2.25 (6H, m), 3.00 (3H, s), 3.19-3.48 (2H, m), 4.18 (2H, s), 6.60 (1H, s), 6.99 (1H, s), 7.43 (1H, br. s.), 7.85 (1H, s)

Example 77

2-[4-({(E)-[Ethyl(methyl)amino]methylidene}amino)-2,5-dimethylbenzyl]-N-[(5-methylpyrazin-2-yl)methyl]-1,3-thiazole-4-carboxamide

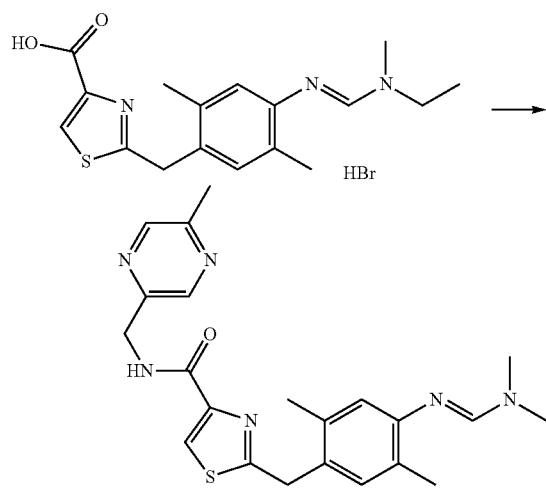

To a N,N-dimethylformamide (2.0 mL) solution of the compound (41 mg) obtained by the technique of Reference Example 37, 1-(5-methylpyrazin-2-yl)methanamine (12 μL) and N,N-diisopropylethylamine (87 μL) were added, then HATU (45 mg) was added, and the resultant was stirred at room temperature for 1 hour. The reaction solution was purified by preparative LC to obtain the title compound (22 mg) as a pale yellow oil.

MS (ESI-APCI): 437 [M+H]+

$^1$H NMR (600 MHz, CHLOROFORM-d) δppm 1.16-1.24 (3H, m), 2.16-2.26 (6H, m), 2.57 (3H, s), 3.00 (3H, br. s.), 3.20-3.49 (2H, m), 4.20 (2H, s), 4.76 (2H, d, J=5.8 Hz), 6.58-6.64 (1H, m), 6.99 (1H, s), 7.42-7.47 (1H, m), 7.95 (1H, s), 8.05-8.10 (1H, m), 8.43 (1H, s), 8.56 (1H, s)

Example 78

2-[4-({(E)-[Ethyl(methyl)amino]methylidene}amino)-2,5-dimethylbenzyl]-N-(2-phenylethyl)-1,3-thiazole-4-carboxamide

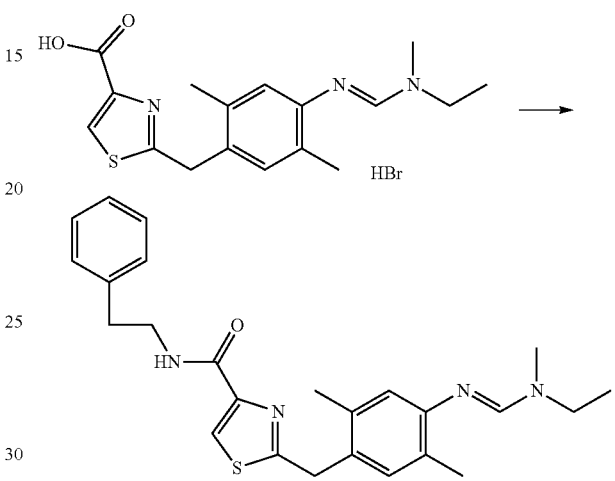

To a N,N-dimethylformamide (2.0 mL) solution of the compound (41 mg) obtained by the technique of Reference Example 37, 2-phenylethanamine (14 μL) and N,N-diisopropylethylamine (87 μL) were added, then HATU (45 mg) was added, and the resultant was stirred at room temperature for 1 hour. The reaction solution was purified by preparative LC to obtain the title compound (39 mg) as a pale yellow oil.

MS (ESI-APCI): 435[M+H]+

$^1$H NMR (600 MHz, CHLOROFORM-d) δppm 1.21 (3H, t, J=7.2 Hz), 2.18-2.25 (6H, m), 2.94 (2H, t, J=7.4 Hz), 3.00 (3H, s), 3.24-3.44 (2H, m), 3.66-3.72 (2H, m), 4.17 (2H, s), 6.59 (1H, s), 6.98 (1H, s), 7.21-7.26 (3H, m), 7.28-7.35 (2H, m), 7.38-7.47 (2H, m), 7.91 (1H, s)

Example 79

2-[4-({(E)-[Ethyl(methyl)amino]methylidene}amino)-2,5-dimethylbenzyl]-N-[2-(pyrazin-2-yl)ethyl]-1,3-thiazole-4-carboxamide

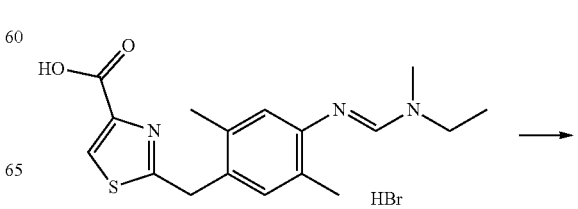

-continued

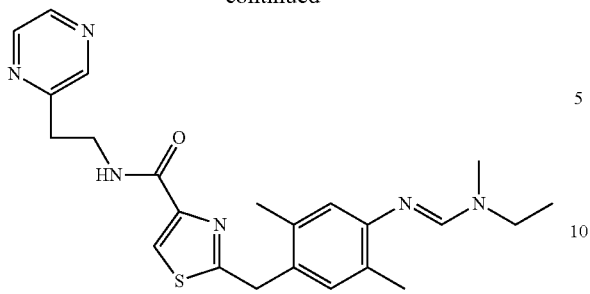

To a N,N-dimethylformamide (2.0 mL) solution of the compound (41 mg) obtained by the technique of Reference Example 37, 2-(pyrazin-2-yl)ethanamine (12 μL) and N,N-diisopropylethylamine (87 μL) were added, then HATU (45 mg) was added, and the resultant was stirred at room temperature for 1 hour. The reaction solution was purified by preparative LC to obtain the title compound (48 mg) as a pale yellow oil.

MS (ESI-APCI): 437[M+H]+
$^1$H NMR (600 MHz, CHLOROFORM-d) δppm 1.21 (3H, t, J=7.0 Hz), 2.15-2.26 (6H, m), 3.00 (3H, br. s.), 3.16 (2H, t, J=6.6 Hz), 3.24-3.44 (2H, m), 3.89 (2H, q, J=6.6 Hz), 4.17 (2H, s), 6.59 (1H, br. s.), 6.98 (1H, s), 7.43 (1H, br. s), 7.71-7.78 (1H, m), 7.91 (1H, s), 8.41-8.56 (3H, m)

Example 80

N-Ethyl-2-[4-({(E)-[ethyl(methyl)amino]methylidene}amino)-2,5-dimethylbenzyl]-N-methyl-1,3-thiazole-4-carboxamide

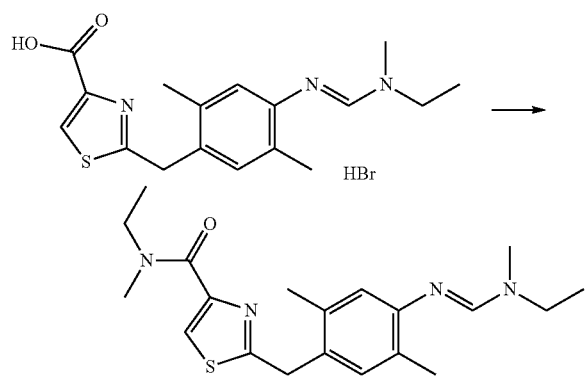

To a 1-methyl-2-pyrrolidone (2.0 mL) solution of the compound (41 mg) obtained by the technique of Reference Example 37, N,N'-carbonyldiimidazole (21 mg) was added, and the resultant was stirred at room temperature for 1 hour. Then, pyrazin-2-amine (14 mg) was added thereto, and the resultant was stirred at room temperature for 1 hour, then at 100° C. for 3.5 hours, then overnight at room temperature, and further at 100° C. for 7.5 hours. A saturated aqueous solution of sodium bicarbonate was added to the reaction solution, followed by extraction with chloroform. An organic layer was separated using a phase separator, and the solvent was distilled off under reduced pressure. The obtained residue was purified by preparative LC to obtain the title compound (2.5 mg) as a pale yellow oil.

MS (ESI-APCI): 373[M+H]+
$^1$H NMR (600 MHz, CHLOROFORM-d) δppm 1.15-1.25 (6H, m), 2.17-2.24 (6H, m), 2.99 (3H, s), 3.01-3.24 (3H, m), 3.25-3.69 (4H, m), 4.22 (2H, s), 6.58 (1H, s), 7.01 (1H, s), 7.43 (1H, br. s.), 7.67 (1H, s)

Example 81

N'-(2,5-Dimethyl-4-{[4-(tetrahydro-2H-pyran-4-yl)-1,3-thiazol-2-yl]methyl}phenyl)-N-ethyl-N-methylimidoformamide

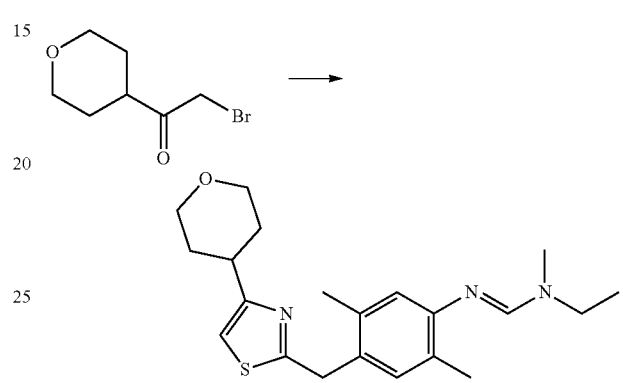

To a 2-propanol (1.0 mL) solution of the compound (30 mg) obtained by the technique of Reference Example 1-5, 2-bromo-1-(tetrahydro-2H-pyran-4-yl)ethanone (56 mg) was added, and the resultant was stirred at 80° C. for 2.5 hours. After standing to cool to room temperature, a saturated aqueous solution of sodium bicarbonate was added thereto, followed by extraction with chloroform. An organic layer was separated using a phase separator, and the solvent was distilled off under reduced pressure. The obtained residue was purified by silica gel column chromatography (OH-type silica gel; chloroform/methanol-gradient elution=99/1→90/10) to obtain the title compound (36 mg) as a yellow oil.

MS (ESI-APCI): 372[M+H]+
$^1$H NMR (600 MHz, CHLOROFORM-d) δppm 1.17-1.25 (3H, m), 1.73-1.82 (2H, m), 1.96-2.02 (2H, m), 2.16-2.26 (6H, m), 2.93-3.04 (4H, m), 3.23-3.44 (2H, m), 3.49-3.57 (2H, m), 4.02-4.09 (2H, m), 4.20 (2H, s), 6.59 (1H, br. s.), 6.70 (1H, s), 7.01 (1H, s), 7.43 (1H, br. s)

Example 82

3-{2-[4-({(E)-[Ethyl(methyl)amino]methylidene}amino)-2,5-dimethylbenzyl]-1,3-thiazol-4-yl}-N-methylbenzamide

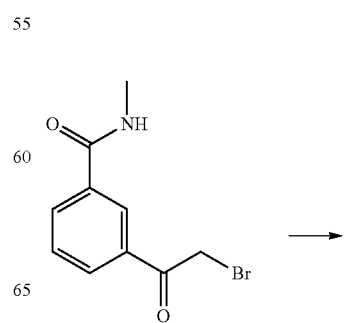

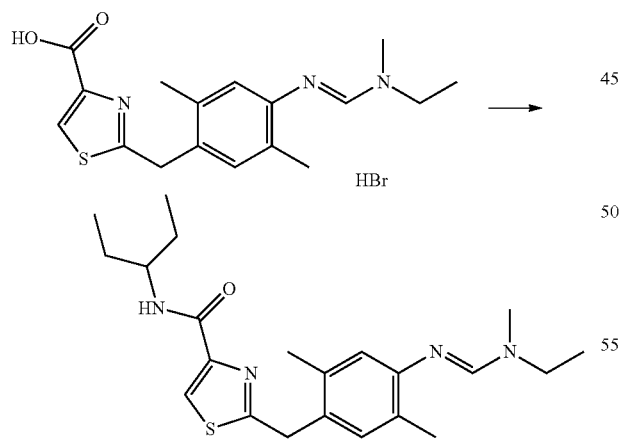

To a 2-propanol (1.0 mL) solution of the compound (30 mg) obtained by the technique of Reference Example 1-5, the compound (65 mg) obtained by the technique of Reference Example 39 was added, and the resultant was stirred at 80° C. for 1 hour. After standing to cool to room temperature, a saturated aqueous solution of sodium bicarbonate was added thereto, followed by extraction with chloroform. An organic layer was separated using a phase separator, and the solvent was distilled off under reduced pressure. The obtained residue was purified by silica gel column chromatography (NH-type silica gel; hexane/ethyl acetate-gradient elution=65/35→12/88) to obtain the title compound (40 mg) as a pale pink oil.

MS (ESI-APCI): 421[M+H]+

$^1$H NMR (600 MHz, CHLOROFORM-d) δppm 1.17-1.29 (3H, m), 2.25 (6H, s), 2.96-3.10 (6H, m), 3.28-3.48 (2H, m), 4.29 (2H, s), 6.27 (1H, br. s.), 6.63 (1H, br. s.), 7.05 (1H, s), 7.39 (1H, s), 7.42-7.52 (2H, m), 7.75 (1H, d, J=7.8 Hz), 7.97-8.03 (1H, m), 8.27 (1H, s)

Example 83

2-[4-({(E)-[Ethyl(methyl)amino]methylidene}amino)-2,5-dimethylbenzyl]-N-(pentan-3-yl)-1,3-thiazole-4-carboxamide

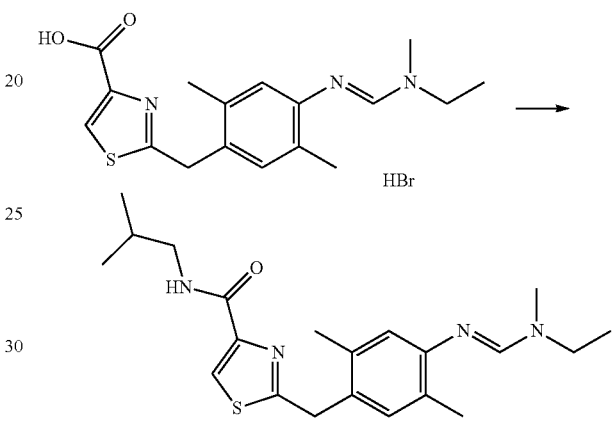

To a N,N-dimethylformamide (2.0 mL) solution of the compound (40 mg) obtained by the technique of Reference Example 37, pentan-3-amine (12 µL) and N,N-diisopropylethylamine (85 µL) were added, then HATU (44 mg) was added, and the resultant was stirred at room temperature for 2 hours. The reaction solution was purified by preparative LC to obtain the title compound (39 mg) as a pale yellow oil.

MS (ESI-APCI): 401[M+H]+

$^1$H NMR (600 MHz, CHLOROFORM-d) δppm 0.96 (6H, t, J=7.4 Hz), 1.21 (3H, t, J=7.2 Hz), 1.45-1.73 (4H, m), 2.18-2.26 (6H, m), 3.00 (3H, s), 3.20-3.46 (2H, m), 3.90-4.02 (1H, m), 4.20 (2H, s), 6.60 (1H, s), 7.00 (1H, s), 7.09 (1H, d, J=8.7 Hz), 7.45 (1H, br. s.), 7.90 (1H, s)

Example 84

2-[4-({(E)-[Ethyl(methyl)amino]methylidene}amino)-2,5-dimethylbenzyl]-N-(2-methylpropyl)-1,3-thiazole-4-carboxamide To a N,N-dimethylformamide (2.0 mL) solution of the compound (40 mg) obtained by the technique of Reference Example 37, 2-methylpropan-1-amine (11 µL) and N,N-diisopropylethylamine (85 µL) were added, then HATU (44 mg) was added, and the resultant was stirred at room temperature for 1 hour. The reaction solution was purified by preparative LC to obtain the title compound (32 mg) as a pale yellow oil.

MS (ESI-APCI): 387[M+H]+

$^1$H NMR (600 MHz, CHLOROFORM-d) δppm 0.99 (6H, d, J=6.6 Hz), 1.17-1.24 (3H, m), 1.86-1.95 (1H, m), 2.18-2.27 (6H, m), 3.00 (3H, s), 3.27 (2H, t, J=6.6 Hz), 3.31-3.44 (2H, m), 4.20 (2H, s), 6.59 (1H, s), 6.99 (1H, s), 7.37-7.48 (2H, m), 7.90 (1H, s)

Example 85

N-(2,2-Dimethylpropyl)-2-[4-({(E)-[ethyl(methyl)amino]methylidene}amino)-2,5-dimethylbenzyl]-1,3-thiazole-4-carboxamide

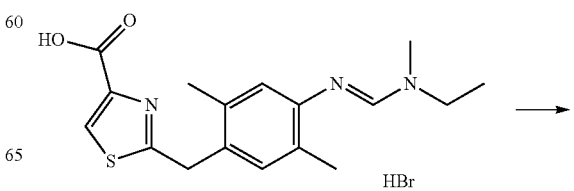

149
-continued

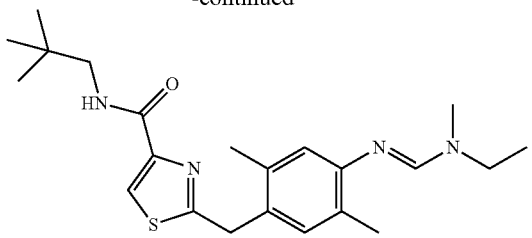

To a N,N-dimethylformamide (2.0 mL) solution of the compound (40 mg) obtained by the technique of Reference Example 37, 2,2-dimethylpropan-1-amine (12 μL) and N,N-diisopropylethylamine (85 μL) were added, then HATU (44 mg) was added, and the resultant was stirred at room temperature for 1 hour. The reaction solution was purified by preparative LC to obtain the title compound (42 mg) as a pale yellow oil.

MS (ESI-APCI): 401[M+H]+

$^1$H NMR (600 MHz, CHLOROFORM-d) δppm 0.99 (9H, s), 1.21 (3H, t, J=7.0 Hz), 2.19-2.26 (6H, m), 3.00 (3H, s), 3.25 (2H, d, J=6.6 Hz), 3.29-3.47 (2H, m), 4.20 (2H, s), 6.59 (1H, s), 7.00 (1H, s), 7.40-7.51 (2H, m), 7.90 (1H, s)

Example 86

2-[4-({(E)-[Ethyl(methyl)amino]methylidene}amino)-2,5-dimethylbenzyl]-N-(2-methylbutan-2-yl)-1,3-thiazole-4-carboxamide

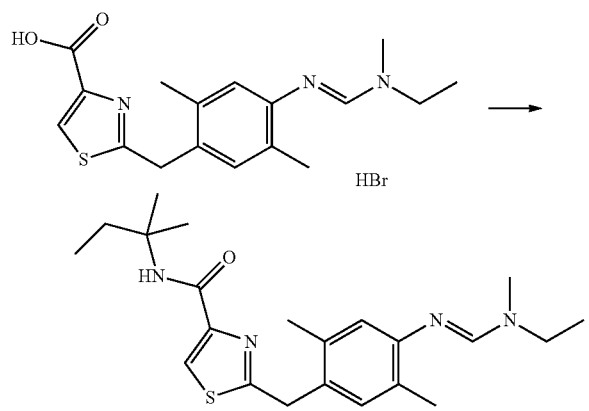

To a N,N-dimethylformamide (2.0 mL) solution of the compound (40 mg) obtained by the technique of Reference Example 37, 2-methylbutan-2-amine (12 μL) and N,N-diisopropylethylamine (85 μL) were added, then HATU (44 mg) was added, and the resultant was stirred at room temperature for 1 hour. The reaction solution was purified by preparative LC to obtain the title compound (40 mg) as a pale yellow oil.

MS (ESI-APCI): 401[M+H]+

$^1$H NMR (600 MHz, CHLOROFORM-d) δppm 0.92 (3H, t, J=7.6 Hz), 1.21 (3H, t, J=7.2 Hz), 1.43 (6H, s), 1.85 (2H, q, J=7.6 Hz), 2.17-2.27 (6H, m), 3.00 (3H, s), 3.21-3.49 (2H, m), 4.19 (2H, s), 6.59 (1H, s), 6.99 (1H, s), 7.20 (1H, br. s.), 7.44 (1H, br. s.), 7.84 (1H, s)

150
Example 87

4-{2-[4-({(E)-[Ethyl(methyl)amino]methylidene}amino)-2,5-dimethylbenzyl]-1,3-thiazol-4-yl}-N-methylcyclohexanecarboxamide

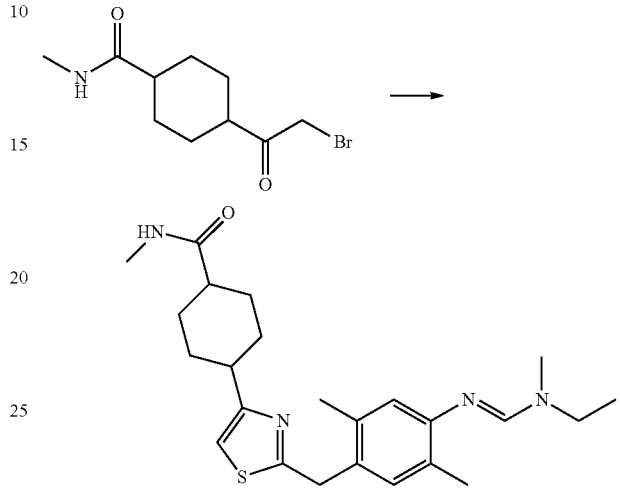

To a 2-propanol (4.0 mL) solution of the compound (60 mg) obtained by the technique of Reference Example 1-5, the compound (0.11 g) obtained by the technique of Reference Example 40 was added, and the resultant was stirred at 70° C. for 1 hour. After standing to cool to room temperature, the solvent in the reaction solution was distilled off under reduced pressure. The obtained residue was purified by preparative LC to obtain the title compound (33 mg) as a yellow oil.

MS (ESI-APCI): 427[M+H]+, 425[M+H]−

$^1$H NMR (600 MHz, CHLOROFORM-d) δppm 1.21 (3H, t, J=7.2 Hz), 1.41-1.53 (1H, m), 1.59-1.78 (2H, m), 1.84-2.06 (4H, m), 2.08-2.16 (1H, m), 2.09-2.40 (7H, m), 2.70-3.02 (6H, m), 3.27-3.46 (2H, m), 4.16-4.22 (2H, m), 5.44-5.53 (1H, m), 6.54-6.74 (2H, m), 6.97-7.02 (1H, m), 7.26 (1H, s), 7.43 (1H, br. s.)

Example 88

2-{2-[4-({(E)-[Ethyl(methyl)amino]methylidene}amino)-2,5-dimethylbenzyl]-1,3-thiazol-4-yl}-N-methylbenzamide

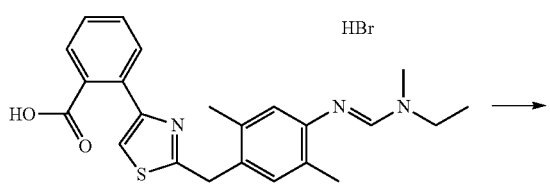

-continued

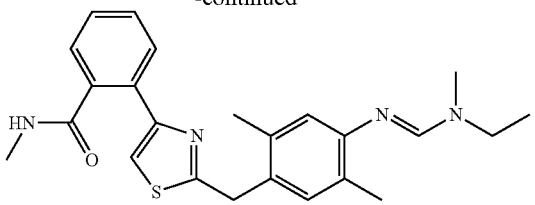

To a N,N-dimethylformamide (4.0 mL) solution of the compound (88 mg) obtained by the technique of Reference Example 41, methylamine hydrochloride (13 mg) and N,N-diisopropylethylamine (0.16 mL) were added, then HATU (82 mg) was added, and the resultant was stirred at room temperature for 1 hour. The reaction solution was purified by preparative LC to obtain the title compound (33 mg) as a white solid.

MS (ESI-APCI): 421[M+H]+, 419[M−H]−
$^1$H NMR (600 MHz, CHLOROFORM-d) δppm 1.17-1.24 (3H, m), 2.22-2.28 (6H, m), 2.78 (3H, d, J=5.0 Hz), 3.00 (3H, br. s.), 3.26-3.43 (2H, m), 4.26 (2H, s), 6.13-6.24 (1H, m), 6.60 (1H, br. s.), 7.04 (1H, s), 7.24 (1H, s), 7.36-7.49 (3H, m), 7.58-7.62 (1H, m), 7.65 (1H, d, J=7.8 Hz)

Example 89

N'-(2,5-Dimethyl-4-{[4-(1-oxo-2,3-dihydro-1H-isoindol-5-yl)-1,3-thiazol-2-yl]methyl}phenyl)-N-ethyl-N-methylimidoformamide

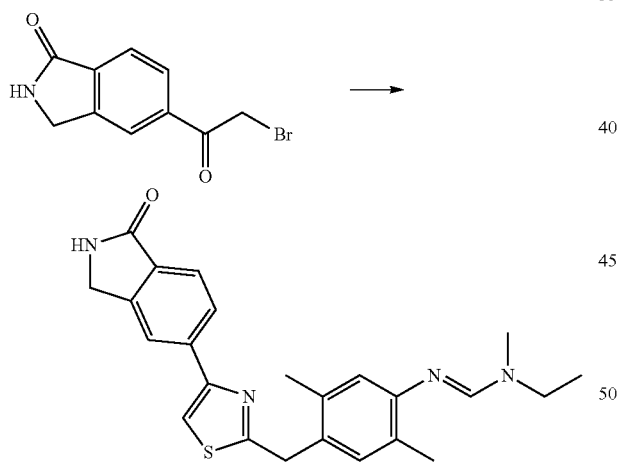

To a 2-propanol (1.0 mL) solution of the compound (26 mg) obtained by the technique of Reference Example 1-5, the compound (22 mg) obtained by the technique of Reference Example 42-4 was added, and the resultant was stirred at 80° C. for 1 hour. After standing to cool to room temperature, a saturated aqueous solution of sodium bicarbonate was added thereto, followed by extraction with chloroform. An organic layer was separated using a phase separator, and the solvent was distilled off under reduced pressure. The obtained residue was purified by silica gel column chromatography (NH-type silica gel; chloroform/methanol-gradient elution=99/1→97/3) and then further purified by preparative LC to obtain the title compound (19 mg) as a colorless solid.

MS (ESI-APCI): 419[M+H]+
$^1$H NMR (600 MHz, DMSO-d$_6$) δppm 1.12 (3H, t, J=7.0 Hz), 2.11-2.23 (6H, m), 2.92 (3H, br. s.), 3.37-3.49 (2H, m), 4.26 (2H, s), 4.43 (2H, s), 6.62 (1H, br. s.), 7.04 (1H, s), 7.52-7.67 (1H, m), 7.71 (1H, d, J=7.8 Hz), 8.05 (1H, d, J=7.8 Hz), 8.08 (1H, s), 8.14 (1H, s), 8.56 (1H, s)

Example 90

5-{2-[4-({(E)-[Ethyl(methyl)amino]methylidene}amino)-2,5-dimethylbenzyl]-1,3-thiazol-4-yl}-N-methylpyrazine-2-carboxamide

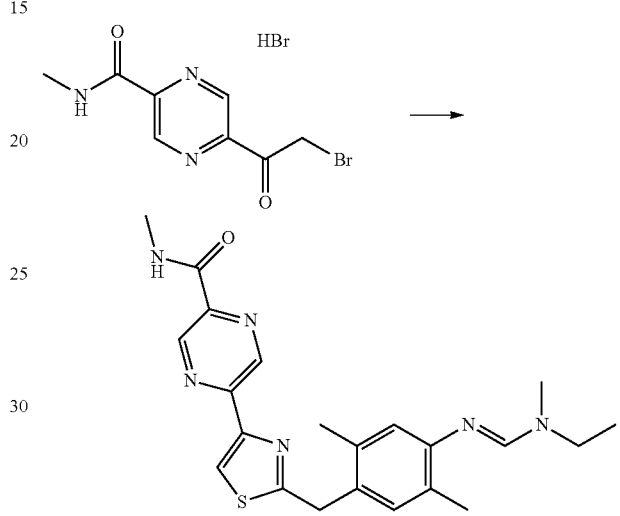

To a 2-propanol (1.0 mL) solution of the compound (30 mg) obtained by the technique of Reference Example 1-5, the compound (46 mg) obtained by the technique of Reference Example 43-3 was added, and the resultant was stirred at 80° C. for 1.5 hours. The reaction solution was concentrated under reduced pressure. The residue was purified by preparative LC to obtain the title compound (38 mg) as a pale yellow solid.

MS (ESI-APCI): 423[M+H]+
$^1$H NMR (600 MHz, CHLOROFORM-d) δppm 1.15-1.26 (3H, m), 2.25 (6H, s), 3.01 (3H, br. s.), 3.07 (3H, d, J=5.0 Hz), 3.20-3.52 (2H, m), 4.31 (2H, s), 6.62 (1H, br. s.), 7.06 (1H, s), 7.46 (1H, br. s.), 7.75-7.84 (1H, m), 8.09 (1H, s), 9.26 (1H, d, J=1.2 Hz), 9.33 (1H, d, J=1.2 Hz)

Example 91

5-{2-[4-({(E)-[Ethyl(methyl)amino]methylidene}amino)-2,5-dimethylbenzyl]-1,3-thiazol-4-yl}-N,2-dimethylbenzamide

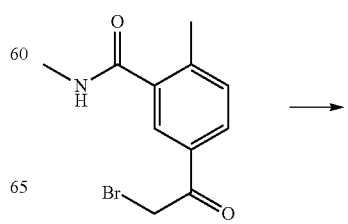

-continued

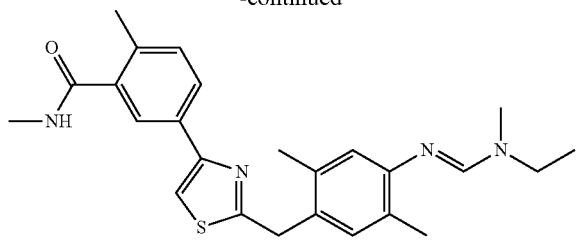

To a 2-propanol (4.0 mL) solution of the compound (78 mg) obtained by the technique of Reference Example 1-5, the compound (70 mg) obtained by the technique of Reference Example 44-2 was added, and the resultant was stirred at 80° C. for 1 hour. After standing to cool to room temperature, a saturated aqueous solution of sodium bicarbonate was added thereto, followed by extraction with chloroform. An organic layer was separated using a phase separator, and the solvent was distilled off under reduced pressure. The obtained residue was purified by silica gel column chromatography (OH-type silica gel; chloroform/methanol-gradient elution=99/1→89/11) to obtain the title compound (103 mg) as a pale yellow foam.

MS (ESI-APCI): 435[M+H]+, 433[M−H]−

$^1$H NMR (600 MHz, CHLOROFORM-d) δppm 1.21 (3H, t, J=7.0 Hz), 2.24 (6H, s), 2.48 (3H, s), 2.94-3.06 (6H, m), 3.25-3.45 (2H, m), 4.28 (2H, s), 5.88 (1H, d, J=4.5 Hz), 6.61 (1H, s), 7.04 (1H, s), 7.20-7.30 (2H, m), 7.45 (1H, br. s.), 7.78 (1H, dd, J=7.8, 1.7 Hz), 7.92 (1H, d, J=1.7 Hz)

Example 92

N'-(4-{[4-(3,5-Dimethylpyrazin-2-yl)-1,3-thiazol-2-yl]methyl}-2,5-dimethylphenyl)-N-ethyl-N-methylimidoformamide

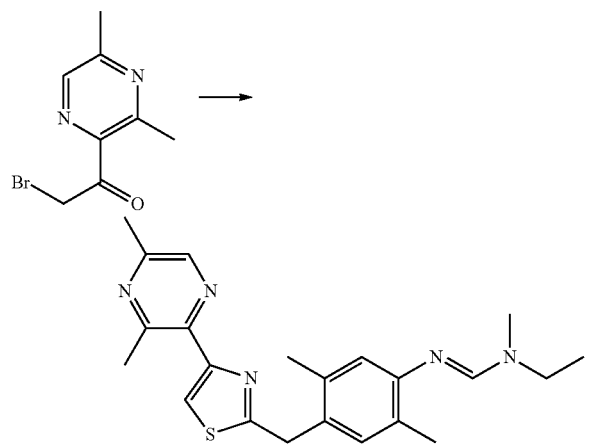

To a 2-propanol (3.0 mL) solution of the compound (18 mg) obtained by the technique of Reference Example 1-5, the compound (14 mg) obtained by the technique of Reference Example 46 was added, and the resultant was stirred at 80° C. for 30 minutes. The reaction solution was concentrated under reduced pressure. The residue was purified by preparative LC to obtain the title compound (13 mg) as a pale yellow oil.

MS (ESI-APCI): 394[M+H]+

$^1$H NMR (600 MHz, CHLOROFORM-d) δppm 1.22 (3H, t, J=6.8 Hz), 2.20-2.29 (6H, m), 2.57 (3H, s), 2.81 (3H, br. s.), 3.01 (3H, br. s.), 3.23-3.45 (2H, m), 4.31 (2H, s), 6.61 (1H, br. s.), 7.06 (1H, s), 7.45 (1H, br. s.), 7.63 (1H, s), 8.32 (1H, s)

Example 93

4-({2-[4-({(E)-[Ethyl(methyl)amino]methylidene}amino)-2,5-dimethylbenzyl]-1,3-thiazol-4-yl}methoxy)-N-methylbenzamide

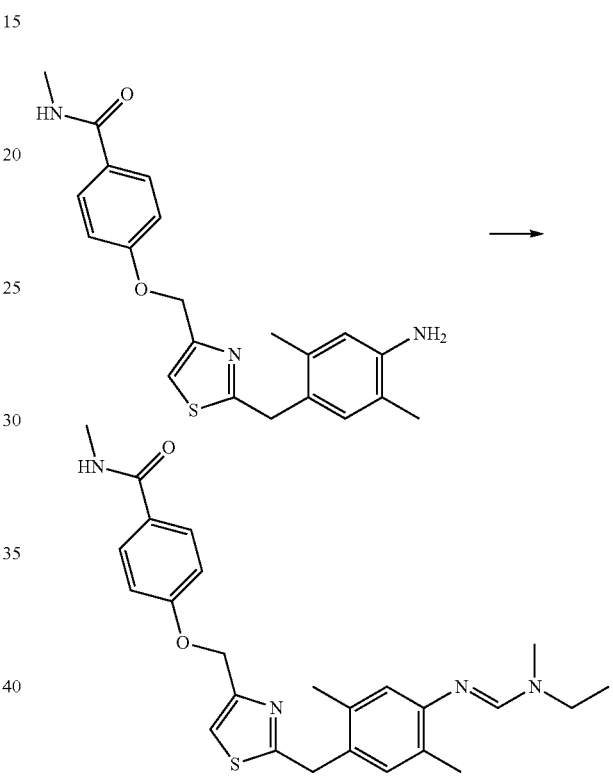

To a chloroform (0.50 mL) solution of N-ethyl-N-methylformamide (12 mg), in a nitrogen atmosphere, oxalyl chloride (10 μL) was added, and the resultant was stirred at room temperature for 10 minutes. Then, a chloroform (0.50 mL) solution of the compound (32 mg) obtained by the technique of Reference Example 47-2 was added thereto, and the resultant was stirred at room temperature for 1 hour. A saturated aqueous solution of sodium bicarbonate was added thereto, followed by extraction with chloroform. The organic layer was dried over magnesium sulfate, and the desiccant was filtered off. Then, the solvent was distilled off under reduced pressure. The obtained residue was purified by silica gel column chromatography (NH-type silica gel; hexane/ethyl acetate-gradient elution=100/0→66/34) to obtain the title compound (16 mg) as a pale yellow solid.

MS (ESI-APCI): 451[M+H]+, 449[M−H]−

$^1$H NMR (600 MHz, CHLOROFORM-d) δppm 1.21 (3H, t, J=7.0 Hz), 2.18-2.25 (6H, m), 2.97-3.03 (6H, m), 3.22-3.44 (2H, m), 4.24 (2H, s), 5.20 (2H, s), 6.03 (1H, br. s.), 6.59 (1H, s), 6.97-7.04 (3H, m), 7.14 (1H, s), 7.44 (1H, br. s.), 7.72 (2H, d, J=8.7 Hz)

Example 94

Methyl 2-{2-[4-({(E)-[ethyl(methyl)amino]methylidene}amino)-2,5-dimethylbenzyl]-1,3-thiazol-4-yl}-5-methylbenzoate

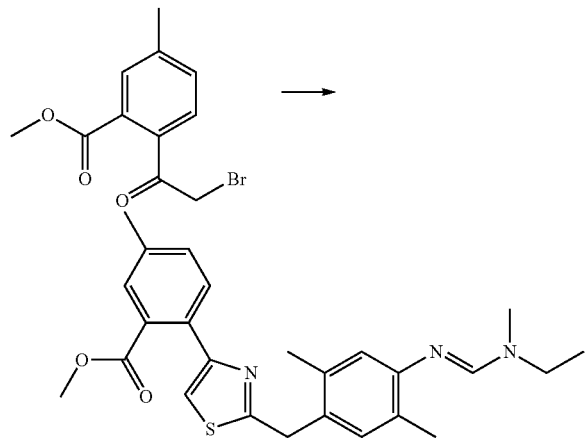

To a 2-propanol (5 mL) solution of the compound (221 mg) obtained by the technique of Reference Example 1-5, the compound (200 mg) obtained by the technique of Reference Example 48-2 was added, and the resultant was stirred at 80° C. for 45 minutes. The reaction solution was allowed to cool to room temperature. A saturated aqueous solution of sodium bicarbonate was added thereto, and the resultant was stirred for 10 minutes, followed by extraction with chloroform. The obtained organic layer was concentrated under reduced pressure. The residue was purified by silica gel column chromatography (OH-type silica gel; hexane/ethyl acetate-gradient elution=67/33→0/100 and chloroform/methanol=90/10) to obtain the title compound (217 mg) as a pale yellow solid.

MS (ESI-APCI): 436[M+H]+, 458[M+Na]+

$^1$H NMR (600 MHz, CHLOROFORM-d) δppm 1.19-1.24 (3H, m), 2.24 (6H, s), 2.40 (3H, s), 3.01 (3H, br. s.), 3.25-3.43 (2H, m), 3.69 (3H, s), 4.23 (2H, s), 6.60 (1H, s), 7.04 (1H, s), 7.13 (1H, s), 7.30 (1H, dd, J=7.8, 1.2 Hz), 7.41-7.47 (1H, m), 7.48-7.53 (2H, m)

Example 95

4-[2-(2,5-Dimethyl-4-{[(E)-(methylamino)methylidene]amino}benzyl)-1,3-thiazol-4-yl]-N-methylbenzamide

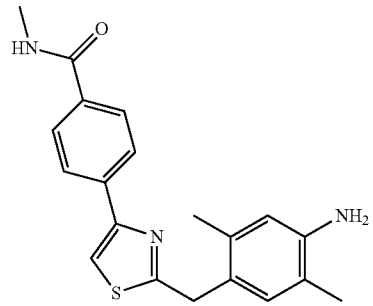

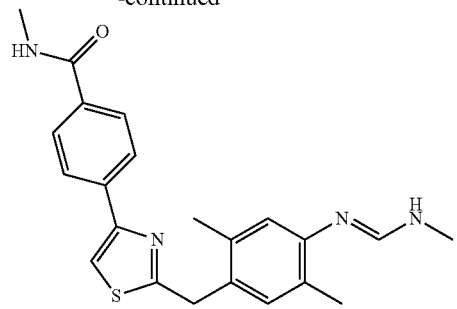

To a N-methylformamide (1.0 mL) solution of the compound (30 mg) obtained by the technique of Reference Example 49-4, p-toluenesulfonyl chloride (19.4 mg) was added, and the resultant was stirred at room temperature for 3 hours. The reaction solution was neutralized by addition to a cooled sodium hydroxide solution, followed by extraction using chloroform. An aqueous layer was separated using a phase separator, and the obtained organic layer was concentrated under reduced pressure. The residue was purified by preparative LC. Then, the obtained mixture was purified by silica gel column chromatography (OH-type silica gel; chloroform/methanol-gradient elution=95/5→50/50) to obtain the title compound (24 mg) as a white solid.

MS (ESI-APCI): 393[M+H]+, 415[M+Na]+

$^1$H NMR (600 MHz, DMSO-d$_6$) δppm 2.14 (3H, s), 2.20 (3H, s), 2.79 (3H, s), 2.80 (3H, s), 4.26 (2H, s), 6.53-6.64 (1H, m), 6.99-7.07 (1H, m), 7.54-7.64 (1H, m), 7.89 (2H, d, J=8.3 Hz), 8.02 (2H, d, J=8.3 Hz), 8.06 (1H, s), 8.43-8.50 (1H, m)

Example 96

N-(4,4-Difluorocyclohexyl)-2-[4-({(E)-[ethyl(methyl)amino]methylidene}amino)-2,5-dimethylbenzyl]-1,3-thiazole-4-carboxamide hydrochloride

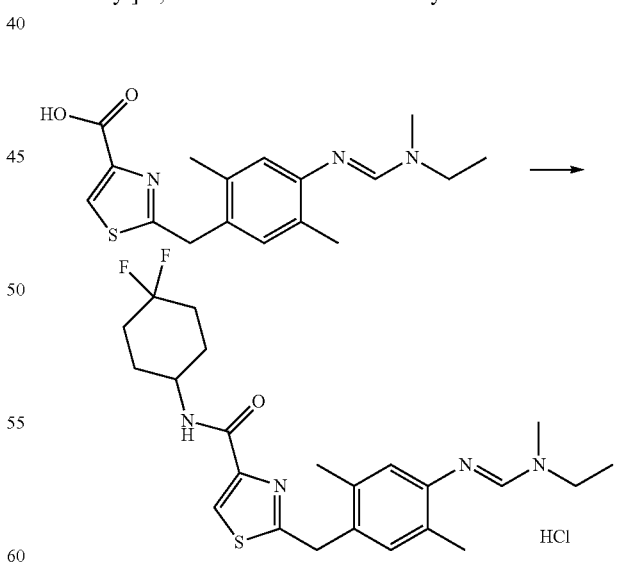

The title compound was obtained by the same technique as in Example 43 from the compound obtained by the technique of Example 39.

$^1$H NMR (400 MHz, DMSO-d$_6$) δ ppm 1.22-1.29 (3H, m), 1.65-2.10 (8H, m), 2.26 (3H, s), 2.28-2.33 (3H, m), 3.23-3.30 (3H, m), 3.58-3.72 (2H, m), 3.90-4.03 (1H, m), 4.36 (2H, s), 7.22-7.26 (1H, m), 7.28 (1H, s), 8.11 (1H, s), 8.25 (1H, d, J=8.3 Hz), 8.28-8.46 (1H, m), 10.76-10.99 (1H, m)

Example 97

Cyclohexyl {2-[4-({(E)-[ethyl(methyl)amino]methylidene}amino)-2,5-dimethylbenzyl]-1,3-thiazol-4-yl}carbamate hydrochloride

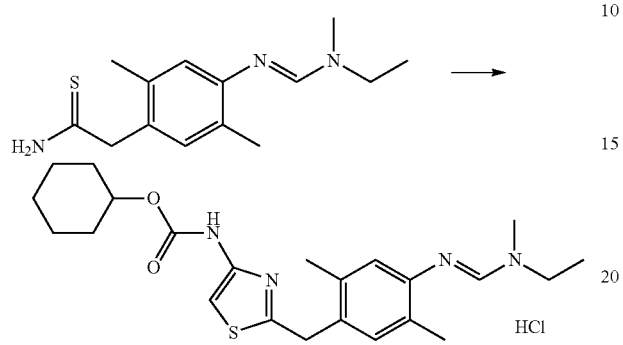

The title compound was obtained by the same technique as in Example 31 from the compound obtained by the technique of Reference Example 1-5.

$^1$H NMR (400 MHz, DMSO-$d_6$) δ ppm 1.20-1.55 (9H, m), 1.64-1.74 (2H, m), 1.80-1.89 (2H, m), 2.24 (3H, s), 2.26-2.32 (3H, m), 3.21-3.29 (3H, m), 3.58-3.69 (2H, m), 4.24 (2H, s), 4.57-4.66 (1H, m), 7.05 (1H, s), 7.19-7.22 (1H, m), 7.23 (1H, s), 8.25-8.45 (1H, m), 10.31 (1H, s), 10.64-10.85 (1H, m)

Example 98

4-{2-[4-({(E)-[Ethyl(methyl)amino]methylidene}amino)-2,5-dimethylbenzyl]-1,3-thiazol-4-yl}-N-(propan-2-yl)benzamide

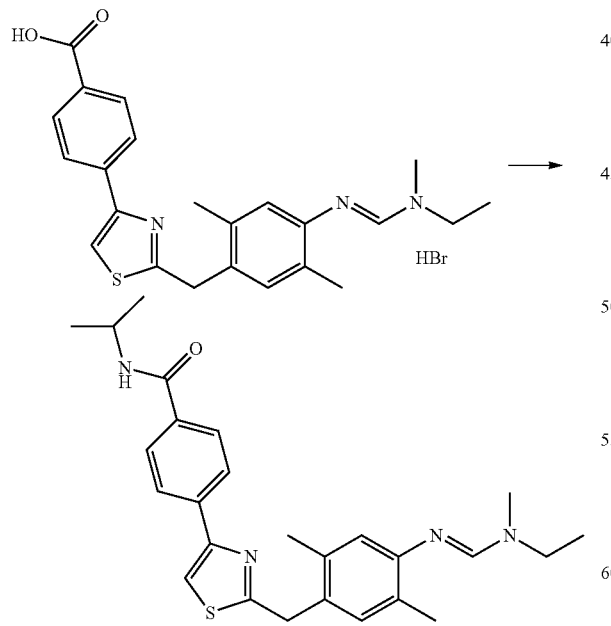

The title compound was obtained by the same technique as in Example 24 from the compound obtained by the technique of Example 15.

$^1$H NMR (400 MHz, DMSO-$d_6$) δ ppm 1.12 (3H, t, J=7.0 Hz), 1.18 (6H, d, J=6.4 Hz), 2.13 (3H, s), 2.20 (3H, s), 2.93 (3H, s), 3.15-3.55 (2H, m), 4.06-4.17 (1H, m), 4.26 (2H, s), 6.63 (1H, s), 7.04 (1H, s), 7.49-7.74 (1H, m), 7.91 (2H, d, J=8.1 Hz), 8.01 (2H, d, J=8.1 Hz), 8.05 (1H, s), 8.25 (1H, d, J=7.6 Hz)

Example 99

N-(2,2-Dimethylpropyl)-4-{2-[4-({(E)-[ethyl(methyl)amino]methylidene}amino)-2,5-dimethylbenzyl]-1,3-thiazol-4-yl}benzamide

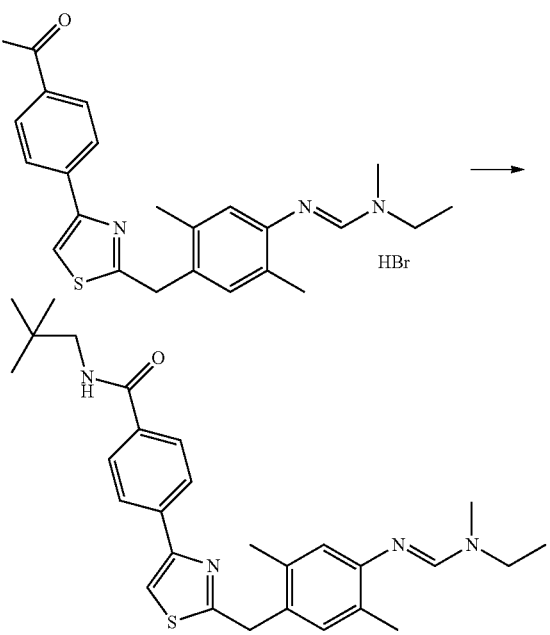

The title compound was obtained by the same technique as in Example 24 from the compound obtained by the technique of Example 15.

$^1$H NMR (400 MHz, DMSO-$d_6$) δ ppm 0.91 (9H, s), 1.13 (3H, t, J=7.1 Hz), 2.15 (3H, s), 2.22 (3H, s), 2.95 (3H, s), 3.12 (2H, d, J=6.3 Hz), 3.28-3.49 (2H, m), 4.27 (2H, s), 6.67 (1H, s), 7.06 (1H, s), 7.53-7.79 (1H, m), 7.92 (2H, d, J=8.3 Hz), 8.02 (2H, d, J=8.3 Hz), 8.05 (1H, s), 8.37 (1H, t, J=6.3 Hz)

Example 100

4-{2-[4-({(E)-[Ethyl(methyl)amino]methylidene}amino)-2,5-dimethylbenzyl]-1,3-thiazol-4-yl}-N,N-dimethylbenzamide hydrochloride

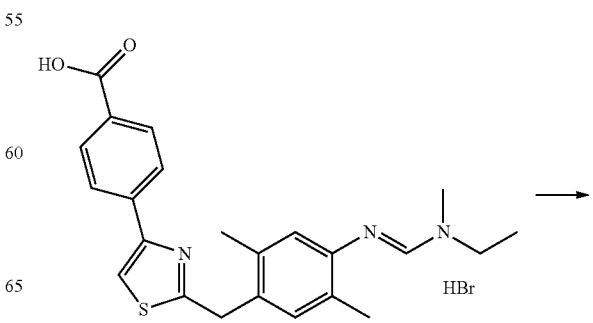

159
-continued

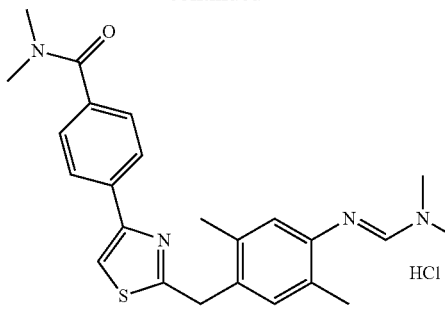

The title compound was obtained by the same technique as in Example 24 from the compound obtained by the technique of Example 15.

$^1$H NMR (400 MHz, DMSO-d$_6$) δ ppm 1.18-1.32 (3H, m), 2.25-2.37 (6H, m), 2.94 (3H, s), 2.99 (3H, s), 3.20-3.33 (3H, m), 3.54-4.00 (2H, m), 4.40 (2H, s), 7.18-7.27 (1H, m), 7.30 (1H, s), 7.47 (2H, d, J=7.6 Hz), 7.98 (2H, d, J=7.6 Hz), 8.06 (1H, s), 8.26-8.48 (1H, m), 10.82-11.07 (1H, m)

Example 101

N'-[4-({4-[4-(Azetidin-1-ylcarbonyl)phenyl]-1,3-thiazol-2-yl}methyl)-2,5-dimethylphenyl]-N-ethyl-N-methylimidoformamide

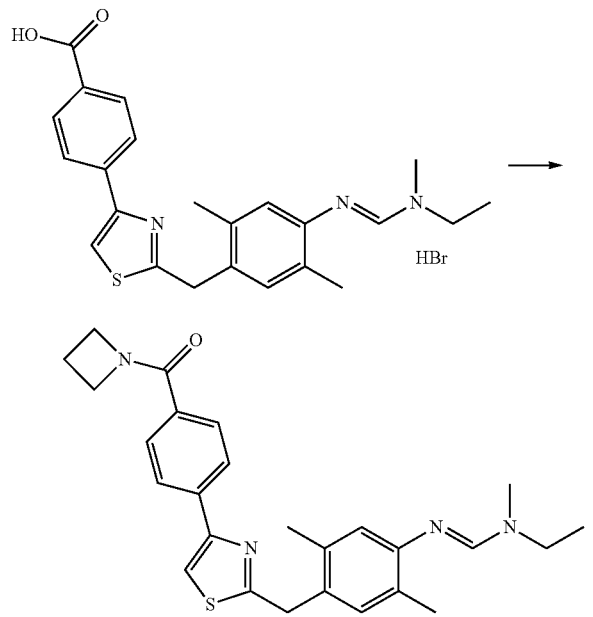

The title compound was obtained by the same technique as in Example 24 from the compound obtained by the technique of Example 15.

$^1$H NMR (400 MHz, DMSO-d$_6$) δ ppm 1.13-1.30 (3H, m), 2.15-2.37 (8H, m), 3.03-3.20 (3H, m), 3.25-3.75 (2H, m), 4.00-4.13 (2H, m), 4.26-4.44 (4H, m), 6.92-7.33 (2H, m), 7.63-7.76 (2H, m), 7.93-8.18 (4H, m)

160
Example 102

Propan-2-yl {2-[4-({(E)-[ethyl(methyl)amino]methylidene}amino)-2,5-dimethylbenzyl]-1,3-thiazol-4-yl}carbamate

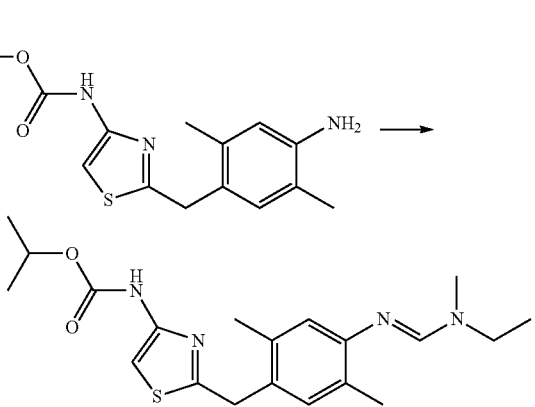

The title compound was obtained by the same technique as in Example 2 from the compound obtained by the technique of Reference Example 50-2.

$^1$H NMR (400 MHz, CHLOROFORM-d) δ ppm 1.20 (3H, t, J=7.2 Hz), 1.29 (6H, d, J=6.4 Hz), 2.19 (3H, s), 2.22 (3H, s), 2.99 (3H, s), 3.19-3.56 (2H, m), 4.12 (2H, s), 4.96-5.07 (1H, m), 6.57 (1H, s), 6.98 (1H, s), 7.02-7.10 (1H, m), 7.36-7.46 (1H, m), 7.46-7.56 (1H, m)

Example 103

N'-[2,5-Dimethyl-4-({4-[4-(pyrrolidin-1-ylcarbonyl)phenyl]-1,3-thiazol-2-yl}methyl)phenyl]-N-ethyl-N-methylimidoformamide hydrochloride

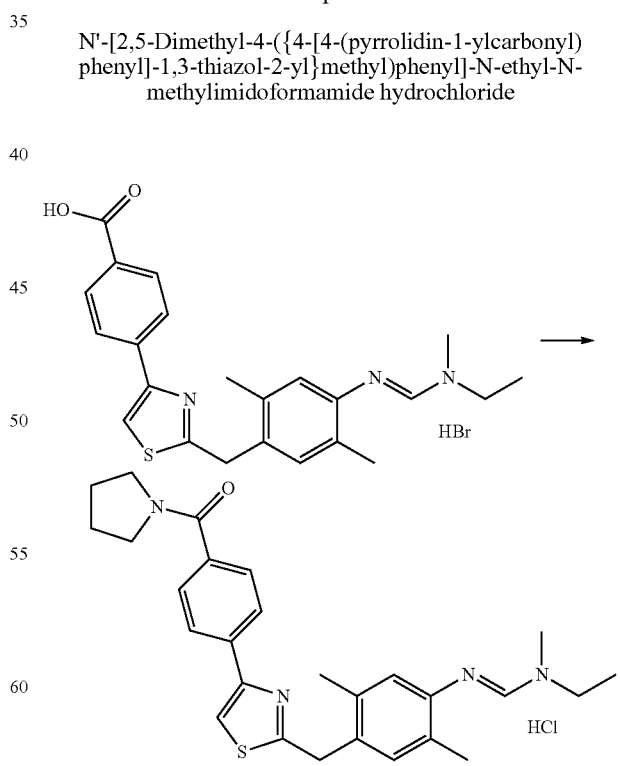

The title compound was obtained by the same technique as in Example 24 from the compound obtained by the technique of Example 15.

¹H NMR (400 MHz, DMSO-d₆) δ ppm 1.22-1.29 (3H, m), 1.77-1.93 (4H, m), 2.31 (3H, s), 2.32 (3H, s), 3.23-3.30 (3H, m), 3.38-3.51 (4H, m), 3.55-3.90 (2H, m), 4.40 (2H, s), 7.21-7.26 (1H, m), 7.30 (1H, s), 7.58 (2H, d, J=8.3 Hz), 7.98 (2H, d, J=8.3 Hz), 8.07 (1H, s), 8.26-8.46 (1H, m), 10.84-11.07 (1H, m)

Example 104

N'-[2,5-Dimethyl-4-({4-[4-(piperidin-1-ylcarbonyl)phenyl]-1,3-thiazol-2-yl}methyl)phenyl]-N-ethyl-N-methylimidoformamide

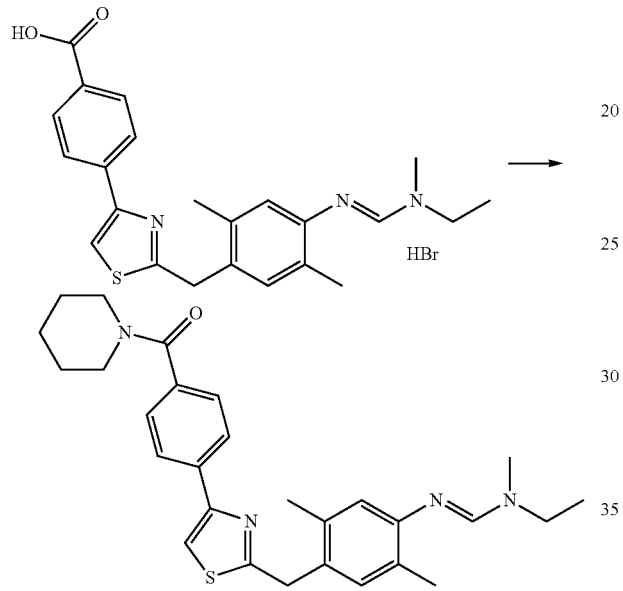

The title compound was obtained by the same technique as in Example 24 from the compound obtained by the technique of Example 15.

¹H NMR (600 MHz, DMSO-d₆) δ ppm 1.14 (3H, t, J=7.2 Hz), 1.40-1.60 (4H, m), 1.60-1.66 (2H, m), 2.15 (3H, s), 2.22 (3H, s), 2.95 (3H, s), 3.25-3.65 (6H, m), 4.27 (2H, s), 6.69 (1H, br. s.), 7.06 (1H, s), 7.42 (2H, d, J=8.4 Hz), 7.54-7.84 (1H, m), 7.99 (2H, d, J=8.4 Hz), 8.01 (1H, s)

Example 105

N'-(2,5-Dimethyl-4-{[4-(5-methylpyrazin-2-yl)-1,3-thiazol-2-yl]methyl}phenyl)-N-ethylimidoformamide hydrochloride

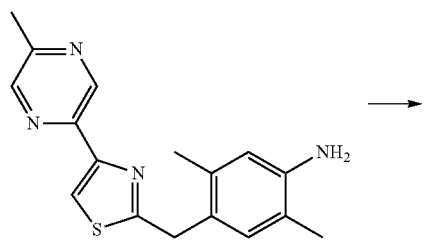

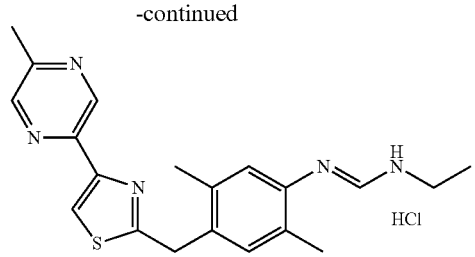

To a N-formylethylamine (1.0 mL) suspension of the compound (50 mg) obtained by the same technique as in Reference Example 3-5, p-toluenesulfonyl chloride (37 mg) was added, and the resultant was stirred at room temperature for 13 hours and 15 minutes and stirred at 75° C. for 2.5 hours. The reaction mixture was cooled to room temperature, and a saturated aqueous solution of sodium bicarbonate and ethyl acetate were added thereto. The organic layer was washed with water and dried over anhydrous sodium sulfate, and the solvent was distilled off under reduced pressure. The obtained residue was purified by silica gel column chromatography (chloroform/acetone=5/1). Ethyl acetate and diethyl ether were added to the obtained oil, then a 4.9 mol/L hydrogen chloride/ethyl acetate solution was added, and the resultant was then concentrated under reduced pressure. Ethyl acetate was added to the obtained residue, and the solid was collected by filtration to obtain the title compound (31 mg) as a brown solid.

¹H NMR (400 MHz, DMSO-d₆) δ ppm 1.09-1.27 (3H, m), 2.13-2.35 (6H, m), 2.52 (3H, s), 3.32-3.56 (2H, m), 4.37-4.45 (2H, m), 7.07-7.37 (2H, m), 8.15-8.70 (2H, m), 8.56 (1H, s), 9.06 (1H, s), 9.98-10.39 (1H, m), 10.97-11.49 (1H, m)

Example 106

4-{2-[4-({(E)-[Ethyl(methyl)amino]methylidene}amino)-2,5-dimethylbenzyl]-1,3-thiazol-4-yl}benzamide

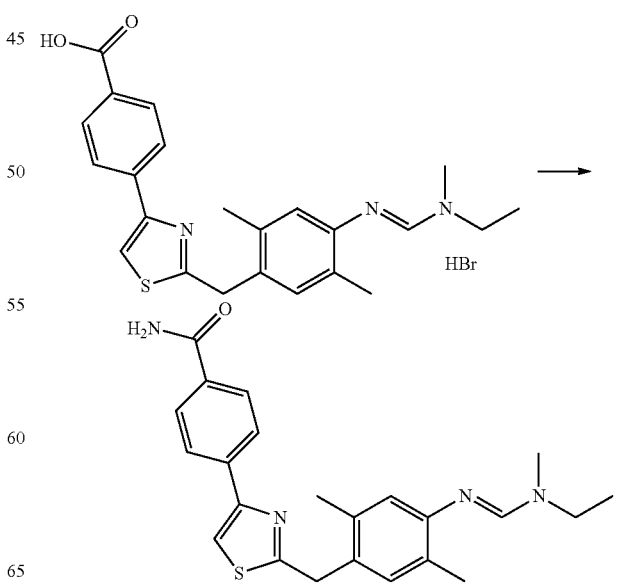

The title compound was obtained by the same technique as in Example 24 from the compound obtained by the technique of Example 15.

¹H NMR (400 MHz, DMSO-d₆) δ ppm 1.20-1.30 (3H, m), 2.30 (3H, s), 2.32 (3H, s), 3.22 (3H, s), 3.57-3.69 (2H, m), 4.40 (2H, s), 7.04-7.41 (5H, m), 7.94 (2H, d, J=8.3 Hz), 8.00 (2H, d, J=8.3 Hz), 8.10 (1H, s)

Example 107

N-Ethyl-4-{2-[4-({(E)-[ethyl(methyl)amino]methylidene}amino)-2,5-dimethylbenzyl]-1,3-thiazol-4-yl}benzamide

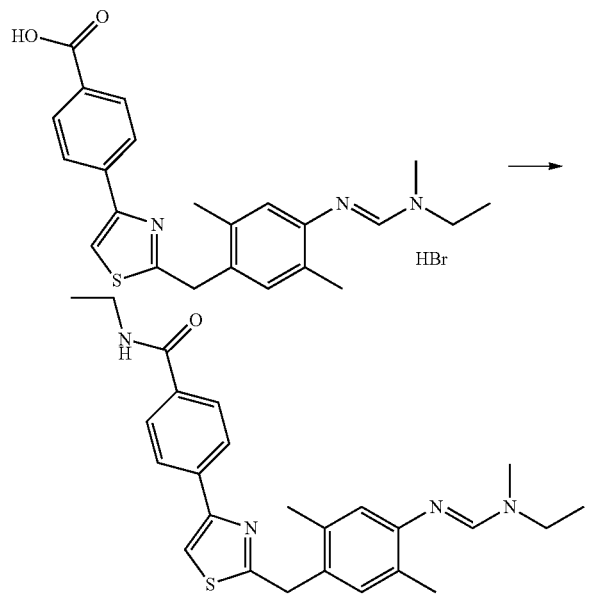

The title compound was obtained by the same technique as in Example 24 from the compound obtained by the technique of Example 15.

¹H NMR (400 MHz, DMSO-d₆) δ ppm 1.09-1.17 (6H, m), 2.14 (3H, s), 2.20 (3H, s), 2.93 (3H, s), 3.33-3.37 (4H, m), 4.26 (2H, s), 6.64 (1H, s), 7.04 (1H, s), 7.51-7.74 (1H, m), 7.90 (2H, d, J=8.4 Hz), 8.02 (2H, d, J=8.4 Hz), 8.05 (1H, s), 8.50 (1H, t, J=5.2 Hz)

Example 108

N'-(4-{[4-(Tert-butoxymethyl)-1,3-thiazol-2-yl]methyl}-2,5-dimethylphenyl)-N-ethyl-N-methylimidoformamide

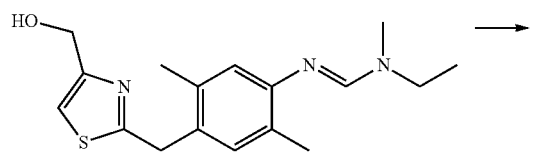

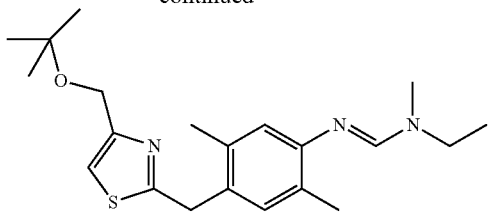

To the compound (56 mg) obtained by the technique of Example 40, a 95% aqueous acetonitrile solution (1.1 mL) was added, then tert-butyl bromide (81 μL) and silver(I) oxide (82 mg) were added in a nitrogen atmosphere under light-shielded conditions, and the resultant was heated to reflux for 6 hours. Methanol was added to the reaction mixture. Insoluble material was removed, and the solvent was distilled off under reduced pressure. The obtained residue was purified by silica gel column chromatography (chloroform/methanol/ammonia water=50/1/0.1) and reverse-phase silica gel column chromatography (35% acetonitrile/0.05 M phosphoric acid-potassium phosphate buffer solution (pH 3)) in this order to obtain the title compound (0.38 mg) as a yellow foam.

¹H NMR (400 MHz, CHLOROFORM-d) δ ppm 1.24-1.28 (3H, m), 1.29 (9H, s), 2.20 (3H, s), 2.23 (3H, s), 3.00 (3H, s), 3.30-3.44 (2H, m), 4.21 (2H, s), 4.57-4.59 (2H, m), 6.58 (1H, s), 6.99-7.01 (1H, m), 7.01-7.03 (1H, m), 7.40-7.47 (1H, m)

Example 109

2-[4-({(E)-[Ethyl(methyl)amino]methylidene}amino)-2,5-dimethylbenzyl]-N-(1,1,1-trifluoro-2-methylpropan-2-yl)-1,3-thiazole-4-carboxamide hydrochloride

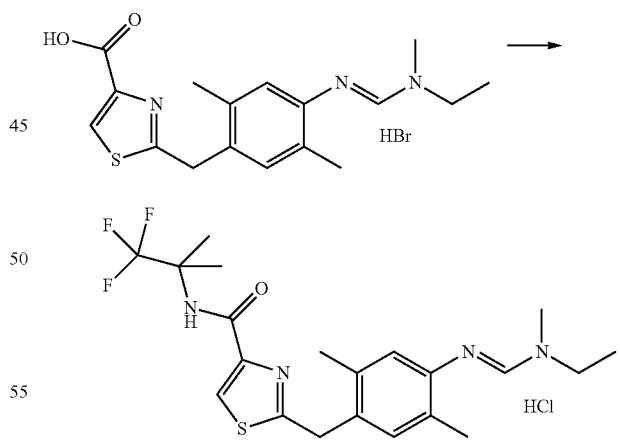

The title compound was obtained by the same technique as in Example 43 from the compound obtained by the technique of Example 39.

¹H NMR (400 MHz, DMSO-d₆) δ ppm 1.21-1.30 (3H, m), 1.64 (6H, s), 2.23-2.31 (6H, m), 3.20-3.30 (3H, m), 3.57-3.67 (2H, m), 4.38 (2H, s), 7.25 (1H, s), 7.29 (1H, s), 7.73 (1H, s), 8.17 (1H, s), 8.28-8.47 (1H, m), 10.53-10.67 (1H, m)

Example 110

N'-[2,5-Dimethyl-4-({4-[4-(morpholin-4-ylcarbonyl)phenyl]-1,3-thiazol-2-yl}methyl)phenyl]-N-ethyl-N-methylimidoformamide hydrochloride

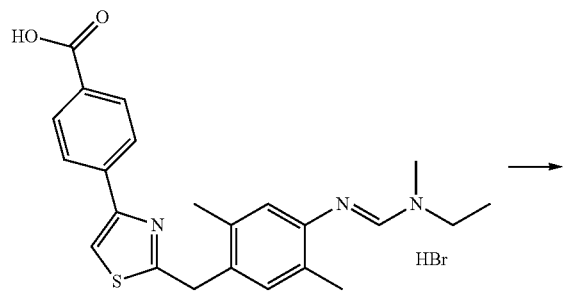

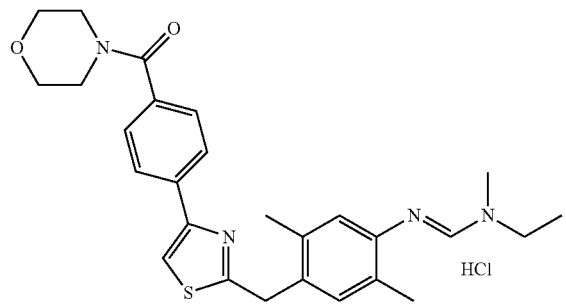

The title compound was obtained by the same technique as in Example 24 from the compound obtained by the technique of Example 15.

$^1$H NMR (400 MHz, DMSO-d$_6$) δ ppm 1.22-1.29 (3H, m), 2.31 (3H, s), 2.32 (3H, s), 3.22-3.30 (3H, m), 3.30-3.93 (10H, m), 4.40 (2H, s), 7.21-7.26 (1H, m), 7.30 (1H, s), 7.48 (2H, d, J=8.3 Hz), 7.99 (2H, d, J=8.3 Hz), 8.07 (1H, s), 8.26-8.46 (1H, m), 10.82-11.03 (1H, m)

Example 111

N'-(2,5-Dimethyl-4-{[4-(5-methylpyrazin-2-yl)-1,3-thiazol-2-yl]methyl}phenyl)-N-methylimidoformamide

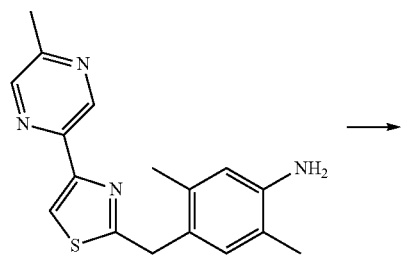

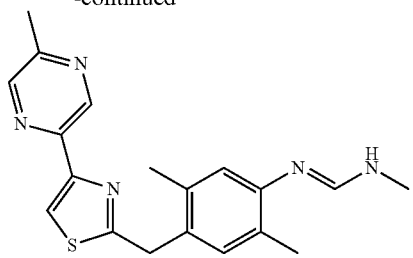

The title compound was obtained by the same technique as in Example 105 from the compound obtained by the technique of Reference Example 3-5.

$^1$H NMR (400 MHz, DMSO-d$_6$) δ ppm 2.12 (3H, s), 2.19 (3H, s), 2.52 (3H, s), 2.77 (3H, d, J=4.4 Hz), 4.27 (2H, s), 6.56 (1H, s), 6.87-6.95 (1H, m), 7.03 (1H, s), 7.53-7.60 (1H, m), 8.13 (1H, s), 8.53-8.57 (1H, m), 9.08 (1H, d, J=1.5 Hz)

Test Example

The fungal susceptibility tests on test substances were conducted by the broth microdilution method equivalent to Clinical and Laboratory Standards Institute method. The medium used in the susceptibility tests was RPMI1640 adjusted to pH 7.0 with 0.165 mol/L morpholinepropanesulfonic acid (MOPS) and 50% sodium hydroxide (RPMI/MOPS). Each test substance was dissolved in DMSO and serially diluted in 2-fold increments with DMSO on a 96-well microplate. Then, the dilutions were dispensed by 1 μL to a 96-well microplate. *Candida albicans* TIMM 1623 cultured overnight at 35° C. in Sabouraud's agar medium was suspended in sterile saline. The number of cells was counted under a biological microscope, and the fungal suspension was diluted with RPMI/MOPS to prepare the inoculum solution (approximately 1×10$^3$ cells/mL). Alternatively, *Candida albicans* TIMM 1623 stored at −80° C. was diluted with RPMI/MOPS to prepare the inoculum solution (approximately 1×10$^3$ CFU/mL). *Aspergillus fumigatus* TIMM 0063 stored at 5° C. was diluted with RPMI/MOPS to prepare the inoculum solution (approximately 1×10$^4$ CFU/mL). *Trichophyton rubrum* NBRC 5467 stored at 5° C. or −80° C. was diluted with RPMI/MOPS to prepare the inoculum solution (approximately 2×10$^3$ CFU/mL). The 199 μL of inoculum solution was dispensed to each well to prepare the microplate containing the designated concentrations of test substance, medium and fungal cells. *Candida albicans* and *Aspergillus fumigatus* were cultured at 35° C. for 2 days. *Trichophyton rubrum* was cultured at 35° C. for 4 days. After the completion of culture, MIC was determined by visual observation. The MICs of *Candida albicans* and *Aspergillus fumigatus* were set to the lowest concentration at which approximately 50% growth inhibition was seen, when compared with a growth control without the addition of the test substance. The MIC of *Trichophyton rubrum* was set to the lowest concentration at which approximately 80% growth inhibition was seen, when compared with a growth control without the addition of the test substance. The results are shown in Tables 1 to 3.

TABLE 1

| Test substance (Example No.) | MIC (μg/mL) C. albicans TIMM1623 |
|---|---|
| 3 | 0.0156 |
| 4 | 0.0313 |
| 14 | 0.0625 |
| 16 | 0.0313 |

TABLE 1-continued

| Test substance (Example No.) | MIC (μg/mL) C. albicans TIMM1623 |
|---|---|
| 17 | 0.0313 |
| 20 | 0.0313 |
| 24 | 0.0313 |
| 26 | 0.0625 |
| 27 | 0.0625 |
| 29 | 0.0625 |
| 36 | 0.0313 |
| 42 | 0.0625 |
| 48 | 0.0625 |
| 49 | 0.0156 |
| 58 | 0.0156 |
| 59 | 0.0156 |
| 60 | 0.0156 |
| 99 | 0.0625 |

TABLE 2

| Test substance (Example No.) | MIC (μg/mL) A. fumigatus TIMM 0063 |
|---|---|
| 1 | 0.0625 |
| 3 | 0.0156 |
| 16 | 0.0313 |
| 26 | 0.0625 |
| 27 | 0.0625 |
| 49 | 0.0625 |
| 58 | 0.0625 |
| 59 | 0.0313 |

TABLE 3

| Test substance (Example No.) | MIC (μg/mL) T. rubrum NBRC5467 |
|---|---|
| 1 | 0.0039 |
| 3 | 0.0005 |
| 4 | 0.002 |
| 7 | 0.25 |
| 16 | 0.002 |
| 17 | 0.002 |
| 19 | 0.0156 |
| 20 | 0.002 |
| 21 | 0.0156 |
| 23 | 0.0039 |
| 24 | 0.0039 |
| 25 | 0.0313 |
| 29 | 0.0039 |
| 30 | 0.0625 |
| 31 | 0.0078 |
| 32 | 0.0039 |
| 34 | 0.0313 |
| 35 | 0.0313 |
| 37 | 0.0039 |
| 38 | 0.0078 |
| 41 | 0.0078 |
| 44 | 0.0625 |
| 45 | 0.0313 |
| 47 | 0.0313 |
| 48 | 0.0078 |
| 51 | 0.25 |
| 58 | 0.001 |
| 59 | 0.0005 |
| 60 | 0.001 |
| 63 | 0.0156 |
| 67 | 0.0625 |
| 71 | 0.0156 |
| 74 | 0.0156 |
| 81 | 0.0156 |
| 86 | 0.0039 |

TABLE 3-continued

| Test substance (Example No.) | MIC (μg/mL) T. rubrum NBRC5467 |
|---|---|
| 87 | 0.0156 |
| 89 | 0.0625 |
| 95 | 0.125 |
| 96 | 0.0313 |
| 97 | 0.0078 |
| 98 | 0.0156 |
| 101 | 0.0625 |
| 102 | 0.0078 |
| 105 | 0.0313 |
| 109 | 0.0039 |

INDUSTRIAL APPLICABILITY

The compound of the present invention or the salt thereof has an antifungal activity against pathogenic fungi and therefore is useful as an antifungal agent.

The invention claimed is:
1. A compound represented by a formula (I):

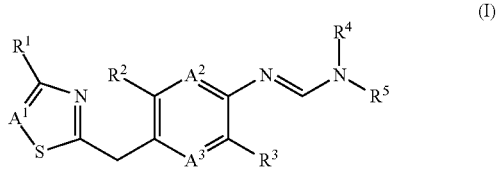

(wherein
$A^1$ represents a nitrogen atom or a group represented by a formula $CR^6$, where $R^6$ represents a hydrogen atom, a halogen atom, a cyano group or a group represented by a formula $COR^7$, where $R^7$ represents a hydroxy group, a $C_{1-6}$ alkoxy group, a $C_{1-6}$ alkyl group, an aryl group or a group represented by a formula $NR^8R^9$, where
$R^8$ and $R^9$ are the same or different and represent a hydrogen atom or a $C_{1-6}$ alkyl group, or
$R^8$ and $R^9$ represent, together with the nitrogen atom bonded thereto, a saturated heterocyclic ring which may be substituted with oxo group;
$A^2$ and $A^3$ each represent CH;
$R^1$ represents a $C_{3-6}$ cycloalkyl group which may be substituted with 1 to 5 substituents selected from Substituent Group 1, a $C_{1-6}$ alkyl group which may be substituted with 1 to 6 substituents selected from Substituent Group 1, an aryl group which may be substituted with 1 to 5 substituents selected from Substituent Group 2, a heterocyclic group which may be substituted with 1 to 5 substituents selected from Substituent Group 2, a group represented by a formula $OR^{10}$, a group represented by a formula $COR^{11}$, a group represented by a formula $NR^{12}CO_2R^{13}$, a group represented by a formula $NR^{14}CONR^{15}R^{16}$, a group represented by a formula $NR^{17}COR^{18}$, a group represented by a formula $NR^{19}SO_2R^{20}$ or a group represented by a formula $OCONR^{21}R^{22}$, where
$R^{10}$, $R^{13}$, $R^{15}$, $R^{16}$, $R^{21}$ and $R^{22}$ are the same or different and represent a hydrogen atom, a $C_{1-6}$ alkyl group which may be substituted with 1 to 6 substituents selected from Substituent Group 1, a $C_{3-6}$ cycloalkyl group which may be substituted with 1 to 5 substituents selected from Substituent Group 1, an adamantyl group, an aryl group which may be substituted with 1 to 5 substituents selected from Substituent Group 2 or a heterocyclic group which may be substituted with 1 to 5 substituents selected from Substituent Group 2, $R^{11}$ represents a hydroxy group, a $C_{1-6}$ alkoxy group, a $C_{1-6}$ alkyl group which may be substituted with 1 to 6 substituents selected from Substituent Group 1, a $C_{3-6}$ cycloalkyl group which may be substituted with 1 to 5 substituents selected from Substituent Group 1, an adamantyl group, an aryl group which may be substituted with 1 to 5 substituents selected from Substituent Group 2, a heterocyclic group which may be substituted with 1 to 5 substituents selected from Substituent Group 2 or a group represented by a formula $NR^{23}R^{24}$, where $R^{23}$ and $R^{24}$ are the same or different and represent a hydrogen atom, a $C_{1-6}$ alkyl group which may be substituted with 1 to 6 substituents selected from Substituent Group 1 or a $C_{3-6}$ cycloalkyl group which may be substituted with 1 to 5 substituents selected from Substituent Group 1, $R^{12}$, $R^{14}$, $R^{17}$ and $R^{19}$ are the same or different and represent a hydrogen atom or a $C_{1-6}$ alkyl group, $R^{18}$ and $R^{20}$ are the same or different and represent a $C_{1-6}$ alkyl group which may be substituted with 1 to 6 substituents selected from Substituent Group 1, a $C_{3-6}$ cycloalkyl group which may be substituted with 1 to 5 substituents selected from Substituent Group 1, an adamantyl group, an aryl group which may be substituted with 1 to 5 substituents selected from Substituent Group 2 or a heterocyclic group which may be substituted with 1 to 5 substituents selected from Substituent Group 2, Substituent Group 1 is the group consisting of a halogen atom, an aryl group which may be substituted with 1 to 5 substituents selected from Substituent Group 2, a heterocyclic group which may be substituted with 1 to 5 substituents selected from Substituent Group 2, a group represented by a formula —$OR^{25}$, a group represented by a formula —$COR^{26}$, a group represented by a formula —$NR^{27}R^{28}$ and a group represented by a formula —$SO_2R^{29}$, where $R^{25}$ represents a hydrogen atom, a $C_{1-6}$ alkyl group, an aryl group which may be substituted with 1 to 5 substituents selected from Substituent Group 2 or a $C_{1-6}$ alkanoyl group, $R^{29}$ represents a hydroxy group, a $C_{1-6}$ alkoxy group or a group represented by a formula $NR^{30}R^{31}$, where $R^{30}$ and $R^{31}$ are the same or different and represent a hydrogen atom or a $C_{1-6}$ alkyl group, or $R^{30}$ and $R^{31}$ represent, together with the nitrogen atom bonded thereto, a saturated heterocyclic ring which may be substituted with oxo group, $R^{27}$ and $R^{28}$ are the same or different and represent a hydrogen atom or a $C_{1-6}$ alkyl group, $R^{29}$ represents a $C_{1-6}$ alkyl group, a $C_{3-6}$ cycloalkyl group, an aryl group which may be substituted with 1 to 5 substituents selected from Substituent Group 2 or a heterocyclic group which may be substituted with 1 to 5 substituents selected from Substituent Group 2, Substituent Group 2 is the group consisting of a halogen atom, an oxo group, a hydroxy group, a $C_{1-6}$ alkoxy group, a $C_{1-6}$ alkyl group, a $C_{1-6}$ haloalkyl group, a cyano group, a $C_{1-6}$ alkylsulfanyl group, a $C_{1-6}$ alkylsulfinyl group, a $C_{1-6}$ alkylsulfonyl group, an aminosulfonyl group, a $C_{1-6}$ alkylaminosulfonyl group and a group represented by a formula $COR^{32}$, where $R^{32}$ represents a hydroxy group, a $C_{1-6}$ alkoxy group or a group represented by a formula $NR^{33}R^{34}$, where $R^{33}$ and $R^{34}$ are the same or different and represent a hydrogen atom or a $C_{1-6}$ alkyl group, or $R^{33}$ and $R^{34}$ represent, together with the nitrogen atom bonded thereto, a saturated heterocyclic ring which may be substituted with oxo group;

$R^2$ and $R^3$ are the same or different and represent a hydrogen atom, a halogen atom, a $C_{1-6}$ alkyl group, a $C_{1-6}$ haloalkyl group or a $C_{1-6}$ alkoxy group;

$R^4$ and $R^5$ are the same or different and represent a hydrogen atom, a $C_{1-6}$ haloalkyl group or a $C_{1-6}$ alkyl group, wherein the $C_{1-6}$ alkyl group may be substituted with 1 to 3 substituents selected from the group consisting of a hydroxy group and a group represented by a formula $COR^{35}$, where $R^{35}$ represents a hydroxy group, a $C_{1-6}$ alkoxy group or a group represented by a formula $NR^{36}R^{37}$, where $R^{36}$ and $R^{37}$ are the same or different and represent a hydrogen atom or a $C_{1-6}$ alkyl group, or $R^{36}$ and $R^{37}$ represent, together with the nitrogen atom bonded thereto, a saturated heterocyclic ring which may be substituted with oxo group, or $R^4$ and $R^5$ represent, together with the nitrogen atom bonded thereto, a saturated heterocyclic ring which may be substituted with oxo group)

or a pharmaceutically acceptable salt thereof.

2. The compound or the pharmaceutically acceptable salt thereof according to claim 1, wherein $R^2$ and $R^3$ are the same or different and represent a hydrogen atom or a $C_{1-6}$ alkyl group.

3. The compound or the pharmaceutically acceptable salt thereof according to claim 1, wherein $R^2$ and $R^3$ are the same or different and represent a $C_{1-6}$ alkyl group.

4. The compound or the pharmaceutically acceptable salt thereof according to claim 1, wherein $A^1$ is a nitrogen atom or a group represented by a formula CH.

5. The compound or the pharmaceutically acceptable salt thereof according to claim 1, wherein $R^1$ is a $C_{3-6}$ cycloalkyl group which may be substituted with 1 to 5 substituents selected from Substituent Group 1, a $C_{1-6}$ alkyl group which may be substituted with 1 to 6 substituents selected from Substituent Group 1, an aryl group which may be substituted with 1 to 5 substituents selected from Substituent Group 2, a heterocyclic group which may be substituted with 1 to 5 substituents selected from Substituent Group 2, a group represented by the formula $OR^{10}$, a group represented by the formula $COR^{11}$ or a group represented by the formula $NR^{12}CO_2R^{13}$.

* * * * *

UNITED STATES PATENT AND TRADEMARK OFFICE
CERTIFICATE OF CORRECTION

PATENT NO. : 9,045,466 B2
APPLICATION NO. : 14/235686
DATED : June 2, 2015
INVENTOR(S) : Tetsuya Tanikawa et al.

Page 1 of 1

It is certified that error appears in the above-identified patent and that said Letters Patent is hereby corrected as shown below:

Title page, item (73) Assignees:

"(73) Assignees: TAISHO PHARMACEUTICAL CO., LTD, Tokyo (JP);
TOYAMA CHEMICAL CO., LTD., Tokyo (JP)"

should be

-- (73) Assignees: TAISHO PHARMACEUTICAL CO., LTD., Tokyo (JP);
TOYAMA CHEMICAL CO., LTD., Tokyo (JP) --

Signed and Sealed this
Eighth Day of December, 2015

Michelle K. Lee
*Director of the United States Patent and Trademark Office*